(12) United States Patent
Rao et al.

(10) Patent No.: US 11,208,683 B2
(45) Date of Patent: *Dec. 28, 2021

(54) METHODS OF EPIGENETIC ANALYSIS

(71) Applicants: The Children's Medical Center Corporation, Boston, MA (US); The United States of America, As Represented by the Secretary, Department of Health & Human Services, Bethesda, MD (US)

(72) Inventors: Anjana Rao, La Jolla, CA (US); Mamta Tahiliani, New York, NY (US); Kian Peng Koh, Jamaica Plain, MA (US); Suneet Agarwal, Belmont, MA (US); Aravind Iyer, Bethesda, MD (US)

(73) Assignees: The Children's Medical Center Corporation, Boston, MA (US); The United States of America, As Represented by the Secretary, Department of Health & Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/231,671

(22) Filed: Apr. 15, 2021

(65) Prior Publication Data

US 2021/0246494 A1  Aug. 12, 2021

Related U.S. Application Data

(63) Continuation of application No. 16/658,195, filed on Oct. 21, 2019, now abandoned, which is a continuation of application No. 16/180,450, filed on Nov. 5, 2018, now Pat. No. 10,767,216, which is a continuation of application No. 16/169,801, filed on Oct. 24, 2018, now Pat. No. 10,465,234, which is a continuation of application No. 15/341,344, filed on Nov. 2, 2016, now Pat. No. 10,533,213, which is a continuation of application No. 15/193,796, filed on Jun. 27, 2016, now Pat. No. 10,443,091, which is a continuation of application No. 13/795,739, filed on Mar. 12, 2013, now Pat. No. 9,447,452, which is a continuation of application No. 13/120,861, filed as application No. PCT/US2009/058562 on Sep. 28, 2009, now Pat. No. 9,115,386.

(60) Provisional application No. 61/121,844, filed on Dec. 11, 2008, provisional application No. 61/100,995, filed on Sep. 29, 2008, provisional application No. 61/100,503, filed on Sep. 26, 2008.

(51) Int. Cl.
C12Q 1/6827 (2018.01)
C12Q 1/26 (2006.01)
C12N 9/10 (2006.01)
G01N 33/53 (2006.01)
C12Q 1/6806 (2018.01)
C12Q 1/6869 (2018.01)

(52) U.S. Cl.
CPC ......... *C12Q 1/6827* (2013.01); *C12N 9/1007* (2013.01); *C12Q 1/26* (2013.01); *C12Q 1/6806* (2013.01); *C12Q 1/6869* (2013.01); *G01N 33/5308* (2013.01); *C12N 2501/70* (2013.01); *C12N 2501/71* (2013.01); *C12N 2501/724* (2013.01); *C12Q 2521/531* (2013.01); *C12Q 2522/10* (2013.01); *C12Q 2537/164* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,115,538 A | 9/1978 | Satoh et al. |
| 4,889,798 A | 12/1989 | Rabbani |
| 5,241,060 A | 8/1993 | Engelhardt et al. |
| 5,260,433 A | 11/1993 | Engelhardt et al. |
| 5,405,760 A | 4/1995 | Raleigh et al. |
| 7,220,854 B1 | 5/2007 | Engelhardt et al. |
| 7,399,614 B2 | 7/2008 | Zon |
| 8,257,950 B2 | 9/2012 | Berlin et al. |
| 8,653,007 B2 | 2/2014 | Zheng et al. |
| 8,679,745 B2 | 3/2014 | Ballhause et al. |
| 8,741,567 B2 | 6/2014 | He et al. |
| 8,822,146 B2 | 9/2014 | Klimasauskas et al. |

(Continued)

FOREIGN PATENT DOCUMENTS

| | | |
|---|---|---|
| CN | 105648537 A | 6/2016 |
| EP | 1394173 A1 | 3/2004 |

(Continued)

OTHER PUBLICATIONS

Hayatsu et al., "Reaction of bisulfite with the 5-hydroxymethyl group in pyrimidines and in phage DNAs", Biochemistry 18(4) 632-637 (1979).

(Continued)

*Primary Examiner* — Susan M Hanley
(74) *Attorney, Agent, or Firm* — Nixon Peabody LLP; David S. Resnick; Mark J. FitzGerald

(57) ABSTRACT

The present invention provides for methods of epigenetic analysis. In some cases, the methods may include obtaining a sample comprising a nucleic acid sequence. In some cases, the nucleic acid sequence may comprise one or more epigenetic marks. The methods may include performing a sequencing. The methods may include distinguishing a hydroxymethylated base from a methylated base.

12 Claims, 53 Drawing Sheets
Specification includes a Sequence Listing.

(56) References Cited

U.S. PATENT DOCUMENTS

| | | |
|---|---|---|
| 8,889,352 B2 | 11/2014 | Klimasauskas et al. |
| 8,951,736 B2 | 2/2015 | Schmidt |
| 8,962,246 B2 | 2/2015 | Ballhause et al. |
| 8,969,061 B2 | 3/2015 | Zhu et al. |
| 9,029,087 B2 | 5/2015 | Zheng et al. |
| 9,034,597 B2 | 5/2015 | Bitinaite et al. |
| 9,040,239 B2 | 5/2015 | Zheng et al. |
| 9,115,386 B2 | 8/2015 | Rao et al. |
| 9,121,061 B2 | 9/2015 | Vaisvila et al. |
| 9,145,580 B2 | 9/2015 | Feehery et al. |
| 9,150,918 B2 | 10/2015 | Turner et al. |
| 9,175,338 B2 | 11/2015 | Flusberg et al. |
| 9,175,341 B2 | 11/2015 | Flusberg et al. |
| 9,175,348 B2 | 11/2015 | Korlach et al. |
| 9,200,260 B2 | 12/2015 | Correa, Jr. et al. |
| 9,200,316 B2 | 12/2015 | Zheng et al. |
| 9,238,836 B2 | 1/2016 | Korlach et al. |
| 9,243,233 B2 | 1/2016 | Rimseliene et al. |
| 9,267,117 B2 | 2/2016 | Guan et al. |
| 9,290,807 B2 | 3/2016 | Booth et al. |
| 9,297,806 B2 | 3/2016 | Yegnasubramanian et al. |
| 9,347,093 B2 | 5/2016 | Klimasauskas et al. |
| 9,447,452 B2 | 9/2016 | Rao et al. |
| 9,464,277 B2 | 10/2016 | Zheng et al. |
| 9,505,797 B2 | 11/2016 | Klimasauskas et al. |
| 9,546,400 B2 | 1/2017 | Turner et al. |
| 9,567,633 B2 | 2/2017 | Gao et al. |
| 9,611,510 B2 | 4/2017 | He et al. |
| 9,650,675 B2 | 5/2017 | Rimseliene et al. |
| 9,677,128 B2 | 6/2017 | Robertson et al. |
| 9,816,986 B2 | 11/2017 | Rao et al. |
| 9,822,394 B2 | 11/2017 | Ost et al. |
| 9,879,315 B2 | 1/2018 | Summerer et al. |
| 9,915,655 B2 | 3/2018 | Bensimon et al. |
| 9,988,673 B2 | 6/2018 | Klimasauskas et al. |
| 10,031,131 B2 | 7/2018 | Rao et al. |
| 10,041,938 B2 | 8/2018 | Rao et al. |
| 10,081,827 B2 | 9/2018 | Guan et al. |
| 10,155,939 B1 | 12/2018 | Vaisvila et al. |
| 10,323,269 B2 | 6/2019 | Rao et al. |
| 10,337,053 B2 | 7/2019 | Rao et al. |
| 10,443,091 B2 | 10/2019 | Rao et al. |
| 10,465,234 B2 | 11/2019 | Rao et al. |
| 10,508,301 B2 | 12/2019 | Rao et al. |
| 10,533,213 B2 | 1/2020 | Rao et al. |
| 10,612,076 B2 | 4/2020 | Rao et al. |
| 10,731,204 B2 | 8/2020 | Rao et al. |
| 10,767,216 B2 | 9/2020 | Rao et al. |
| 10,774,373 B2 | 9/2020 | Rao et al. |
| 10,793,899 B2 | 10/2020 | Rao et al. |
| 11,072,818 B2 | 7/2021 | Rao et al. |
| 2003/0017454 A1 | 1/2003 | Sukumar et al. |
| 2003/0211522 A1 | 11/2003 | Landes et al. |
| 2004/0048279 A1 | 3/2004 | Olek et al. |
| 2004/0132026 A1 | 7/2004 | Olek |
| 2004/0175826 A1 | 9/2004 | Maor |
| 2004/0219580 A1 | 11/2004 | Dunn et al. |
| 2005/0019815 A1* | 1/2005 | Gladyshev ............ C07K 14/47 435/6.14 |
| 2005/0106690 A1* | 5/2005 | Hirata ................... C12P 17/10 435/107 |
| 2005/0153296 A1 | 7/2005 | Berlin |
| 2005/0245737 A1 | 11/2005 | Cummings |
| 2006/0183128 A1 | 8/2006 | Berlin et al. |
| 2006/0257905 A1 | 11/2006 | Freije et al. |
| 2007/0026393 A1 | 2/2007 | Berlin et al. |
| 2007/0243161 A1 | 10/2007 | Olek |
| 2007/0269824 A1 | 11/2007 | Albrecht et al. |
| 2009/0136998 A1* | 5/2009 | Gambhir ................ C12Q 1/66 435/69.1 |
| 2010/0167942 A1 | 7/2010 | Zheng et al. |
| 2010/0197510 A1 | 8/2010 | Spain et al. |
| 2010/0221716 A1 | 9/2010 | Flusberg et al. |
| 2011/0059432 A1 | 3/2011 | Ballhause et al. |
| 2011/0236894 A1 | 9/2011 | Rao et al. |
| 2011/0301045 A1 | 12/2011 | He et al. |
| 2012/0064521 A1 | 3/2012 | Yen et al. |
| 2013/0230856 A1 | 9/2013 | Schneider et al. |
| 2013/0323728 A1 | 12/2013 | Robertson et al. |
| 2014/0030727 A1 | 1/2014 | Pfeifer et al. |
| 2014/0127677 A1 | 5/2014 | Correa, Jr. et al. |
| 2014/0178873 A1 | 6/2014 | Brachmann et al. |
| 2014/0179564 A1 | 6/2014 | Korlach et al. |
| 2014/0228231 A1 | 8/2014 | Vilain et al. |
| 2014/0272970 A1 | 9/2014 | Zegzouti et al. |
| 2014/0322707 A1 | 10/2014 | He et al. |
| 2014/0363815 A1 | 12/2014 | Dahl et al. |
| 2015/0004596 A1 | 1/2015 | Zhu et al. |
| 2015/0011403 A1 | 1/2015 | Lo et al. |
| 2015/0056616 A1 | 2/2015 | He et al. |
| 2015/0240310 A1 | 8/2015 | Bitinaite et al. |
| 2015/0259742 A1 | 9/2015 | Zhang et al. |
| 2015/0285807 A1 | 10/2015 | Shi et al. |
| 2015/0299781 A1 | 10/2015 | Ost |
| 2015/0307542 A1 | 10/2015 | Roy et al. |
| 2016/0046981 A1 | 2/2016 | Correa, Jr. et al. |
| 2016/0115525 A1 | 4/2016 | Ebenstein et al. |
| 2016/0186207 A1 | 6/2016 | Reik et al. |
| 2016/0194696 A1 | 7/2016 | Guan et al. |
| 2016/0222448 A1 | 8/2016 | Horvath |
| 2016/0258014 A1 | 9/2016 | Booth et al. |
| 2016/0304552 A1 | 10/2016 | Roy et al. |
| 2017/0051354 A1 | 2/2017 | Davis et al. |
| 2017/0067093 A1 | 3/2017 | Klimasauskas et al. |
| 2017/0145484 A1 | 5/2017 | Rao et al. |
| 2017/0168043 A1 | 6/2017 | Rao et al. |
| 2017/0175085 A1 | 6/2017 | Rao et al. |
| 2017/0175129 A1 | 6/2017 | Roy et al. |
| 2017/0176420 A1 | 6/2017 | Rao et al. |
| 2017/0176421 A1 | 6/2017 | Rao et al. |
| 2017/0191119 A1 | 7/2017 | Rao et al. |
| 2017/0198344 A1 | 7/2017 | Vaisvila et al. |
| 2017/0218338 A1 | 8/2017 | Rao et al. |
| 2017/0219589 A1 | 8/2017 | Rao et al. |
| 2017/0253924 A1 | 9/2017 | Lu et al. |
| 2017/0283863 A1 | 10/2017 | Robertson et al. |
| 2017/0283870 A1 | 10/2017 | Ost et al. |
| 2017/0298422 A1 | 10/2017 | Song et al. |
| 2018/0044632 A1 | 2/2018 | Rao et al. |
| 2018/0044633 A1 | 2/2018 | Rao et al. |
| 2018/0105884 A1 | 4/2018 | Lo et al. |
| 2018/0112206 A1 | 4/2018 | Forsyth et al. |
| 2018/0119113 A1 | 5/2018 | Rao et al. |
| 2018/0119225 A1 | 5/2018 | Rao et al. |
| 2018/0120304 A1 | 5/2018 | Rao et al. |
| 2018/0171397 A1 | 6/2018 | Vaisvila et al. |
| 2018/0179587 A1 | 6/2018 | Rao et al. |
| 2018/0180602 A1 | 6/2018 | Rao et al. |
| 2018/0201993 A1 | 7/2018 | Turner et al. |
| 2018/0223332 A1 | 8/2018 | Ost et al. |
| 2018/0224434 A9 | 8/2018 | Rao et al. |
| 2018/0237839 A1 | 8/2018 | Rao et al. |
| 2018/0245128 A1 | 8/2018 | He et al. |
| 2018/0251815 A1 | 9/2018 | Okamoto et al. |
| 2018/0258149 A1 | 9/2018 | Motz et al. |
| 2018/0258474 A1 | 9/2018 | Jain et al. |
| 2018/0291435 A1 | 10/2018 | Rao et al. |
| 2018/0298431 A1 | 10/2018 | Rao et al. |
| 2018/0312914 A1 | 11/2018 | Vaisvila et al. |
| 2018/0327855 A1 | 11/2018 | Ebenstein et al. |
| 2019/0017109 A1 | 1/2019 | Song et al. |
| 2019/0048405 A1 | 2/2019 | Rao et al. |
| 2019/0048407 A1 | 2/2019 | Rao et al. |
| 2019/0055593 A1 | 2/2019 | Rao et al. |
| 2019/0062817 A1 | 2/2019 | Rao et al. |
| 2019/0233885 A1 | 8/2019 | Rao et al. |
| 2019/0300941 A1 | 10/2019 | Rao et al. |
| 2019/0390261 A1 | 12/2019 | Rao et al. |
| 2020/0040381 A1 | 2/2020 | Rao et al. |

(56) References Cited

U.S. PATENT DOCUMENTS

| | | | |
|---|---|---|---|
| 2020/0087715 A1 | 3/2020 | Rao et al. | |
| 2020/0087716 A1 | 3/2020 | Rao et al. | |

FOREIGN PATENT DOCUMENTS

| | | | |
|---|---|---|---|
| EP | 1568786 A2 | 8/2005 | |
| EP | 1614149 A4 | 4/2006 | |
| EP | 1394173 B9 | 10/2008 | |
| EP | 2292797 A1 | 3/2011 | |
| EP | 2292797 B1 | 7/2013 | |
| EP | 1614149 B1 | 11/2013 | |
| EP | 2414528 B1 | 5/2014 | |
| EP | 2414527 B1 | 5/2015 | |
| EP | 2470675 B1 | 3/2016 | |
| EP | 3053585 A1 | 8/2016 | |
| EP | 3061764 A1 | 8/2016 | |
| EP | 2737085 B1 | 10/2016 | |
| EP | 2825645 B1 | 10/2016 | |
| EP | 2376632 B1 | 11/2016 | |
| EP | 3124605 A1 | 2/2017 | |
| EP | 2776575 B1 | 3/2017 | |
| EP | 3013979 B1 | 4/2017 | |
| EP | 3214183 A1 | 6/2017 | |
| EP | 2630257 B1 | 8/2017 | |
| EP | 2694686 B1 | 11/2017 | |
| EP | 2948774 B1 | 7/2018 | |
| GB | 1603778 A | 11/1981 | |
| WO | 2006109300 A1 | 10/2006 | |
| WO | 2008150853 A1 | 12/2008 | |
| WO | 2009092035 A2 | 7/2009 | |
| WO | 2010037001 A2 | 4/2010 | |
| WO | 2013017853 A2 | 2/2013 | |
| WO | 2014083118 A1 | 6/2014 | |
| WO | 2015124955 A1 | 8/2015 | |
| WO | 2015145133 A1 | 10/2015 | |
| WO | 2016016639 A1 | 2/2016 | |
| WO | 2016034908 A1 | 3/2016 | |
| WO | 2016063034 A1 | 4/2016 | |
| WO | 2016063059 A1 | 4/2016 | |
| WO | 2016079509 A1 | 5/2016 | |
| WO | 2016170319 A1 | 10/2016 | |
| WO | 2016189288 A1 | 12/2016 | |
| WO | 2017190215 A1 | 11/2017 | |
| WO | 2018129120 A1 | 7/2018 | |
| WO | 2018165459 A1 | 9/2018 | |

OTHER PUBLICATIONS

Hayatsu et al., "Reaction of sodium bisulfite with uracil, cytosine, and their derivatives", Biochemistry 9(14) 2858-2865 (1970).
He et al., "Tet-mediated formation of 5-carboxylcytosine and its excision by TDG in mammalian DNA", Science 333(6047) 1303-1307 (2011).
Hegde et al., "Early steps in the DNA base excision/single-strand interruption repair pathway in mammalian cells", Cell Res 18(1) 27-47 (2008).
Hochedlinger et al., "Nuclear reprogramming and pluripotency", Nature 441(7097) 1061-1067 (2006).
International Search Report with Written Opinion for PCT/US2009/058562, dated May 20, 2010.
Ito et al., "Tet proteins can convert 5-methylcytosine to 5-formylcytosine and 5-carboxylcytosine", Science 333(6047) 1300-1303 (2011).
Jabbari et al., "Evolutionary changes in CpG and methylation levels in the genome of vertebrates", Gene 205(1-2) 109-118 (1997).
Jiricny et al., "DNA Cytosine demethylation: are we getting close?", Cell 135(7) 1167-1169 (2008).
Johnson et al., "5-Hydroxymethylcytosine localizes to enhancer elements and is associated with survival in glioblastoma patients", Nat Commun 7: 13177 (2016).
Kangaspeska et al., "Transient cyclical methylation of promoter DNA", Nature 452(7183) 112-115 (2008).
Kawasaki et al., "A Novel method for the simultaneous identification of methylcytosine and hydroxymethylcytosine at a single base resolution", Nucleic Acids Res 45(4) e24 (2017).
Kim, et al., "CREB/ATF-dependent T cell receptor-induced FoxP3 gene expression: a role for DNA methylation", The Journal of Experimental Medicine 204(7):1543-1551 (2007).
Kothari et al., "5-Methylcytosine content in the vertebrate deoxyribonucleic acids: species specificity", J Mol Evol 7(4) 625-629 (1976).
Kriaucionis et al., "The nuclear DNA base 5-hydroxymethylcytosine is present in Purkinje neurons and the brain", Science 324(5929) 929-930 (2009).
Kriukiene et al., "5-Hydroxymethylcytosine—the elusive epigenetic mark in mammalian DNA", Chem Soc Rev 41(21) 6916-6930 (2012).
Lariviere et al., "Crystal structures of the T4 phage beta-glucosyltransferase and the D100A mutant in complex with UDP-glucose: glucose binding and identification of the catalytic base for a direct displacement mechanism", J Mol Biol 330(5) 1077-1086 (2003).
Lariviere et al., "Structural evidence of a passive base-flipping mechanism for AGT, an unusual GT-B glycosyltransferase", J Mol Biol 352(1) 139-150 (2005).
Lariviere et al., "Structural evidence of a passive base-flipping mechanism for beta-glucosyltransferase", J Biol Chem 279(33) 34715-34720 (2004).
Lee et al., "Th2 lineage commitment and efficient IL-4 production involves extended demethylation of the IL-4 gene", Immunity 16(5) 649-660 (2002).
Leonhardt et al., "A targeting sequence directs DNA methyltransferase to sites of DNA replication in mammalian nuclei", Cell 71(5) 865-873 (1992).
Li et al., "Mechanisms and functions of DNA mismatch repair", Cell Res 18(1) 85-98 (2008).
Loenarz et al., "Expanding chemical biology of 2-oxoglutarate oxygenases", Nat Chem Biol 4(3) 152-156 (2008).
Lorsbach et al., "TET1, a member of a novel protein family, is fused to MLL in acute myeloid leukemia containing the t(10;11)(q22;q23)", Leukemia 17(3) 637-641 (2003).
Lu et al., "TET family proteins: oxidation activity, interacting molecules, and functions in diseases.", Chem Rev 115(6) 2225-2239 (2015).
Luscombe et al., "An overview of the structures of protein-DNA complexes", Genome Biol 1(1) REVIEWS001 (2000).
Mayer et al., "Demethylation of the zygotic paternal genome", Nature 403(6769) 501-502 (2000).
Mellen et al., "MeCP2 binds to 5hmC enriched within active genes and accessible chromatin in the nervous system", Cell 151(7) 1417-1430 (2012).
Metivier et al., "Cyclical DNA methylation of a transcriptionally active promoter", Nature 452(7183) 45-50 (2008).
Morera et al., "T4 phage beta-glucosyltransferase: substrate binding and proposed catalytic mechanism", J Mol Biol 292(3) 717-730 (1999).
Morris, "Liquid", Academic Press Dictionary of Science and Technology (4th Ed.),Elsevier Science & Technology (1992).
Netto et al., "The iron-catalyzed oxidation of dithiothreitol is a biphasic process: hydrogen peroxide is involved in the initiation of a free radical chain of reactions", Arch Biochem Biophys 333(1) 233-242 (1996).
Notice of Allowance issued during the prosecution of U.S. Appl. No. 13/120,861, dated Apr. 22, 2015.
Notice of Allowance issued during the prosecution of U.S. Appl. No. 13/795,739, dated Apr. 22, 2016.
Notice of Allowance issued during the prosecution of U.S. Appl. No. 15/440,284, dated Apr. 4, 2018.
Notice of Allowance issued during the prosecution of U.S. Appl. No. 15/440,408, dated Sep. 18, 2017.
Notice of Allowance issued during the prosecution of U.S. Appl. No. 15/440,408, dated Aug. 23, 2017.
Notice of Allowance issued during the prosecution of U.S. Appl. No. 15/440,826, dated Jun. 1, 2018.
Notice of Allowance issued during the Prosecution of U.S. Appl. No. 15/193,796, dated Oct. 16, 2018.

(56) References Cited

OTHER PUBLICATIONS

Notice of Allowance issued during the prosecution of U.S. Appl. No. 15/440,826, dated Nov. 22, 2017.
Office Action issued during the prosecution of U.S. Appl. No. 13/120,861, dated Mar. 13, 2013.
Office Action issued during the prosecution of U.S. Appl. No. 13/795,739, dated Mar. 24, 2014.
Office Action issued during the prosecution of U.S. Appl. No. 14/235,707, dated Aug. 4, 2015.
Office Action issued during the prosecution of U.S. Appl. No. 14/363,442, dated Nov. 10, 2016.
Office Action issued during the prosecution of U.S. Appl. No. 14/363,442, dated Jul. 11, 2017.
Office Action issued during the prosecution of U.S. Appl. No. 14/363,442, dated Mar. 7, 2016.
Office Action issued during the prosecution of U.S. Appl. No. 14/648,527, dated Jan. 18, 2018.
Office Action issued during the prosecution of U.S. Appl. No. 15/054,227, dated Oct. 3, 2016.
Office Action issued during the prosecution of U.S. Appl. No. 15/193,796, dated Jun. 20, 2018.
Office Action issued during the prosecution of U.S. Appl. No. 15/341,344, dated Apr. 16, 2018.
Dunican et al. "The CXXC-TET bridge—mind the methylation gap!." Cell Research 23(8): 973-974 (2013).
Office Action issued during the prosecution of U.S. Appl. No. 17/208,940; dated Jun. 22, 2021.
Alegria et al., "Hydroxymethylation of pyrimidine mononucleotides with formaldehyde", Biochim Biophys Acta 149(2) 317-324 (1967).
Allen et al., "Solution structure of the nonmethyl-CpG-binding CXXC domain of the leukaemia-associated MLL histone methyltransferase", EMBO J 25(19) 4503-4512 (2006).
Aller et al., "A structural rationale for stalling of a replicative DNA polymerase at the most common oxidative thymine lesion, thymine glycol", Proc Natl Acad Sci USA 104(3) 814-818 (2007).
An et al., "TET family dioxygenases and DNA demethylation in stem cells and cancers", Exp Mol Med 49(4) e323 (2017).
Aravind et al., "The DNA-repair protein AlkB, EGL-9, and leprecan define new families of 2-oxoglutarate- and iron-dependent dioxygenases", Genome Biol 2(3): 1-8 (2001).
Arita et al., "Recognition of hemi-methylated DNA by the SRA protein UHRF1 by a base-flipping mechanism", Nature 455(7214) 818-822 (2008).
Avvakumov et al., "Structural basis for recognition of hemi-methylated DNA by the SRA domain of human UHRF1", Nature 455(7214) 822-826 (2008).
Bird et al., "DNA methylation patterns and epigenetic memory", Genes Dev 16(1) 6-21 (2002).
Blelloch et al., "Reprogramming efficiency following somatic cell nuclear transfer is influenced by the differentiation and methylation state of the donor nucleus", Stem Cells 24(9) 2007-2013 (2006).
Booth et al., "Oxidative bisulfite sequencing of 5-methylcytosine and 5-hydroxymethylcytosine", Nat Protoc 8(1) 1841-1851 (2013).
Booth et al., "Quantitative sequencing of 5-methylcytosine and 5-hydroxymethylcytosine at single-base resolution", Science 336(6083) 934-937 (2012).
Borst et al., "Base J: discovery, biosynthesis, and possible functions", Annu Rev Microbiol 62: 235-251 (2008).
Breton et al., "Structures and mechanisms of glycosyltransferases", Glycobiology 16(2) 29R-37R (2006).
Bullard et al., "Identification of the glucosyltransferase that converts hydroxymethyluracil to base J in the trypanosomatid genome", J Biol Chem 289(29) 20273-20282 (2014).
Cannon et al., "5-Hydroxymethylcytosine DNA glycosylase activity in mammalian tissue", Blochem Biophys Res Commun 151(3) 1173-1179 (1988).
Castro et al. "5-Methylcytosine attack by hydroxyl free radicas and during carbon tetrachloride promoted liver microsomal lipid peroxidation." Chemico-Biological Interactions 99(1-3): 289-299 (1996).
Cedar et al., "Gene expression. The amazing demethylase", Nature 397(6720) 568-569 (1999).
Chuang et al., "Human DNA-(cytosine-5) methyltransferase-PCNA complex as a target for p21WAF1", Science 277(5334) 1996-2000 (1997).
Clark et al., "Enhanced 5-methylcytosine detection in single-molecule, real-time sequencing via Tet1 oxidation", BMC Biol 11:4 (2013).
Cliffe et al., "JBP1 and JBP2 are two distinct thymidine hydroxylases involved in J biosynthesis in genomic DNA of African trypanosomes", Nucleic Acids Res 37(5) 1452-1462 (2009).
Coulter et al., "Hydroquinone increases 5-hydroxymethylcytosine formation through ten eleven translocation 1 (TET1) 5-methylcytosine dioxygenase", The Journal of Biological Chemistry 288(40):28792-28800 (2013).
Dai et al., "Evaluation of UDP-GlcN derivatives for selective labeling of 5-(hydroxymethyl)cytosine", Chembiochem 14(16) 2144-2152 (2013).
De Kort et al., "Chemical and Enzymatic Synthesis of DNA Fragments Containing 5-($\beta$-D-Glucopyranosyloxymethyl)-2'-deoxycytidine—a Modified Nucleoside in T4 Phage DNA", European Journal of Organic Chemistry 2075-2082 (2001).
De Waard et al., "On the specificity of bacteriophage-induced hydroxymethylcytosine glucosyltransferases. II. Specificities of hydroxymethylcytosine alphaand beta-glucosyltransferases induced by bacteriophage T4", Eur J Biochem 2(3) 303-308 (1967).
Delhommeau et al., "TET2 Is a Novel Tumor Suppressor Gene Inactivated in Myeloproliferative Neoplasms: Identification of a Pre-JAK2 V617F Event" Blood 112(11) 1ba-3 (2008). Paper presented at the Americna Society of Hematology Annual Meeting and Exposition, San Francisco, CA, Dec. 9, 2008.
Ehrlich et al., "5-Methylcytosine in eukaryotic DNA", Science 212(4501) 1350-1357 (1981).
Esteller et al., "Cancer epigenomics: DNA methylomes and histone-modification maps", Nat Rev Genet 8(4) 286-298 (2007).
Esteller et al., "Epigenetics in cancer", N Engl J Med 358(11) 1148-1159 (2008).
Farthing et al., "Global mapping of DNA methylation in mouse promoters reveals epigenetic reprogramming of pluripotency genes", PLoS Genet 4(6) e1000116 1-8 (2008).
Ficz et al., "Reprogramming by cell fusion: boosted by Tets", Mol Cell 49(6) 1017-1018 (2013).
Flaks et al., "Virus-induced acquisition of metabolic function. I. Enzymatic formation of 5-hydroxymethyldeoxycytidylate", J Biol Chem 234(6) 1501-1506 (1959).
Flusberg et al., "Direct detection of DNA methylation during single-molecule, real-time sequencing", Nat Methods 7(6) 461-465 (2010).
Fraga et al., "DNA methylation: a profile of methods and applications", Biotechniques 33(3) 632, 634, 636-649 (2002).
Franco et al., "Oxidative stress, DNA methylation and carcinogenesis", Cancer Lett 266(1) 6-11 (2008).
Frommer et al., "A genomic sequencing protocol that yields a positive display of 5-methylcytosine residues in individual DNA strands", Proc Natl Acad Sci USA 89(5) 1827-1831 (1992).
Fu et al., "Nucleic acid modifications with epigenetic significance", Curr Opin Chem Biol 16(5-6) 516-524 (2012).
Fukushige et al., "Methyl-CpG targeted transcriptional activation allows re-expression of tumor suppressor genes in human cancer cells", Biochem Biophys Res Commun 377(2) 600-605 (2008).
Gal-Yam et al., "Cancer epigenetics: modifications, screening, and therapy", Annu Rev Med 59: 267-280 (2008).
Geijsen et al., "Derivation of embryonic germ cells and male gametes from embryonic stem cells", Nature 427(6970) 148-154 (2004).
Globisch et al., "Tissue distribution of 5-hydroxymethylcytosine and search for active demethylation intermediates", PLoS One 5(12) e15367 (2010).
Goll et al., "Eukaryotic cytosine methyltransferases", Annu Rev Biochem 74: 481-514 (2005).
Goode et al. "Identification of Promiscuous Small Molecule Activators in High-Throughput Enzyme Activation Screens." Journal of Medicinal Chemistry 51(8): 2346-2349 (2008).

(56) References Cited

OTHER PUBLICATIONS

Green, "General PCR Protocol", http://labs.mcbd.lsa.umich.edu/labs/maddock/protocols/PCR/general_pcr_protocol.html, 2 pages, 1996.
Gros et al., "The major human AP endonuclease (Ape1) is involved in the nucleotide incision repair pathway", Nucleic Acids Res 32(1) 73-81 (2004).
Gruenbaum et al., "Methylation of CpG sequences in eukaryotic DNA", FEBS Lett 124(1) 67-71 (1981).
Gruenewald et al., "The role of antigenic determinants in the control of IgM and IgG antibody responses to denatured DNA", J Immunol 111(1) 106-113 (1973).
Guerrero et al., "Determination of 5-methyl-cytosine and cytosine in tumor DNA of cancer patients", Electrophoresis 26(6) 1057-1062 (2005).
Gurdon et al., "From nuclear transfer to nuclear reprogramming: the reversal of cell differentiation", Annu Rev Cell Dev Biol 22: 1-22 (2006).
Hajkova et al., "Chromatin dynamics during epigenetic reprogramming in the mouse germ line", Nature 452(7189) 877-881 (2008).
Hannum et al., "Genome-wide methylation profiles reveal quantitative views of human aging rates", Mol Cell 49(2) 259-267 (2013).
Vrielink et al., "Crystal structure of the DNA modifying enzyme beta-glucosyltransferase in the presence and absence of the substrate uridine diphosphoglucose", EMBO J 13(15) 3413-3422 (1994).
Wang et al. "Antibody Structure, Instability, and Formulation." Journal of Pharmaceutical Sciences 96(1): 1-26 (2007).
Wang et al., "Chemoenzymatic synthesis and antibody detection of DNA glycoconjugates", Bioconjug Chem 14(6) 1314-1322 (2003).
Wang et al., "Comparison of bisulfite modification of 5-methyldeoxycytidine and deoxycytidine residues", Nucleic Acids Res 8(20) 4777-4790 (1980).
Wu et al., "Mechanisms and functions of Tet protein-mediated 5-methylcytosine oxidation", Gene Dev 25(23) 2436-2452 (2011).
Wyatt et al., "The bases or the nucleic acids of some bacterial and animal viruses: the occurrence of 5-hydroxymethylcytosine", Biochem 55(5) 774-782 (1953).
Xia et al., "Bisulfite-free, base-resolution analysis of 5-formylcytosine at the genome scale", Nat Methods 12(11) 1047-1050 (2015).
Xiong et al., "Cooperative Action between SALL4A and TET Proteins in Stepwise Oxidation of 5-Methylcytosine", Mol Cell 64(5) 913-925 (2016).
Yu et al., "Base-resolution analysis of 5-hydroxymethylcytosine in the mammalian genome", Cell 149(6) 1368-1380 (2012).
Yu et al., "Induced Pluripotent Stem Cell Lines Derived from Human Somatic Cells", Science 318(5858) 1917-1920 (2007).
Yu et al., "Tet-assisted bisulfite sequencing of 5-hydroxymethylcytosine", Nat Protoc 7(12) 2159-2170 (2012).
Yu et al., "The protein that binds to DNA base J in trypanosomatids has features of a thymidine hydroxylase", Nucleic Acids Res 35(7) 2107-2115 (2007).
Zhu et al., "5-methylcytosine-DNA glycosylase activity is present in a cloned G/T mismatch DNA glycosylase associated with the chicken embryo DNA demethylation complex", Proc Natl Acad Sci USA 97(10) 5135-5139 (2000).
Bair et al., "Exclusion of Glucosyl-Hydroxymethylcytosine DNA Containing Bacteriophages", J. Mol. Biol. 366(3) 779-789 (2007).
Comeau et al., "Modular architecture of the T4 phage superfamily: A conserved core genome and a plastic periphery", Virology 362 384-396 (2007).
Office Action issued during the prosecution of U.S. Appl. No. 16/012,280 dated Aug. 27, 2018.
Petrov et al., "Plasticity of the Gene Functions for DNA Replication in the T4-like Phages", J. Mol. Biol. 361 46-68 (2006).
Office Action issued during the prosecution of U.S. Appl. No. 15/440,319, dated Oct. 26, 2018.
Office Action issued during the prosecution of U.S. Appl. No. 15/952,352, dated Nov. 14, 2018.
Office Action issued during the prosecution of U.S. Appl. No. 15/341,344, dated Dec. 17, 2018.
Office Action issued during the prosecution of U.S. Appl. No. 15/725,917, dated Dec. 27, 2018.
Notice of Allowance issued during the prosecution of U.S. Appl. No. 15/440,815; dated Jan. 10, 2019.
Li et al., "CD4 CD25+ regulatory T-Cell lines from human cord blood have functional and molecular properties of T-Cell anergy", Blood 106(9) 3068-3073 (2005).
Office Action issued duing the prosecution of U.S. Appl. No. 15/483,282; dated Feb. 13, 2019.
Notice of Allowance issued during the prosecution of U.S. Appl. No. 16/012,280; dated Feb. 13, 2019.
Office Action issued during the prosecution of U.S. Appl. No. 16/169,801; dated Feb. 15, 2019.
Office Action issued during the prosecution of U.S. Appl. No. 16/172,369; dated Feb. 19, 2019.
Office Action issued during the prosecution of U.S. Appl. No. 16/175,353; dated Mar. 6, 2019.
Hori et al., "Identification of high excision capacity for 5-hydroxymethyluracil mispaired with guanine in DNA of *Escherichia coli* MutM, Nei and Nth DNA glycosylases" Nucleic Acids Research 31(4) 1191-1196 (2003).
GenBank "*Homo sapiens* SATB homeobox 1 (SATB1), transcript variant 3, mRNA" https://www.ncbi.nlm.nih.gov/nuccore/306518683?sat=14&satkey=4225583 1-4 (Feb. 25, 2019).
GenBank "Predicted: *Homo sapiens* uncharacterized LOC101927603 (LOC101927603), ncRNA" https://www.ncbi.nlm.nih.gov/nuccore/1034672260?sat=46&satkey=133762724 1-2 (2019).
Office Action issued during the prosecution of U.S. Appl. No. 15/890,034; dated Mar. 7, 2019.
Notice of Allowance during the prosecution of U.S. Appl. No. 16/012,510; dated Mar. 13, 2019.
Office Action issued during the prosecution of U.S. Appl. No. 16/180,450; dated Mar. 19, 2019.
Notice of Allowance during the prosecution of U.S. Appl. No. 15/193,796; dated Apr. 16, 2019.
Office Action issued during the prosecution of U.S. Appl. No. 15/722,183; dated Apr. 24, 2019.
Office Action issued during the prosecution of U.S. Appl. No. 15/440,424; dated May 1, 2019.
Office Action issued during the prosecution of U.S. Appl. No. 15/722,202; dated May 2, 2019.
Office Action issued during the prosecution of U.S. Appl. No. 15/725,917; dated May 14, 2019.
Notice of Corrected Allowability during the prosecution of U.S. Appl. No. 15/440,815; dated May 15, 2019.
Chun-Xiao Song et al., "The hunt for 5-hydroxymethylcytosine: the sixth base", Epigenomics, vo. 3, No. 5, 521-523, Oct. 1, 2011.
European Search Report dated Oct. 10, 2018 for EP Application No. 18174572.
Saori Takahashi et al., "A novel method to analyze 5-hydroxymethylcytosine in CpG sequences using maintenance DNA methyltransferase, DNMT1", FEBS Open Bio, vol. 5, No. 1, 741-747, Jan. 1, 2015.
Notice of Allowance during the prosecution of U.S. Appl. No. 16/012,510; dated Jul. 15, 2019.
Notice of Allowance during the prosecution of U.S. Appl. No. 16/169,801; dated Jul. 25, 2019.
Office Action issued during the prosecution of U.S. Appl. No. 15/952,352; dated Aug. 8, 2019.
Office Action issued during the prosecution of U.S. Appl. No. 16/180,450; dated Aug. 6, 2019.
Office Action issued during the prosecution of U.S. Appl. No. 16/172,369; dated Aug. 6, 2019.
Office Action issued during the prosecution of U.S. Appl. No. 16/175,353; dated Aug. 15, 2019.
Office Action issued during the prosecution of U.S. Appl. No. 16/411,998; dated Aug. 19, 2019.
Office Action issued during the prosecution of U.S. Appl. No. 15/440,284, dated Jan. 19, 2018.
Office Action issued during the prosecution of U.S. Appl. No. 15/440,284; dated Aug. 8, 2017.
Office Action issued during the prosecution of U.S. Appl. No. 15/440,319, dated Jul. 25, 2017.

(56) References Cited

OTHER PUBLICATIONS

Office Action issued during the prosecution of U.S. Appl. No. 15/440,319, dated Apr. 30, 2018.
Office Action issued during the prosecution of U.S. Appl. No. 15/440,408, dated May 31, 2017.
Office Action issued during the prosecution of U.S. Appl. No. 15/440,424, dated Jan. 23, 2018.
Office Action issued during the prosecution of U.S. Appl. No. 15/440,815, dated Jun. 12, 2018.
Office Action issued during the prosecution of U.S. Appl. No. 15/440,822, dated Jun. 13, 2017.
Office Action issued during the prosecution of U.S. Appl. No. 15/440,822, dated Nov. 22, 2017.
Office Action issued during the prosecution of U.S. Appl. No. 15/440,826, dated Jun. 28, 2017.
Office Action issued during the prosecution of U.S. Appl. No. 15/952,352, dated Jun. 27, 2018.
Ohki et al., "Solution structure of the methyl-CpG-binding domain of the methylation-dependent transcriptional repressor MBD1", EMBO J 18(23) 6653-6661 (1999).
Ono et al., "LCX, leukemia-associated protein with a CXXC domain, is fused to MLL in acute myeloid leukemia with trilineage dysplasia having t(10; 11)(q22;q23)", Cancer Res 62(14) 4075-4080 (2002).
Ooi et al., "The colorful history of active DNA demethylation", Cell 133(7) 1145-148 (2008).
Oswald et al., "Active demethylation of the paternal genome in the mouse zygote", Curr Biol 10(8) 475-478 (2000).
Pacific Biosciences, "Detecing DNA Base Modifications Using Single Molecule, Real-Time Sequencing", White Paper Base Modifications (2015). 5 pp.
Pais et al., "Biochemical characterization of a Naegleria TET-like oxygenase and its application in single molecule sequencing of 5-methylcytosine", Proc Natl Acad Sci 112(14) 4316-4321 (2015).
Penn et al., "The presence of 5-hydroxymethylcytosine in animal deoxyribonucleic acid", Biochem J 126(4) 781-790 (1972).
Pfaffeneder et al., "Tet oxidizes thymine to 5-hydroxymethyluracil in mouse embryonic stem cell DNA", Nat Chem Bil 10(7) 574-581 (2014).
Pfeifer et al., "5-hydroxymethylcytosine and its potential roles in development and cancer", Epigenetics Chromatin 6(1) 10 (2013).
Que et al., "Dioxygen Activation by Enzymes with Mononuclear Non-Heme Iron Active Sites", Chem Res 96(7) 2607-2624 (1996).
Rai et al., "DNA demethylation in zebrafish involves the coupling of a deaminase, a glycosylase, and gadd45", Cell 135(7) 1201-1212 (2008).
Ramsahoye et al., "Non-CpG methylation is prevalent in embryonic stem cells and may be mediated by DNA methyltransferase 3a", Proc Natl Acad Sci USA 97(10) 5237-5242 (2000).
Rapisarda et al. "Identification of Small Molecule Inhibitors of Hypoxia-inducible Factor 1 Transcriptional Activation Pathway." Cancer Research 62(15): 4316-4324 (2002).
Rauch et al., "Methylated-CpG island recovery assay: a new technique for the rapid detection of methylated-CpG islands in cancer", Lab Invest 85(9) 1172-1180 (2005).
Reik et al., "Stability and flexibility of epigenetic gene regulation in mammalian development", Nature 447(7143) 425-432 (2007).
Rein et al., "Identifying 5-methylcytosine and related modifications in DNA genomes", Nucleic Acids Res 26(10) 2255-2264 (1998).
Rodic et al., "Diagnostic utility of 5-hydroxymethylcytosine immunohistochemistry in melanocytic proliferations", J Cutan Pathol 42(11) 807-814 (2015).
Rusmintratip et al., "An unexpectedly high excision capacity for mispaired 5-hydroxymethyluracil in human cell extracts", Proc Natl Acad Sci USA 97(26) 14183-14187 (2000).
Scourzic et al., "TET proteins and the control of cytosine demethylation in cancer", Genome Med 7(1) 9 (2015).
Sedgwick et al., "Repair of alkylated DNA: recent advances", DNA Repair (Amst) 6(4) 429-442 (2007).

Seisenberger et al., "The dynamics of genome-wide DNA methylation reprogramming in mouse primordial germ cells", Mol Cell 48(6) 849-862 (2012).
Sela et al., "Uridine-Specific Antibodies Obtained With Synthetic Antigens", Proc Natl Acad Sci USA 52: 285-292 (1964).
Shin et al., "Seeking a roadmap toward neuroepigenetics", Neuron 86(1) 12-15 (2015).
Shrivastav et al., "Regulation of DNA double-strand break repair pathway choice", Cell Res 18(1) 134-147 (2008).
Shuck et al., "Eukaryotic nucleotide excision repair: from understanding mechanisms to influencing biology", Cell Res 18(1) 64-72 (2008).
Simonsson et al., "DNA demethylation is necessary for the epigenetic reprogramming of somatic cell nuclei", Nat Cell Biol 6(10) 984-990 (2004).
Smith et al., "Unraveling the epigenetic code of cancer for therapy", Trends Genet 23(9) 449-456 (2007).
Song et al., "Detection of 5-hydroxymethylcytosine in DNA by transferring a keto-glucose by using T4 phage β-glucosyltransferase", Chembiochem 12(11) 1682-1685 (2011).
Song et al., "Simultaneous single-molecule epigenetic imaging of DNA methylation and hydroxymethylation", Proc Natl Acad Sci 113(16) 4338-4343 (2016).
Surani et al., "Genetic and epigenetic regulators of pluripotency", Cell 128(4) 747-762 (2007).
Tahiliani et al., "Conversion of 5-methylcytosine to 5-hydroxymethylcytosine in mammalian DNA by MLL partner TET1", Science 324(5929) 930-935 (2009).
Takahashi et al., "Induction of pluripotent stem cells from adult human fibroblasts by defined factors", Cell 131(5) 861-872 (2007).
Takahashi et al., "Induction of pluripotent stem cells from mouse embryonic and adult fibroblast cultures by defined factors", Cell 126(4) 663-676 (2006).
Tan et al., "Tet family proteins and 5-hydroxymethylcytosine in development and disease", Development 139(11) 1895-1902(2012).
Tomaschewski et al., "T4-induced alpha- and beta-glucosyltransferase: cloning of the genes and a comparison of their products based on sequencing data", Nucleic Acids Res 13(21) 7551-7568 (1985).
Unligil et al., "Glycosyltransferase structure and mechanism", Curr Opin Struct Biol 10(5) 510-517 (2000).
Valinluck et al., "Endogenous cytosine damage products alter the site selectivity of human DNA maintenance methyltransferase DNMT1", Cancer Res 67(3) 946-950 (2007).
Valinluck et al., "Oxidative damage to methyl-CpG sequences inhibits the binding of the methyl-CpG binding domain (MBD) of methyl-CpG binding protein 2 (MeCP2)", Nucleic Acids Res 32(14) 4100-4108 (2004).
Viguie et al., "Common 4q24 deletion in four cases of hematopoietic malignancy: early stem cell involvement?", Leukemia 19(8) 1411-1415 (2005).
Office Action issued during the prosecution of U.S. Appl. No. 16/541,857; dated Nov. 27, 2019.
Office Action issued during the prosecution of U.S. Appl. No. 15/440,424; dated Dec. 5, 2019.
Office Action issued during the prosecution of U.S. Appl. No. 15/890,034; dated Dec. 11, 2019.
Office Action issued during the prosecution of U.S. Appl. No. 15/722,183; dated Dec. 20, 2019.
Office Action issued during the prosecution of U.S. Appl. No. 16/658,195; dated Jan. 27, 2020.
Office Action issued during the prosecution of U.S. Appl. No. 16/691,247; dated Feb. 6, 2020.
Notice of Allowance issued during the prosecution of U.S. Appl. No. 15/483,282; dated Feb. 10, 2020.
Office Action issued during the prosecution of U.S. Appl. No. 16/180,450; dated Mar. 17, 2020.
Office Action issued during the prosecution of U.S. Appl. No. 16/411,998; dated Mar. 30, 2020.
Office Action issued during the prosecution of U.S. Appl. No. 16/175,353; dated Apr. 7, 2020.
Office Action issued during the prosecution of U.S. Appl. No. 16/541,857; dated Apr. 10, 2020.

(56) References Cited

OTHER PUBLICATIONS

Notice of Allowance issued during the prosecution of U.S. Appl. No. 15/725,917; dated Apr. 27, 2020.
Office Action issued during the prosecution of U.S. Appl. No. 16/658,195; dated May 22, 2020.
Notice of Allowance issued during the prosecution of U.S. Appl. No. 16/180,450; dated Jul. 17, 2020.
Office Action issued during the prosecution of U.S. Appl. No. 15/952,352; dated Jul. 28, 2020.
Notice of Allowance issued during the prosecution of U.S. Appl. No. 16/541,857; dated Jul. 29, 2020.
Office Action issued during the prosecution of U.S. Appl. No. 15/440,424; dated Jul. 30, 2020.
Notice of Allowance issued during the prosecution of U.S. Appl. No. 16/411,998; dated Aug. 6, 2020.
Office Action issued during the prosecution of U.S. Appl. No. 16/380,846; dated Aug. 28, 2020.
Office Action issued during the prosecution of U.S. Appl. No. 16/691,247; dated Oct. 6, 2020.
Office Action issued during the prosecution of U.S. Appl. No. 16/658,195; dated Jan. 19, 2021.
Office Action issued during the prosecution of U.S. Appl. No. 16/691,255; dated Mar. 1, 2021.
Notice of Allowance issued during the prosecution of U.S. Appl. No. 16/380,846; dated Mar. 19, 2021.
Office Action issued during the prosecution of U.S. Appl. No. 16/691,247; dated Apr. 13, 2021.
Notice of Allowance issued during the prosecution of U.S. Appl. No. 15/193,796; dated Aug. 29, 2019.
Notice of Allowance issued during the prosecution of U.S. Appl. No. 16/169,801; dated Sep. 16, 2019.
Office Action issued during the prosecution of U.S. Appl. No. 15/483,282; dated Oct. 7, 2019.
Office Action issued during the prosecution of U.S. Appl. No. 15/483,297; dated Oct. 10, 2019.
Notice of Allowance issued during the prosecution of U.S. Appl. No. 16/012,510; dated Oct. 22, 2019.
Office Action issued during the prosecution of U.S. Appl. No. 15/725,917; dated Oct. 24, 2019.
Office Action issued during the prosecution of U.S. Appl. No. 15/722,202; dated Nov. 12, 2019.
Notice of Allowance issued during the prosecution of U.S. Appl. No. 15/341,344; dated Nov. 19, 2019.
Alves et al. "Differential methylation of human LINE-1 retrotransposons in malignant cells." Gene 176(1-2): 39-44 (1996).
Bastian et al. "Prognostic value of preoperative serum cell-free circulating DNA in men with prostate cancer undergoing radical prostatectomy." Clinical Cancer Research 13(18): 5361-5367 (2007).
Bayer et al. "[55] The avidin-biotin complex in affinity cytochemistry." Methods in enzymology. Academic Press Bol. 62: 308-315 (1979).
Bogani et al. "Hypermethylation of CXCR4 promoter in CD34+ cells from patients with primary myelofibrosis." Stem Cells 26(8): 1920-1930 (2008).
Ciccarone et al. "DNA hydroxymethylation levels are altered in blood cells from Down syndrome persons enrolled in the MARK-AGE project." The Journals of Gerontology: Series A 73(6): 737-744 (2018).
Cliffe et al. "JBP1 and JBP2 proteins are Fe2+/2-oxoglutarate-dependent dioxygenases regulating hydroxylation of thymidine residues in trypanosome DNA." Journal of Biological Chemistry 287(24): 19886-19895 (2012).
Cross et al. "J-binding protein increases the level and retention of the unusual base J in trypanosome DNA." Molecular microbiology 46(1): 37-47 (2002).
Deligezer et al. "Frequent copresence of methylated DNA and fragmented nucleosomal DNA in plasma of lymphoma patients." Clinica Chimica Acta 335(1-2): 89-94 (2003).
Gao et al. "Integrated detection of both 5-mC and 5-hmC by high-throughput tag sequencing technology highlights methylation reprogramming of bivalent genes during cellular differentiation." Epigenetics 8(4): 421-430 (2013).
Gilat et al. "Single-molecule quantification of 5-hydroxymethylcytosine for diagnosis of blood and colon cancers." Clinical Epigenetics 9(70): 1-8 (2017).
Goldstein et al. "Carbohydrate binding properties of banana (*Musa acuminata*) lectin: II. Binding of laminaribiose oligosaccharides and β-glucans containing β1, 6-glucosyl end groups." European Journal of Biochemistry 268(9): 2616-2619 (2001).
Gommers-Ampt et al. "A novel DNA nucleotide in Trypanosoma brucei only present in the mammalian phase of the life-cycle." Nucleic acids research 19(8): 1745-1751 (1991).
Gommers-Ampt et al. "β-D-glucosyl-hydroxymethyluracil: a novel modified base present in the DNA of the parasitic protozoan T. brucei." Cell 75(6): 1129-1136 (1993).
Gommers-Ampt et al. "The identification of hydroxymethyluracil in DNA of Trypanosoma brucei." Nucleic acids research 21(9): 2039-2043 (1993).
Hatfull et al. "Bacteriophages and their genomes." Current opinion in virology 1(4): 298-303 (2011).
Jesaitis. "Differences in the chemical composition of the phage nucleic acids." Nature 178(4534): 637-637 (1956).
Josse et al. "Glucosylation of Deoxyribonucleic Acid III. β- and β-Glucosyl Transferases From T4-Infected *Escherichia coli*" Journal of Biological Chemistry 237(6): 1968-1976 (1962).
Kinney et al. "Tissue-specific distribution and dynamic changes of 5-hydroxymethylcytosine in mammalian genomes." Journal of Biological Chemistry 286(28): 24685-24693 (2011).
Koressaar et al. "Enhancements and modifications of primer design program Primer3." Bioinformatics 23(10): 1289-1291 (2007).
Kornberg et al. "Glucosylation of deoxyribonucleic acid by enzymes from bacteriophage-infected *Escherichia coli*." Journal of Biological Chemistry 236(5): 1487-1493 (1961).
Kuno et al. "Gentiobiose, a constituent of deoxyribonucleic acid from coliphage T6." J Biol Chem 237: 1266-1270 (1962).
Lehman et al. "On the structure of the glucosylated hydroxymethylcytosine nucleotides of coliphages T2, T4, and T6." Journal of Biological Chemistry 235(11): 3254-3259 (1960).
Leone et al. "Inhibitors of DNA methylation in the treatment of hematological malignancies and MDS." Clinical Immunology 109(1): 89-102 (2003).
Lisowska et al. "Preparation of biotinylated lectins and application in microtiter plate assays and Western blotting." BioMethods 7: 115-129 (1996).
Monod et al. "The genome of the pseudo T-even bacteriophages, a diverse group that resembles T4." Journal of Molecular Biology 267(2): 237-249 (1997).
Panigrahi et al. "Four related proteins of the Trypanosoma brucei RNA editing complex." Molecular and cellular biology 21(20): 6833-6840 (2001).
Ren et al. "Phage T4 SOC and HOC display of biologically active, full-length proteins on the viral capsid." Gene 215(2): 439-444 (1998).
Sabatini, et al. "Recognition of base J in duplex DNA by J-binding protein." Journal of Biological Chemistry 277(2): 958-966 (2002).
Sigma-Aldrich (Product Specification, Product No. B4501), www.sigmaaldrich.com, retrieved 2019.
Strand et al. "High levels of 5-hydroxymethylcytosine (5hmC) is an adverse predictor of biochemical recurrence after prostatectomy in ERG-negative prostate cancer." Clinical Epigenetics 7(1): 111 pp. 1-12 (2015).
Storebjerg et al. "Dysregulation and prognostic potential of 5-methylcytosine (5mC), 5-hydroxymethylcytosine (5hmC), 5-formylcytosine (5fC), and 5-carboxylcytosine (5caC) levels in prostate cancer." Clinical Epigenetics 10(1): 105 pp. 1-16 (2018).
Taylor et al. "Ultradeep bisulfite sequencing analysis of DNA methylation patterns in multiple gene promoters by 454 sequencing." Cancer Research 67(18): 8511-8518 (2007).
Teofili et al. "Epigenetic alteration of SOCS family members is a possible pathogenetic mechanism in JAK2 wild type myeloproliferative diseases." International Journal of Cancer 123(7): 1586-1592 (2008).

(56) References Cited

OTHER PUBLICATIONS

USB Thermo Sequenase Dye Primer Manual Cycle Sequencing Kit: Product No. 79260. Affymetrix, Inc. (2015).
Vafadar-Isfahani et al. "Decoupling of DNA methylation and activity of intergenic LINE-1 promoters in colorectal cancer." Epigenetics 12(6): 465-475 (2017).
Van Leeuwen et al. "The Modified DNA Base β-d-Glucosylhydroxymethyluracil Confers Resistance to Micrococcal Nuclease and is Incompletely Recovered by32P-Postlabeling." Analytical biochemistry 258(2): 223-229 (1998).
Volkin. "The Linkage of Glucose in Coliphage Nucleic Acids1." Journal of the American Chemical Society 76(22): 5892-5893 (1954).
Wernig-Zorc et al. "Global distribution of DNA hydroxymethylation and DNA methylation in chronic lymphocytic leukemia." Epigenetics & Chromatin 12(4): 1-15 (2019).
Supplemental Data File 2A: Excerpts of Additional File 3 from Wernig-Zorc et al. "Global distribution of DNA hydroxymethylation and DNA methylation in chronic lymphocytic leukemia." Epigenetics & Chromatin 12(4): 1-15 (2019).
Wick et al. "Trapping covalent Intermediates on beta-glycosidases." Methods in Enzymology 354: 84-105 (2002).
Winkler et al. "Cloning and sequencing of the genes of beta-glucosyl-HMC-alpha-glucosyl-transferases of bacteriophages T2 and T6." Nucleic Acids Research 21(6): 1500 (1993).
Zilberman et al. "Genome-wide analysis of DNA methylation patterns." Development 134(22): 3959-3965 (2007).

\* cited by examiner

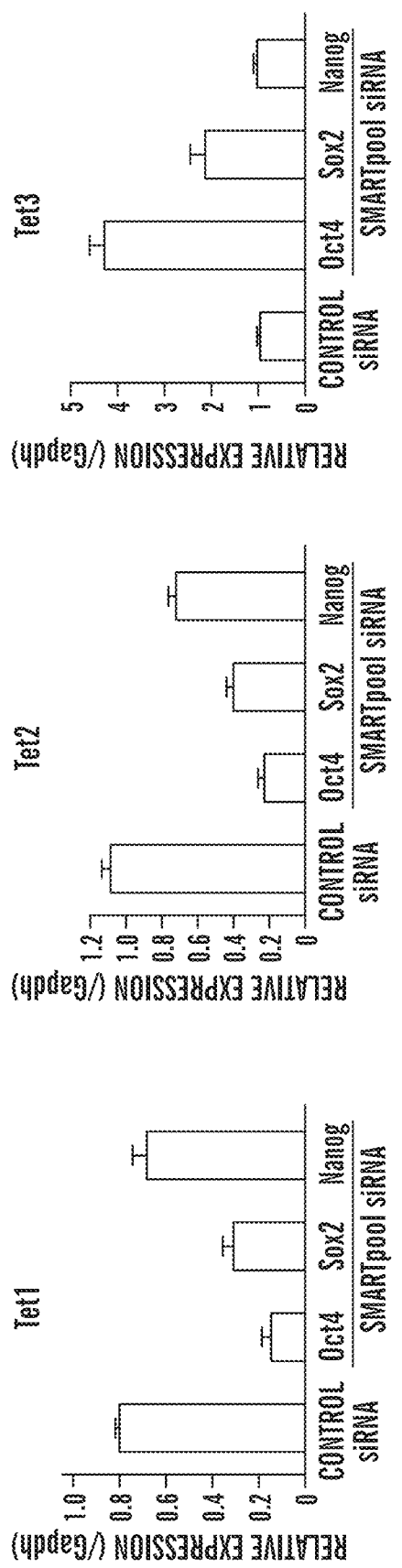
FIG. 16A  FIG. 16B  FIG. 16C  FIG. 16D  FIG. 16E

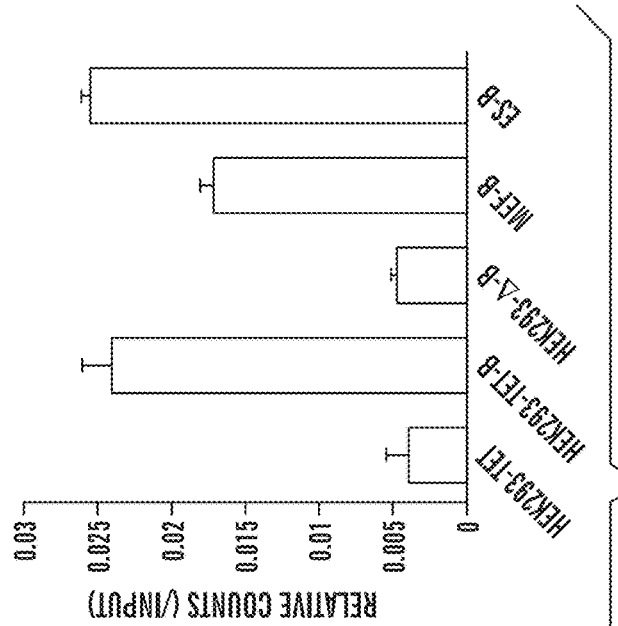
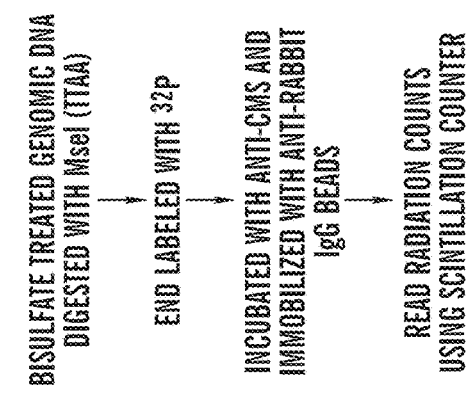
FIG. 19
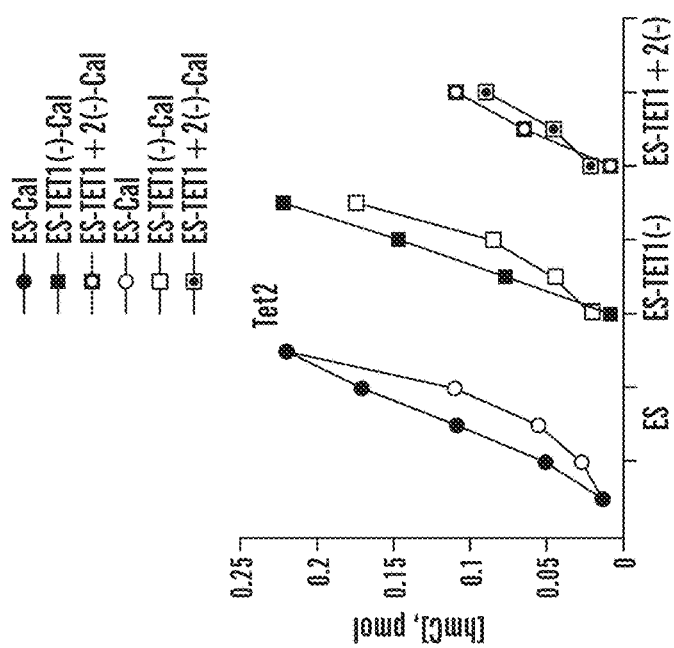
FIG. 18

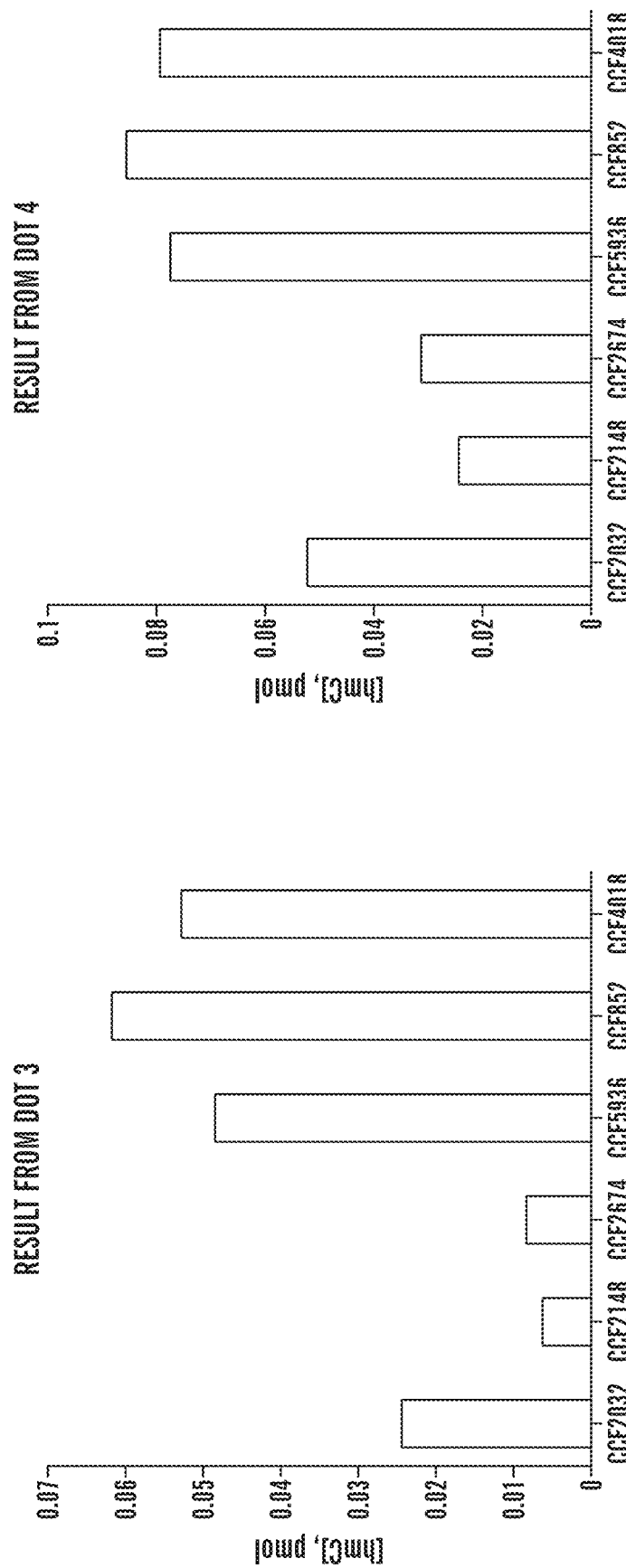

5' ATTGTGGTAGGTTAAGTGGATTGTAAGGAGGTAGGTGTGATATCTGTAGCCATCGAGGAAGATTAAATACTG

GAATTCCACAATCAGAACTTTAGGGACCAGGCTCTCCGGGA CCTT ATAAC TTCC AAGGTGTTGGTGACCGACTGTGAA
                                         *          *              *

GTGGCCGCGGGGAGCTCTGTGGAGAAAGAAGTAAGGAGAGTGGTAGTGAAT 3' SEQ ID NO:18
       *

Reverse primer (used for primer extension):

5' ATTCACTACCACTCTCCTTACTTCTCTTTCTCC 3' SEQ ID NO:8

FIG. 24A

5' GTGAAATATTGTGGTAGGTTAAGTGGATTGTAAGGAGGTAGGTGTTGTAGAGATCGAGGAAGAGATTTAAATAGT

GGAGAATGAGAAGTTTAGAAGAGGATGTTXXXXATGTGTTTATAAGAGAAGAGAAGTAAGGAGAGTGGTAGTGTT

AATTAAGATG 3'   SEQ ID NO:19

1-CG:    XXXX = GGAT
2-CG:    XXXX = CGAT
CGCG:    XXXX = CGCG
CC:      XXXX = CCAT
CCGG:    XXXX = CCGG

Reverse primer (used for primer extension):

5' CATCTTAATTAACCACTACCACTCTCCTTACTTCTCTTTCT 3'   SEQ ID NO:10

FIG. 24B

SEQUENCE OF NO CG AMPLICON AND PRIMERS

GTGAATTAAGGATTTTTTTGTGTGTTTTTGGTTTTTAGGAGAGTTTTTATTTGTGTGATTGATTTGAGGTTT
TAAAAGTTTTTGAGTAATATTAAGAATGTTTTATTAGGATTTTTTAAAATATTTAAAGATTTTT
TTTTGTTTTTGTTGGTGAAGTTTTTAGGGAATTAGAGATATGGAAGATGAATTGGAGGTTAAGAAG
TATTAGAGAGAGGATTTGTAAGAAAAGTTGGGGTTAGAGTGTATTTGAGTGGTATGAAGTAGGGAAATG
TTTTTT  SEQ ID NO:20

Primers:

Forward:  GTGAATTAAGGATTTTTTTTGTGTG  SEQ ID NO:11

Reverse:  AAAAAACATTTCCCTACTTC  SEQ ID NO:12

*FIG. 26A*

SEQUENCE OF MLH1 AMPLICON1

GTTAGATTATTTTAGTAGAGGTATATAAGTTCGGTTTCGGTATTTTTGTTTTTATTGGTTGGATATTTCG
TATTTTTCGAGTTTTTAAAAAXGAATTAATAGGAAGAGCGATTTTTAACGCGTAAGCGTATAT
TTTTTTAGGTAGCGGGTAGTAGTCGTTTTAGGGAGGGACGAAGAGATTTAGTAATTTATAGAGTTGAGAA
ATTTGATTGGT SEQ ID NO:21

Primers:
Forward: GTTAGATTATTTTAGTAGAGGTATATAAGT SEQ ID NO:13
Reverse: ACCAATCAAATTTCTCAACTCTAT SEQ ID NO:14

FIG. 26B

SEQUENCE OF MLH AMPLICON2

TGAGAAATTTGATTGGTATTTAAGTTGTTTAATTAATAGTTGTCGTTGAAGGGTGGGTTGGATGGCGTA
AGTTATAGTTGAAGGAAGAACGTGAGTAYGAGGTATTGAGGTGATTGGTTGAAGGTATTTCGTTGAGTA
TTTAGACGTTTTTTTGGTTTTTTGGCGTTAAAATGTCGTTCGTGGTAGGGGTTATTCGGCGGTTGGACG
AGATAGTGGTGAATCGTATCCGCGGGCGGGGAAGTTATTTAGXGGTTAGTTAATGTTATTAAAGAGATGAT
TG SEQ ID NO:22

Primers:

Forward: TGAGAAATTTGATTGGTATTTAAGTTG SEQ ID NO:15

Reverse: CAATCATCTCTTTAATAACATTAACTAACC SEQ ID NO:16

FIG. 26C

METHODS OF EPIGENETIC ANALYSIS

CROSS REFERENCE TO RELATED APPLICATIONS

This application is a continuation application under 35 U.S.C. § 120 of co-pending U.S. application Ser. No. 16/658,195 filed Oct. 21, 2019, which is a continuation application of U.S. application Ser. No. 16/180,450 filed Nov. 5, 2018, now U.S. Pat. No. 10,767,216, issued Sep. 8, 2020, which is a continuation application under 35 U.S.C. § 120 of U.S. application Ser. No. 16/169,801 filed Oct. 24, 2018, now U.S. Pat. No. 10,465,234, issued Nov. 5, 2019, which is a continuation application under 35 U.S.C. § 120 of U.S. application Ser. No. 15/341,344 filed Nov. 2, 2016, now U.S. Pat. No. 10,533,213, issued Jan. 14, 2020, which is a continuation application under 35 U.S.C. § 120 of U.S. application Ser. No. 15/193,796 filed Jun. 27, 2016, now U.S. Pat. No. 10,443,091, issued Oct. 15, 2019, which is a continuation application under 35 U.S.C. § 120 of U.S. application Ser. No. 13/795,739 filed Mar. 12, 2013, now U.S. Pat. No. 9,447,452, issued Sep. 20, 2016, which is a continuation application under 35 U.S.C. § 120 of U.S. application Ser. No. 13/120,861 filed on Jun. 7, 2011, now U.S. Pat. No. 9,115,386, issued Aug. 25, 2015, which is a 35 U.S.C. § 371 National Phase Entry Application of International Application No. PCT/US2009/058562 filed Sep. 28, 2009, which designates the United States, and which claims benefit under 35 U.S.C. § 119(e) of U.S. Provisional Patent Application Ser. No. 61/100,503 filed Sep. 26, 2008, U.S. Provisional Patent Application Ser. No. 61/100,995 filed Sep. 29, 2008, and U.S. Provisional Patent Application Ser. No. 61/121,844 filed on Dec. 11, 2008, the contents of which are incorporated herein in their entirety by reference.

GOVERNMENT SUPPORT

This invention was made with government support under grant numbers AI044432 and HL089150 awarded by The National Institutes of Health. The government has certain rights in the invention.

FIELD OF THE INVENTION

The present invention relates to enzymes with novel hydroxylase activity and methods for uses thereof, and methods of labeling and detecting methylated residues.

SEQUENCE LISTING

The instant application contains a Sequence Listing which has been submitted in ASCII format via EFS-Web and is hereby incorporated by reference in its entirety. Said ASCII copy, created on Mar. 24, 2011, is named 20110324_Seq_List_TXT_033393_063004_US.TXT and is 147,751 bytes in size.

BACKGROUND OF THE INVENTION

DNA methylation and demethylation play vital roles in various aspects of mammalian development, as well as in somatic cells during differentiation and aging. Importantly, these processes are known to become highly aberrant during tumorigenesis and cancer (A. Bird, Genes Dev 16: 6-21 (2002); W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006)).

In mammals, DNA methylation occurs primarily on cytosine in the context of the dinucleotide CpG. DNA methylation is dynamic during early embryogenesis and plays crucial roles in parental imprinting, X-inactivation, and silencing of endogenous retroviruses. Embryonic development is accompanied by major changes in the methylation status of individual genes, whole chromosomes and, at certain times, the entire genome (A. Bird, Genes Dev 16: 6-21 (2002); W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006)). For example, there is active genome-wide demethylation of the paternal genome shortly after fertilization (W. Mayer, Nature 403: 501-502 (2000); J. Oswald, Curr Biol 10: 475-478 (2000)). DNA demethylation is also an important mechanism by which germ cells are reprogrammed: the development of primordial germ cells (PGC) during early embryogenesis involves widespread DNA demethylation mediated by an active (i.e. replication-independent) mechanism (A. Bird, Genes Dev 16: 6-21 (2002); W. Reik, Nature 447: 425-432 (2007); K. Hochedlinger, Nature 441: 1061-1067 (2006); M. A. Surani Cell 128: 747-762 (2007); P. Hajkova, Nature 452: 877-881 (2008); N. Geijsen, Nature 427: 148-154 (2004)).

De novo DNA methylation and demethylation mechanisms are also prominent in somatic cells during differentiation and aging. Expression of differentiation-specific genes in somatic cells is often accompanied by progressive DNA demethylation (W. Reik, Nature 447: 425-432 (2007); K. Hochedlinger, Nature 441: 1061-1067 (2006); M. A. Surani Cell 128: 747-762 (2007)). Tight regulation of DNA demethylation is a feature of pluripotent stem cells and progenitor cells in cellular differentiation pathways, which could contribute to the ability of these cells to self-renew, as well as give rise to daughter differentiating cells (W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006); S. Simonsson Nat Cell Biol 6: 984-990 (2004); R. Blelloch, Stem Cells 24: 2007-2013 (2006)).

It is believed that two important aspects of stem cell function, pluripotency and self-renewal ability, require proper DNA demethylation, and hence, the ability to manipulate these stem cell functions could be improved by controlled expression of enzymes in the DNA demethylation pathway. The epigenetic reprogramming of somatic nuclei during somatic cell nuclei transfer (SCNT) may also require proper control of DNA demethylation pathways (W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006); S. Simonsson (2004); R. Blelloch (2006)). For optimal efficiency of cloning by SCNT, regulated DNA demethylation may be required for nuclear reprogramming in the transferred somatic cell nucleus. Moreover, correct regulation of DNA demethylation could improve the efficiency with which induced pluripotent stem cells (iPS cells) are generated from adult fibroblasts or other somatic cells using pluripotency factors (K. Takahashi, Cell 126: 663-676 (2006); K. Takahashi, Cell 131: 861-872 (2007); J. Yu, Science 318: 1917-1920 (2007)).

DNA methylation processes are known to be highly aberrant in cancer. Overall, the genomes of cancer cells show a global loss of methylation, but additionally tumor suppressor genes are often silenced through increased methylation (L. T. Smith, Trends Genet 23: 449-456 (2007); E. N. Gal-Yam, Annu Rev Med 59: 267-280 (2008); M. Esteller, Nature Rev Cancer 8: 286-298 (2007); M. Esteller, N Engl J Med 358: 1148-1159 (2008)). Thus, oncogenesis is associated with aberrant regulation of the DNA methylation/demethylation pathway. Moreover, the self-renewing population of cancer stem cells can be characterized by high levels of DNA demethylase activity. Furthermore, in cultured breast cancer cells, gene expression in response to oestrogen has been shown to be accompanied by waves of apparent DNA demethylation and remethylation not coupled to replication (R. Métivier, Nature 452: 45-50 (2008); S. Kangaspeska, Nature 452:112-115 (2008)). It is presently unknown whether this apparent demethylation is due to full conversion of 5-methylcytosine (5mC) to cytosine, or whether it reflects a partial modification of 5-methylcytosine to a base not recognized by methyl-binding proteins or antibodies to 5-methylcytosine.

DNA demethylation can proceed by two possible mechanisms—a "passive" replication-dependent demethylation, or a process of active demethylation for which the molecular basis is still unknown. The passive demethylation mechanism is fairly well understood and is typically observed during cell differentiation, where it accompanies the increased expression of lineage-specific genes (D. U. Lee, Immunity, 16: 649-660 (2002)). Ordinarily, hemimethylated CpG's are generated during cell division as a result of replication of symmetrically-methylated DNA. These hemimethylated CpGs are recognized by the DNA methyltransferase (Dnmt) 1, which then transfers a methyl group to the opposing unmethylated cytosine to restore the symmetrical pattern of DNA methylation (H. Leonhardt, Cell 71: 865-873 (1992); L. S. Chuang, Science 277: 1996-2000 (1997)). If Dnmt1 activity or localization is inhibited, remethylation of the CpG on the opposite strand does not occur and only one of the two daughter strands retains cytosine methylation.

In contrast, enzymes with the ability to demethylate DNA by an active mechanism have not been identified as molecular entities. There is evidence that active DNA demethylation occurs in certain carefully-controlled circumstances, such as shortly after fertilization, and during early development of primordial germ cells (PGC) (W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006); P. Hajkova, Nature 452: 877-881 (2008); N. Geijsen, Nature 427: 148-154 (2004)). The mechanism of active demethylation is not known, though various disparate mechanisms have been postulated (reviewed in (H. Cedar, Nature 397: 568-569 (1999); .S. K. Ooi, Cell 133:1145-1148 (2008)). However, no proteins with these postulated activities have been reliably identified to date.

Overall, identification of molecules that play a role in active demethylation and methods to screen for changes in the methylation status of DNA would be important for the development of novel therapeutic strategies that interfere with or induce demethylation and monitor changes in the methylation status of cellular DNA.

SUMMARY OF THE INVENTION

The present invention provides for novel methods for regulating and detecting the cytosine methylation status of DNA. The invention is based upon identification of a novel and surprising catalytic activity for the family of TET proteins, namely TET1, TET2, TET3, and CXXC4. The novel activity is related to the enzymes being capable of converting the cytosine nucleotide 5-methylcytosine into 5-hydroxymethylcytosine by hydroxylation.

The invention provides, in part, novel methods and reagents to promote the reprogramming of somatic cells into pluripotent cells, for example, by increasing the rate and/or efficiency by which induced pluripotent stem (iPS) cells are generated, and for modulating pluripotency and cellular differentiation status. The inventors have made the surprising discovery that members of the TET family of enzymes are highly expressed in ES cells and iPS cells, and that a gain in pluripotency is associated with induction of members of the TET family of enzymes and the presence of 5-hydroxymethylcytosine, while a loss of pluripotency suppresses TET family enzyme expression and results in a loss of 5-hydroxymethylcytosine. Thus, the TET family of enzymes provide a novel set of non-transcription factor targets that can be used to modulate and regulate the differentiation status of cells. Accordingly, the invention provides novel reagents, such as TET family enzymes, functional TET family derivatives, or TET catalytic fragments for the reprogramming of somatic cells into pluripotent stem cells. This novel and surprising activity of the TET family proteins, and derivatives thereof, could also provide a way of improving the function of stem cells generally—any kind of stem cell, not just iPS cells. Examples include, but are not limited to, neuronal stem cells used to create dopaminergic neurons administered to patients with Parkinson's or other neurodegenerative diseases etc, muscle stem cells administered to patients with muscular dystrophies, skin stem cells useful for treating burn patients, and pancreatic islet stem cells administered to patients with type I diabetes.

The invention also provides novel methods of diagnosing and treating individuals at risk for or having a myeloid cancer, such as a myeloproliferative disorder (MPD), a myelodysplatic syndrome (MDS), an acute myeloid leukemia (AML), a systemic mastocytosis, and a chronic myelomonocytic leukemia (CMML). The inventors have made the surprising discovery that TET family mutations have significant and profound effects on the hydroxymethylation status of DNA in cells, and that such defects can be detected using the methods of the invention, such as bisulfate treatment of nucleic acids and antibody-based detection of cytosine methylene sulfonate.

One aspect of the present invention also provides a method for improving the generation of stable human regulatory Foxp3+ T cells, the method comprising contacting a human T cell with, or delivering to a human T cell, an effective 5-methylcytosine to 5-hydroxymethylcytosine converting amount of at least one catalytically active TET family enzyme, functional TET family derivative, TET catalytic fragment or combination thereof. In one embodiment, one uses the entire protein of TET1, TET2, TET3, and CXXC4, or a nucleic acid molecule encoding such protein.

In one embodiment, the method of generating human regulatory Foxp3+ T cells further comprises contacting the human T cell with a composition comprising cytokines, growth-factors, and activating reagents. In one embodiment, the composition comprising cytokines, growth factors, and activating reagents comprises TGF-β.

Accordingly, in one aspect, the invention provides a method for improving the efficiency or rate with which induced pluripotent stem (iPS) cells can be produced from adult somatic cells. In one embodiment of this aspect, the method comprises contacting a somatic cell with, or delivering to a somatic cell being treated to undergo reprogramming, an effective amount of at least one catalytically active TET family enzyme, functional TET family derivative, TET catalytic fragment, or combination thereof, in combination with one or more known pluripotency factors, in vitro or in vivo. In one embodiment, one uses the entire catalytically active TET1, TET2, TET3, or CXXC4 protein, or a nucleic acid encoding such protein. In one embodiment, only a functional TET1, TET2, TET3, or CXXC4 derivative is used. In one embodiment, only a TET1, TET2, TET3, or CXXC4 catalytic fragment is used.

In one embodiment of the aspect, reprogramming is achieved by delivery of a combination of one or more nucleic acid sequences encoding Oct-4, Sox2, c-Myc, and Klf4 to a somatic cell. In another embodiment, the nucleic acid sequences of Oct-4, Sox2, c-MYC, and Klf4 are delivered using a viral vector, such as an adenoviral vector, a lentiviral vector, or a retroviral vector.

Another object of the invention is to provide a method for improving the efficiency of cloning mammals by nuclear transfer or nuclear transplantation.

Accordingly, in one aspect, the invention provides a method for improving the efficiency of cloning mammals by nuclear transfer or nuclear transplantation, the method comprising contacting a nucleus isolated from a cell during a typical nuclear transfer protocol with an effective hydroxylation-inducing amount of a catalytically active TET family enzyme, a functional TET family derivative, or a TET catalytic fragment thereof.

The invention is based, in part, upon identification of a novel and surprising hydroxylase activity for the family of TET proteins, namely TET1, TET2, TET3, and CXXC4, wherein the hydroxylase activity converts the cytosine nucleotide 5-methylcytosine into 5-hydroxymethylcytosine. However, because 5-hydroxymethylcytosine is not recognized either by the 5-methylcytosine binding protein MeCP2 (V. Valinluck, Nucleic Acids Research 32: 4100-4108 (2004)), or specific monoclonal antibodies directed against 5-methylcytosine, novel and inventive methods to detect 5-hydroxymethylcytosine are required.

Accordingly, one object of the present invention is directed to methods for the detection of the 5-hydroxymethylcytosine nucleotide in a sample.

In one aspect of the invention, an assay based on thin-layer chromatography (TLC) is used to detect 5-hydroxymethyl cytosine in a sample. In other aspects, the methods described herein generally involve direct detection of 5-hydroxymethyl cytosine with agents that recognize and specifically bind to it. These methods can be used singly or in combination to determine the hydroxymethylation status of cellular DNA or sequence information. In one aspect, these methods can be used to detect 5-hydroxymethylcytosine in cell nuclei for the purposes of immunohistochemistry. In another aspect, these methods can be used to immunoprecipitate DNA fragments containing 5-hydroxymethylcytosine from crosslinked DNA by chromatin immunoprecipitation (ChIP).

Accordingly, in one embodiment of the aspects described herein, an antibody or antigen-binding portion thereof that specifically binds to 5-hydroxymethylcytosine is provided. In one embodiment, a hydroxymethyl cytosine-specific antibody, or hydroxymethyl cytosine-specific binding fragment thereof is provided to detect a 5-hydroxymethylcytosine nucleotide. Levels of unmethylated cytosine, methylated cytosine and hydroxymethylcytosine can also be assessed by using proteins that bind CpG, hydroxymethyl-CpG, methyl-CpG, hemi-methylated CpG as probes. Examples of such proteins are known (Ohki et al., EMBO J 1999; 18: 6653-6661; Allen et al., EMBO J 2006; 25: 4503-4512; Arita et al., Nature 2008; doi:10.1038/nature07249; Avvakumov et al., Nature 2008; doi:10.1038/nature07273). In some embodiments of these aspects, it may be desirable to engineer the antibody or antigen-binding portion thereof to increase its binding affinity or selectivity for the 5-hydroxymethylcytosine target site. In one embodiment, an antibody or antigen-fragment thereof that specifically binds cytosine-5-methylsulfonate is used to detect a 5-hydroxymethylcytosine nucleotide in a sample.

In one aspect, the invention also provides methods for screening for signaling pathways that activate or inhibit TET family enzymes at the transcriptional, translational, or post-translational levels.

In one aspect, one or more catalytically active TET family enzymes, functional TET family derivatives, or TET catalytic fragments thereof, or DNA encoding one or more catalytically active TET family enzymes, functional TET family derivatives, or TET catalytic fragments thereof, is used to generate nucleic acids containing hydroxymethylcytosine from nucleic acids containing 5-methylcytosine, or in an alternative embodiment other oxidized pyrimidines from appropriate free or nucleic acid precursors.

Yet another object of the present invention provides a kit comprising materials for performing methods according to the aspects of the invention as described herein.

In one embodiment, the kit comprises one or more catalytically active TET family enzymes, functional TET family derivatives, or TET catalytic fragments thereof, or DNA encoding one or more catalytically active TET family enzymes, functional TET family derivatives, or TET catalytic fragments thereof, to be contacted with or delivered to a cell, or plurality of cells.

In one embodiment, the kit comprises one or more catalytically active TET family enzymes, functional TET family derivatives, or TET catalytic fragments thereof, and one or more compositions comprising cytokines, growth factors, and activating reagents for the purposes of generating stable human regulatory T cells. In one preferred embodiment, the compositions comprising cytokines, growth factor, and activating reagents, comprises TGF-β. In a preferred embodiment, the kit includes packaging materials and instructions therein to use said kits.

In one embodiment, the kit comprises one or more catalytically active TET family enzymes, functional TET family derivatives, or TET catalytic fragments, or DNA encoding one or more catalytically active TET family enzymes, functional TET family derivatives, or TET catalytic fragments, and a combination of the nucleic acid sequences for Oct-4, Sox2, c-MYC, and Klf4, for the purposes of improving the efficiency or rate of the generation of induced pluripotent stem cells. In one embodiment, the nucleic acid sequences for Oct-4, Sox2, c-MYC, and Klf4 are delivered in a viral vector, selected from the group consisting of an adenoviral vector, a lentiviral vector, or a retroviral vector. In a further embodiment, the kit includes packaging materials and instructions therein to use said kit.

In one embodiment, the kit comprises one or more catalytically active TET family enzymes, functional TET family derivatives, or TET catalytic fragments thereof, or DNA encoding one or more catalytically active TET family enzymes, functional TET family derivatives, or TET catalytic fragments thereof, to be contacted with or delivered to a cell, or plurality of cells for the purposes of improving the efficiency of cloning mammals by nuclear transfer. In a further embodiment, the kit includes packaging materials and instructions therein to use said.

In some embodiments, the kit also comprises reagents suitable for the detection of the activity of one or more catalytically active TET family enzymes, functional TET family derivatives, or TET catalytic fragments thereof, namely the production of 5-hydroxymethylcytosine from 5-methylcytosine. In one embodiment, the kit comprises an antibody or binding portion thereof or CxxC domain of a TET family protein or another DNA-binding protein that specifically binds to 5-hydroxymethylcytosine. In other embodiments, the kit includes packaging materials and instructions therein to use said kits. In other embodiments, recombinant TET proteins are provided in a kit to generate nucleic acids containing hydroxymethylcytosine from nucleic acids containing 5-methylcytosine or other oxidized pyrimidines from appropriate free or nucleic acid precursors.

The present invention, in part, relates to novel methods and compositions that enhance stem cell therapies. One aspect of the present invention includes compositions and methods of inducing stem cells to differentiate into a desired cell type by contacting with or delivering to, a stem cell one or more catalytically active TET family enzymes, functional TET family derivatives, or TET catalytic fragments thereof, or nucleic acid encoding one or more catalytically active TET family enzymes, functional TET family derivatives, or TET catalytic fragments thereof, or any combination thereof, to increase pluripotency of said cell being contacted. Such cells, upon contact with or delivery of one or more catalytically active TET family enzymes, functional TET family derivatives, or TET catalytic fragments thereof, or DNA encoding one or more catalytically active TET family enzymes, functional TET family derivatives, or TET catalytic fragments thereof, or any combination thereof, can then be utilized for stem cell therapy treatments, wherein said contacted cell can undergo further manipulations to differentiate into a desired cell type for use in treatment of a disorder requiring cell or tissue replacement.

The present invention also provides, in part, improved methods for the treatment of cancer by the administration of compositions modulating catalytically active TET family enzymes, functional TET family derivatives, or TET catalytic fragments thereof. Also encompassed in the methods of the present invention are methods for screening for the identification of TET family modulators.

Accordingly, in one aspect, the invention provides a method for treating an individual with, or at risk for, cancer using a modulator(s) of the activity of the TET family of proteins. In one embodiment, the method comprises selecting a treatment for a patient affected by, or at risk for developing, cancer by determining the presence or absence of hypermethylated CpG island promoters of tumor suppressor genes, wherein if hypermethylation of tumor suppressor genes is detected, one administers to the individual an effective amount of a tumor suppressor activity reactivating catalytically active TET family enzyme, a functional TET family derivative, a TET catalytic fragment therein, or an activating modulator of TET family activity.

In one embodiment of this aspect, the treatment involves the administration of a TET family inhibiting modulator. In particular, the TET family inhibiting modulator is specific for TET1, TET2, TET3, or CXXC4. In one embodiment of the invention, the cancer being treated is a leukemia. In one embodiment, the leukemia is acute myeloid leukemia caused by the t(10:11)(q22:q23) Mixed Lineage Leukemia translocation of TET1.

In one embodiment of the present aspect, and other aspects described herein, the TET family targeting modulator is a TET family inhibitor. In one embodiment, the TET targeting treatment is specific for the inhibition of TET1, TET2, TET3, or CXXC4. For example, a small molecule inhibitor, a competitive inhibitor, an antibody or antigen-binding fragment thereof, or a nucleic acid that inhibits TET1, TET2, TET3, or CXXC4.

In one embodiment of the present aspect, and other aspects described herein, the TET family targeting modulator is a TET family activator. Alternatively and preferably, the TET targeting treatment is specific for the activation of TET1, TET2, TET3, or CXXC4. For example, a small molecule activator, an agonist, an antibody or antigen-binding fragment thereof, or a nucleic acid that activates TET1, TET2, TET3, or CXXC4.

Also encompassed in the methods and assays of the present invention are methods to screen for the identification of a TET family modulator for use in anti-cancer therapies. The method comprises a) providing a cell comprising a TET family enzyme, recombinant TET family enzyme thereof, TET family functional derivative, or TET family fragment thereof; b) contacting said cell with a test molecule; c) comparing the relative levels of 5-hydroxymethylated cytosine in cells expressing the TET family enzyme, recombinant TET family enzyme thereof, TET family functional derivative, or TET family fragment thereof in the presence of the test molecule, with the level of 5-hydroxymethylated cytosine expressed in a control sample in the absence of the test molecule; and d) determining whether or not the test molecule increases or decreases the level of 5-hydroxymethylated cytosine, wherein a statistically significant decrease in the level of 5-hydroxymethylated cytosine indicates the molecule is an inhibitor, and a statistically significant increase in the level of 5-hydroxymethylated cytosine indicates the molecule is an activator.

In another embodiment of this aspect, a method for high-throughput screening for anti-cancer agents is provided. The method comprises screening for and identifying TET family modulators. For example, providing a combinatorial library containing a large number of potential therapeutic compounds (potential modulator compounds). Such "combinatorial chemical libraries" are then screened in one or more assays to identify those library members (particular chemical species or subclasses) that display a desired characteristic activity (e.g., inhibition of TET family mediated 5-methylcytosine to 5-hydroxymethylcytosine conversion, or activation of TET family mediated 5-methylcytosine to 5-hydroxymethylcytosine conversion).

BRIEF DESCRIPTION OF DRAWINGS

FIGS. 3A-3B show that alpha-glucosyltransferases add glucose in the alpha configuration, and beta-glucosyltransferases add glucose in the beta configuration. FIGS. 3A-3B also show that beta-glucosyl-HMC-alpha-glucosyl-transferases add another glucose molecule in the beta-configuration to glucosylated 5-hydroxymethylcytosine.

FIG. 5 is a schematic diagram of the domain structure of the TET subfamily proteins, which includes the CXXC domain, the "C" or Cys-rich domain, and the 2OG-Fe(II) oxygenase domain containing a large, low complexity insert.

FIG. 6 shows the relation between 5-methylcytosine staining and high expression of HA on a per-cell basis using the Cell Profiler program. FIG. 6 depicts that the mean intensity of 5-methylcytosine staining decreases in the presence of catalytically active full-length TET1 (FL) or the C+D domains of TET1 (C+D), but not when the catalytic activity is abrogated (FL mut or C+D mut). FIG. 6 expresses the 5-methylcytosine staining data of FIG. 6B normalized to the levels of the mock transfected sample.

FIG. 7 depicts line scans of labeled spots on a TLC plate, obtained using phosphorimaging of the results of assays to detect a novel nucleotide in genomic DNA of cells transfected with various constructs. FIG. 7A shows the line scan from mock transfected cells. FIG. 7B shows the line scan from cells transfected with catalytically active full-length TET1 (FL). FIG. 7C shows the line scan from cells transfected with catalytically inactive TET1 (FL mut). FIG. 7D shows the line scan from cells transfected with TET1 catalytic fragment (C+D). FIG. 7E shows the line scan from cells transfected with mutant TET1 catalytic fragment (C+D mut).

FIG. 8 depicts line scans of labeled spots on a TLC plate, obtained using a phosphorimager, and shows that a novel nucleotide is only observed in DNA from cells transfected with the catalytically-active (C+D) fragment of TET1, as in FIG. 8B, and not in DNA from cells transfected with empty vector, as in FIG. 8A, or the catalytically-inactive mutant version of (C+D), as in FIG. 8C.

FIG. 9 depicts the results of LC/MS/MS runs using mass spectroscopy analysis with a collision energy of 15V.

FIG. 11A shows that TET1 mRNA is strongly upregulated after 8 h of stimulation of mouse dendritic cells (DC) with LPS. FIGS. 11B-11I show the changes in Tet1, Tet2 and Tet3 mRNA levels in mouse ES cells that have been induced to differentiate by withdrawal of leukemia inhibitory factor (LIF) and addition of retinoic acid, and shows that Tet1, Tet2, and the positive control pluripotency gene Oct4 are downregulated (FIGS. 11B-11E, and FIGS. 11H-11I), whereas Tet3 is upregulated, during RA-induced differentiation (FIGS. 11F-11G).

FIG. 12A shows that Tet siRNA inhibits Tet1 expression. FIG. 12B shows the effect of siRNA-mediated Tet1 inhibition on Oct4.

FIG. 12C shows the effect of siRNA-mediated Tet1 inhibition on Sox2. FIG. 12D shows the effect of siRNA-mediated Tet1 inhibition on Nanog. FIG. 12E shows the effect of siRNA-mediated Tet1 inhibition on Cdx2. FIG. 12F shows the effect of siRNA-mediated Tet1 inhibition on Gata6.

FIG. 13A shows a schematic diagram of predicted domain structure of TET1, comprising the CXXC domain [Allen, M. D., et al., Embo J, 2006. 25(19): p. 4503-12], cysteine-rich and double-stranded beta-helix (DSBH) regions. FIG. 13B depicts the TLC data of cells overexpressing full-length (FL) TET1 or the predicted catalytic domain (CD) that reveals the appearance of an additional nucleotide species identified by mass spectrometry as 5-hydroxymethylcytosine. H1671Y, D1673A mutations at the residues predicted to bind Fe(II) abrogate the ability of TET1 to generate 5-hydroxymethylcytosine. FIG. 13C shows that 5-hydroxymethylcytosine is detected in the genome of mouse ES cells.

FIG. 14A depicts that the mouse genome expresses three family members—Tet1, Tet2 and Tet3—that share significant sequence homology with the human homologs (Lorsbach, R. B., et al., Leukemia, 2003. 17(3): p. 637-41). Tet1 and Tet3 encode within their first conserved coding exon the CXXC domain. FIG. 14B shows that mouse ES cells express high levels of Tet1 and Tet2, which can be specifically depleted with RNAi.

FIG. 15A shows that the mRNA levels of Tet1 rapidly decline upon LIF withdrawal. FIG. 15B shows that the mRNA levels of Tet2 rapidly decline upon LIF withdrawal.

FIG. 15C demonstrates that Tet3 levels remain low upon LIF withdrawal but increase 10-fold with addition of retinoic acid. FIG. 15D shows that the mRNA levels of Oct4 rapidly decline upon LIF withdrawal, as expected.

FIG. 16A-E shows that Tet1, Tet2 and 5-hydroxymethylcytosine are associated with pluripotency. FIGS. 16A-16C show the loss of pluripotency induced by RNAi-mediated depletion of Oct4 potently suppresses Tet1 (FIG. 16A) and Tet2 expression (FIG. 16B) and upregulates Tet3 (FIG. 16C). Sox2 RNAi was found to cause a similar, though weaker, effect as Oct4 RNAi, and Nanog RNAi had almost no effect. FIGS. 16D-16E show that the gain of pluripotency in iPS clones derived from mouse tail-tip fibroblasts (TTF) by viral transduction of Oct4, Sox2, Klf4 and c-Myc is associated with up-regulation of Tet1 (FIG. 16D) and Tet2 (FIG. 16E) and appearance of 5-hydroxymethylcytosine in the genome.

FIGS. 17A-17C show that RNAi-mediated knockdown of each Tet member does not affect expression of the pluripotency factors Oct4 (FIG. 17A), Sox2 (FIG. 17B) and Nanog (FIG. 17C). FIGS.

17D-17F demonstrate that RNAi-depletion of Tet1, but not of Tet2 or Tet3, increases the expression of the trophectodermal genes Cdx2 (FIG. 17D), Eomes (FIG. 17E) and Hand1 (FIG. 17F). FIGS. 17G-17I demonstrate that RNAi-depletion of Tet family members produces small insignificant changes in expression of extraembryonic endoderm, mesoderm and primitive ectoderm markers Gata6 (FIG. 17G), Brachyury (FIG. 17H), and Fgf5 (FIG. 17I).

FIG. 18 shows the theoretical vs. quantified by bisulfite sequencing amount of 5-hydroxymethylcytosine present in samples in the absence or presence of various TET family siRNA inhibitors.

FIG. 19 illustrates an assay to detect cytosine methylene sulfonate from bisulfite treated samples.

FIGS. 21A-21B show the result of analyses of 5-hydroxymethylcytosine present in samples obtained from patients diagnosed with cancer with or without mutations in TET2, by analysis of dot 3 (FIG. 21A) and dot 4 (FIG. 21B) from TLC plates.

FIG. 22A shows the amplification plots under the various experimental conditions, and FIG. 22B summarizes that data expressed as change in the cycle threshold (Ct).

FIGS. 24A-24B shows the sequences (SEQ ID NO: 18 and SEQ ID NO: 19, respectively) and primers (SEQ ID NO: 8 and SEQ ID NO: 10, respectively) used to determine whether cytosine methylene sulfonate impedes PCR amplification of DNA.

FIGS. 26A-26C shows the sequences (SEQ ID NOS 20-22, respectively) and primers (SEQ ID NOS 11-16, respectively) used to sequence bisulfite treated genomic DNA from HEK293T cells and the sequences and primers used to sequence the bisulfite treated MLH amplicon. FIG. 26A depicts the sequence of the no CG amplicon (SEQ ID NO:20); FIG. 26B shows the sequence of the MLH1 amplicon 1 (SEQ ID NO:21), and FIG. 26C (SEQ ID NO:22) shows the sequence of the MLH1 amplicon 2.

FIG. 27A shows the line traces of MspI sites in the presence or absence of TET1. FIG. 27B shows the line traces of Tag$^{\alpha}$I sites in the presence or absence of TET1.

FIG. 27C compares the mean cycle threshold for various amplicons in the absence or presence of TET1 treatment.

FIG. 35A shows Tet2 expression in myeloid lineage subpopulations and FIG. 35B shows Tet2 expression in various lymphoid lineage subpopulations.

FIG. 36A shows Tet1 expression in myeloid lineage subpopulations and FIG. 36B shows Tet1 expression in various lymphoid lineage subpopulations.

FIG. 37A shows the reduction in mRNA expression, and FIG. 37B shows the reduction in Myc-tagged Tet2 protein.

DETAILED DESCRIPTION OF THE INVENTION

Figure 1:
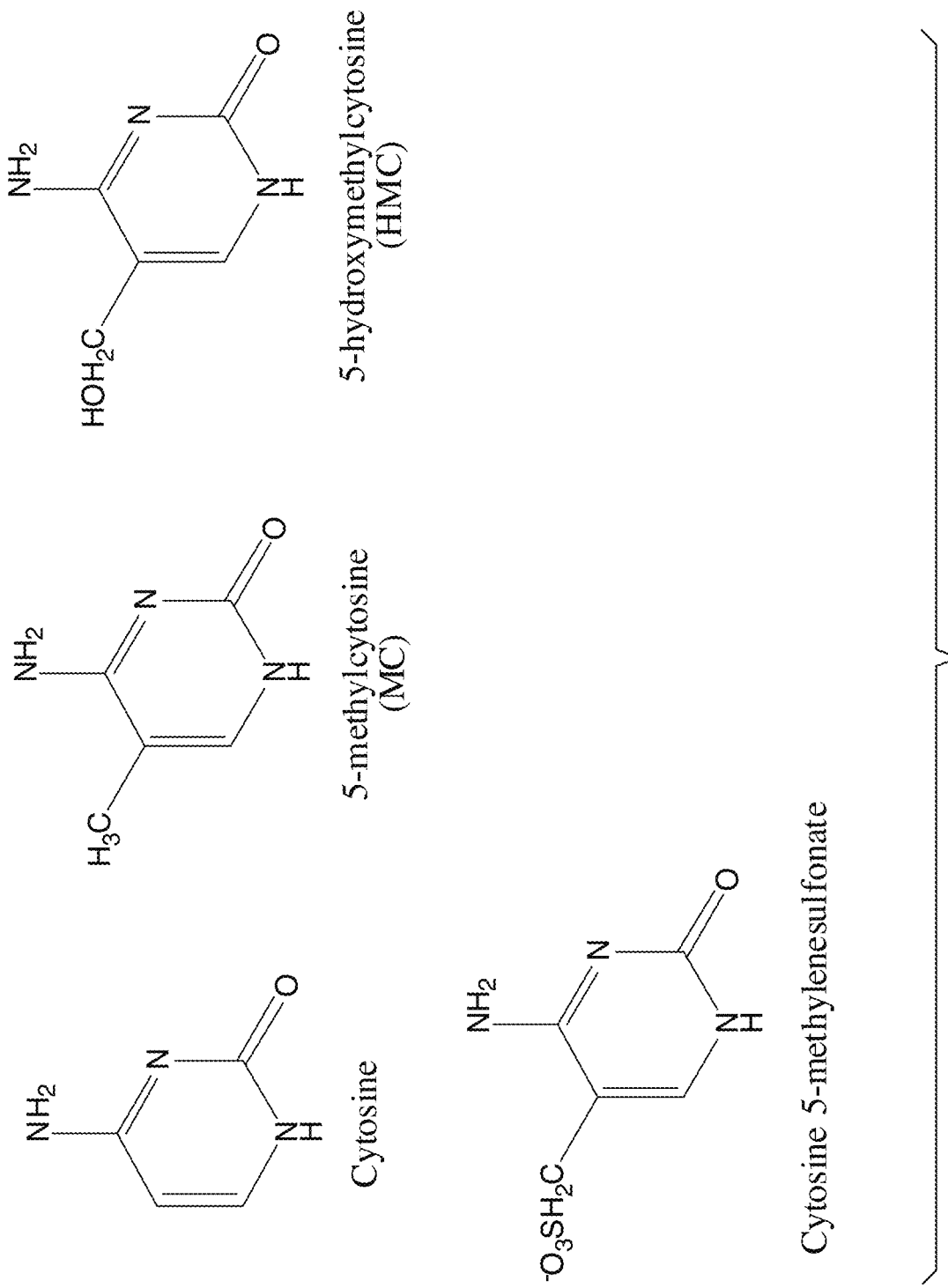
FIG. 1 depicts the chemical structures for cytosine, 5-methylcytosine, 5-hydroxymethylcytosine, and 5-methylenesulfonate.
Figure 2:
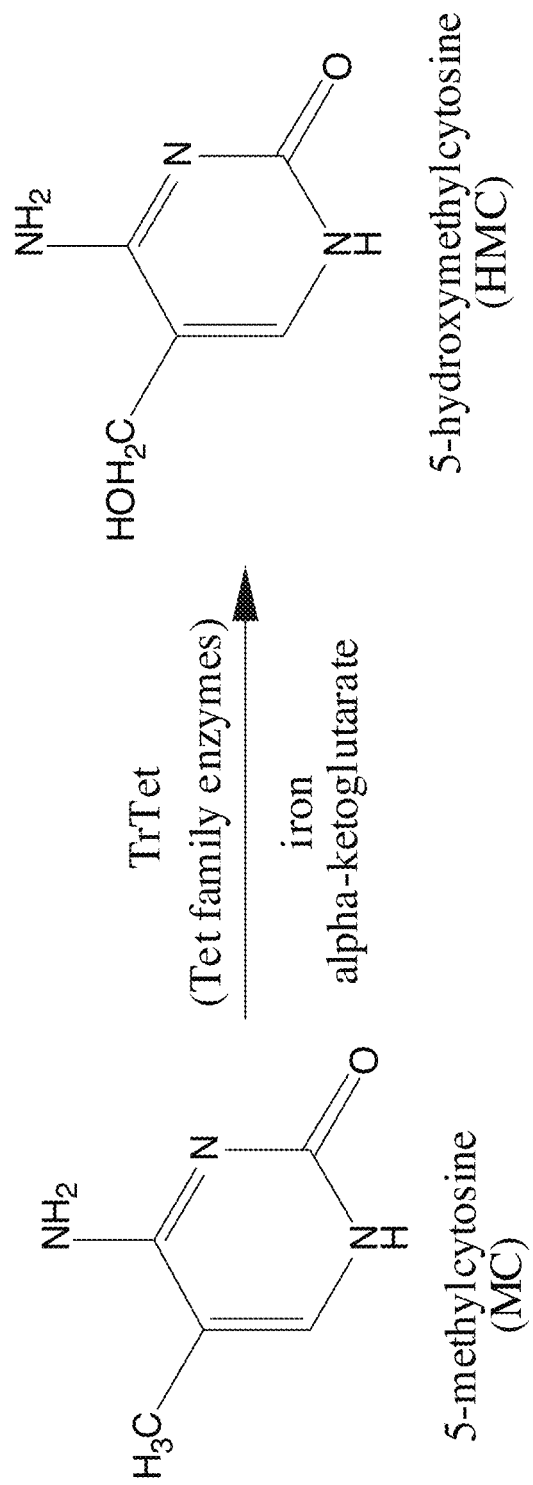
FIG. 2 depicts the conversion of 5-methylcytosine to 5-hydroxymethylcytosine that can be mediated by a catalytically active TET family enzyme, functional TET family derivative, or TET catalytic fragment.
Figure 3A:
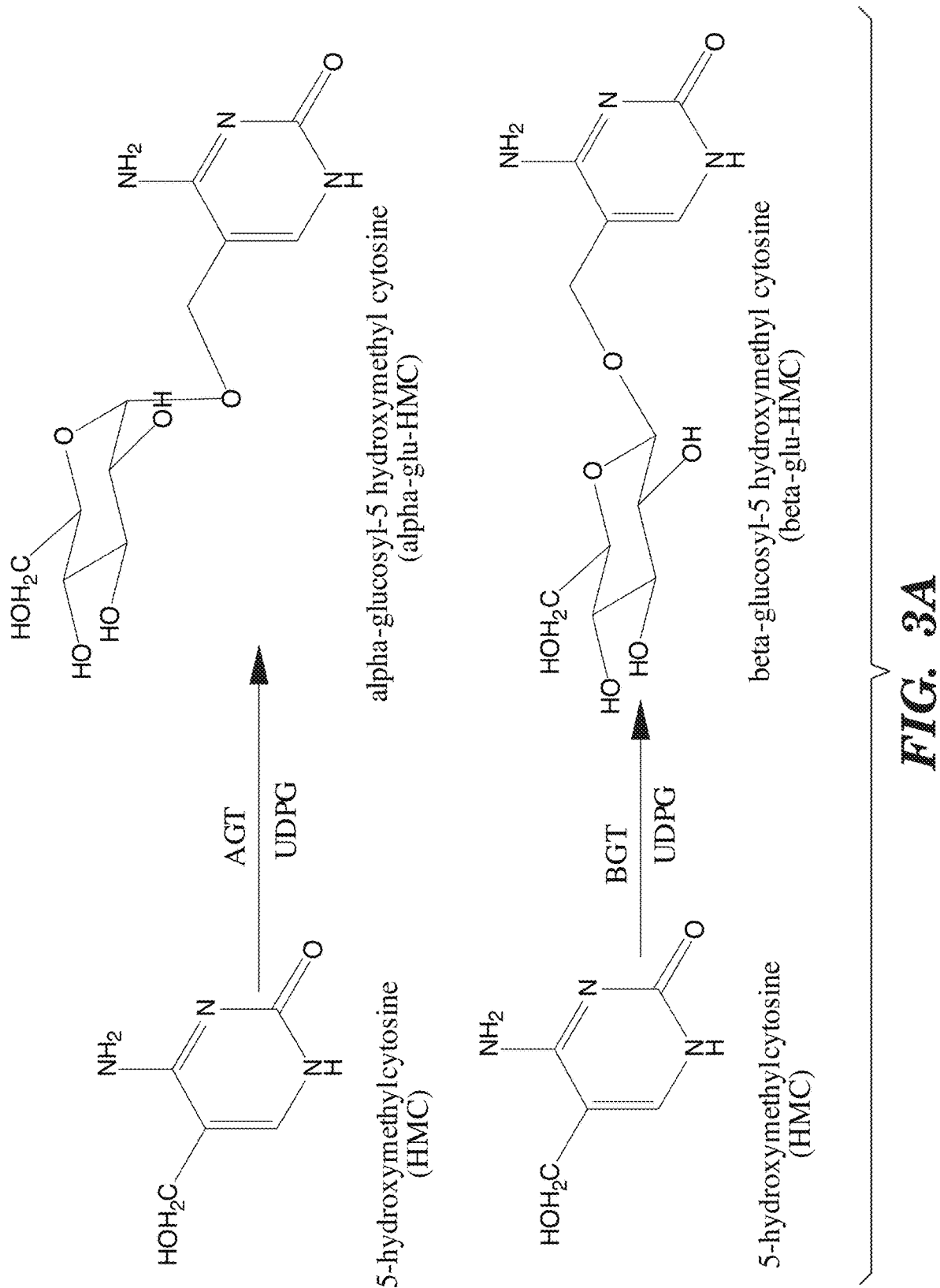
FIGS. 3A-3B shows the various conversions mediated by enzymes encoded by the "T even" family of bacteriophages.
Figure 3B:
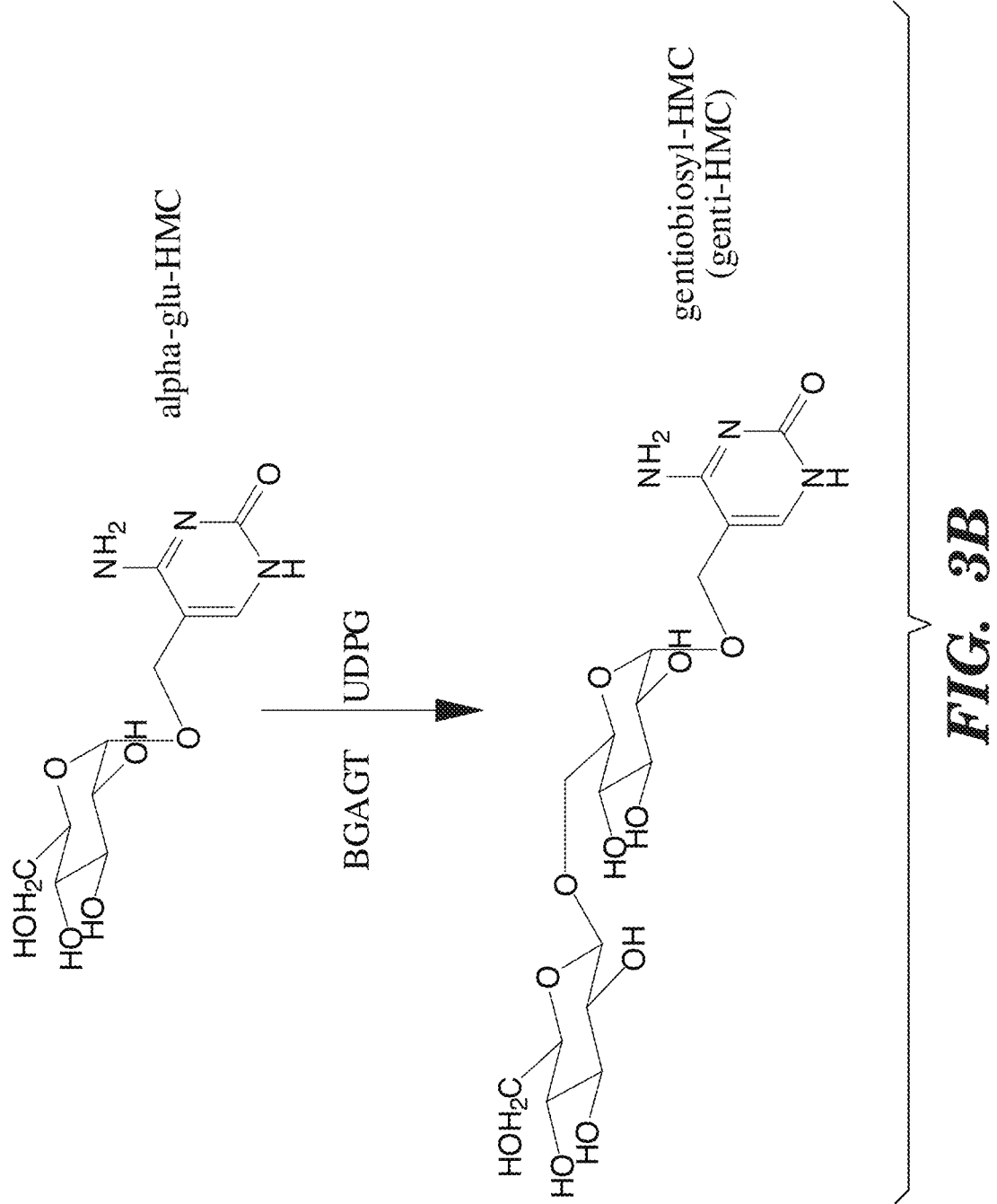

The present invention provides novel and improved methods for modulating pluripotency and differentiation status of cells, novel methods for reprogramming somatic cells, novel research tools for use in the modulation of cellular gene transcription and methylation studies, novel methods for detecting and isolating 5-methylcytosine and 5-hydroxymethylcytosine in nucleic acids, and novel methods for cancer treatment and screening methods therein.

The invention is based upon identification of a novel and surprising enzymatic activity for the family of TET proteins, namely TET1, TET2, TET3, and CXXC4. This novel enzymatic activity relates to the conversion of the cytosine nucleotide 5-methylcytosine into 5-hydroxymethylcytosine via a process of hydroxylation by the TET family of proteins. Accordingly, the invention provides novel tools for regulating the DNA methylation status of mammalian cells. Specifically, these enzymatic activities can be harnessed in methods for use in human Foxp3+ regulatory T cell generation, in the reprogramming of somatic cells, in stem cell therapy, in cancer treatment, in the modulation of cellular transcription, and as research tools for DNA methylation studies.

DNA methylation is catalyzed by at least three DNA methyltransferases (DNMTs) that add methyl groups to the 5' portion of the cytosine ring to form 5' methyl-cytosine. During S-phase of the cell cycle, DNMTs, found at the replication fork, copy the methylation pattern of the parent strand onto the daughter strand, making methylation patterns heritable over many generations of cell divisions. In mammalian genomes, this modification occurs almost exclusively on cytosine residues that precede guanine—i.e., CpG dinucleotides. CpGs occur in the genome at a lower frequency than would be statistically predicted because methylated cytosines can spontaneously deaminate to form thymine. This substitution is not efficiently recognized by the DNA repair machinery, so C-T mutations accumulate during evolution. As a result, 99% of the genome is CpG depleted.

The other 1% is composed of discrete regions that have a high (G+C) and CpG content, and are known as CpG islands.

CpG islands are mostly found at the 5' regulatory regions of genes, and 60% of human gene promoters are embedded in CpG islands. Although most of the CpG dinucleotides are methylated, the persistence of CpG islands suggests that they are not methylated in the germ line and thus did not undergo CpG depletion during evolution. Around 90% of CpG islands are estimated to be unmethylated in somatic tissues, and the expression of genes that contain CpG islands is not generally regulated by their methylation. However, under some circumstances CpG islands do get methylated, resulting in long-term gene silencing.

Regulated DNA methylation is essential for normal development, as mice lacking any one of the enzymes in these pathways die in the embryonic stages or shortly after birth. As a silencing mechanism, DNA methylation plays a role in the normal transcriptional repression of repetitive and centromeric regions, X chromosome inactivation in females, and genomic imprinting. The silencing mediated by DNA methylation occurs in conjunction with histone modifications and nucleosome remodeling, which together establish a repressive chromatin structure. In addition, it has been shown that many cancerous cells possess aberrant patterns of DNA methylation.

As 5-hydroxymethylcytosine is not recognized by the 5-methylcytosine-binding protein MeCP2 (V. Valinluck, Nucleic Acids Research 32: 4100-4108 (2004)), without wishing to be limited by a theory, conversion of 5-methylcytosine into 5-hydroxymethylcytosine could result in loss of binding of MeCP2 and other 5-methylcytosine-binding proteins (MBDs) to DNA, and interfere with chromatin condensation, and therefore result in loss of gene silencing dependent on MBDs.

Additionally, because 5-hydroxymethylcytosine is not recognized by DNA methyltransferase 1 (Dnmt1), which remethylates hemi-methylated regions of DNA, particularly during DNA replication (V. Valinluck and L. C. Sowers, Cancer Research 67: 946-950 (2007)), the oxidative conversion of 5-methylcytosine to 5-hydroxymethylcytosine would result in net loss of 5-methylcytosine in favor of unmethylated cytosine during successive cycles of DNA replication, therefore facilitating the "passive" demethylation of DNA.

Finally, conversion of 5-methylcytosine to 5-hydroxymethylcytosine could also lie in the pathway of "active" demethylation if one postulates, without wishing to be bound by a theory, that a specific DNA repair mechanism exists that recognizes 5-hydroxymethylcytosine and replaces it with cytosine. Without wishing to be limited by a theory, the DNA repair mechanisms that could be utilized for recognition of 5-hydroxymethylcytosine include, but are not limited to: direct repair (B. Sedgwick, DNA Repair (Amst). 6(4):429-42 (2007)), base excision repair (M. L. Hedge, Cell Res. 18(1):27-47 (2008)), nucleotide incision repair (L. Gros, Nucleic Acids Res. 32(1):73-81 (2004)), nucleotide excision repair (S. C. Shuck, Cell Res. 18(1):64-72 (2008)), mismatch repair (G. M. Li, Cell Res. 18(1):85-98 (2008)), homologous recombination, and non-homologous end-joining (M. Shrivastav, Cell Res. 18(1):134-47 (2008)).

We identified a novel enzymatic activity for the TET family of proteins, namely that the TET family of proteins mediate the conversion of 5-methylcytosine in cellular DNA to yield 5-hydroxymethylcytosine by hydroxylation.

Methods of Improving the Reprogramming of Somatic Cells for the Production of Induced Pluripotent Stem Cells and for Use in Somatic Nuclear Cell Transfer The present invention provides, in part, improved methods for the reprogramming of somatic cells into pluripotent stem cells by the administration of a composition containing at least one catalytically active TET family enzyme, functional TET family derivative, TET catalytically active fragment, or combination thereof.

The data demonstrate a novel catalytic activity for the TET family of enzymes, specifically the ability to hydroxylate 5-methylcytosine (5mC) to an intermediate, 5-hydroxymethylcytosine (HMC), and methods wherein to detect this modification.

Accordingly, in one aspect, the invention provides a method for improving the efficiency or rate with which induced pluripotent stem (iPS) cells can be produced from adult somatic cells, comprising contacting a somatic cell being treated to undergo reprogramming with or delivering to a somatic cell being treated to undergo reprogramming an effective amount of one or more catalytically active TET family enzyme, one or more functional TET family derivatives, one or more TET catalytic fragments therein, or a combination thereof, in combination with one or more known pluripotency factors, in vitro or in vivo. In one embodiment, one uses at least one entire catalytically active TET1, TET2, TET3, or CXXC4 protein, or a nucleic acid encoding such protein. In one embodiment, one uses at least one functional TET1, TET2, TET3, or CXXC4 derivative, or at least one nucleic acid encoding such functional derivatives. In one embodiment, one uses at least one TET1, TET2, TET3, or CXXC4 catalytically active fragment or a nucleic acid encoding at least one such catalytically active fragment.

In another aspect, the invention provides a method for improving the efficiency or rate with which induced pluripotent stem (iPS) cells can be produced from adult somatic cells, comprising contacting a somatic cell being treated to undergo reprogramming with, or delivering to, a somatic cell being treated to undergo reprogramming, an effective amount of one or more catalytically active TET family enzymes, one or more functional TET family derivatives, or one or more TET catalytic fragments, and an effective amount of one or more inhibitors of TET family catalytic activity, in combination with one or more known pluripotency factors, in vitro or in vivo. In one embodiment, the catalytically active TET family enzyme, functional TET family derivatives, or TET catalytic fragments, is a catalytically active TET1 and/or TET2 enzyme, and/or functional TET1 and/or TET2 derivative, and/or a TET1 and/or TET2 catalytic fragment, and the inhibitor of TET family catalytic activity is a TET3 inhibitor that is specific for only TET3. In one embodiment, the inhibitor of TET3 is an siRNA or shRNA sequence specific for inhibiting TET3.

The TET family of proteins as referred to in this aspect, and all aspects and embodiments described herein in this application, comprises the nucleotide sequences of TET1, TET2, TET3, and CXXC4 with GenBank nucleotide sequence IDs: GeneID: NM_030625.2 (TET1) (SEQ ID NO:23), GeneID: NM_001127208.1 (TET2) (SEQ ID NO:24), GeneID: NM_144993.1 (TET3) (SEQ ID NO:25), and GeneID: NM_025212.1 (CXXC4) (SEQ ID NO:26) and the protein sequences of TET1, TET2, and CXCC4 with GenBank peptide sequence IDs: NP_085128 (TET1) (SEQ ID NO:27), NP_001120680 (TET2) (SEQ ID NO:28), and NP_079488 (CXXC4) (SEQ ID NO:29).

As used herein, a "TET family protein" refers to the sequences of human TET1, TET2, TET3, and CXXC4, and to proteins having at least 70%, at least 75%, at least 80%, at least 85%, at least 90%, at least 95%, at least 98%, at least 99%, or more, homology to human TET1, TET2, or TET3, and displaying a catalytic (hydroxylating) activity of the TET family of proteins. A "functional TET family derivative", as used herein, refers to a protein comprising a signature sequence, SEQ ID NO:1, from the catalytic site of the TET family proteins and having a catalytic activity of TET proteins.

SEQ ID NO: 1: GVAzAPxHGSzLIECAbxEzHATT
where x=any residue, z=aliphatic residue in the group (L, I, V) and b=basic residue in the group (R, K)

A "TET catalytically active fragment", as referred to herein, comprises a protein having a catalytic activity of TET family proteins and a sequence meeting one of the following criteria: (1) Identical to the sequence of SEQ ID NO: 2 or one of the empirically verified catalytic fragments; or having homology of at least 70%, at least 75%, at least 80%, at least 85%, at least 90%, at least 95%, at least 98%, at least 99%, or more, to such a sequence; or (2) incorporating a linear succession of the TET signature sequences of SEQ ID NO: 2, SEQ ID NO: 3, and SEQ ID NO: 4 in a defined order, that are predicted to form the core of the beta-stranded double helix catalytic domain; or having homology of at least 70%, at least 75%, at least 80%, at least 85%, at least 90%, at least 95%, at least 98%, at least 99%, or more, to such a linear succession of TET family signature sequences, and preserving the linear order thereof.

SEQ ID NO: 3: PFxGxTACxDFxAHxHxDxxN-$[X]_5$-TxVxTL-$[X]_{13}$-DEQxHVLPxY-$[X]_{0-780}$-GVAx-APxHGSxLIECAxxExHATT-$[X]_{11}$-RxSLVxYQH, wherein X is any amino acid residue.

SEQ ID NO: 4: PFxGxTACxDFxAHxHxDxxN-$[X]_5$-TxVxTL-$[X]_{12}$-DEQxHVLPxY-$[X]_{0-780}$-GVAx-APxHGSxLIECAxxExHATT-$[X]_{11}$-RxSLVxYQH, wherein X is any amino acid residue.

SEQ ID NO: 5: PFxGxTACxDFxxHxHxDxxN-$[X]_{2-11}$-TxVxTL-$[X]_{9-13}$-DEQxHVLPxY-$[X]_{0-780}$-GVAx-APxHGSxLIECAxxExHATT-$[X]_{5-13}$-RxSLVxYQH, wherein X is any amino acid residue.

The human TET3 peptide sequence, as described herein, comprises: SEQ ID NO: 6, as well as that described by GenBank Peptide ID: NP_659430.

In connection with contacting a cell with, or delivering to, a catalytically active TET family enzyme, a functional TET family derivative, or a TET catalytically active fragment therein, the phrase "increasing the efficiency" of induced pluripotent stem (iPS) cell production indicates that the proportion of reprogrammed cells in a given population is at least 5% higher in populations treated with a catalytically active TET family enzyme, a functional TET family derivative, or a TET catalytically active fragment thereof, is present. In one embodiment, the proportion of reprogrammed cells in a catalytically active TET family enzyme, a functional TET family derivative, or a TET catalytically active fragment therein treated cell population is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 98% higher, at least 1-fold higher, at least 1.5-fold higher, at least 2-fold higher, at least 5-fold higher, at least 10 fold higher, at least 25 fold higher, at least 50 fold higher, at least 100 fold higher, at least 1000-fold higher, or more than a control treated cell population of comparable size and culture conditions. The phrase "control treated cell population of comparable size and culture conditions" is used herein to describe a population of cells that has been treated with identical media, viral induction, nucleic acid sequences, temperature, confluency, flask size, pH, etc., with the exception of the addition of the catalytically active TET family enzyme, a functional TET family derivative, or a TET catalytically active fragment therein.

By the phrase "increasing the rate" of iPS cell production is meant that the amount of time for the induction of iPS cells is at least 6 hours less, at least 12 hours less, at least 18 hours less, at least 1 day less, at least 2 days less, at least 3 days less, at least 4 days less, at least 5 days less, at least 6 days less, at least 1 week less, at least 2 weeks less, at least 3 weeks less, or more, in the presence of a catalytically active TET family enzyme, a functional TET family derivative, or a TET catalytically active fragment therein, than in a control treated population of comparable size and culture conditions.

The production of iPS cells, as practiced by those skilled in the art, is generally achieved by the introduction of nucleic acid sequences encoding stem cell-associated genes into an adult, somatic cell. In general, these nucleic acids are introduced using retroviral vectors and expression of the gene products results in cells that are morphologically and biochemically similar to pluripotent stem cells (e.g., embryonic stem cells). This process of altering a cell phenotype from a somatic cell phenotype to a stem cell-like phenotype is referred to herein as "reprogramming".

Reprogramming can be achieved by introducing a combination of stem cell-associated genes including, or pluripotency inducing factors, such as Oct3/4 (Pouf51), Sox1, Sox2, Sox3, Sox 15, Sox 18, NANOG, Klf1, Klf2, Klf4, Klf5, c-Myc, 1-Myc, n-Myc and LIN28. In general, successful reprogramming is accomplished by introducing Oct-3/4, a member of the Sox family, a member of the Klf family, and a member of the Myc family to a somatic cell (K. Takahashi, Cell 126: 663-676 (2006); K. Takahashi, Cell 131: 861-872 (2007); J. Yu, Science 318: 1917-1920 (2007)). Oct-3/4 (Pou5f1): Oct-3/4 is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells.

Sox family: The Sox family of genes is associated with maintaining pluripotency similar to Oct-3/4, although it is also associated with multipotent and unipotent stem cells in contrast with Oct-3/4, which is exclusively expressed in pluripotent stem cells. While Sox2 was the initial gene used for induction by Yamanaka et al., Jaenisch et al., and Thomson et al., other genes in the Sox family have been found to work as well in the induction process. Sox1 yields iPS cells with a similar efficiency as Sox2, and genes Sox3, Sox15, and Sox18 also generate iPS cells, although with decreased efficiency.

Klf family: Klf4 of the Klf family of genes was initially identified by Yamanaka et al. and confirmed by Jaenisch et al. as a factor for the generation of mouse iPS cells and was demonstrated by Yamanaka et al. as a factor for generation of human iPS cells. However, Thomson et al. reported that Klf4 was unnecessary for generation of human iPS cells and in fact failed to generate human iPS cells. Klf2 and Klf4 have been found to be factors capable of generating iPS cells, and related genes Klf1 and Klf5 did as well, although with reduced efficiency.

Myc family: The Myc family of genes are proto-oncogenes implicated in cancer. Yamanaka et al. and Jaenisch et al. demonstrated that c-myc is a factor implicated in the generation of mouse iPS cells and Yamanaka et al. demonstrated it was a factor implicated in the generation of human iPS cells. However, Thomson et al., Yamanaka et al., and unpublished work by Johns Hopkins University have reported that c-myc is unnecessary for generation of human iPS cells. N-myc and L-myc have been identified to induce instead of c-myc with similar efficiency.

Nanog: In embryonic stem cells, Nanog, along with Oct-3/4 and Sox2, is necessary in promoting pluripotency. Yamanaka et al. has reported that Nanog is unnecessary for induction although Thomson et al. has reported it is possible to generate iPS cells with Nanog as one of the factors.

LIN28: LIN28 is an mRNA binding protein expressed in embryonic stem cells and embryonic carcinoma cells associated with differentiation and proliferation. Thomson et al. demonstrated it is a factor in iPS generation, although it is unnecessary.

In one embodiment of the methods described herein, reprogramming is achieved by delivery of Oct-4, Sox2, c-Myc, Klf4, or any combination thereof, to a somatic cell (e.g., a fibroblast). In one embodiment of the methods described herein, reprogramming is achieved by delivery of at least one of Sox-2, Oct-4, Klf-4, c-Myc, Nanog, or Lin-28 to a somatic cell (e.g., a fibroblast). In one embodiment, reprogramming is achieved by delivery of the following four transcription factors, Sox-2, Oct-4, Klf-4, and c-Myc, to a somatic cell. In one embodiment, reprogramming is achieved by delivery of three of the following four transcription factors: Sox-2, Oct-4, Klf-4, and c-Myc, to a somatic cell. In one embodiment, reprogramming is achieved by delivery of two of the following four transcription factors: Sox-2, Oct-4, Klf-4, and c-Myc, to a somatic cell. In one embodiment, reprogramming is achieved by delivery of one of the following four transcription factors: Sox-2, Oct-4, Klf-4, and c-Myc to a somatic cell. In one embodiment, reprogramming of a somatic cell is achieved in the absence of the following four transcription factors: Sox-2, Oct-4, Klf-4, and c-Myc.

In one embodiment, reprogramming is achieved by delivery of the following four transcription factors, Sox-2, Oct-4, Nanog, and Lin-28, to a somatic cell. In one embodiment, reprogramming is achieved by delivery of any three of the following four transcription factors: Sox-2, Oct-4, Nanog, or Lin-28 to a somatic cell. In one embodiment, reprogramming is achieved by delivery of two of the following four transcription factors: Sox-2, Oct-4, Nanog, or Lin-28 to a somatic cell. In one embodiment, reprogramming is achieved by delivery of one of the following four transcription factors: Sox-2, Oct-4, Nanog, or Lin-28 to a somatic cell. In one embodiment, reprogramming is achieved in the absence of the following four transcription factors: Sox-2, Oct-4, Nanog, or Lin-28.

In one embodiment, the nucleic acid sequences of one or more of Oct-4, Sox2, c-MYC, Klf4, Nanog, or Lin-28 are delivered using a viral vector or a plasmid. The viral vector can be, for example, a retroviral vector, a lentiviral vector or an adenoviral vector. In some embodiments, the viral vector is a non-integrating viral vector. In one embodiment, reprogramming is achieved by introducing more than one non-integrating vector (e.g., 2, 3, 4, or more vectors) to a cell, wherein each vector comprises a nucleic acid sequence encoding a different reprogramming factor (e.g., Oct2, Sox2, c-Myc, Klf4, etc). In an alternate embodiment, more than one reprogramming factor is encoded by a non-integrating vector and expression of the reprogramming factors is controlled using a single promoter, polycistronic promoters, or multiple promoters.

Non-viral approaches to the introduction of nucleic acids known to those skilled in the art can also be used with the methods described herein. Alternatively, activation of the endogenous genes encoding such transcription factors can be used. In another embodiment, one or more proteins that reprogram the cell's differentiation state can be introduced to the cell. For example, proteins such as c-Myc, Oct4, Sox2 and/or Klf4 can be introduced to the cell through the use of HIV-TAT fusion. The TAT polypeptide has characteristics that permit it to penetrate the cell, and has been used to introduce exogenous factors to cells (see, e.g., Peitz et al., 2002, Proc. Natl. Acad. Sci. USA. 99:4489-94). This approach can be employed to introduce factors for reprogramming the cell's differentiation state. While it is understood that reprogramming is usually accomplished by viral delivery of stem-cell associated genes, it is also contemplated that reprogramming can be induced using other delivery methods, such as delivery of the native, purified proteins (K. Takahashi, Cell 126: 663-676 (2006); K. Takahashi, Cell 131: 861-872 (2007); J. Yu, Science 318: 1917-1920 (2007)). In some embodiments, the reprogramming can be induced using plasmid delivery methods, such as described in Okita K, et al., 2008 Nov. 7; 322(5903):949-53. In other embodiments, reprogramming is achieved by the use of recombinant proteins, such as via a repeated treatment of the cells with certain proteins channeled into the cells to be reprogrammed via poly-arginine anchors. Such cells are termed herein as "protein-induced pluripotent stem cells" or piPS cells, as described in H. Zhou et al., Cell Stem Cell, 4 (5), 8 May 2009, p. 381-384.

The efficiency of reprogramming (i.e., the number of reprogrammed cells) can be enhanced by the addition of various small molecules as shown by Shi, Y., et al (2008) Cell-Stem Cell 2:525-528, Huangfu, D., et al (2008) Nature Biotechnology 26(7):795-797, Marson, A., et al (2008) Cell-Stem Cell 3:132-135, which are incorporated herein by reference in their entirety. It is contemplated that the methods to increase efficiency or rate of iPS cell formation through the novel catalytic activity of one or more members of the TET family described herein can also be used in combination with a single small molecule (or a combination of small molecules) that enhances the efficiency of induced pluripotent stem cell production. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), trichostatin (TSA), and inhibitors of the TGF-β signaling pathway, among others.

It is thus contemplated that inhibitors can be used alone or in combination with other small molecule(s) to replace one or more of the reprogramming factors used in the methods to improve the efficiency or rate of iPS cell production by modulating TET family enzymatic activity as described. In some embodiments, one or more small molecules or other agents are used in the place of (i.e. to replace or substitute) exogenously supplied transcription factors, either supplied as a nucleic acid encoding the transcription factor or a protein or polypeptide of the exogenously supplied transcription factor, which are typically used in the production of iPS cells. As discussed herein, "exogenous" or "exogenous supplied" refer to addition of a nucleic acid encoding a reprogramming transcription factor (e.g. a nucleic acid encoding Sox2, Klf4, Oct4, c-Myc, Nanog, or Lin-28) or a polypeptide of a reprogramming factor (e.g. proteins of Sox2, Klf4, Oct4, c-Myc, Nanog, or Lin-28 or biologically active fragments thereof) which is normally used in production of iPS cells. In some embodiments, reprogramming of a cell is achieved by contacting a cell with one or more agents, such as small molecules, where the agent (i.e. small molecules) replaces the need to reprogram the differentiated cell with one or more of exogenous Sox2, Klf4, Oct4, c-Myc, Nanog, or Lin-28.

In one embodiment, replacement of exogenous transcription factor Sox2 is by an agent which is an inhibitor of the TGFβ signalling pathway, such as a TGFBR1 inhibitor. In other embodiments, a cell to be reprogrammed is contacted with small molecules or other agents which replace exogenous supplied Oct-4 and Klf-4.

Thus, the methods described herein include methods for producing reprogrammed cells from differentiated cells (i.e. from fibroblasts e.g., MEFs) without using exogenous oncogenes, for example c-Myc or oncogenes associated with introduction of nucleic acid sequences encoding one or more of the transcription factors selected from Sox-2, Oct-4 or Klf-4 into the differentiated cell to be reprogrammed (i.e. viral oncogenes). For example, chemically mediated reprogramming of differentiated cells makes it possible to create reprogrammed cells (i.e. iPS cells) from small numbers of differentiated cells, such as those obtained from hair follicle cells from patients, blood samples, adipose biopsy, fibroblasts, skin cells, etc). In some embodiments, the addition of small molecule compounds allows successful and safe generation of reprogrammed cells (i.e. iPS cells) from human differentiated cells, such as skin biopsies (fibroblasts or other nucleated cells) as well as from differentiated cells from all and any other cell type. In one embodiment, an agent which is an agonist of MEK or Erk cell signalling replaces exogenous transcription factor Klf-4. Examples of such agonists include prostaglandin J2, an inhibitor of Ca2+/calmodulin signaling, EGF receptor tyrosine kinase inhibitor, or HDBA. In one embodiment, exogenous transcription factor Oct-4 is replaced by an agent that is an inhibitor of Na2+ channels, an agonist of ATP-dependent potassium channels, or an agonist of MAPK signalling pathways.

In general, iPS cells are produced by viral or non-viral delivery of said stem cell-associated genes into adult somatic cells (e.g., fibroblasts). While fibroblasts are preferred, essentially any primary somatic cell type can be used. Some non-limiting examples of primary somatic cells include, but are not limited to, epithelial cells, endothelial cells, neuronal cells, adipose cells, cardiac cells, skeletal muscle cells, immune cells (T, B, NK, NKT, dendritic, monocytes, neutrophils, eosinophils), hepatic cells, splenic cells, lung cells, circulating blood cells, gastrointestinal cells, renal cells, bone marrow cells, and pancreatic cells. The cell can be a primary cell isolated from any somatic tissue including, but not limited to bone marrow, brain, pancreas, liver, lung, gut, stomach, intestine, fat, muscle, uterus, skin, spleen, thymus, kidney, endocrine organ, bone, etc. Where the cell is maintained under in vitro conditions, conventional tissue culture conditions and methods can be used, and are known to those of skill in the art. Isolation and culture methods for various cells are well within the abilities of one skilled in the art. Further, the parental cell can be from any mammalian species, with non-limiting examples including a murine, bovine, simian, porcine, equine, ovine, or human cell. The parental cell should not express embryonic stem cell (ES) markers, e.g., Nanog mRNA or other ES markers, thus the presence of Nanog mRNA or other ES markers indicates that a cell has been re-programmed. Where a fibroblast is used, the fibroblast is flattened and irregularly shaped prior to the re-programming, and does not express Nanog mRNA. The starting fibroblast will preferably not express other embryonic stem cell markers. The expression of ES-cell markers can be measured, for example, by RT-PCR. Alternatively, measurement can be by, for example, immunofluorescence or other immunological detection approaches that detect the presence of polypeptides or other features that are characteristic of the ES phenotype.

To confirm the induction of pluripotent stem cells, isolated clones can be tested for the expression of a stem cell marker. Such expression identifies the cells as induced pluripotent stem cells. Stem cell markers can be selected from the non-limiting group including SSEA1, CD9, Nanog, Fbx15, Ecat1, Esg1, Eras, Gdf3, Fgf4, Cripto, Dax1, Zpf296, Slc2a3, Rex1, Utf1, and Natl. Methods for detecting the expression of such markers can include, for example, RT-PCR and immunological methods that detect the presence of the encoded polypeptides. The pluripotent stem cell character of the isolated cells can be confirmed by any of a number of tests evaluating the expression of ES markers and the ability to differentiate to cells of each of the three germ layers. As one non-limiting example, teratoma formation in nude mice can be used to evaluate the pluripotent character of the isolated clones. The cells are introduced to nude mice and histology is performed on a tumor arising from the cells. The growth of a tumor comprising cells from all three germ layers (endoderm, mesoderm and ectoderm) further indicates that the cells are pluripotent stem cells. The pluripotent stem cell character of the isolated cells can also be confirmed by the creation of chimeric mice. For example, the cells can be injected by micropipette into a trophoblast, and the blastocyst transferred to a recipient females, where resulting chimeric living mouse pups (with, for example, 10%-90% chimerism) are indicative of successful generation of iPS cells. Tetraploid complementation can also be used to determine the pluripotent stem cell character of the isolated cells, such that the cells are injected into tetraploid blastocysts, which themselves can only form extra-embryonic tissues, and the formation of whole, non-chimeric, fertile mice, is indicative of successful generation of iPS cells (X-y Zhao et al., 2009, Nature. doi:10.1038/nature08267; L. Kang, et al. 2009. Cell Stem Cell. doi:10.1016/j.stem.2009.07.001; and M. J. Boland et al. Nature. 2009 Aug. 2; 461(7260):91-94).

Another object of the invention is to provide a method for improving the efficiency of cloning mammals by nuclear transfer or nuclear transplantation.

Accordingly, in one aspect the invention provides a method for improving the efficiency of cloning mammals by nuclear transfer or nuclear transplantation, the method comprising contacting a nucleus isolated from a cell during a typical nuclear transfer protocol with an effective hydroxylating-inducing amount of one or more catalytically active TET family enzymes, one or more functional TET family derivatives, one or more TET catalytically active fragments thereof, or any combination thereof.

In another aspect, the invention provides a method for improving the efficiency of cloning mammals by nuclear transfer or nuclear transplantation, the method comprising contacting a nucleus isolated from a cell during a typical nuclear transfer protocol with an effective one or more catalytically active TET family enzymes, one or more functional TET family derivatives, one or more TET catalytic fragments, or any combination thereof, and an effective amount of one or more inhibitors of TET family catalytic activity, in combination with at least one known factors that induces pluripotency, in vitro or in vivo. In one embodiment, the catalytically active TET family enzyme, functional TET family derivatives, or TET catalytic fragments, is a catalytically active TET1 and/or TET2 enzyme, and/or functional TET1 and/or TET2 derivative, and/or a TET1 and/or TET2 catalytic fragment, or any combination thereof, and the inhibitor of TET family catalytic activity is a TET3 inhibitor. In one embodiment, the inhibitor of TET3 is an siRNA or shRNA sequence specific for TET3.

In one embodiment, the method comprises a typical nuclear transfer protocol. In a non-limiting example, the method comprises the steps of: (a) enucleating an oocyte; (b) isolating and permeabilizing a nucleated cell, thereby generating a permeabilized cell having pores in its plasma membrane or a partial plasma membrane or no remaining plasma membrane; (c) dedifferentiating the permeabilized cell containing a nucleus of step (b), comprising contacting the nucleus with an effective hydroxylation inducing amount of one or more catalytically active TET family enzymes, one or more functional TET family derivatives, and/or one or more TET catalytically active fragments thereof, under dedifferentiating conditions utilized by ones skilled in the art; (d) transplanting the dedifferentiated nucleus formed in step (c) into a nucleated or enucleated egg such that the dedifferentiated nucleus is exposed to an activating egg cytoplasm, thereby forming a reconstituted oocyte, wherein the recipient egg is from the same species as the somatic reprogrammed cell nucleus; and (e) transferring the reconstituted oocyte or an embryo formed from the reconstituted oocyte into a host animal, thus allowing the egg to develop under direction of genetic information contained in the transplanted activated nucleus.

In connection with the administration of a catalytically active TET family enzyme, a functional TET family derivative, or a TET catalytically active fragment thereof, "improving the efficiency of cloning mammals by nuclear transfer or nuclear transplantation", indicates that the proportion of cloned mammals produced in the presence of exogenous catalytically active TET family enzymes, functional TET family derivatives, or TET catalytically active fragments therein, is at least 5% higher than a comparable, control treated population. In one embodiment, the proportion of viable cloned mammals in a catalytically active TET family enzyme, a functional TET family derivative, or a TET catalytically active fragment, treated population is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 98% higher, at least 99% higher, or more than a control treated population under comparable conditions, wherein no catalytically active TET family enzyme, no functional TET family derivative, or no TET catalytically active fragment is present. The term "control treated population under comparable conditions" is used herein to describe a population of permeabilized, nucleated cells that have been treated with identical media, viral induction, nucleic acid sequence, temperature, confluency, flask size, pH, etc., with the exception of the addition of the catalytically active TET family enzymes, functional TET family derivatives, or TET catalytically active fragments therein, with all other steps in the protocol remaining identical.

In one embodiment, somatic cells are cultured for 5 or more passages (about 10 doublings in cell number), more preferably for 7 or more passages (about 14 doublings in cell number), more preferably for 10 (about 20 doublings in cell number) or more passages and yet more preferably for 15 (about 30 doublings in cell number) passages on a suitable growth medium. Cells are cultured until confluent, disaggregated by chemical and/or mechanical means, and allocated to new growth media upon each passage.

It is preferred that the donor cells of the invention be induced to quiescence prior to fusion or microinjection into the recipient cell. In accord with the teachings of PCT/GB96/02099 and WO 97/07668, both assigned to the Roslin Institute (Edinburgh), it is preferred that the donor nucleus be in either the G0 or G1 phase of the cell cycle at the time of transfer. Donors must be diploid at the time of transfer in order to maintain correct ploidy. It is particularly preferred that the donor cells be in the G0 phase of the cell cycle.

While it is preferred that the recipient of the donor cell nucleus be an oocyte at metaphase I to metaphase II, the present invention may be used with other recipients known to those of ordinary skill in the art, including zygotes and two-cell embryos. Activation of oocytes can be by fertilization with sperm or by parthenogenetic activation schemes known in the art. It is particularly preferred that the recipient be enucleate. A preferred oocyte is an enucleated metaphase II oocyte, non-activated or pre-activated. When a recipient is an enucleated metaphase II oocyte, activation may take place at the time of transfer.

It is preferred that the reconstituted oocyte be activated prior to implantation into the host using techniques known to those of ordinary skill in the art, such as electrical stimulation. As would be understood by one of ordinary skill in the art, activation techniques should be optimized for the particular cell type being used. Non-electrical means for activation known in the art include, but are not limited to, ethanol, protein kinase inhibitors (e.g., 6-dimethylpurine (DMAP), ionophores (e.g., ionomycin), temperature change, protein synthesis inhibitors (e.g. cyclohexamide), thapsigargin, phorbol esters (e.g. phorbol 12-myristate 13-acetate ("PMA")), and mechanical means (See, e.g., Susko-Parrish., U.S. Pat. No. 5,496,720, issued Mar. 5, 1996).

Cultured donor cells may be genetically altered by methods well-known to those of ordinary skill in the art (see, Molecular Cloning a Laboratory Manual, 2nd Ed., 1989, Sambrook, Fritsch and Maniatis, Cold Spring Harbor Laboratory Press; U.S. Pat. No. 5,612,205, Kay et al., issued Mar. 18, 1997; U.S. Pat. No. 5,633,067, to DeBoer et al., issued May 27, 1997). Any known method for inserting, deleting or modifying a desired gene from a mammalian cell may be used to alter the nuclear donor. Included is the technique of homologous recombination, which allows the insertion, deletion or modification of a gene or genes at specific site or sites in the cell genome. Examples for modifying a target DNA genome by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

Human Regulatory T Cell Production Using TET Family Proteins

The mechanisms underlying the methylation and demethylation status of mammalian cells are areas of active research. Most gene regulation is transitory, depending on the current state of the cell and changes in external stimuli. Persistent regulation, on the other hand, is a primary role of epigenetic modifications, i.e., heritable regulatory patterns that do not alter the basic genetic coding of the DNA. DNA methylation is the archetypical form of epigenetic regulation, and performs a crucial role in maintaining the long-term identity of various cell types.

Tissue-specific methylation also serves in regulating adult cell types/stages, and in some cases a causal relationship between methylation and gene expression has been established. A much studied example for such a cell type and cell status specific modification of certain gene regions is found during the lineage commitment of naïve T cells to differentiated helper T cells (Th1 or Th2). Naïve (unstimulated) $CD4^+$ T cells become activated upon encountering an antigen and become committed to alternative cell fates through further stimulation by interleukins. The two types of helper T cells show reciprocal patterns of gene expression: Th1 cells produce Interferon-gamma (IFN-gamma) and silence IL-4, while Th2 cells produce IL-4 and silence IFN-gamma (K. M. Ansel, Nature Immunology 4:616-623, (2003)). For both alternative cell fates, the expression of these genes is inversely correlated with methylation of proximal CpG sites. In Th2 and naive T cells the IFN-gamma promoter is methylated, but not in IFN-gamma expressing Th1 cells (J. T. Attwood, CMLS 59:241-257, (2002)). Conversely, the entire transcribed region of IL-4 becomes demethylated under Th2-inducing conditions, strongly correlating with efficient transcription of IL-4, whereas in Th1 cells, specific untranscribed regions gradually become heavily methylated and IL-4 is not expressed (D. U. Lee, Immunity 16:649-660, (2002)). Furthermore, it has been demonstrated that in naive T cells, the IL-2 promoter is heavily methylated and inactive, but after activation of the naive T cell, the IL-2 gene undergoes rapid and specific demethylation at six consecutive CpGs. This alteration in methylation patterns occurs concomitantly with cell differentiation and increased production of the IL-2 gene product (D. Bruniquel and R. H. Schwartz, Nat. Immunol. 4:235-40, (2003)). In developing immune cells, demethylation during cell fate decisions occurs either passively through exclusion of maintenance methylases from the replication fork, or actively as in the case of IL-2 where a yet not identified enzyme is able to actively demethylate the promoter region upon TCR stimulation.

Regulatory T cells or Treg cells play an important role for the maintenance of immunological tolerance by suppressing the action of autoreactive effector cells and are critically involved in preventing the development of autoimmune reactions, thus making them important and attractive targets for therapeutic applications (S. Sakaguchi, Nat Immunol 6:345-352, (2005)). While a number of cell surface molecules are used to characterize and define Treg cells, the most common being CD4+CD25hi, the transcription factor FOXP3 is specifically expressed in these cells and has been shown to be a critical factor for the development and function of Treg cells.

It has been demonstrated that a conserved 348 bp fragment upstream of the FOXP3 transcription start site contains a minimal promoter necessary for induction of FOXP3 expression (P. Y. Mantel, J. Immunol. 176(6):3593-602 (2006)). Analysis of the methylation status in a stretch of 8 tightly positioned CpG dinucleotides demonstrated that naturally occurring regulatory T cells display a completely demethylated promoter region. In contrast, induced CD4+ CD25hi cells, as well unstimulated and restimulated CD4+ CD25lo cells displayed a partially methylated promoter region (P. C. Janson, PLoS ONE. 3(2) (2008)). Various data demonstrate that activation of CD4+CD25lo cells results in partial demethylation of the human FOXP3 promoter, and that the speed of demethylation correlates with proliferation, thus indicating a mechanism of passive demethylation. Importantly, in contrast to the mouse system, the addition of TGF-β during cell culture of human regulatory T cells does not result in a Treg-like demethylation at the human FOXP3 promoter, highlighting the need for alternative mechanisms of modulating the methylation status at the FOXP3 locus for the generation of stable human regulatory T cell lines.

The importance of demethylation at the FOXP3 locus was demonstrated by the fact that the addition of DNA methylation-inhibiting 5-azacytidine to in vitro derived human regulatory T cell cultures was sufficient to induce stable FOXP3 expression, and 5-azacytidine also stabilized TGF-β induced FOXP3+ Treg cells in restimulation cultures. Similarly, blocking the maintenance of DNA methylation, by pharmacological inhibition of DNA methyltransferase-1, induced significant and stable activation-dependent FOXP3 expression in cycling conventional T cells, which was further amplified by co-treatment with TGF-β.

Taken together, the results thus far demonstrate that epigenetic modification, which results in imprinting of FOXP3 expression and stable Treg populations, is not restricted to naturally occurring Treg cells differentiating within the thymus, but can still be initiated in peripheral FOXP3− T cells. Furthermore, the data indicate that stable conversion of CD25-CD4+ T cells into FOXP3+ Treg can only occur under conditions that also induce epigenetic fixation of the Treg phenotype by modulating the methylation status of the DNA at the FOXP3 locus. However, the biological signals leading to this modulation of the methylation status at the FOXP3 locus remain elusive.

One object of the present invention to provide an improved method of generating stable regulatory T cells.

Accordingly, one aspect of the present invention provides a method for improving the generation of stable human regulatory FOXP3+ T cells, the method comprising contacting a human T cell with or delivering to a human T cell an effective 5-methylcytosine to 5-hydroxymethylcytosine converting amount of one or more catalytically active TET family enzymes, functional TET family derivatives, TET catalytic fragments, or any combination thereof. In one embodiment, one uses the entire protein of TET1, TET2, TET3, or CXXC4, or a nucleic acid encoding such a protein, or any combination thereof. In one embodiment, one uses only the active hydroxylation-inducing portion of TET1, TET2, TET3, or CXXC4, or a nucleic acid encoding such a fragment, or any combination thereof.

In connection with "contacting with" or "delivering to" a cell a TET family enzyme, functional TET family derivative, TET catalytic fragment thereof, or any combination thereof, the phrase "improving the generation of stable human regulatory FOXP3+ cells" indicates that the percentage of stable human regulatory FOXP3+ cells in a given population is at least 5% higher in populations treated with a catalytically active TET family enzyme, a functional TET family derivative, or a TET catalytic fragment thereof, relative to a comparable, control population, where no TET family enzyme, functional TET family derivative, or TET catalytic fragment is present. In one embodiment, the percentage of stable human regulatory FOXP3+ cells in a catalytically active TET family enzyme, a functional TET family derivative, or a TET catalytic fragment thereof, treated population is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 1-fold higher, at least 1.5-fold higher, at least 2-fold higher, at least 5-fold higher, at least 10 fold higher, at least 25 fold higher, at least 50 fold higher, at least 100 fold higher, at least 1000-fold higher, or more than a control treated population of comparable size and culture conditions. The phrase "control treated population of comparable size and culture conditions" is used herein to describe a population of cells that has been treated with identical media, viral induction, nucleic acid sequences, temperature, confluency, flask size, pH, etc., with the exception of the addition of a catalytically active TET family enzyme, a functional TET family derivative, or a TET catalytic fragment thereof.

By the phrase "stable human regulatory FOXP3+ T cells" is meant a population of CD4 T cells that maintain expression of the transcription factor FOXP3 upon repeated T cell stimulation in the absence of exogenous regulatory T cell differentiation factors, such as, but not limited to, TGF-β. Such "stable human regulatory FOXP3+ T cells" possess functions known to be characteristic of human regulatory T cells, for example, but not limited to, the ability to suppress the proliferation of naïve CD4+CD25− cells in a dose-dependent manner, as assayed by techniques familiar to those in the art, including, but not limited to, tritiated-thymidine incorporation and CFSE assays.

The production of human regulatory FOXP3+ T cells, as practiced by those skilled in the art, is generally achieved by purifying CD4+ cells from a human source and culturing and expanding the CD4+ cells in the presence of agents that non-specifically activate the T cell receptor, and cytokines and/or growth factors known to promote survival, growth, function, differentiation, or a combination thereof, of the regulatory T cell lineage. It is to be understood that the CD4+ T cells may be obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells may be obtained. It is to be understood that any technique, which enables separation of the CD4 T cells for use in the methods and assays invention may be employed, such as flow cytometric sorting, or through the use of magnetic bead assays (negative or positive selection), or a combination of such methods, and is to be considered as part of this invention.

Cytokines and growth factors, it is to be understood, may include polypeptides and nonpolypeptide factors. As defined herein, a "cytokine" is any of a number of substances which are secreted by specific cells of the immune system which carry signals locally between cells, and thus have an effect on other cells, and include proteins, peptides, or glycoproteins.

A cytokine, may include lymphokines, interleukins, and chemokines, and can be classified into: (1) the four α-helix bundle family, which is further divided into three subfamilies (IL-2 subfamily, interferon (IFN) subfamily, and the IL-10 subfamily); (2) the IL-1 family, which primarily includes IL-1 and IL-18; and (3) the IL-17 family, which has yet to be completely characterized, though member cytokines have a specific effect in promoting proliferation of T-cells that cause cytotoxic effects.

A "growth factor", as the term is defined herein, refers to a naturally occurring substance capable of stimulating cellular growth, proliferation and cellular differentiation. A growth factor may be a protein or a steroid hormone. A cytokine may be a growth factor. Some non-limiting examples of growth factor families include: Bone morphogenetic proteins (BMPs), Epidermal growth factor (EGF), Erythropoietin (EPO), Fibroblast growth factor (FGF), Granulocyte-colony stimulating factor (G-CSF), Granulocyte-macrophage colony stimulating factor (GM-CSF), Growth differentiation factor-9 (GDF9), Hepatocyte growth factor (HGF), Hepatoma derived growth factor (HDGF), Insulin-like growth factor (IGF), Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), and Vascular endothelial growth factor (VEGF).

In general, successful generation of human regulatory FOXP3+ T cells, as practiced by one of skill in the art, is accomplished by culturing purified CD4+ T cells in the presence of anti-CD3 and anti-CD28 antibodies as T cell receptor stimulating agents, and promoting the differentiation of human regulatory FOXP3+ T cells by the addition of TGF-β to the culture medium. The isolated CD4+ cells cultured under such conditions can then be assessed for expression of cell-surface markers characteristic of the regulatory T cell lineage, such as, but not limited to, CD25, using techniques standard in the art. It is to be understood that the isolated culture-expanded human regulatory FOXP3+ T cells of this invention may express in addition to CD25 and CD4 any number or combination of cell surface markers, as described herein, and as is well known in the art, and are to be considered as part of this invention. The isolated CD4+ T cells cultured under such conditions can also be assessed for expression of the transcription factor defining the regulatory T cell lineage, FOXP3, using techniques known in the art, for example, but not limited to, intracellular flow cytometric analysis using a labeled FOXP3 specific monoclonal antibody that can be detected using a flow cytometer.

Accordingly, in one embodiment, the method of generating human regulatory FOXP3+ T cells further comprises contacting the human T cell with a composition comprising at least one cytokine, growth-factor, or activating reagents. In one embodiment, the composition comprises TGF-β.

Compositions and Methods for Detecting 5-Methylcytosine and 5-Hydroxymethylcytosine The invention is based, in part, upon identification of a novel and surprising enzymatic activity for the family of TET proteins, namely TET1, TET2, TET3, and CXXC4. The novel activity is related to the hydroxylase activity of the TET family enzymes, wherein the hydroxylase activity converts the cytosine nucleotide 5-methylcytosine into 5-hydroxymethylcytosine. There are currently no techniques or reagents to detect or map 5-hydroxymethylcytosine residues in genomes, as it is not recognized either by the 5-methylcytosine binding protein MeCP2 (V. Valinluck, Nucleic Acids Research 32: 4100-4108 (2004)), or existing specific monoclonal antibodies directed against 5-methylcytosine. Hence, reagents and methods to detect 5-hydroxymethylcytosine are required.

Accordingly, one object of the present invention is directed towards compositions and methods for the detection of 5-methylcytosine and 5-hydroxymethylcytosine nucleotides in a nucleic acid, such as DNA, in a biological sample.

In one embodiment, an assay based on thin-layer chromatography (TLC) is used. Briefly, DNA is extracted from cells and digested with a methylation insensitive enzyme that cuts the DNA regardless of whether the internal cytosine in the CG dinucleotide is methylated. Preferably, the restriction enzyme cuts within CCGG sequences, and more preferably the enzyme is MspI. Alternatively, the enzyme cuts within TCGA, and the restriction enzyme used is Taqα1. The restricted DNA is then treated with an agent to remove the newly exposed 5' phosphate, such as calf intestinal phosphatase. The DNA is then treated to yield fragments that are almost exclusively labeled on the newly exposed 5' cytosine, regardless of methylation status, by, for example, end-labeling the DNA with T4 polynucleotide kinase and [γ32P]ATP. The DNA fragments are then digested to liberate dNMPs (dinucleotide monophosphates), using agents such as, for example, snake venom phosphodiesterase and DNase I. The dNMPs can then be separated on cellulose TLC plates and excised for nucleotide identification. As a means of confirming the presence of 5-hydroxymethylcytosine nucleotide in a sample, a known biological source of the nucleotide may be used, such as T-even phages grown in *E. coli* lacking GalU (the enzyme that catalyses formation of the glucose donor UDP-Glucose) and the McrA and McrB1 components of McrBC, which results in the exclusive production of 5-hydroxymethylcytosine, and can be used to compare migration patterns with that of the nucleotides present in the sample.

In addition, the methods and compositions described herein generally involve direct detection of 5-methylcytosine and 5-hydroxymethylcytosine nucleotides, with agents that recognize and specifically bind to 5-methylcytosine and 5-hydroxymethylcytosine nucleotides in a nucleic acid sequence. These methods and compositions can be used singly or in combination to determine the hydroxymethylation status of cellular DNA or sequence information. In one embodiment, these methods and compositions can be used to detect 5-hydroxymethylcytosine in cell nuclei for the purposes of immunohistochemistry. In another embodiment, these methods and compositions can be used to immunoprecipitate DNA fragments containing 5-hydroxymethylcytosine from crosslinked DNA by chromatin immunoprecipitation (ChIP). The identity of such fragments can then be determined by deep-sequencing (ChIPseq) or by hybridizing the fragments to genomic tiling arrays.

Accordingly, one embodiment comprises providing an antibody or antigen-binding fragment thereof that specifically binds to 5-hydroxymethylcytosine. The antibody or antigen-binding portion thereof can be contacted with a biological sample under conditions effective to yield a detectable signal if 5-hydroxymethylcytosine is present in the sample, and the antibody or antigen-binding portion thereof binds to the 5-hydroxymethylcytosine. A determination can be made as to whether the sample yields a detectable signal, where the presence of the detectable signal indicates that the sample contains the 5-hydroxymethylcytosine. Such a determination can be made using any equipment that detects the signal, such as a microscope (fluorescent, electron) or flow cytometric device.

In one embodiment, the 5-hydroxymethylcytosine nucleotide is detected using a hydroxymethylation-specific antibody, hydroxymethylation-specific antigen-binding fragment thereof, or hydroxymethylation-specific protein.

The methylation of cytosine residues occurs in the DNA of many organisms from plants to mammals and is believed to play a critical role in gene regulation. There is considerable research into the mechanisms by which patterns of cytosine methylation change during the differentiation of cells and in states of disease. Furthermore, cytosine methylation patterns are believed to serve as a functional "fingerprint" of different normal and diseased cell types and of the same cell type at various stages of differentiation, and thus mapping the sites of cytosine methylation on a genome-wide scale is a subject of research.

Novel compositions and methods are provided herein that (1) enable covalent enzymatic tagging of methylcytosine in polynucleotides, and detection of the covalent tag; (2) enable covalent enzymatic tagging of 5-hydroxymethylcytosine in polynucleotides, and detection of the covalent tag; and (3) enable detection of 5-hydroxymethylcytosine through chemical modification, such as bisulfite treatment. The compositions and methods for tagging, modification, detection and isolation further provide, in part, numerous downstream applications for analysis of methylcytosine and 5-hydroxymethylcytosine in polynucleotides, including but not limited to, genome-wide analysis of methylcytosine and 5-hydroxymethylcytosine patterns in normal and diseased DNA. The compositions and methods of the invention significantly expand the current state of the art, and can be immediately applied to basic research, clinical diagnostics, and drug screening applications.

This invention describes, in part, a method to covalently tag and detect naturally occurring 5-hydroxymethylcytosine in nucleic acids, such as DNA, for multiple applications. As has been described herein, we have shown that 5-hydroxymethylcytosine is present in mammalian DNA, which, without wishing to be bound by a theory, may exist as an intermediate during changes in methylation status of the genome. As described herein, modification of methylcytosine to 5-hydroxymethylcytosine is catalyzed through the action of the novel TET family of enzymes. Without wishing to be bound by a theory, we believe that 5-hydroxymethylcytosine in DNA is subsequently converted into unmethylated cytosine. 5-hydroxymethylcytosine in DNA may also serve other functions.

As is described herein, in some aspects, methods are provided wherein a catalytically active TET family enzyme, a functional TET family derivative, or a TET catalytically active fragment thereof is contacted with a nucleic acid, such as DNA or RNA, to convert methylcytosine in nucleic acids to 5-hydroxymethylcytosine. In some embodiments, the nucleic acids are contacted in vitro. In some embodiments, the nucleic acids are contacted in a cell. In some embodiments, the nucleic acids are contacted in vivo, in a living animal, preferably a mammal, for example, a human.

Compositions and methods to detect and map methylated and hydroxymethylated cytosine residues in genomes have numerous applications. Several techniques are currently utilized to map methylated cytosine residues. One method involves a chemical reaction of nucleic acids with sodium hydrogen sulfite (bisulfite), which sulfonates unmethylated cytosine but does not efficiently sulfonate methylated cytosine. The sulfonated unmethylated cytosine is prone to spontaneous deamination, which yields sulfonated uracil.

The sulfonated uracil can then be desulfonated to uracil at low pH. The base-pairing properties of the pyrimidines uracil and cytosine are fundamentally different: uracil in DNA is recognized as the equivalent of thymine and therefore is paired with adenine during hybridization or polymerization of DNA, whereas cytosine is paired with guanosine during hybridization or polymerization of DNA. Performance of genomic sequencing or PCR on bisulfite treated DNA can therefore be used to distinguish unmethylated cytosine in the genome, which has been converted to uracil by bisulfite/deamination/desulfonation, versus methylated cytosine, which has remained unconverted. This technique is amenable to large-scale screening approaches when combined with other technologies such as microarray hybridization and high-throughput sequencing.

As described, the invention provides, in one aspect, a method of detecting 5-hydroxymethylcytosine in complex genomes using bisulfite treatment of nucleic acids, such as DNA. The method comprises, in part, contacting a nucleic acid of interest, such as isolated genomic DNA or an oligonucleotide, with an effective amount of sodium bisulfite to convert any 5-hydroxymethylcytosine present in the nucleic acid to cytosine-5-methylenesulfonate. The bisulfite treated nucleic acid is then digested with an enzyme, such as a methyl sensitive enzyme, and the nucleic acid is end-labeled. In one embodiment, the enzyme is MseI. In one embodiment, the nucleic acid is end-labeled, for example, using $^{32}P$. The digested and labeled nucleic acid is then contacted with an antiserum, antibody or antigen-fragment thereof specific for cytosine-5-methylenesulfonate. The contacted nucleic acid can then be immobilized using, for example, beads specific for the species and isotype of antiserum, antibody or antigen-fragment thereof. In one embodiment, the beads comprise anti-rabbit IgG beads. The amount of 5-hydroxymethylcytosine in the immobilized nucleic acid can then be determined by obtaining the radiation counts, by, for example, a scintillation counter. In other embodiments of the aspect, the antibody or antigen-binding fragment is directly labeled. In some embodiments, the label is a fluorescent label or an enzymatic substrate. In some embodiments, the nucleic acid is contacted in vitro. In some embodiments, the nucleic acid is contacted in a cell. In some embodiments, the nucleic acid is contacted in vivo.

In some embodiments, the ability of a test inhibitor to inhibit TET family enzymatic activity can be determined using the methods described herein. For example, genomic DNA is isolated from cells treated with one or more test inhibitors of TET family enzymatic activity, such as siRNAs, and undergoes bisulfite treatment as described herein. The presence of less cytosine-5-methylenesulfonate in a sample treated with the test inhibitor(s) of TET family enzymatic activity compared with a sample to which no test inhibitor(s) was added is indicative of the ability of the test inhibitor to inhibit TET family activity.

In other embodiments, the methods described herein to detect cytosine-5-methylenesulfonate in a sample can be used to test whether a patient having a mutation, single nucleotide polymorphism, or other genetic difference in a TET family member genomic sequence has decreased 5-hydroxymethylcytosine.

In other embodiments, the methods of the aspect can be used to isolate a nucleic acid having one or more 5-hydroxymethylcytosine residues, for use, for example, in chromatin immunoprecipitation assays. Such isolated nucleic acids can then be sequenced or subjected to PCR amplification and subsequent sequencing to identify the genomic regions having 5-hydroxymethylcytosine residues.

As described herein, the invention provides, in one aspect, novel and significant improvements for detecting 5-methylcytosine and 5-hydroxymethylcytosine in complex genomes. In some embodiments, a catalytically active TET family enzyme, a functional TET family derivative, or a TET catalytically active fragment thereof is provided to efficiently convert methylcytosine in nucleic acids to 5-hydroxymethylcytosine. In some embodiments, compositions and methods are provided for using specific and efficient enzymes to convert methylcytosine residues in nucleic acids to glucosylated-5-hydroxymethylcytosine residues and gentibiose-containing-5-hydroxymethylcytosine residues. In some embodiments, the nucleic acids are contacted in vitro. In some embodiments, the nucleic acids are contacted in a cell. In some embodiments, the nucleic acids are contacted in vivo.

Another method currently used to distinguish methylated versus unmethylated cytosine in genomes is by use of methylation sensitive restriction enzymes (MSRE). Cytosine methylation in certain sequence contexts prevents cleavage by MSRE, whereas other enzymes are able to cleave the identical sequence regardless of cytosine methylation status. This differential sensitivity to cytosine methylation can be used to quantitatively determine the degree of methylation in particular stretches of sequence in the genome. Limitations of this method are that it is less amenable to large-scale approaches, and analysis is limited to methylation within recognition sites of the restriction enzymes.

As described herein, the invention provides, in one aspect, novel and significant improvements for detecting methylcytosine in complex genomes. The compositions and methods, as described herein, will allow tagging and analysis of all methylated cytosine residues in the genome, as opposed to the limited analysis obtained with MSRE.

A third method used to distinguish methylated versus unmethylated cytosine in genomes is via affinity purification of methylated cytosine using antibodies or protein domains (e.g. MBD2) that specifically bind to the methylated cytosine residue. Methylated cytosine containing DNA is bound by these affinity reagents and then enriched by binding of the affinity reagent to a solid support or other separation strategy. Further analysis such as microarray hybridization and high-throughput sequencing can be performed on either the bound fraction enriched for methylated cytosine-containing DNA, or the unbound fraction enriched for unmethylated cytosine. This technique has the advantage of enriching regions of interest for further analysis, such as high-throughput sequencing of methylated or unmethylated cytosine in genomes. One limitation of this method is that it depends heavily on the binding affinity and specificity of the given methylated cytosine binding protein, since the binding of these reagents is noncovalent. Another limitation of this method is that it measures density of methylation in a given genomic region, and will not be as sensitive to areas with sparse methylation target sites.

The compositions and methods of the invention provide, in one aspect, improved affinity purification of DNA containing methylated cytosine, by adding covalent tags and/or chemical modifications to methylated cytosine and 5-hydroxymethylated cytosine residues. This is because, as described herein, detection reagents against glucosylated 5-hydroxymethyl cytosine, gentibiose containing 5-hydroxymethylcytosine DNA and chemically modified 5-methylenesulfonate hydroxymethylcytosine are either covalently bound or non-covalently bound with a much higher affinity and specificity than that currently achievable by methylcytosine affinity reagents.

In addition, as described herein, novel compositions and methods are provided for detecting methylated and hydroxymethylated cytosine in complex genomes. Such compositions and methods utilize the properties of certain enzymes to efficiently and specifically add glucose residues to hydroxymethylcytosine in DNA. Enzymes encoded by bacteriophages of the "T even" family have these properties, and those enzymes that add glucose in the alpha configuration are called alpha-glucosyltransferases (AGT), while those enzymes that add glucose in the beta configuration are called beta-glucosyltransferases (BGT). T2, T4, and T6 bacteriophages encode AGTs, but only T4 bacteriophages encode BGT. Amino acids important for the activity of T4 alpha-glucosyltransferases are His-Asp-His (114-116) ((L. Lariviere, J Mol Biol (2005) 352, 139). Amino acids important for the activity of T4 beta-glucosyltransferases are Asp-Ile-Arg-Leu (amino acids 100-103) (SEQ ID NO: 17), Met (amino acid 231) and Glu (amino acid 311) (L. Lariviere, (2003) J Mol Biol 330, 1077). T2 and T6 bacteriophages possess an additional activity that further modifies glucosylated hydroxymethylcytosine by adding another glucose molecule in the beta-configuration. This enzyme is called beta-glucosyl-alpha-glucosyl-transferase (BGAGT). Addition of the second glucose results in the formation of a disaccharide containing two glucose molecules linked in a beta-1-6 configuration, which is known as gentibiose or gentiobiose. The glucose donor used by AGT, BGT, and BGAGT is called uridine diphosphate glucose (UDPG).

In some embodiments of this aspect, enzymes encoded by bacteriophages of the "T even" family are provided that add glucose molecules to 5-hydroxymethylcytosine residues in nucleic acids. In one embodiment, the 5-hydroxymethylcytosine is naturally occurring. In one embodiment, the 5-hydroxymethylcytosine occurs through contacting DNA with a catalytically active TET family enzyme, a functional TET family derivative, or a TET catalytically active fragment thereof, thereby converting methylcytosine to hydroxymethylcytosine. In one embodiment, the enzyme provided is an alpha-glucosyltransferase. In one embodiment, the alpha-glucosyltransferases provided are encoded by a bacteriophage selected from the group consisting of T2, T4, and T6 bacteriophages. In one embodiment, the enzyme is a beta-glucosyltransferase. In one embodiment, the beta-glucosyltransferase is encoded by a bacteriophage selected from T4 bacteriophages. In some embodiments, enzymes encoded by bacteriophages of the "T even" family add two glucose molecules linked in a beta-1-6 configuration to hydroxymethylcytosine to form gentibiose-containing-hydroxymethylcytosine. In one embodiment, the enzyme is a beta-glucosyl-alpha-glucosyl-transferase. In one embodiment, the beta-glucosyl-alpha-glucosyl-transferase is encoded by a bacteriophage selected from the group consisting of T2 and T6 bacteriophages. In some embodiments, the nucleic acids are in vitro. In some embodiments, the nucleic acids are in a cell. In some embodiments, the nucleic acids are in vivo.

As defined herein, a "naturally occurring" 5-hydroxymethylcytosine residue is one which is found in a sample in the absence of any external manipulation, or activity. For example, a "naturally occurring 5-hydroxymethylcytosine residue" is one found in an isolated nucleic acid that is present due to normal genomic activities, such as, for example, gene silencing mechanisms.

In some embodiments of this aspect, the addition of glucose or gentibiose molecules to 5-hydroxymethylcytosine residues provides a method to detect nucleic acids containing hydroxymethylated cytosines. In some embodiments, the method to detect the hydroxymethylated cytosine utilizes radiolabeled glucose and glucose derivative donor substrates. In one such embodiment, the nucleic acid is incubated with an alpha-glucosyltransferases, a beta-glucosyltransferase, or a beta-glucosyl-alpha-glucosyl-transferase in the presence of radiolabeled uridine diphosphate glucose (UDPG), and the DNA purified and analyzed by liquid scintillation counting, autoradiography or other means. In one such embodiment, the UDPG is radiolabeled with 14C. In one embodiment, the UDPG is radiolabeled with 3H.

In some embodiments of this aspect, proteins that recognize glucose residues are used as a method to detect 5-hydroxymethylated cytosine. In some embodiments, the proteins recognize only the glucose residue. In some embodiments, the proteins recognize the residue in the context of hydroxymethyl cytosine. In one embodiment, the protein that recognizes glucose residues is a lectin. In one embodiment, the protein that recognizes glucose residues is an antibody or antibody fragment thereof. In one embodiment, the antibody is modified with several tags and used for solid-phase purification of gentibiose-containing-hydroxymethylcytosine in DNA. In one embodiment, the tags are a biotin molecules or beads. In one embodiment, the antibody is modified with gold or fluorescent tags. In one embodiment, the protein that recognizes glucose residues is an enzyme. In one embodiment, the enzyme is a hexokinase or a beta-glucosyl-alpha-glucosyl-transferase.

In other embodiments of this aspect, the addition of glucose to the 5-hydroxymethylcytosine residues provides a method to detect nucleic acids containing hydroxymethylated cytosines. In such embodiments, naturally occurring 5-hydroxymethylcytosine, or 5-hydroxymethylcytosine occurring through contacting DNA with a catalytically active TET family enzyme, a functional TET family derivative, or a TET catalytically active fragment thereof, undergoes conversion to glucosylated 5-hydroxymethylcytosine using the methods described herein. The glucosylated 5-hydroxymethylcytosine is then contacted with sodium periodate to generate aldehyde residues, and the DNA isolated and precipitated by any method known to one of skill in the art, such as ethanol precipitation. The quantity of aldehyde residues, as determined by one of skill in the art, can then be used to determine the quantity of 5-hydroxymethylcytosine residues. For example, in one embodiment, aldehye residues can be detected using an aldehyde specific probe conjugated to a tag, such as an enzyme, non-fluorescent moiety, or fluorescent label. In one embodiment, the aldehyde specific probe is an aldehyde reactive biotin, and can be detected by streptavidin conjugated to an enzyme. In some embodiments, the enzyme is horseradish peroxidase. In some embodiments of the aspect, the aldehyde specific probe can be used to perform specific pulldown of the glucosylated DNA residues, which can be used, for example, to perform chromatin immunoprecipitation assays to determine in vivo sites of genomic 5-hydroxymethylation.

In some embodiments of this aspect, proteins that recognize gentibiosyl residues are used as a method to detect 5-hydroxymethylated cytosine. In some embodiments, enzymes encoded by bacteriophages of the "T even" family add two glucose molecules linked in a beta-1-6 configuration to hydroxymethylcytosine to form gentibiose-containing-hydroxymethylcytosine. In one embodiment, the enzyme is a beta-glucosyl-alpha-glucosyl-transferase. In one embodiment, the beta-glucosyl-alpha-glucosyl-transferase is encoded by a bacteriophage selected from the group consisting of T2 and T6 bacteriophages. In some embodiments, the gentibiosyl residue in gentibiose-containing-hydroxymethylcytosine is detected non-covalently. In some embodiments, the non-covalent detection methods utilizes proteins with an affinity for the gentibiosyl residue. In one embodiment, the protein is an antibody specific to gentibiose-containing-hydroxymethylcytosine. In one embodiment, the antibody is modified with several tags and used for solid-phase purification of gentibiose-containing-hydroxymethylcytosine in DNA. In one embodiment, the tags are a biotin molecules or beads. In one embodiment, the antibody is modified with gold or fluorescent tags. In one embodiment, the protein is a lectin with affinity to gentibiosyl residues. In one embodiment, the lectin is Musa *acuminata* lectin (BanLec). In one embodiment, the lectin is modified with gold or fluorescent tags. In some embodiments, the proteins with an affinity for the gentibiosyl residue are used to identify gentibiose-containing-hydroxymethylcytosine in DNA using electron microscopy or immunofluorescent detection.

In some embodiments of the aspect, glucose substrates that trap the covalent enzyme-DNA intermediates are used as a method to detect 5-hydroxymethylated cytosine. In some embodiments, enzymes encoded by bacteriophages of the "T even" family add glucose substrates that trap the covalent enzyme-DNA intermediates to 5-hydroxymethylcytosine in DNA. In some embodiments, the glucose substrate is a UDPG analog. In one embodiment, the UDPG analog is uridine-2-deoxy-2-fluoro-glucose. In some embodiments, the enzyme encoded by bacteriophages of the "T even" family is labeled with a tag to facilitate detection and isolation of the covalently linked enzyme-DNA intermediate. In one embodiment, the tag is a protein. In one embodiment, the tag is not a protein.

In some embodiments of this aspect, the method to detect the hydroxymethylated cytosine uses a chemical that recognizes sugar residues and catalyzes further reactions that enable additional tags to be placed on these sugar residues. In one embodiment, the sugar residue is a glucose or a glucose derivative. In one embodiment, the sugar residue is a gentibiose molecule.

In some embodiments of this aspect, the addition of glucose molecules to hydroxymethylcytosine serves to covalently tag hydroxymethylcytosine for downstream applications. In one such embodiment, the downstream application involves the detection and purification of DNA containing methylcytosine and hydroxymethylcytosine. In some embodiments the glucose and glucose derivative donor substrates are radiolabeled for detection.

In some embodiments of this aspect, the 5-hydroxymethyl residue of 5-hydroxymethylcytosine residues in nucleic acids is converted to a methylenesulfonate residue after treatment with sodium hydrogen sulfite. In some embodiments, the addition of sulfonate to 5-hydroxymethylcytosine provides a method to detect the hydroxymethylated cytosine residue. In one embodiment, antibodies specific for the 5-methylenesulfonate residue in nucleosides are used. In some embodiments, the nucleic acids are in vitro. In some embodiments, the nucleic acids are in a cell. In some embodiments, the nucleic acids are in vivo.

In some embodiments of this aspect, the addition of glucose, glucose analogs, or sulfonate molecules to methylcytosine and hydroxymethylcytosine serves to covalently or non-covalently tag methylcytosine and hydroxymethylcytosine for downstream applications. In one such embodiment, the downstream application involves the detection and purification of nucleic acids containing methylcytosine and hydroxymethylcytosine. In some embodiments the glucose and glucose derivative donor substrates are radiolabeled for detection. In some embodiments, the downstream application involves detection of methylcytosine and 5-hydroxymethylcytosine in cells or tissues directly by fluorescence or electron microscopy. In some embodiments, the downstream application involves detection of methylcytosine and 5-hydroxymethylcytosine by assays such as blotting or linked enzyme mediated substrate conversion with radioactive, colorimetric, luminescent or fluorescent detection. In some embodiments, the downstream application involves separation of the tagged nucleic acids away from untagged nucleic acids by enzymatic, chemical or mechanical treatments, and fractionation of either the tagged or untagged DNA by precipitation with beads, magnetic means, fluorescent sorting. In some embodiments, this is followed by application to whole genome analyses such as microarray hybridization and high-throughput sequencing.

Another object of the present invention is to provide methods and assays to screen for signaling pathways that activate or inhibit TET family enzymes at the transcriptional, translational, or posttranslational levels.

Accordingly, one aspect of the invention provides assays for detecting the activity of the TET family of proteins. In one embodiment, an assay for detecting increased hydroxymethylcytosine in vitro using an oligonucleotide containing 5-methylcytosine is provided. In one embodiment, an assay for detecting an increased cytosine-to-methylcytosine ratio in vitro in an oligonucleotide containing 5-methylcytosine is provided. In one embodiment, an assay for detecting increased hydroxymethylcytosine in cellular DNA is provided. In one embodiment, an assay for detecting an increased cytosine-to-methylcytosine ratio in cellular DNA is provided. In another embodiment, an assay for detecting increased hydroxymethylcytosine in transfected plasmid DNA is provided. In one embodiment, an assay for detecting an increased cytosine-to-methylcytosine ratio in transfected plasmid DNA is provided. In another embodiment, an assay for detecting increased activity of a reporter gene that is initially silenced by promoter methylation is provided. In one embodiment, an assay for the detection of other oxidative modifications of pyrimidines in RNA or DNA, in vitro, in cells or in plasmid DNA, is provided.

Another aspect provides a method for detecting factors involved in decreasing the amount of 5-hydroxymethylcytosine residues in a nucleic acid. In some embodiments, the decrease in the amount of 5-hydroxymethylcytosine residues is caused by conversion of 5-hydroxymethylcytosine to cytosine. In some embodiments, the decrease in 5-hydroxymethylcytosine residues is mediated by a DNA repair protein, such as, for example, a glycosylase. In some embodiments, the DNA repair protein is one or more proteins selected from MBD4, SMUG1, TDG. NTHL1, NEIL1, NEIL2, or APEX1. In some embodiments, the method comprises expressing a test factor in a mammalian cell and determining whether any 5-hydroxymethylcytosine residue decreasing activity is present in a cellular lysate by monitoring cleavage of a 5-hydroxymethylcytosine residue containing oligonucleotide. In one embodiment, the method comprises expressing a test glycosylase in a mammalian cell, such as, for example, a 293T cell. Oligonucleotides can then be generated and end-labeled, whereby at least one oligonucleotide comprises one or more 5-hydroxymethylcytosine residues, and at least one oligonucleotide has a known substrate for the test glycosylase. The test glycosylase expressing cells are then lysed, and the oligonucleotides are added to the lysate. In one embodiment, the oligonucleotides are exposed to alkaline conditions to generate abasic sites, and then run on a denaturing gel to detect breaks in the oligonucleotides. For example, if both the oligonucleotide comprising 5-hydroxymethylcytosine residue and the oligonucleotide having a known substrate for the test glycosylase are cut, it indicates that the test glycosylase recognizes 5-hydroxymethylcytosine.

A Kit for Enhancing Gene Transcription, Assessment of 5-Methylcytosine to 5-Hydroxymethylcytosine Conversion, and Purification of Nucleotides Other aspects of the present invention provide kits comprising materials for performing methods according to the invention as above. A kit can be in any configuration well known to those of ordinary skill in the art and is useful for performing one or more of the methods described herein for the conversion of 5-methylcytosine to 5-hydroxymethylcytosine in cells, and the detection of 5-methylcytosine and 5-hydroxymethylcytosine in a nucleic acid.

In one embodiment of this aspect, the kit comprises one or more catalytically active TET family enzymes, functional TET family derivatives, or TET catalytically active fragments thereof, or engineered nucleic acids encoding such catalytically active TET family enzymes, functional TET family derivatives, or TET catalytically active fragments thereof, to be contacted with a cell, or plurality of cells.

In one embodiment of this aspect, the kit comprises one or more catalytically active TET family enzymes, functional TET family derivatives, or TET catalytically active fragments thereof, and one or more compositions comprising cytokines, growth factors, and activating reagents for the purposes of generating stable human regulatory T cells. In one preferred embodiment, the compositions comprising cytokines, growth factor, and activating reagents, comprises TGF-β. In one embodiment of this aspect, the kit includes packaging materials and instructions therein to use said kits.

In one embodiment of this aspect, the kit comprises one or more catalytically active TET family enzymes, functional TET family derivatives, or TET catalytically active fragments, or engineered nucleic acids encoding such catalytically active TET family enzymes, functional TET family derivatives, or TET catalytically active fragments thereof, and the nucleic acid sequences for one or more of Oct-4, Sox2, c-MYC, and Klf4, for the purposes of improving the efficiency or rate of the generation of induced pluripotent stem cells. In some embodiments, the nucleic acid sequences for one or more of Oct-4, Sox2, c-MYC, and Klf4 are delivered in a viral vector. In some embodiments, the vector is an adenoviral vector, a lentiviral vector, or a retroviral vector. In one embodiment of this aspect, the kit includes packaging materials and instructions therein to use said kits.

In one embodiment of this aspect, the kit comprises one or more catalytically active TET family enzymes, functional TET family derivatives, or TET catalytically active fragments thereof, to be contacted with a cell, or plurality of cells for the purposes of improving the efficiency of cloning mammals by nuclear transfer. In preferred embodiments, the kit includes packaging materials and instructions therein to use said kits.

In some embodiments, the kit also comprises reagents suitable for the detection of the activity of one or more catalytically active TET family enzymes, functional TET family derivatives, or TET catalytically active fragments thereof, namely the production of 5-hydroxymethylcytosine from 5-methylcytosine. In one preferred embodiment, the kit comprises an antibody, antigen-binding portion thereof, or protein that specifically binds to 5-hydroxymethylcytosine. In other embodiments, one or more catalytically active TET family enzymes, functional TET family derivatives, or TET catalytically active fragments thereof are provided in a kit to generate nucleic acids containing hydroxymethylcytosine from nucleic acids containing 5-methylcytosine or other oxidized pyrimidines from appropriate free or nucleic acid precursors. In all such embodiments of the aspect, the kit includes packaging materials and instructions therein to use said kits.

In some embodiments of this aspect, the kit also comprises, or consists essentially of, or consists of, reagents suitable for the detection and purification of methylcytosine for use in downstream applications. In one embodiment, the kit comprises, consists essentially of, or consists of, one or more catalytically active TET family enzymes, functional TET family derivatives, or TET catalytically active fragments thereof for the conversion of methylcytosine to 5-hydroxymethylcytosine; one or more enzymes encoded by bacteriophages of the "T even" family; one or more glucose or glucose derivative substrates; one or more proteins to detect glucose or glucose derivative modified nucleotides; and standard DNA purification columns, buffers, and substrate solutions, as known to one of skill in the art.

In some embodiments of this aspect, the enzymes encoded by bacteriophages of the "T even" family are selected from the group consisting of alpha-glucosyltransferases, beta-glucosyltransferases, and beta-glucosyl-alpha-glucosyl-transferases. In one embodiment, the alpha-glucosyltransferases are encoded by a bacteriophage selected from the group consisting of T2, T4, and T6 bacteriophages. In one embodiment, the beta-glucosyltransferase is encoded by a bacteriophage selected from T4 bacteriophages. In one embodiment, the beta-glucosyl-alpha-glucosyl-transferase is encoded by a bacteriophage selected from the group consisting of T2 and T6 bacteriophages.

In some embodiments, the glucose and glucose derivative donor substrates are radiolabeled. In one such embodiment, the radiolabeled glucose and glucose derivative donor substrate is uridine diphosphate glucose (UDPG). In one such embodiment, the UDPG is radiolabeled with 14C. In one embodiment, the UDPG is radiolabeled with 3H.

In some embodiments, the proteins that recognize glucose or glucose derivative modified nucleotides are selected from a group comprising a lectin, an antibody or antigen-binding fragment thereof, or an enzyme. In some embodiments, the proteins recognize only the glucose residue. In some embodiments, the proteins recognize the residue in the context of hydroxymethyl cytosine. In one embodiment, the antibody or antibody fragment thereof is modified with several tags. In one embodiment, the tags are biotin molecules or beads. In one embodiment, the antibody is modified with gold or fluorescent tags. In one embodiment, the enzyme is a hexokinase or a beta-glucosyl-alpha-glucosyl-transferase. In one embodiment, the lectin is Musa *acuminata* lectin (BanLec). In one embodiment, the lectin is modified with gold or fluorescent tags.

In all such embodiments of the aspect, the kit includes the necessary packaging materials and informational material therein to use said kits. The informational material can be descriptive, instructional, marketing or other material that relates to the methods described herein and/or the use of a compound(s) described herein for the methods described herein. In one embodiment, the informational material can include information about production of the compound, molecular weight of the compound, concentration, date of expiration, batch or production site information, and so forth. In one embodiment, the informational material relates to methods for culturing the compound. In one embodiment, the informational material can include instructions to culture a compound(s) (e.g., a TET family enzyme) described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a compound(s) described herein to a suitable subject, e.g., a human, e.g., a human having or at risk for a disorder described herein or to a cell in vitro.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In all embodiments of the aspects described herein, the kit will typically be provided with its various elements included in one package, e.g., a fiber-based, e.g., a cardboard, or polymeric, e.g., a styrofoam box. The enclosure can be configured so as to maintain a temperature differential between the interior and the exterior, e.g., it can provide insulating properties to keep the reagents at a preselected temperature for a preselected time. The kit can include one or more containers for the composition containing a compound(s) described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight. The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

Methods of Improving Stem Cell Therapies Using TET Family Proteins

Stem cell bioengineering is an emerging technology that holds great promise for the therapeutic treatment of a wide range of disorders. A fundamental problem in the field relates to understanding mechanisms whereby stem cell differentiation and lineage commitment can be controlled in vitro so that the bioengineered stem cells may be used in vivo. A method that could easily be adapted to generate a wide range of stem cell types would allow a multitude of therapeutic applications to be developed. Human embryonic stem cell research and consequent therapeutic applications could provide treatments for a variety of conditions and disorders, including Alzheimer's disease, spinal cord injuries, amyotrophic lateral sclerosis, Parkinson's disease, type-1 diabetes, and cardiovascular diseases. Stem cells that could be readily differentiated into desired cell types could also be useful for a number of tissue engineering applications such as the production of complete organs, including livers, kidneys, eyes, hearts, or even parts of the brain. In addition, the ability to control stem cell proliferation and differentiation has applicability in developing targeted drug treatments.

The present invention relates, in part, to novel methods and compositions that enhance stem cell therapies. One aspect of the present invention includes compositions and methods of inducing stem cells to differentiate into a desired cell type by contacting a stem cell or a plurality of stem cells, with, or delivering to a stem cell or a plurality of stem cells, one or more catalytically active TET family enzymes, one or more functional TET family derivatives, or one or more TET catalytically active fragments thereof, or engineered nucleic acids encoding one or more of such catalytically active TET family enzymes, functional TET family derivatives, or TET catalytically active fragments thereof, to increase pluripotency of said cell being contacted or delivered to.

As defined herein, "stem cells" are primitive undifferentiated cells having the capacity to differentiate and mature into other cell types, for example, brain, muscle, liver and blood cells. Stem cells are typically classified as either embryonic stem cells, or adult tissue derived-stem cells, depending on the source of the tissue from which they are derived. "Pluripotent stem cells", as defined herein, are undifferentiated cells having the potential to differentiate to derivatives of all three embryonic germ layers (endoderm, mesoderm, and ectoderm). Adult progenitor cells are adult stem cells which can give rise to a limited number of particular types of cells, such as hematopoetic progenitor cells. Stem cells for use with the present invention may be obtained from any source. By way of example, pluripotent stem cells can be isolated from the primordial germinal ridge of the developing embryo, from teratocarcinomas, and from non-embryonic tissues, including but not limited to the bone marrow, brain, liver, pancreas, peripheral blood, fat tissue, placenta, skeletal muscle, chorionic villus, and umbilical cord blood. The methods and compositions of the present invention may be used with and include embryonic stem cells. Embryonic stem cells are typically derived from the inner cell mass of blastocyst-stage embryos (Odorico et al. 2001, Stem Cells 19:193-204; Thomson et al. 1995. Proc Natl Acad Sci USA. 92:7844-7848; Thomson et al. 1998. Science 282:1145-1147). The distinguishing characteristics of stem cells are (i) their ability to be cultured in their non-differentiated state and (ii) their capacity to give rise to differentiated daughter cells representing all three germ layers of the embryo and the extra-embryonic cells that support development. Embryonic stem cells have been isolated from other sites in the embryo. Embryonic stem cells may be induced to undergo lineage specific differentiation in response to soluble factors.

According to certain embodiments, the stem cells are of human origin. According to one embodiment, the stem cells are selected from embryonic stem cells and adult stem cells. The adult stem cell can be a pluripotent cell or a partially committed progenitor cell.

According to certain embodiments, the composition comprises genetically modified stem cells. Typically, the cells are transformed with a suitable vector comprising a nucleic acid sequence for effecting the desired genetic alteration, as is known to a person skilled in the art.

According to certain embodiments, the stem cells may be partially committed progenitors isolated from several tissue sources. In some embodiments, the partially committed progenitors are hematopoietic cells, neural progenitor cells, oligodendrocyte cells, skin cells, hepatic cells, muscle cells, bone cells, mesenchymal cells, pancreatic cells, chondrocytes or marrow stromal cells.

Such stem cells, upon contact with, or delivery of, one or more catalytically active TET family enzymes, functional TET family derivatives, or TET catalytically active fragments thereof, can then be utilized for stem cell therapy treatments, wherein said contacted cell can undergo further manipulations to differentiate into a desired cell type for use in treatment of a disorder requiring cell or tissue replacement.

The differentiated stem cells of the present invention may be used as any other differentiated stem cell. By way of a non-limiting example, differentiated stem cells of the present invention can be used for tissue reconstitution or regeneration in a human patient in need thereof. The differentiated stem cells are administered in a manner that permits them to graft to the intended tissue site and reconstitute or regenerate the functionally deficient area. One method of administration is delivery through the peripheral blood vessel of the subject, given that stem cells are preferentially attracted to damaged areas. Another form of administration is by selective catheterization at or around the site of damage, which can lead to almost complete delivery of the stem cells into a damaged area.

Methods of Diagnosing and Treating Cancer

The present invention also provides, in part, improved methods for the diagnosis and treatment of cancer by the administration of compositions modulating catalytically active TET family enzymes, functional TET family derivatives, or TET catalytically active fragments thereof. Also encompassed in the methods of the present invention are methods for screening for the identification of TET family modulators. Such methods can be used to modify or determine, for example, treatments to be administered to an individual having or being predisposed to cancer.

Deregulation of gene expression is a hallmark of cancer. Although genetic lesions have been the focus of cancer research for many years, it has become increasingly recognized that aberrant epigenetic modifications also play major roles in the tumorigenic process. These modifications are imposed on chromatin, do not change the nucleotide sequence of DNA, and are manifested by specific patterns of gene expression that are heritable through many cell divisions. When a general role for DNA methylation in gene silencing was established more than 25 years ago, it was proposed that aberrant patterns of DNA methylation might play a role in tumorigenesis. Initial studies found evidence for a decrease in the total 5-methylcytosine content in tumor cells, and the occurrence of global hypomethylation in cancer was firmly established in subsequent studies. Hypomethylation occurs primarily at DNA repetitive elements and is believed to contribute to the genomic instability frequently seen in cancer. Hypomethylation can also contribute to overexpression of oncogenic proteins, as was shown to be associated with loss of imprinting of IGF2 (insulin growth factor 2), leading to aberrant activation of the normally silent maternally inherited allele. This was found to be associated with an increased risk for colon cancer. The mechanisms underlying global hypomethylation patterns are the focus of intensive research (E. N. Gal-Yam, Annu Rev Med 59: 267-280 (2008)).

Aberrant hypermethylation at normally unmethylated CpG islands occurs parallel to global hypomethylation. The CpG island promoter of the Rb (Retinoblastoma) gene, found to be hypermethylated in retinoblastoma, was the first tumor suppressor shown to harbor such a modification. This discovery was soon followed by studies showing promoter hypermethylation and silencing of other tumor suppressor genes, including, but not limited to VHL (von Hippel-Lindau) in renal cancer, the cell cycle regulator CDKN2 A/p16 in bladder cancer, and the mismatch repair gene hMLH1 in colon cancer. It is now established that aberrant hypermethylation at CpG island promoters is a hallmark of cancer. Notably, not only protein-coding genes undergo these modifications; CpG island promoters of noncoding microRNAs were shown to be hypermethylated in tumors, possibly contributing to their proposed roles in carcinogenesis (Id.).

The origin for the dysregulated methylation patterns in cancer are an active area of research. Initially it was suggested that like genetic mutations, de novo hypermethylation events are stochastically generated, and that the final patterns observed are a result of growth advantage and selection. However, several observations made in recent years should be noted: First, hypermethylation events are already apparent at precancerous stages, such as in benign tumors and in tumor-predisposing inflammatory lesions. Second, there seem to be defined sets of hypermethylated genes in certain tumors. These differential methylation signatures, or "methylomes," may even differentiate between tumors of the same type, as was recently shown for the CpG island methylator phenotype (CIMP) in colon cancer. Third, although many hypermethylated genes have tumor-suppressing functions, not all are involved in cell growth or tumorigenesis (Id.).

One object of the present invention relates to methods for treating an individual with, or at risk for, cancer by using an agent that modulates the hydroxylase activity of the catalytically active TET family enzymes, functional TET family derivatives, or TET catalytically active fragments.

Accordingly, in one aspect the invention provides a method for treating an individual with or at risk for cancer using an effective amount of one or more modulators of the activity of the TET family of proteins. In one embodiment of the aspect, the method includes selecting a treatment for a patient affected by or at risk for developing cancer by determining the presence or absence of hypermethylated CpG island promoters of tumor suppressor genes, wherein if hypermethylation of tumor suppressor genes is detected, one administers to the individual an effective amount of a tumor suppressor activity reactivating catalytically active TET family enzyme, a functional TET family derivative, a TET catalytically active fragment therein, an activating modulator of TET family activity, or any combination thereof.

In one embodiment, the treatment involves the administration of a TET family inhibiting modulator. In particular, the TET family inhibiting modulator is specific to TET1, TET2, TET3, or CXXC4. In one embodiment of the aspect, the cancer being treated is a leukemia. In one embodiment, the leukemia is acute myeloid leukemia caused by the t(10:11)(q22:q23) Mixed Lineage Leukemia translocation of TET1. In one embodiment, the TET family inhibiting modulator is specific to TET2.

The present invention also provides, in another aspect, improved methods for the diagnosis of disease conditions by creating methylome or hydroxymethylome signatures for stratifying subjects at risk for a disease condition, and for directing therapy and monitoring the response to the therapy in subjects. In some embodiments of the aspect, methods to detect methylcytosine and 5-hydroxymethylcytosine in DNA from a subject diagnosed with or at risk for a disease condition are provided, wherein enzymes encoded by bacteriophages of the "T even" family are contacted with the DNA and the global level of methylation and hydroxymethylation determined. In one embodiment, the DNA is obtained from a diseased tissue sample of the subject. In one embodiment, the enzyme provided is an alpha-glucosyltransferase. In one embodiment, the alpha-glucosyltransferase provided is encoded by a bacteriophage selected from the group consisting of T2, T4, and T6 bacteriophages. In one embodiment, the enzyme is a beta-glucosyltransferase. In one embodiment, the beta-glucosyltransferase is encoded by a bacteriophage selected from T4 bacteriophages. In some embodiments, enzymes encoded by bacteriophages of the "T even" family add two glucose molecules linked in a beta-1-6 configuration to hydroxymethylcytosine to form gentibiose-containing-hydroxymethylcytosine. In one embodiment, the enzyme is a beta-glucosyl-alpha-glucosyl-transferase. In one embodiment, the beta-glucosyl-alpha-glucosyl-transferase is encoded by a bacteriophage selected from the group consisting of T2 and T6 bacteriophages. In one embodiment, the disease condition is a myeloproliferative disorder, myelodysplatic disorders, acute myelogenous leukemia, or other malignant and pre-malignant conditions.

In some embodiments of the aspect, methods to detect global levels of methylcytosine and 5-hydroxymethylcytosine in DNA from a subject with familial predisposition for a disease condition are provided, wherein enzymes encoded by bacteriophages of the "T even" family are contacted with the DNA. In one embodiment, the enzyme provided is an alpha-glucosyltransferase. In one embodiment, the alpha-glucosyltransferase provided is encoded by a bacteriophage selected from the group consisting of T2, T4, and T6 bacteriophages. In one embodiment, the enzyme is a beta-glucosyltransferase. In one embodiment, the beta-glucosyltransferase is encoded by a bacteriophage selected from T4 bacteriophages. In some embodiments, enzymes encoded by bacteriophages of the "T even" family add two glucose molecules linked in a beta-1-6 configuration to hydroxymethylcytosine to form gentibiose-containing-hydroxymethylcytosine. In one embodiment, the enzyme is a beta-glucosyl-alpha-glucosyl-transferase. In one embodiment, the beta-glucosyl-alpha-glucosyl-transferase is encoded by a bacteriophage selected from the group consisting of T2 and T6 bacteriophages. In one embodiment, the disease condition is a myeloproliferative disorder, myelodysplatic disorders, acute myelogenous leukemia, or other malignant and pre-malignant conditions. In one embodiment, the DNA is isolated from the CD34+ hematopoietic cells of a family member of a subject with a disease condition, to determine if there is a familial predisposition.

Also encompassed in the methods of the present invention are methods for screening for and identifying drugs that cause alterations in the methylcytosine and 5-hydroxymethylcytosine residues in genomic DNA using the compositions and methods described herein.

As defined herein, the phrase "genetic predisposition" refers to the genetic makeup of a subject or cell, that makes or predetermines the subject's or cells' likelihood of being susceptible to a particular disease, disorder or malignancy, or likelihood of responding to a treatment for a disease disorder or malignancy. Accordingly, as defined herein, an individual having a "familial predisposition" refers to the subject or individual having one or more family members that have had, have, or have an increased likelihood of developing, a particular disease, disorder or malignancy, such as, cancer. The familial predisposition may be due to one or more underlying genetic mutations, or can be caused by shared environmental risk factors in the family members, or be a combination thereof.

As defined herein, a "cancer", "malignancy", or "malignant condition" refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a patient, or may be a non-tumorigenic cancer cell, such as a leukemia cell. In some circumstances, cancer cells will be in the form of a tumor; such cells may exist locally, or circulate in the blood stream as independent cells, for example, leukemic cells. Examples of cancers, wherein methylation status plays a role, include, but are not limited to, breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

"Leukemia" is a cancer of the blood or bone marrow and is characterized by an abnormal proliferation of white blood cells i.e., leukocytes. There are four major classifications of leukemia comprising of Acute lymphoblastic leukemia (ALL), Chronic lymphocytic leukemia (CLL), Acute myelogenous leukemia or acute myeloid leukemia (AML), and Chronic myelogenous leukemia (CML).

"Acute myeloid leukemia" (AML), also known as acute myelogenous leukemia, is a cancer of the myeloid line of white blood cells, characterized by the rapid proliferation of abnormal myeloid cells that accumulate in the bone marrow and interfere with the production of normal blood cells. AML is the most common acute leukemia affecting adults, and its incidence increases with age. The World Health Organization (WHO) classification of subtypes of acute myeloid leukemia comprises of: a) AML with characteristic genetic abnormalities, including, but not limited to AML with translocations between chromosome 10 and 11 [t(10, 11)], chromosome 8 and 21 [t(8;21)], chromosome 15 and 17 [t(15;17)], and inversions in chromosome 16 [inv(16)]; b) AML with multilineage dysplasia, which includes patients who have had a prior myelodysplastic syndrome (MDS) or myeloproliferative disease that transforms into AML; c) AML and myelodysplastic syndrome (MDS), therapy-related, which category includes patients who have had prior chemotherapy and/or radiation and subsequently develop AML or MDS. These leukemias may also be characterized by specific chromosomal abnormalities; d) AML not otherwise categorized, which includes subtypes of AML that do not fall into the above categories; and e) Acute leukemias of ambiguous lineage, which occur when the leukemic cells can not be classified as either myeloid or lymphoid cells, or where both types of cells are present. Acute myeloid leukemias can further be classified or diagnosed as: minimally differentiated acute myeloblastic leukemia (M0), acute myeloblastic leukemia, without maturation (M1), acute myeloblastic leukemia, with granulocytic maturation (M2) (caused by t(8;21)(q22;q22), t(6;9)), promyelocytic, or acute promyelocytic leukemia (APL) (M3), (caused by t(15;17)), acute myelomonocytic leukemia (M4), (caused by inv(16) (p13q22), del(16q)), myelomonocytic together with bone marrow eosinophilia (M4eo), (caused by inv(16), t(16;16)), acute monoblastic leukemia (M5a) or acute monocytic leukemia (M5b) (caused by del (11q), t(9;11), t(11;19)), acute erythroid leukemias, including erythroleukemia (M6a) and very rare pure erythroid leukemia (M6b), acute megakaryoblastic leukemia (M7), (caused by t(1;22)), and acute basophilic leukemia (M8).

In connection with the administration of a TET family modulator, a drug which is "effective against" a cancer indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

In connection with determining or modifying a treatment to be administered to an individual having a cancer, or having familial predisposition to a cancer, such as a leukemia, the treatment can include, for example, imatinib (Gleevac), all-trans-retinoic acid, a monoclonal antibody treatment (gemtuzumab ozogamicin), chemotherapy (for example, chlorambucil, prednisone, prednisolone, vincristine, cytarabine, clofarabine, farnesyl transferase inhibitors, decitabine, inhibitors of MDR1, rituximab, interferon-α, anthracycline drugs (such as daunorubicin or idarubicin), L-asparaginase, doxorubicin, cyclophosphamide, doxorubicin, bleomycin, fludarabine, etoposide, pentostatin, or cladribine), bone marrow transplant, stem cell transplant, radiation therapy, anti-metabolite drugs (methotrexate and 6-mercaptopurine), or any combination thereof. The modification of the treatment based upon, for example, determination of the hydroxymethylation status of a cell, or TET family activity, includes, but is not limited, to changing the dosage, frequency, duration, or type of treatment(s) being administered to a patient in need thereof.

A "TET family modulator" is a molecule that acts to either increase or reduce the production and/or accumulation of TET family gene product activity in a cell. The molecule can thus either enhance or prevent the accumulation at any step of the pathway leading from the TET family gene to TET family enzymatic activity, e.g. transcription, mRNA levels, translation, or the enzyme itself. As used interchangeably herein, an "inhibitor", "inhibiting modulator" or "inhibitory modulator" of the TET family is a molecule that acts to reduce the production and/or accumulation of TET family gene product activity in a cell. The inhibitor, inhibiting modulator or inhibitory modulator molecule can thus prevent the accumulation at any step of the pathway leading from the TET family gene to the TET family enzymatic activity e.g. preventing transcription, reducing mRNA levels, preventing translation, or inhibiting the enzyme itself. Similarly, as used interchangeably herein, an "activator" or "activating modulator" of the TET family is a molecule that acts to increase the production and/or accumulation of TET family gene product activity in a cell. The TET family activator or activating modulator molecule can thus enhance the accumulation at any step of the pathway leading from the TET family gene to TET family enzymatic activity e g enhancing transcription, increasing mRNA levels, enhancing translation, or activating the enzyme itself.

In one embodiment of the present aspect, the TET family targeting treatment is a TET family inhibitor. In a preferred embodiment, the TET targeting treatment is specific for the inhibition of TET1, TET2, TET3, or CXXC4. For example, a small molecule inhibitor, a competitive inhibitor, an antibody or antigen-binding fragment thereof, or a nucleic acid that inhibits TET1, TET2, TET3, or CXXC4, as encompassed under "Definitions".

In one embodiment of the present aspect, the TET family targeting treatment is a TET family activator. Alternatively and preferably, the TET targeting treatment is specific for the activation of TET1, TET2, TET3, or CXXC4. For example, a small molecule activator, an agonist, an antibody or antigen-binding fragment thereof, or a nucleic acid that activates TET1, TET2, TET3, or CXXC4, as defined under "Definitions".

Also encompassed in the methods of the present aspect are methods to screen for the identification of a TET family modulator for use in anti-cancer therapies. The method comprises a) providing a cell comprising a TET family enzyme or recombinant TET family enzyme thereof; b) contacting said cell with a test molecule; c) comparing the relative levels of 5-hydroxymethylated cytosine in cells expressing the TET family enzyme or recombinant TET family enzyme thereof in the presence of the test molecule with the level of 5-hydroxymethylated cytosine expressed in a control sample in the absence of the test molecule; and d) determining whether or not the test molecule increases or decreases the level of 5-hydroxymethylated cytosine, wherein a statistically significant decrease in the level of 5-hydroxymethylated cytosine indicates the molecule is an inhibitor and a statistically significant increase in the level of 5-hydroxymethylated cytosine indicates the molecule is an activator.

In another embodiment of the aspect, a method for high-throughput screening for anti-cancer agents is provided. The method comprises screening for and identifying TET family modulators. For example, providing a combinatorial library containing a large number of potential therapeutic compounds (potential modulator compounds). Such "combinatorial chemical libraries" are then screened in one or more assays to identify those library members (particular chemical species or subclasses) that display a desired characteristic activity (e.g., inhibition of TET family mediated 5-methylcytosine to 5-hydroxymethylcytosine conversion or activation of TET family mediated 5-methylcytosine to 5-hydroxymethylcytosine conversion). The compounds thus identified can serve as conventional "lead compounds" or "candidate therapeutic agents," and can be derivatized for further testing to identify additional TET family modulators.

Once identified, such compounds are administered to patients in need of TET family targeted treatment, for example, patients affected with, or at risk for, developing cancer or cancer metastasis. The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered parenterally by injection or by gradual infusion over time and can be delivered by peristaltic means. Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics. For topical administration, the pharmaceutical composition (e.g., inhibitor of TET family activity) is formulated into ointments, salves, gels, or creams, as is generally known in the art. The therapeutic compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Any formulation or drug delivery system containing the active ingredients required for TET family modulation, suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Definitions

As used herein, the term "drug" or "compound" refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including, without limitation, proteins, oligonucleotides, ribozymes, DNAzymes, glycoproteins, siRNAs, lipoproteins, aptamers, and modifications and combinations thereof.

The terms "effective" and "effectiveness", as used herein, includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

As used herein, the phrase "therapeutically effective amount" or "effective amount" are used interchangeably and refer to the amount of an agent that is effective, at dosages and for periods of time necessary to achieve the desired therapeutic result, e.g., for an increase in hydroxymethylation for a TET family activator, or a decrease or prevention of hydroxymethylation for a TET family inhibitor. An effective amount for treating such a disease related to defects in methylation is an amount sufficient to result in a reduction or amelioration of the symptoms of the disorder, disease, or medical condition. By way of example only, an effective amount of a TET family inhibitor for treatment of a disease characterized by an increase in hydroxymethylation will cause a decrease in hydroxymethylation. An effective amount for treating such an hydroxymethylation-related disease (i.e. one characterized by an increase in hydroxymethylation) is an amount sufficient to result in a reduction or amelioration of the symptoms of the disorder, disease, or medical condition. The effective amount of a given therapeutic agent (i.e. TET family inhibitor or TET family activator,) will vary with factors such as the nature of the agent, the route of administration, the size and species of the animal, such as a human, to receive the therapeutic agent, and the purpose of the administration.

A therapeutically effective amount of the agents, factors, or inhibitors described herein, or functional derivatives thereof, can vary according to factors such as disease state, age, sex, and weight of the subject, and the ability of the therapeutic compound to elicit a desired response in the individual or subject. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. Efficacy of treatment can be judged by an ordinarily skilled practitioner. Efficacy can be assessed in animal models of cancer and tumor, for example treatment of a rodent with an experimental cancer, and any treatment or administration of an TET family inhibitor in a composition or formulation that leads to a decrease of at least one symptom of the cancer, for example a reduction in the size of the tumor.

As used herein, the phrase "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. A pharmaceutically acceptable carrier typically will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

The terms "subject" and "individual" are used interchangeably herein, and refer to an animal, for example, a human from whom cells can be obtained (i.e. differentiated cells can be obtained which are reprogrammed) and/or to whom treatment, including prophylactic treatment, with the reprogrammed cells (or their differentiated progeny) as described herein, is provided. For treatment of conditions or disease states which are specific for a specific animal such as a human subject, the term subject refers to that specific animal. The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

As used herein the terms "sample" or "biological sample" means any sample, including but not limited to cells, organisms, lysed cells, cellular extracts, nuclear extracts, or components of cells or organisms, extracellular fluid, and media in which cells are cultured.

The term "in vitro" as used herein refers to refers to the technique of performing a given procedure in a controlled environment outside of a living organism. The term "in vivo", as used herein refers to experimentation using a whole, living organism as opposed to a partial or dead organism, or in an in vitro controlled environment. "Ex vivo" as the term is used herein, means that which takes place outside an organism. The term ex vivo is often differentiated from the term in vitro in that the tissue or cells need not be in culture; these two terms are not necessarily synonymous.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art. In the context of cell ontogeny, the adjective "differentiated", or "differentiating" is a relative term meaning a "differentiated cell" is a cell that has progressed further down the developmental pathway than the cell it is being compared with. Thus, a reprogrammed cell, as this term is defined herein can differentiate to lineage-restricted precursor cells (such as a mesodermal stem cell), which in turn can differentiate into other types of precursor cells further down the pathway (such as an tissue specific precursor, for example, a cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like. The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue.

The term "progenitor cell" is used herein to refer to cells that have a cellular phenotype that is more primitive (i.e., is at an earlier step along a developmental pathway or progression than is a fully differentiated cell) relative to a cell which it can give rise to by differentiation. Typically, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "differentiated cell" refers to a primary cell that is not pluripotent as that term is defined herein. It should be noted that placing many primary cells in culture can lead to some loss of fully differentiated characteristics. However, simply culturing such cells does not, on its own, render them pluripotent. The transition to pluripotency requires a reprogramming stimulus beyond the stimuli that lead to partial loss of differentiated character in culture. Reprogrammed pluripotent cells also have the characteristic of the capacity of extended passaging without loss of growth potential, relative to primary cell parents, which generally have capacity for only a limited number of divisions in culture. Stated another way, the term "differentiated cell" refers to a cell of a more specialized cell type derived from a cell of a less specialized cell type (e.g., a stem cell such as an induced pluripotent stem cell) in a cellular differentiation process.

As used herein, the term "somatic cell" refers to a cell forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell can be performed both in vivo and in vitro (where in vivo is practiced when an differentiated cell is present within a subject, and where in vitro is practiced using isolated differentiated cell maintained in culture). In some embodiments, where a differentiated cell or population of differentiated cells are cultured in vitro, the differentiated cell can be cultured in an organotypic slice culture, such as described in, e.g., meneghel-Rozzo et al., (2004), Cell Tissue Res, 316(3); 295-303. As used herein, the term "adult cell" refers to a cell found throughout the body after embryonic development.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be, for example, a nucleic acid encoding a protein of interest, a polynucleotide, an oligonucleotide, a nucleic acid analogue, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example, but not limited to, RNAi, shRNAi, siRNA, micro RNAi (mRNAi), antisense oligonucleotides etc.

As used herein, the term "DNA" is defined as deoxyribonucleic acid. The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term "variant" as used herein refers to a polypeptide or nucleic acid that is "substantially similar" to a wild-type polypeptide or polynucleic acid. A molecule is said to be "substantially similar" to another molecule if both molecules have substantially similar structures (i.e., they are at least 50% similar in amino acid sequence as determined by BLASTp alignment set at default parameters) and are substantially similar in at least one relevant function (e.g., effect on cell migration). A variant differs from the naturally occurring polypeptide or nucleic acid by one or more amino acid or nucleic acid deletions, additions, substitutions or side-chain modifications, yet retains one or more specific functions or biological activities of the naturally occurring molecule.

Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality or size. Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide). Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, including but not limited to insertion of ornithine which does not normally occur in human proteins.

The term "derivative" as used herein refers to peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

Recombinant Proteins

Typically, the proteins or polypeptides of the present invention are secreted into the growth medium of recombinant *E. coli*. To isolate the desired protein, the *E. coli* host cell carrying a recombinant plasmid is propagated, homogenized, and the homogenate is centrifuged to remove bacterial debris. The supernatant is then subjected to sequential ammonium sulfate precipitation. The fraction containing the desired protein of the present invention is subjected to gel filtration in an appropriately sized dextran or polyacrylamide column to separate the proteins. If necessary, the protein fraction may be further purified by HPLC. Alternative methods may be used as suitable. Mutations or variants of the above polypeptides or proteins are encompassed by the present invention. Variants may be modified by, for example, the deletion or addition of amino acids that have minimal influence on the properties, secondary structure, and hydropathic nature of the desired polypeptide. For example, a polypeptide may be conjugated to a signal (or leader)

sequence at the N-terminal end of the protein which co-translationally or post-translationally directs transfer of the protein. The polypeptide may also be conjugated to a linker or other sequence for ease of synthesis, purification, or identification of the polypeptide.

Fragments of the above proteins are also encompassed by the present invention. Suitable fragments can be produced by several means. In the first, subclones of the gene encoding the desired protein of the present invention are produced by conventional molecular genetic manipulation by subcloning gene fragments. The subclones then are expressed in vitro or in vivo in bacterial cells to yield a smaller protein or peptide. In another approach, based on knowledge of the primary structure of the proteins of the present invention, fragments of the genes of the present invention may be synthesized by using the polymerase chain reaction ("PCR") technique together with specific sets of primers chosen to represent particular portions of the protein. These then would be cloned into an appropriate vector for increased expression of an accessory peptide or protein. Chemical synthesis can also be used to make suitable fragments. Such a synthesis is carried out using known amino acid sequences for the proteins of the present invention. These fragments can then be separated by conventional procedures (e.g., chromatography, SDS-PAGE) and used in the methods of the present invention.

The nucleic acid molecule encoding a catalytically active TET family enzyme, a functional TET family derivative, or a TET catalytically active fragment thereof of the present invention can be introduced into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5' to 3') orientation and correct reading frame. Alternatively, the nucleic acid may be inserted in the "anti-sense" orientation, i.e, in a 3' to 5' prime direction. The vector contains the necessary elements for the transcription and translation of the inserted protein-coding sequences.

Recombinant genes may also be introduced into viruses, including vaccinia virus, adenovirus, and retroviruses, including lentivirus. Recombinant viruses can be generated by transfection of plasmids into cells infected with virus. Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," Gene Expression Technology Vol. 185 (1990), and any derivatives thereof.

Recombinant molecules can be introduced into cells via transformation, particularly transduction, conjugation, mobilization, or electroporation. The DNA sequences are cloned into the vector using standard cloning procedures in the art, as described by Sambrook et al., Molecular Cloning: A Laboratory Manual, Cold Springs Laboratory, Cold Springs Harbor, N.Y. (1989), which is hereby incorporated by reference in its entirety. A variety of host-vector systems may be utilized to express the protein-encoding sequence of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

The expression elements of these vectors vary in their strength and specificities. Depending upon the host-vector system utilized, any one of a number of suitable transcription and translation elements can be used. Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells. Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, Methods in Enzymology, 68:473 (1979), which is hereby incorporated by reference in its entirety. Promoters vary in their "strength" (i.e., their ability to promote transcription). For the purposes of expressing a cloned gene, it is desirable to use strong promoters in order to obtain a high level of transcription and, hence, expression of the gene.

Depending upon the host cell system utilized, any one of a number of suitable promoters may be used. For instance, when cloning in *E. coli*, its bacteriophages, or plasmids, promoters such as the T7 phage promoter, lac promoter, trp promoter, rec A promoter, ribosomal RNA promoter, the PR and PL promoters of coliphage lambda and others, including but not limited, to lac UV5, omp F, bla, lpp, and the like, may be used to direct high levels of transcription of adjacent DNA segments. Additionally, a hybrid trp-lac UV5 (tac) promoter or other *E. coli* promoters produced by recombinant DNA or other synthetic DNA techniques may be used to provide for transcription of the inserted gene. Bacterial host cell strains and expression vectors may be chosen which inhibit the action of the promoter unless specifically induced. In certain operons, the addition of specific inducers is necessary for efficient transcription of the inserted DNA.

For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used. Depending on the vector system and host utilized, any number of suitable transcription and/or translation elements, including constitutive, inducible, and repressible promoters, as well as minimal 5' promoter elements may be used. The nucleic acid molecule(s) of the present invention, a promoter molecule of choice, a suitable 3' regulatory region, and if desired, a reporter gene, are incorporated into a vector-expression system of choice to prepare the nucleic acid construct of present invention using standard cloning procedures known in the art, such as described by Sambrook et al., Molecular Cloning: A Laboratory Manual, Third Edition, Cold Spring Harbor: Cold Spring Harbor Laboratory Press, New York (2001), which is hereby incorporated by reference in its entirety.

In one aspect of the present invention, a nucleic acid molecule encoding a protein of choice is inserted into a vector in the sense (i.e 5' to 3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct of the present invention. Once the isolated nucleic acid molecule encoding, for example, the catalytically active TET family protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., Molecular Cloning: A Laboratory Manual, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Accordingly, another aspect of the present invention relates to a method of making a recombinant cell. Essentially, this method is carried out by transforming a host cell with a nucleic acid construct of the present invention under conditions effective to yield transcription of the DNA molecule in the host cell. In one embodiment, a nucleic acid construct containing the nucleic acid molecule(s) of the present invention is stably inserted into the genome of the recombinant host cell as a result of the transformation. Transient expression in protoplasts allows quantitative studies of gene expression since the population of cells is very high (on the order of $10^6$). To deliver DNA inside protoplasts, several methodologies have been proposed, but the most common are electroporation (Neumann et al., "Gene Transfer into Mouse Lyoma Cells by Electroporation in High Electric Fields," EMBO J. 1: 841-45 (1982); Wong et al., "Electric Field Mediated Gene Transfer," Biochem Biophys Res Commun 30; 107(2):584-7 (1982); Potter et al, "Enhancer-Dependent Expression of Human Kappa Immunoglobulin Genes Introduced into Mouse pre-B Lymphocytes by Electroporation," Proc. Natl. Acad. Sci. USA 81: 7161-65 (1984), and polyethylene glycol (PEG) mediated DNA uptake, Sambrook et al., Molecular Cloning: A Laboratory Manual, Chap. 16, Second Edition, Cold Springs Laboratory, Cold Springs Harbor, N.Y. (1989). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene. Fraley, et al., Proc. Natl. Acad. Sci. USA, 79:1859-63 (1982).

Stable transformants are preferable for the methods of the present invention, using variations of the methods above as described in Sambrook et al., Molecular Cloning: A Laboratory Manual, Chap. 16, Second Edition, Cold Springs Laboratory, Cold Springs Harbor, N.Y. (1989). Typically, an antibiotic or other compound useful for selective growth of the transformed cells only is added as a supplement to the media. The compound to be used will be dictated by the selectable marker element present in the plasmid with which the host cell was transformed. Suitable selective marker genes are those which confer resistance to, e.g., gentamycin, G418, hygromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually. An example of a marker suitable for the present invention is the green fluorescent protein (GFP) gene. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (Prasher et al., "Primary Structure of the *Aequorea Victoria* Green-Fluorescent Protein," Gene 111 (2):229-233 (1992); U.S. Pat. No. 5,491,084 to Chalfie et al.). A plasmid encoding the GFP of *Aequorea victoria* is available from the ATCC as Accession No. 75547. Mutated forms of GFP that emit more strongly than the native protein, as well as forms of GFP amenable to stable translation in higher vertebrates, are commercially available from Clontech Laboratories, Inc. (Palo Alto, Calif.) and can be used for the same purpose. The plasmid designated pTa1-

GFPh (ATCC Accession No. 98299) includes a humanized form of GFP. Indeed, any nucleic acid molecule encoding a fluorescent form of GFP can be used in accordance with the subject invention. Standard techniques are then used to place the nucleic acid molecule encoding GFP under the control of the chosen cell specific promoter. The selection marker employed will depend on the target species and/or host or packaging cell lines compatible with a chosen vector.

An "inhibitor" of a TET family enzyme, as the term is used herein, can function in a competitive or non-competitive manner, and can function, in one embodiment, by interfering with the expression of the TET family polypeptides. A TET family inhibitor includes any chemical or biological entity that, upon treatment of a cell, results in inhibition of the biological activity caused by activation of the TET family enzymes in response to cellular signals. Such an inhibitor can act by binding to the Cys-rich and double-stranded β-helix domains of the enzymes and blockade of their enzymatic activity. Alternatively, such an inhibitor can act by causing conformationals shifts within or sterically hindering the enzymes, such that enyzmatic activity is abolished or reduced.

Inhibitors of TET Family Proteins and Activity

A "TET family inhibitor", as used herein, refers to a chemical entity or biological product, or combination of a chemical entity or a biological product. The chemical entity or biological product is preferably, but not necessarily a low molecular weight compound, but can also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. The term "inhibitor" refers to any entity selected from a group comprising; chemicals; small molecules; nucleic acid sequences; nucleic acid analogues; proteins; peptides; aptamers; antibodies; or fragments thereof.

A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

A protein and/or peptide agent can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Inhibitors can be known to have a desired activity and/or property, or can be selected from a library of diverse compounds.

Antibody Inhibitors of TET Family Enzymes: Antibodies that specifically bind TET family enzymes can be used for inhibition in vivo, in vitro, or ex vivo. The TET family inhibitory activity of a given antibody, or, for that matter, any TET family inhibitor, can be assessed using methods known in the art or described herein. An antibody that inhibits TET family enzymes causes a decrease in the conversion of 5-methylcytosine to 5-hydroxymethylcytosine in the DNA of a cell. Specific binding is typically defined as binding that does not recognize other antigens, such as a protein, nucleotide, chemical residue, etc., at a detectable level in an assay used.

Antibody inhibitors of TET family enzymes can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. As used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)].

Nucleic Acid Inhibitors of TET Family Enzymes: A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is a double stranded RNA (dsRNA). In another embodiment, the RNA is a single stranded DNA. This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex,"

or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i. e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the TET1 sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003.

In addition to expression profiling, one may also screen the target sequences for similar sequences in the sequence databases to identify sequences that may have off-target effects. For example, according to Jackson et al. (Id.) 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the, for example, TET1 mRNA.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents, such as RNAi molecules that effectively target mRNA of a TET family enzyme. In some embodiments of the aspects described herein, examples of siRNA and shRNA sequences that can be used to inhibit TET family activity include, but are not limited to: SEQ ID NO: 36, SEQ ID NO: 37, SEQ ID NO: 40, SEQ ID NO: 41, SEQ ID NO: 48, SEQ ID NO: 49, SEQ ID NO: 52, SEQ ID NO: 53, SEQ ID NO: 70, SEQ ID NO:

74, SEQ ID NO: 75, SEQ ID NO: 78, SEQ ID NO: 79, SEQ ID NO: 82, SEQ ID NO: 83, SEQ ID NO: 86, SEQ ID NO: 98, and SEQ ID NO: 92.

siRNAs useful for targeting expression of a TET family enzyme can be readily designed and tested. Chalk et al. (Nucl. Acids Res. 33: D131-D134 (2005)) describe a database of siRNA sequences and a predictor of siRNA sequences. Linked to the sequences in the database is information such as siRNA thermodynamic properties and the potential for sequence-specific off-target effects. The database and associated predictive tools enable the user to evaluate an siRNA's potential for inhibition and non-specific effects. The database is available at on the world wide web at siRNA.cgb.ki.se. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al., Nature 411:494-498 (2001); Elbashir, S. M., et al., Genes & Development 15:188-200 (2001); Harborth, J. et al., J. Cell Science 114:4557-4565 (2001); Masters, J. R. et al., Proc. Natl. Acad. Sci., USA 98:8012-8017 (2001); and Tuschl, T. et al., Genes & Development 13:3191-3197 (1999)).

Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al., Genes Dev. 16:948-958 (2002); McManus, M. T. et al., RNA 8:842-850 (2002); Paul, C. P. et al., Nat. Biotechnol. 20:505-508 (2002); Miyagishi, M. et al., Nat. Biotechnol. 20:497-500 (2002); Sui, G. et al., Proc. Natl. Acad. Sci., USA 99:5515-5520 (2002); Brummelkamp, T. et al., Cancer Cell 2:243 (2002); Lee, N. S., et al., Nat. Biotechnol. 20:500-505 (2002); Yu, J. Y., et al., Proc. Natl. Acad. Sci., USA 99:6047-6052 (2002); Zeng, Y., et al., Mol. Cell 9:1327-1333 (2002); Rubinson, D. A., et al., Nat. Genet. 33:401-406 (2003); Stewart, S. A., et al., RNA 9:493-501 (2003)).

In one embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, a TET family enzyme.

In one embodiment, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

The RNA interference agents, e.g., the siRNAs targeting TET family enzyme mRNA, may be delivered singly, or in combination with other RNA interference agents, e.g., siRNAs, such as, for example siRNAs directed to other cellular genes. TET family enzyme siRNAs may also be administered in combination with other pharmaceutical agents which are used to treat or prevent diseases or disorders, as described herein.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; *Sui*, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., a TET family enzyme coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (SEQ ID NO: 102) (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

Delivery of RNA Interfering Agents: In general, any method of delivering a nucleic acid molecule can be adapted for use with an RNAi interference molecule (see e.g., Akhtar S. and Julian R L. (1992) Trends Cell. Biol. 2(5):139-144; WO94/02595, which are incorporated herein by reference in their entirety). Methods of delivering RNA interference agents, e.g., an siRNA, or vectors containing an RNA interference agent, to the target cells, e.g., a cancer cell or other desired target cells, for uptake can include injection of a composition containing the RNA interference agent, e.g., an siRNA, or directly contacting the cell, e.g., a lymphocyte, with a composition comprising an RNA interference agent, e.g., an siRNA.

However, there are factors that are important to consider in order to successfully deliver an RNAi molecule in vivo. For example, one should consider: (1) biological stability of the RNAi molecule, (2) preventing non-specific effects, and (3) accumulation of the RNAi molecule in the target tissue. The non-specific effects of an RNAi molecule can be minimized by local administration by e.g., direct injection into a tumor, cell, target tissue, or topically. Local administration of an RNAi molecule to a treatment site limits the exposure of the e.g., siRNA to systemic tissues and permits a lower dose of the RNAi molecule to be administered. Several studies have shown successful knockdown of gene products when an RNAi molecule is administered locally. For example, intraocular delivery of a VEGF siRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of an siRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55).

For administering an RNAi molecule systemically for the treatment of a disease, the RNAi molecule can be either be modified or alternatively delivered using a drug delivery system—both methods act to prevent the rapid degradation of the RNAi molecule by endo- and exo-nucleases in vivo. Modification of the RNAi molecule or the pharmaceutical carrier can also permit targeting of the RNAi molecule to the target tissue and avoid undesirable off-target effects.

RNA interference molecules can be modified by chemical conjugation to lipophilic groups such as cholesterol to enhance cellular uptake and prevent degradation. For example, an siRNA directed against ApoB conjugated to a lipophilic cholesterol moiety was injected systemically into mice and resulted in knockdown of apoB mRNA in both the liver and jejunum (Soutschek, J., et al (2004) Nature 432: 173-178). Conjugation of an RNAi molecule to an aptamer has been shown to inhibit tumor growth and mediate tumor regression in a mouse model of prostate cancer (McNamara, J O., et al (2006) Nat. Biotechnol. 24:1005-1015).

In an alternative embodiment, the RNAi molecules can be delivered using drug delivery systems such as e.g., a nanoparticle, a dendrimer, a polymer, liposomal, or a cationic delivery system. Positively charged cationic delivery systems facilitate binding of an RNA interference molecule (negatively charged) and also enhance interactions at the negatively charged cell membrane to permit efficient uptake of an siRNA by the cell. Cationic lipids, dendrimers, or polymers can either be bound to an RNA interference molecule, or induced to form a vesicle or micelle (see e.g., Kim S H., et al (2008) Journal of Controlled Release 129(2):107-116) that encases an RNAi molecule. The formation of vesicles or micelles further prevents degradation of the RNAi molecule when administered systemically. Methods for making and administering cationic-RNAi complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205).

Some non-limiting examples of drug delivery systems useful for systemic administration of RNAi include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an RNAi molecule forms a complex with cyclodextrin for systemic administration. Methods for administration and pharmaceutical compositions of RNAi molecules and cyclodextrins can be found in U.S. Pat. No. 7,427,605, which is herein incorporated by reference in its entirety. Specific methods for administering an RNAi molecule for the inhibition of angiogenesis can be found in e.g., U.S. Patent Application No. 20080152654.

In other embodiments, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agents may be used simultaneously. In one embodiment, only one siRNA that targets a human TET family enzyme is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., TET1, TET2, TET3, or CXXC4. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

Small Molecule Inhibitors and Activators: As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Antibodies Specific for TET Family Enzymes and Detecting TET Family Activity

Antibodies that can be used according to the methods described herein, for example, for detecting TET family activity, such as hydroxymethylation of cytosine, include complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred.

Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a nucleotide, polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

The term "intrabodies" as used herein, refers to a method wherein to target intracellular endogenous proteins as described in U.S. Pat. No. 6,004,940. Briefly, the method comprises the intracellular expression of an antibody capable of binding to the target. A DNA sequence is delivered to a cell, the DNA sequence contains a sufficient number of nucleotides coding for the portion of an antibody capable of binding to the target operably linked to a promoter that will permit expression of the antibody in the cell(s) of interest. The antibody is then expressed intracellularly and binds to the target, thereby disrupting the target from its normal actions.

The terms "label" or "tag", as used herein, refer to a composition capable of producing a detectable signal indicative of the presence of the target, such as, for example, a 5-hydroxymethylcytosine, in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means. The terms "labeled antibody" or "tagged antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of, for example, 5-hydroxymethylcytosine residues present in a nucleic acid sample correlate to the intensity of the signal emitted from the detectably labeled antibody. In one embodiment, the label is a detectable marker, e.g., incorporation of a radiolabeled amino acid. Various methods of labeling polypeptides and glycoproteins are known in the art and may be used.

Examples of labels or tags for polypeptides include, but are not limited to, the following: radioisotopes or radionuclides (e.g., 3H, 14C, 15N, 35S, 43K, 52Fe, 57Co, 67Cu, 67Ga, 68 Ga, 90Y, 99Tc, 111In, 123I, 125I, 131I, or 132I), fluorescent labels (e.g., FITC, phycoerythrin, rhodamine, lanthanide phosphors), enzymatic labels (e.g., horseradish peroxidase, beta-galactosidase, luciferase, alkaline phosphatase), quantum dots, chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, the label for the antibody is a fluorescent label.

A fluorescent label or tag for labeling the antibody may be Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., non-integrating viral vectors or replication defective retroviruses, lentiviruses, adenoviruses and adeno-associated viruses), which serve equivalent functions. In one embodiment, lentiviruses are used to deliver one or more siRNA molecule of the present invention to a cell.

As used herein, the term "non-integrating viral vector" refers to a viral vector that does not integrate into the host genome; the expression of the gene delivered by the viral vector is temporary. Since there is little to no integration into the host genome, non-integrating viral vectors have the advantage of not producing DNA mutations by inserting at a random point in the genome. For example, a non-integrating viral vector remains extra-chromosomal and does not insert its genes into the host genome, potentially disrupting the expression of endogenous genes. Non-integrating viral vectors can include, but are not limited to, the following: adenovirus, alphavirus, picornavirus, and vaccinia virus. These viral vectors are "non-integrating" viral vectors as the term is used herein, despite the possibility that any of them may, in some rare circumstances, integrate viral nucleic acid into a host cell's genome. What is critical is that the viral vectors used in the methods described herein do not, as a rule or as a primary part of their life cycle under the conditions employed, integrate their nucleic acid into a host cell's genome. It goes without saying that an iPS cell generated by a non-integrating viral vector will not be administered to a subject unless it and its progeny are free from viral remnants.

As used herein, the term "viral remnants" refers to any viral protein or nucleic acid sequence introduced using a viral vector. Generally, integrating viral vectors will incorporate their sequence into the genome; such sequences are referred to herein as a "viral integration remnant". However, the temporary nature of a non-integrating virus means that the expression, and presence of, the virus is temporary and is not passed to daughter cells. Thus, upon passaging of a re-programmed cell the viral remnants of the non-integrating virus are essentially removed.

As used herein, the phrases "free of viral integration remnants" and "substantially free of viral integration remnants" refers to iPS cells that do not have detectable levels of an integrated adenoviral genome or an adenoviral specific protein product (i.e., a product other than the gene of interest), as assayed by PCR or immunoassay. Thus, the iPS cells that are free (or substantially free) of viral remnants have been cultured for a sufficient period of time that transient expression of the adenoviral vector leaves the cells substantially free of viral remnants.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the disclosed invention. Various changes and modifications to the disclosed embodiments, which will be apparent to those of skill in the art, may be made without departing from the spirit and scope of the present invention.

As used herein, the term "comprising" or "comprises" is used in reference to compositions, methods, and respective component(s) thereof, that are essential to the invention, yet open to the inclusion of unspecified elements, whether essential or not.

As used herein, the term "consisting essentially of" refers to those elements required for a given embodiment. The term permits the presence of additional elements that do not materially affect the basic and novel or functional characteristic(s) of that embodiment of the invention.

As used herein, the term "consisting of" refers to compositions, methods, and respective components thereof as described herein, which are exclusive of any element not recited in that description of the embodiment.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

DNA Methylation and Demethylation

DNA methylation and demethylation play a vital role in mammalian development. In mammals, DNA methylation occurs primarily on cytosine in the context of the dinucleotide CpG. DNA methylation is dynamic during early embryogenesis and has a crucial role in parental imprinting, X-inactivation and silencing of endogenous retroviruses. Embryonic development is accompanied by remarkable changes in the methylation status of individual genes, whole chromosomes and, at times, the entire genome (A. Bird, Genes Dev 16: 6-21 (2002); W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006)). There is active genome-wide demethylation of the paternal genome shortly after fertilization (W. Mayer, Nature 403: 501-502 (2000); J. Oswald, Curr Biol 10: 475-478 (2000)). DNA demethylation is also an important mechanism by which germ cells are reprogrammed: the development of primordial germ cells (PGC) during early embryogenesis involves widespread DNA demethylation that may be mediated by an active (i.e. replication-independent) mechanism (A. Bird, Genes Dev 16: 6-21 (2002); W. Reik, Nature 447: 425-432 (2007); K. Hochedlinger, Nature 441: 1061-1067 (2006); M. A. Surani Cell 128: 747-762 (2007); J. B. Gurdon, Annu Rev Cell Dev Biol 22: 1-22 (2006); W. Mayer, Nature 403: 501-502 (2000); J. Oswald, Curr Biol 10: 475-478 (2000)).

De novo DNA methylation and demethylation are also prominent in somatic cells during differentiation, tumorigenesis and aging. Expression of differentiation-specific genes in somatic cells is often accompanied by progressive DNA demethylation (W. Reik, Nature 447: 425-432 (2007); K. Hochedlinger, Nature 441: 1061-1067 (2006); M. A. Surani Cell 128: 747-762 (2007)), but it is not clear whether this process reflects an "active" process (see below) or "passive" demethylation occurring as a result of exclusion of Dnmt1 during replication. In cultured breast cancer cells, gene expression in response to oestrogen has been shown to be accompanied by waves of apparent DNA demethylation and remethylation that are clearly not coupled to replication (H. Cedar, Nature 397: 568-569 (1999); .S. K. Ooi, Cell 133:1145-1148 (2008)). Moreover, tight regulation of DNA demethylation is a likely feature of pluripotent stem cells and progenitor cells in cellular differentiation pathways, that could plausibly contribute to the ability of these cells to self-renew as well as to give rise to daughter differentiating cells. In fact, it has been proposed that pluripotency and the ability to self-renew, two important aspects of stem cell function, involve (or require) proper DNA demethylation (W. Reik, Nature 447: 425-432 (2007); K. Hochedlinger, Nature 441: 1061-1067 (2006); M. A. Surani Cell 128: 747-762 (2007); S. Simonsson, Nat. Cell. Biol. 6: 984-990 (2004); R. Blelloch, Stem Cells 24: 2007-2013 (2006)) and as such, could be improved by controlled expression of enzymes in the DNA demethylation pathway. Furthermore, DNA methylation is highly aberrant in cancer, with global loss of methylation as well as increased methylation leading to silencing of tumor suppressor genes (L. T. Smith, Trends Genet 23: 449-456 (2007); E. N. Gal-Yam, Annu Rev Med 59: 267-280 (2008); M. Esteller Nature Rev Cancer; 8: 286-298 (2007); M. Esteller, N Engl J Med, 358: 1148-1159 (2008)), thus it seems possible that cancer cells aberrantly turn on the DNA demethylation pathway, and that the self-renewing population of cancer stem cells is characterized by high levels of DNA demethylase activity. Overall, therefore, an understanding of the mechanism of active DNA demethylation has broad implications for our understanding of mammalian development, cell differentiation, cancer, stem cell function and aging.

DNA demethylation can proceed by two possible mechanisms—"passive" replication-dependent demethylation and a postulated process of active demethylation for which the molecular basis is still unknown (see below). The passive mechanism is fairly well understood. Normally, cytosine methylation in CpG dinucleotides is symmetric, i.e. occurs on both strands. Hemimethylated CpG's, which are generated during replication of symmetrically-methylated DNA, are recognized by DNA methyltransferase (Dnmt) 1 and are rapidly remethylated. This process is facilitated by interaction of Dnmt1 with proliferating cell nuclear antigen PCNA, which targets Dnmt1 to the replication fork and ensures rapid restoration of the symmetrical pattern of DNA methylation (H. Leonhardt, 1: 865-873, (1992), L. S. Chuang, Science, 277: 1996-2000 (1997).

If Dnmt1 activity is inhibited or Dnmt1 is excluded from the replication fork for any reason, remethylation of the CpG on the opposite strand does not occur and only one of the two daughter strands retains cytosine methylation. "Passive" demethylation is typically observed during cell differentiation, where it accompanies the increased expression of lineage-specific genes (D. U. Lee, Immunity, 16: 649-660 (2002)). Over a prolonged time period (3-7 cycles of DNA replication), cytosine methylation is progressively lost from genes whose expression increases as a result of cell differentiation.

So far, enzymes with the ability to demethylate DNA by an active mechanism have not been identified as molecular entities. There is evidence that active DNA demethylation occurs in certain carefully-controlled circumstances: for instance, the paternal genome is actively demethylated shortly after fertilization, well prior to DNA replication (J. B. Gurdon, Annu Rev Cell Dev Biol 22: 1-22 (2006); W. Mayer, Nature 403: 501-502 (2000)). Early development of primordial germ cells (PGC) also involves widespread demethylation that may be mediated by active DNA demethylation (W. Reik, Nature 447: 425-432 (2007); K. Hochedlinger, Nature 441: 1061-1067 (2006); M. A. Surani Cell 128: 747-762 (2007); P. Hajkova, Nature, 452: 877-881 (2008); N. Geijsen, Nature, 427: 148-154 (2004)). The mechanism of active demethylation is not known, and various disparate mechanisms have been postulated, including direct removal of the methyl group (i.e. direct conversion of 5-methylcytosine (5mC) into cytosine, a thermodynamically unfavourable process that involves cleavage of a carbon-carbon bond and results in release of the methyl moiety), and methylcytosine-specific DNA repair through the activity of methylcytosine-specific or T/G mismatch-specific DNA glycosylases, and methylcytosine-specific DNA deamination or other modification such as glycosylation or hydroxymethylation, also followed by DNA repair (reviewed in (H. Cedar, Nature, 397: 568-569 (1999), S. K. Ooi, Cell 133: 1145-1148 (2008)). However, no proteins (or set of proteins) with these postulated activities have been reliably identified to date.

Identification of a Novel Family of 2OG-Fe(II) Oxygenases with Predicted DNA Modification Activities 5-methylcytosine (5mC) is a minor base in mammalian DNA: It constitutes ~1% of all DNA bases and is found almost exclusively as symmetrical methylation of the dinucleotide CpG (M. Ehrlich and R. Y. Wang, Science 212, 1350 (1981)). The majority of methylated CpG is found in repetitive DNA elements, suggesting that cytosine methylation evolved as a defense against transposons and other parasitic elements (M. G. Goll, et al., Annu. Rev. Biochem. 74, 481 (2005)). Methylation patterns change dynamically in early embryogenesis, when CpG methylation is essential for X-inactivation and asymmetric expression of imprinted genes (W. Reik, Nature 447, 425 (2007)). In somatic cells, promoter methylation often shows a correlation with gene expression: CpG methylation may directly interfere with the binding of certain transcriptional regulators to their cognate DNA sequences or may enable recruitment of methyl-CpG binding proteins that create a repressed chromatin environment (A. Bird, Genes Dev. 16, 6 (2002)). DNA methylation patterns are highly dysregulated in cancer: Changes in methylation status have been postulated to inactivate tumor suppressors and activate oncogenes, thus contributing to tumorigenesis (E. N. Gal-Yam, et al., Annu. Rev. Med. 59, 267 (2008)).

Trypanosomes contain base J (b-D-glucosylhydroxymethyluracil), a modified thymine produced by sequential hydroxylation and glucosylation of the methyl group of thymine (P. Borst and R. Sabatini, Annu. Rev. Microbiol. 62, 235 (2008)). J biosynthesis requires JBP1 and JBP2, enzymes of the 2OG- and Fe(II) dependent oxygenase superfamily predicted to catalyze the first step of J biosynthesis (Z. Yu et al., Nucleic Acids Res. 35, 2107 (2007); L. J. Cliffe et al., Nucleic Acids Res. 37, 1452 (2009)). Like 5-methylcytosine, base J has an association with gene silencing: It is present in silenced copies of the genes encoding the variable surface glycoprotein (VSG) responsible for antigenic variation in the host but is absent from the single expressed copy (P. Borst and R. Sabatini, Annu. Rev. Microbiol. 62, 235 (2008)).

We used bioinformatic analysis to predict that the putative mammalian oncogenes TET1, TET2 and TET3 belong to the class of enzymes containing 2OG-Fe(II) oxygenase domains. To identify homologs of the 2OG-Fe(II) oxygenase domain of JBP1 and JBP2, they were included in a profile of 2OG-Fe(II) oxygenases and a systematic search of the non-redundant database, as well as the protein sequence database of microbes from environmental samples, with their conserved catalytic domain using the PSI-BLAST program, was conducted. A further search of the non-redundant database, with proteins newly detected as a result of this search also included in the profile, and using iterative sequence profile searches, using the predicted oxygenase domains of JBP1 and JBP2, was used to recover homologous regions in three paralogous human proteins (oncogenes) TET1 (CXXC6), TET2, and TET3 (R. B. Lorsbach, Leukemia, 17(3):637-41 (2003)) and their orthologs found throughout metazoa (e<10-5), as well as homologous domains in fungi and algae. In PSI-BLAST searches of these groups of homologous domains consistently recovered each other prior to recovering any other member of the 2OG-Fe (II) oxygenase superfamily, indicating that they formed a distinctive family within it.

To confirm the relationship of the newly-identified proteins (hereinafter referred to as the JBP1/2 family) with classical 2OG-Fe(II) oxygenases, a multiple alignment of their shared conserved domains was prepared.

Secondary structure predictions pointed to a continuous series of β-strands with an N-terminal α-helix, which is typical of the double-stranded β-helix (DSBH) fold of the 2OG-Fe(II) oxygenases (L. Aravind and E. V. Koonin, Genome Biol. 2, RESEARCH 0007 (2001)). A multiple sequence alignment showed that the new TET/JBP family displayed all of the typical features of 2OG-Fe(II) oxygenases, including conservation of residues predicted to be important for coordination of the cofactors Fe(II) and 2OG. The metazoan TET proteins contain a unique conserved cysteine-rich region, contiguous with the N terminus of the DSBH region. Vertebrate TET1 and TET3, and their orthologs from all other animals, also possess a CXXC domain, a binuclear Zn-chelating domain, found in several chromatin-associated proteins, that in certain cases has been shown to discriminate between methylated and unmethylated DNA (M. D. Allen et al., EMBO J. 25, 4503 (2006)).

Thus, we have identified the TET subfamily as having structural features characteristic of enzymes that oxidize 5-me thylpyrimidines. We have shown that the domain structure of the TET subfamily proteins, includes the CXXC domain, the "C" or Cys-rich domain, and the 2OG-Fe(II) oxygenase domain containing a large, low complexity insert.

The conserved features of the TET family of proteins include: (i) the HxD sequence (where x is any amino acid) associated with the extended region after the first strand which chelates Fe(II); (ii) the GG sequence at the beginning of strand 4 which helps in positioning the active site arginine; (iii) the HXs sequence (where s is a small residue) in the penultimate conserved strand, in which the H chelates the Fe(II) and the small residue helps in binding the 2-oxo acid; (iv) the RX5a sequence (where a is an aromatic residue: F,Y,W) in the last conserved strand of the domain. The R in this motif forms a salt bridge with the 2 oxo acid and the aromatic residue helps in position the first metal-chelating histidine. The JBP1/2 family is unified by the presence of a distinctive proline in the N-terminal conserved helix (which might result in a characteristic kink in the first helix of this subfamily) and a conserved aromatic residue (typically part of a sX2F sequence; 's' being a small residue) in the first conserved strand. These observations indicated that TET1, TET2, and TET3, as well as the majority of JBP1/2 homologs from diverse phage, fungal, algal and animal sources, are catalytically-active 2OG-Fe(II) oxygenases. We have shown that when the conserved HxD motif is mutated to YxA catalytic activity is eliminated.

Figure 5:
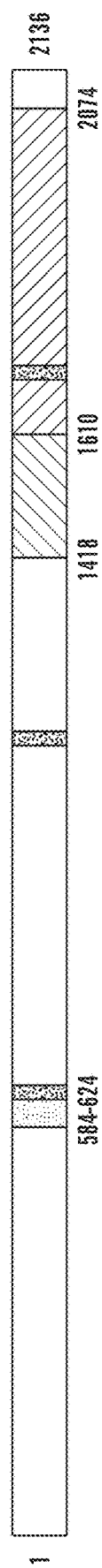
FIG. 5 identifies the TET subfamily as having structural features characteristic of enzymes that oxidize 5-methylpyrimidines.

We have shown that the vertebrate TET1 and TET3 and their orthologs (the TET subfamily) from all other animals show a fusion of the 2OG-Fe(II) oxygenase domain with a N-terminal CXXC domain, as depicted in FIG. 5. The CXXC domain is a binuclear Zn-chelating domain with 8 conserved cysteines and 1 histidine that is found in several chromatin-associated proteins, including the animal DNA methylase DNMT1 and the methylated DNA-binding MBD1. Different versions of this domain have been shown to bind specifically to DNA containing methylated cytosine, either on both strands or just a single strand. This feature, when seen in light of the relationship with JBP1/2 and the phage proteins, suggested to us that the TET subfamily operates on methylcytosine to catalyze oxidation or oxidative removal of the methyl group.

Additionally, the TET subfamily is characterized by a unique conserved domain (here termed the Cys-rich or "C" domain). This domain is contiguous with the N-terminus of the 2OG-Fe(II) oxygenase domain, and contains at least 8 conserved cysteines and 1 histidine that are likely to comprise a binuclear metal cluster. Based on the position of the N-terminal extensions of the AlkB protein, at least a part of the "C" domain could be similarly positioned and form an extended DNA recognition surface. The 2OG-Fe(II) oxygenase domain of the TET family contains a large, low complexity insert predicted to have a predominantly unstructured conformation. It occurs within the DSBH fold exactly in the same position as an unstructured insert seen in the prolyl hydroxylases. Based on the structure of the prolyl hydroxylases, this insert is likely to be located on the exterior surface of the protein, stacked against one face of the DSBH. Its persistence across the entire family despite lack of sequence conservation indicates that it might form a generalized protein-protein interaction surface.

Thus, the total weight of the contextual information available for the JBP1/2 family supports a conserved modification function for the entire family, namely oxidation of 5-methylpyrimidines in DNA or RNA. Without wishing to be limited or bound by a theory, we envision that the activity of this family of enzymes need not be restricted to hydroxymethylation of 5-methylcytosine; certain family members could act as dioxygenases for other pyrimidines, either free, in small nucleic acids such as microRNAs, in DNA or in RNA; or could mediate further oxidation steps beyond hydroxymethylation, for instance to an aldehyde or an acid.

Experimental Analysis of the TET Subfamily: Cells Expressing TET1 Show Decreased Staining for 5-Methylcytosine To test the computational predictions for the human TET subfamily, all three human TET proteins were subcloned into mammalian expression vectors with tandem FLAG and HA tags. Importantly, TET1/CXXC6 is known to be associated with the development of acute myeloid leukemia in the context of t(10;11)(q22;23) translocations, which result in the expression of TET1:MLL fusion proteins that maintain the predicted catalytic domain of TET1 while losing the SET methyltransferase domain of MLL (R. B. Lorsbach, Leukemia, 17(3):637-41 (2003); R. Ono, Cancer Res 62: 4075-4080 (2002)).

To examine the effect of TET1 on overall DNA methylation levels, FLAG- and HA-tagged full-length TET1 or its C-terminal Cys-rich+DSBH domains (hereafter referred to as the C+D domain) was expressed in human embryonic kidney (HEK) 293 cells. Two days later, we stained the cells for 5-methylcytosine content using a 5-methylcytosine-specific antibody and for TET1 expression using an antibody to the HA epitope tag. We showed that mock-transfected cells showed substantial variation in 5-methylcytosine staining intensity (FIG. 6), either because 5-methylcytosine levels vary from cell to cell or because the accessibility of 5-methylcytosine to the antibody differs among cells because of technical considerations (e.g., incomplete denaturation of DNA).

Figure 6:
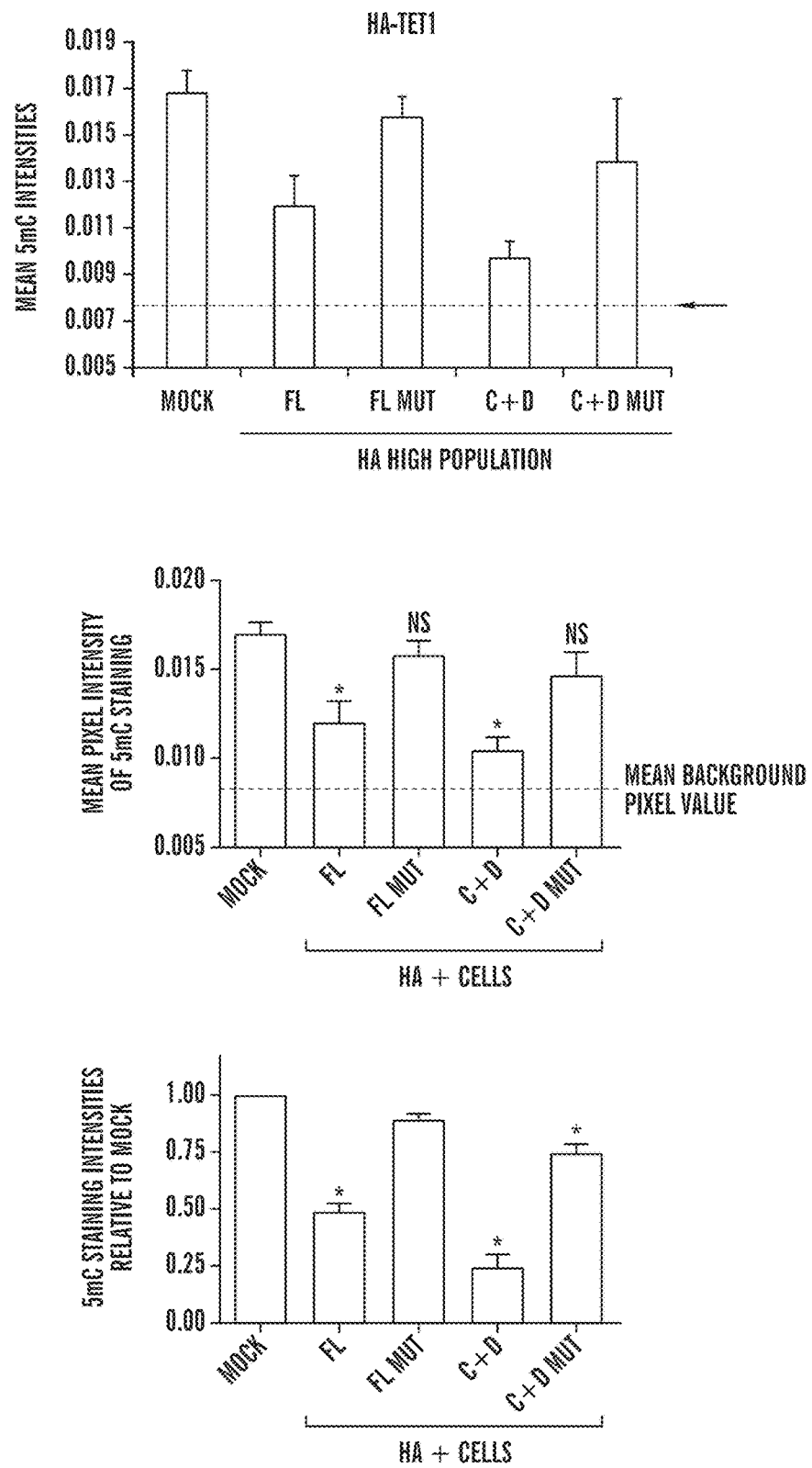
FIG. 6 demonstrates that overexpression of catalytically active TET subfamily proteins leads to decreased staining with a monoclonal antibody directed against 5-methylcytosine.
Figure 7A:
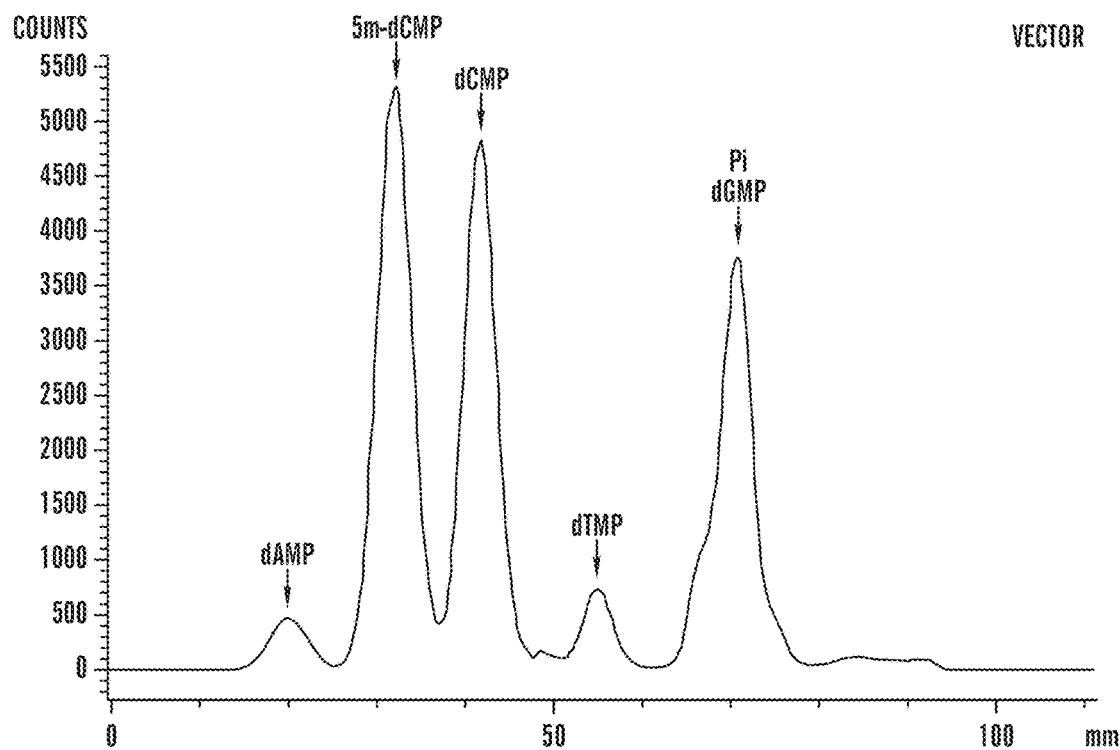
FIGS. 7A-E demonstrate that TET1 expression leads to the generation of a novel nucleotide.
Figure 7B:
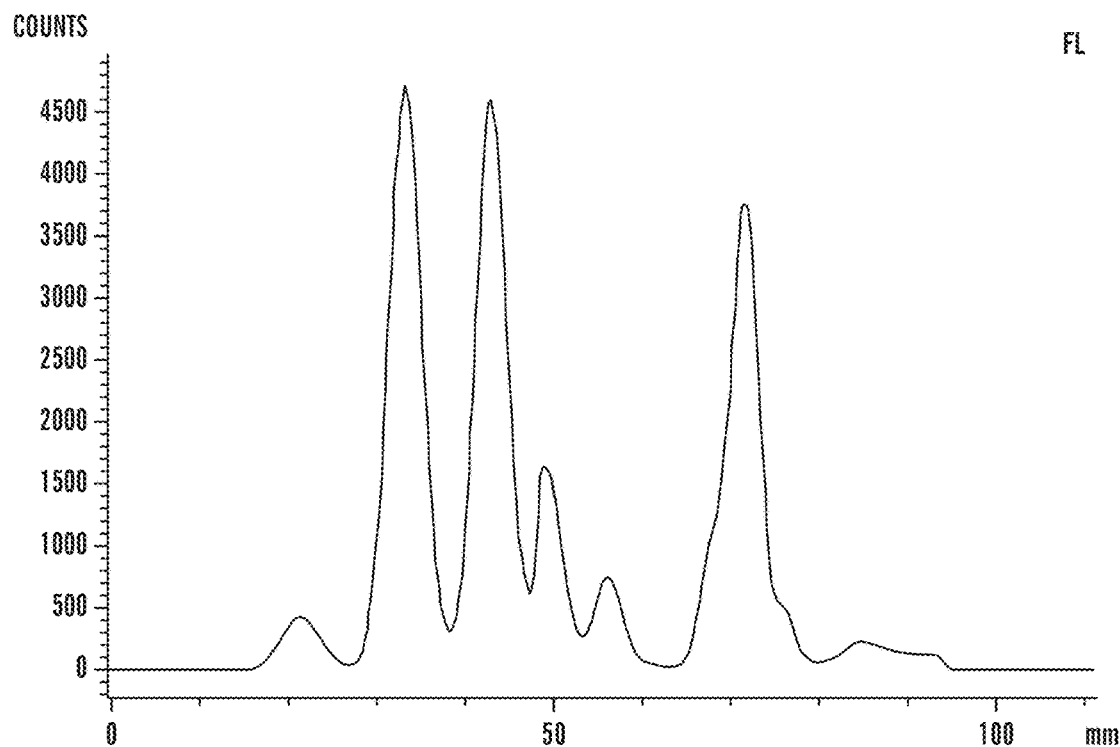
Figure 7C:
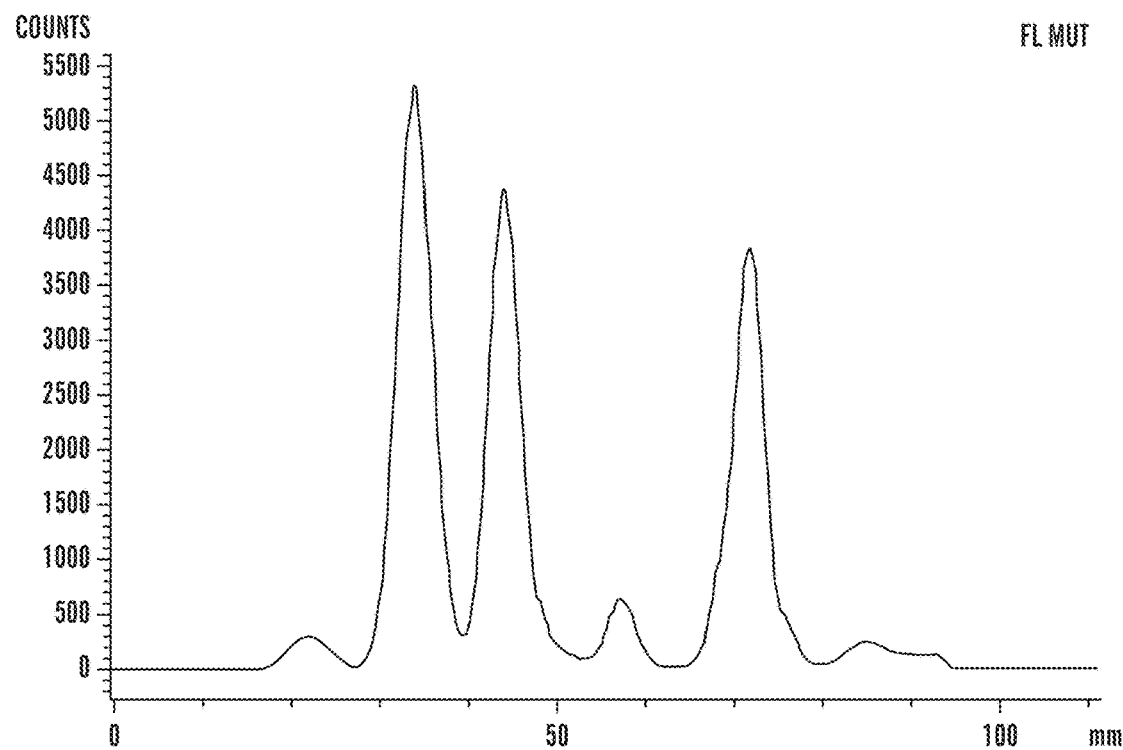
Figure 7D:
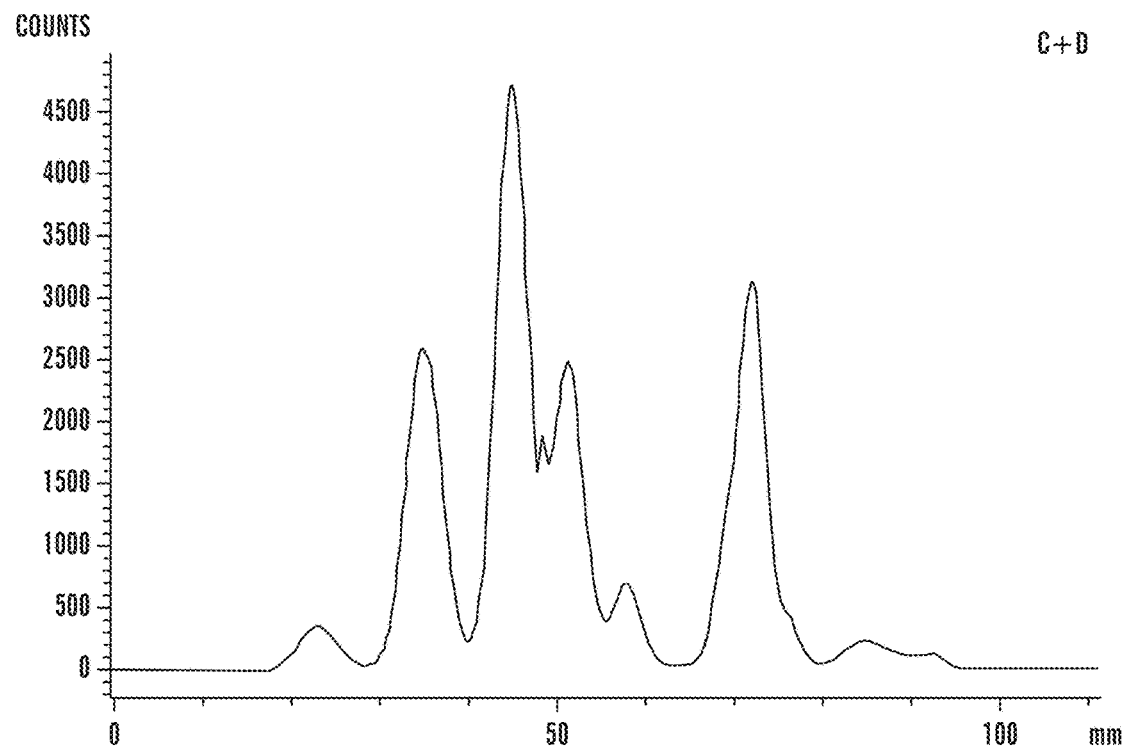
Figure 7E:
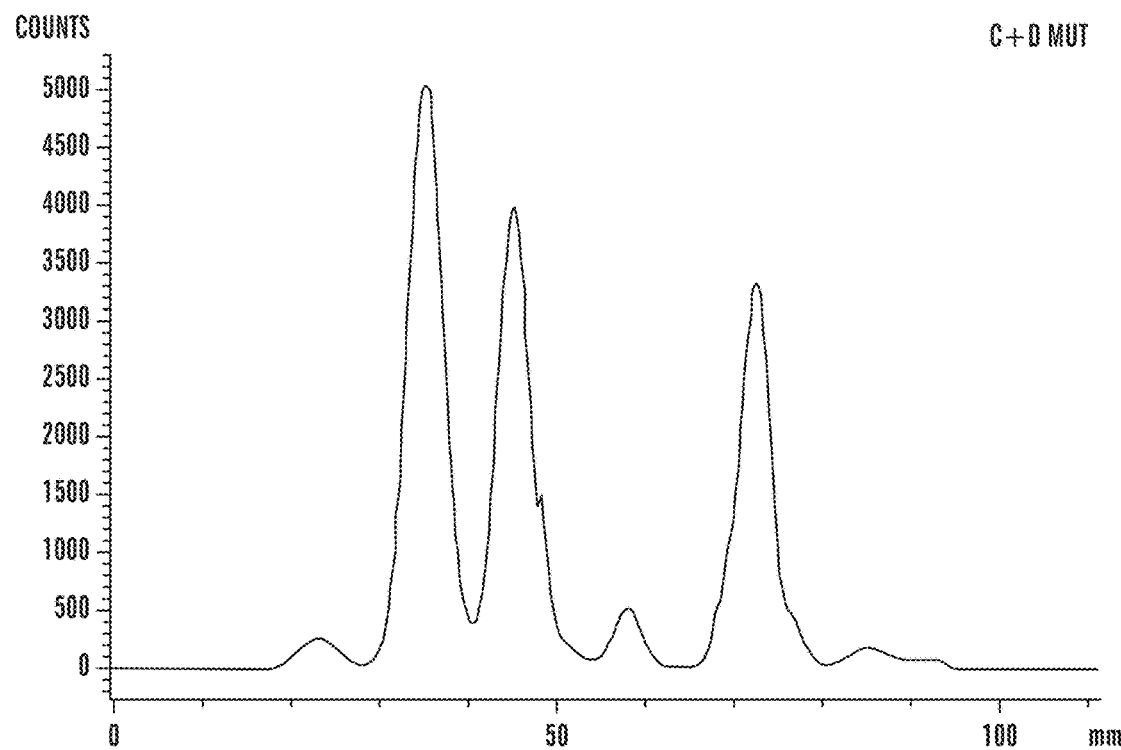

We found that cells transfected with wild-type TET1 showed a strong correlation of HA positivity with decreased staining for 5-methylcytosine, both visually and by quantification (FIG. 6). Untransfected HA-low cells showed a spread of 5-methylcytosine staining intensity similar to that of mock-transfected cells, whereas productively transfected HA-high cells showed uniformly low 5-methylcytosine staining intensity (FIG. 6).

We have demonstrated that overexpression of catalytically active TET subfamily proteins leads to decreased staining with a monoclonal antibody directed against 5-methylcytosine. We have shown that catalytically active TET1 causes a substantial decrease in nuclear staining for 5-methylcytosine (5mC) in transfected HEK293 cells. We have also quantified the relation between 5-methylcytosine staining and HA/TET1 staining on a per-cell basis using the Cell Profiler program. We found that cells expressing full-length TET1 show a substantial decrease in 5-methylcytosine staining relative to mock-transfected cells (FIG. 6). The loss of 5-methylcytosine staining is even more striking in cells expressing only the C+D domain of TET1, but is far less apparent in cells expressing a mutant C+D domain in which two of the predicted catalytic residues of the predicted 2OG-Fe(II) oxygenase domain, His1672 and Asp1674, are mutated to tyrosine and alanine respectively (numbers refer to residues in full-length TET1).

We used the Cell Profiler program to quantify the relation between 5-methylcytosine staining and HA staining on a per-cell basis. We found that mock-transfected cells show a wide spread in 5-methylcytosine staining intensity, most likely because access of the anti-5-methylcytosine antibody to the methylated cytosine requires complete denaturation of the DNA. In the population of cells transfected with full-length TET1 or the C+D domain of TET1, we found that the 5-methylcytosine staining intensity of the untransfected (HA-low) subpopulation overlaps with that of the mock-transfected population, but the productively transfected (HA-high) population shows a clear decrease in the intensity of 5-methylcytosine staining (FIG. 6). In contrast, we found that HA-positive cells expressing the mutant H1672Y, D1674A C+D domain show a distribution of 5-methylcytosine staining intensity that is much more similar to that of the mock-transduced cells.

We also found that, notably, cells expressing the C+D domain display a distinct increase in nuclear size, which again is much less apparent in cells expressing the mutant protein, and we also quantified this effect.

A Novel Nucleotide in DNA from Cells Expressing TET1

The loss of 5-methylcytosine staining in TET1-expressing cells suggested to us that the 5-methylcytosine in these cells was being modified in some way. To detect the modified nucleotide, we developed an assay based on thin-layer chromatography (TLC) to detect the relative levels of cytosine and 5-methylcytosine in cells. Herein, we demonstrate that TET1 expression leads to the generation of a novel nucleotide. Briefly, DNA is subjected to cleavage with MspI, a methylation-insensitive enzyme that cuts at the sequence CCGG regardless of whether or not the internal CpG is methylated on cytosine. The resulting fragments, whose 5' ends derive from the dinucleotide CpG, contain either cytosine or 5-methylcytosine (H. Cedar et al., Nucleic Acids Res. 6, 2125 (1979)). The DNA is then treated with calf intestinal phosphatase (CIP), end-labeled with polynucleotide kinase (PNK), hydrolysed to dNMPs with snake venom phosphodiesterase (SVPD) and DNase I, and the nucleotides are separated by thin-layer chromatography.

We demonstrate that our TLC assay detected a novel nucleotide in genomic DNA of cells transfected with catalytically active full-length TET1 or its catalytic fragment (C+D)—the appearance of this novel nucleotide depended both on 5-methylcytosine and on the expression of catalytically active full-length TET1 or its catalytic fragment (C+D) in HEK293 cells. To determine if TET1 altered the relative levels of unmethylated and methylated cytosine in cells, HEK293 cells were transfected with control vector or vector encoding full-length or C+D TET1 or their mutant versions, following which DNA was extracted from the entire transfected population and subjected to digestion, end-labeling and TLC. Compared to MspI-digested DNA from cells transfected with the control vector, MspI-digested DNA from cells expressing wildtype, but not mutant, full-length or C+D TET1 yielded a novel labeled spot migrating between dCMP and dTMP. We showed that catalytically active (wt) but not catalytically inactive (mut) TET1 alters the relative levels of unmethylated and methylated cytosine in transfected HEK293 cells and results in the appearance of the novel nucleotide, and this was particularly apparent with the catalytic C+D fragment. We show that the intensity of this spot correlated with a decrease in the intensity of the 5-methyl-dCMP (5m-dCMP) spot, suggesting strongly that the spot was derived from 5-methyl-dCMP and not from dCMP. We also demonstrate that neither the 5-methylcytosine spot nor the new spot were observed when the DNA was digested with HpaII, a methylation-sensitive isoschizomer of MspI which cuts DNA at the sequence CCGG but only if the internal CpG dinucleotide is unmethylated, again indicating that the spot was likely to be a derivative of 5-methyl-dCMP; this is because both 5-methylcytosine and cytosine are present at the 5' end of MspI fragments and are therefore labeled by polynucleotide kinase, but only cytosine is represented at the 5' end of DNA fragments produced by the methylation-sensitive isoschizomer HpaII.

To confirm that the spot was not an artefact of MspI digestion, we tested another methylation-insensitive enzyme, Taqα1, whose restriction site (TCGA) includes a central CG dinucleotide. As with MspI, both 5-methylcytosine and cytosine are present at the 5' end of DNA fragments produced by Taqα1, and are therefore labeled. We show that Taqα1, a methylation-insensitive enzyme which cuts at the sequence TCGA, gives the same results as MspI, a methylation-insensitive enzyme which cuts at the sequence CCGG. Once again, the novel spot was observed in Taqα1-digested DNA from cells expressing wildtype, but not mutant, full-length or C+D TET1, and again the intensity of the spot correlated with a decrease in the intensity of the 5-methyl-dCMP spot.

FIG. 7 shows these experiments represented using line scans of the phosphorimaging of the labeled spots on the TLC plate. These experiments confirmed the correlation between loss of 5-methylcytosine and appearance of the novel nucleotide in cells expressing full-length (FL) or C+D TET1, but not FL mut or C+D mut.

Identification of the Novel Nucleotide as 5-Hydroxymethyl-dCMP

We identified the novel nucleotide produced by TET1 expression as 5-hydroxymethyl-dCMP. We subcloned full-length and C+D TET1 and their mutant versions into a vector containing an cassette in which expression of human CD25 was driven by an internal ribosome entry site (IRES).

This strategy allowed identification and sorting of transfected cells that co-expressed TET1 and CD25, and the acquisition of samples from a preparative TLC.

Figure 8A:
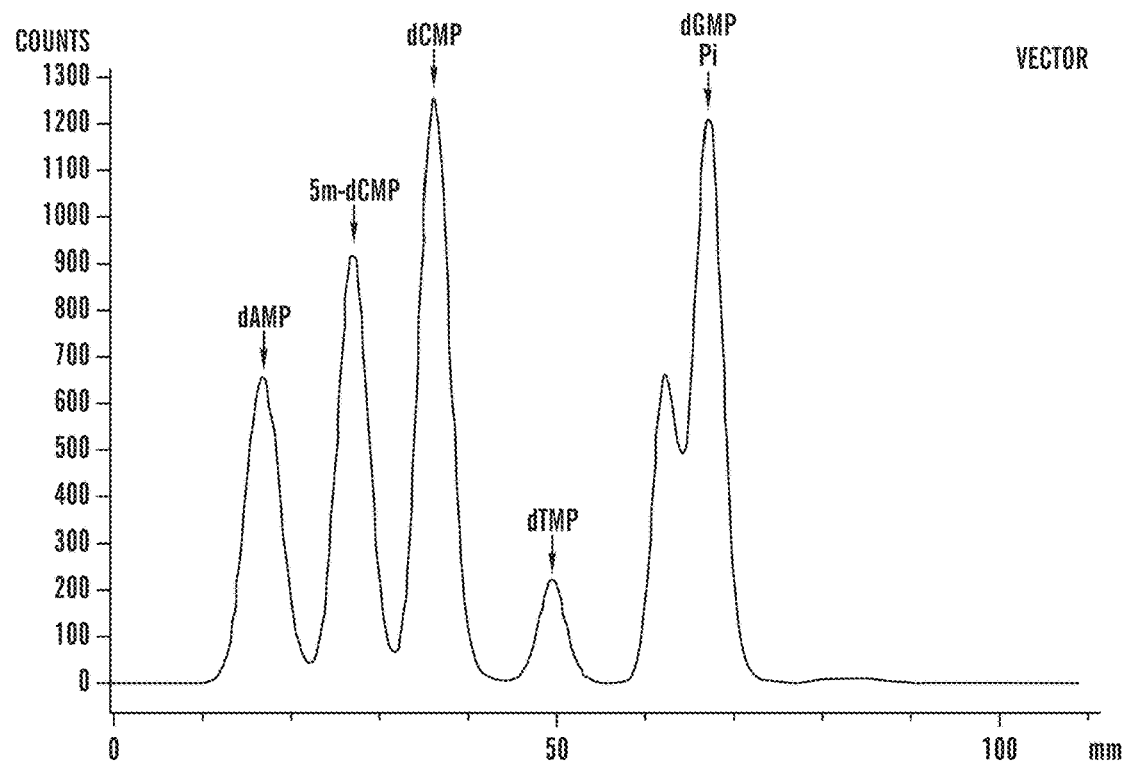
FIGS. 8A-8C demonstrate that TET1 expression leads to the generation of a novel nucleotide.
Figure 8B:
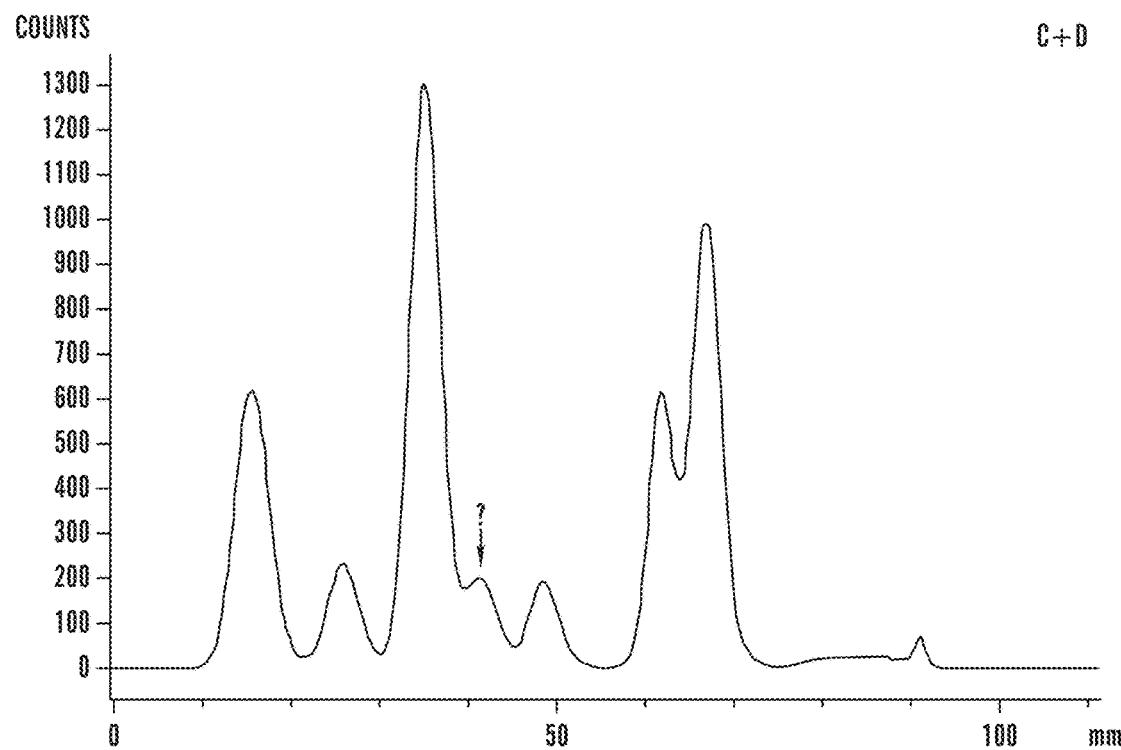
Figure 8C:
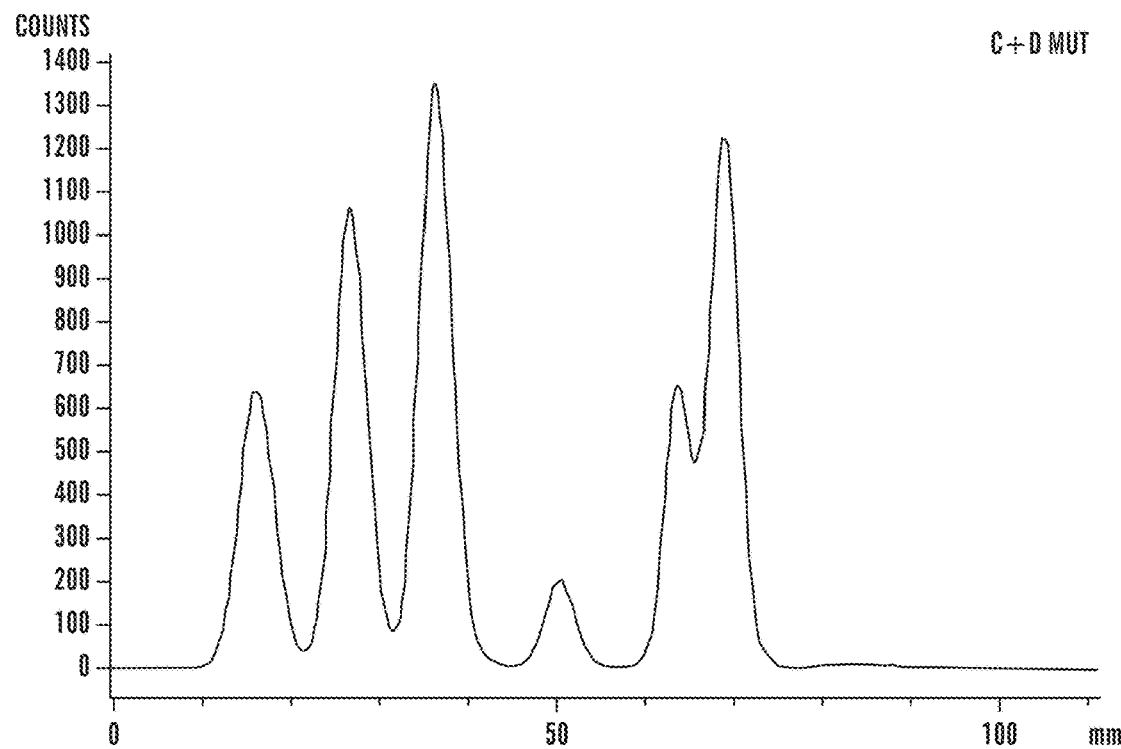

We showed the generation of expression plasmids based on pEF1 and used to express full-length TET1 or its C+D catalytic domain, either wildtype (wt) or mutant (mut), together with an IRES-human CD25 cassette, and we demonstrated that successfully-transfected cells were marked with CD25 expression. The cells were sorted for CD25 expression to enrich for the TET1-expressing cell population, genomic DNA was isolated and subjected to MspI cleavage, treatment with calf intestinal phosphatase (CIP) end-labeling with polynucleotide kinase (PNK), hydrolysis to dNMPs with snake venom phosphodiesterase (SVPD) and DNase I, and thin-layer chromatography. The results of the TLC assay showed that the novel nucleotide ("new spot") is only observed in DNA from cells transfected with the catalytically-active (C+D) fragment of TET1, and not in DNA from cells transfected with empty vector or the catalytically-inactive mutant version of (C+D). FIG. 8 depicts theses experiments as line scans of the labeled spots on the TLC plate, using phosphorimager analysis.

Experiments to determine the identity of the unknown nucleotide by mass spectrometry were performed. Ultra performance liquid chromatography was carried out using Acquity UPLC system (Waters Corp., Milford, Mass.). Waters HSS C18 column (1.0 mm i.d.×50 mm, 1.8-um particles) was used. The mobile phases were 0.1% aqueous ammonium formate (A, pH6.0) and Methanol (B). After initial equilibration at 100% A, the methanol was increased linearly from 0% to 50% over 15 minutes and then to 100% within 10 minutes and stay at 100% MeOH for 2 minutes before getting back to 0% methanol in 10 min to flush the column. The column was then allowed to re-equilibrate by holding 100% A for 7 min prior to subsequent analyses. The flow rate was 0.05 ml min-1 and the eluant was directly injected into the mass spectrometer. Mass spectrometry analysis was carried out using a Q-tof Premier mass spectrometer (Waters Corp., Milford, Mass.) fitted with an electrospray interface. Data were acquired and processed with Masslynx 4.1 software. Instrument tuning and mass calibration were carried out using 1 mM sodium acetate solution (in 1:4 H2O: ACN). Mass spectra were recorded in the negative mode within m/z 300-500 for LC/MS runs, and within 50-350 for LC/MS/MS runs. The quad was set to allow all ions to pass through in the LC/MS runs, and was set to focus on the specific mass of the targeted parent ions for fragmentation in the LC/MS/MS runs. For all characterizations, Ultra pure water was obtained from a Milli-Q water purification system (Millipore). All solvents and modifiers used were mass spectrometry grade. Methanol was purchase from Fisher Scientific. Ammonium formate was obtained from Sigma. To determine the identity of the unknown nucleotide (336.06 Da signal in negative mode), LC/MS and LC/MS/MS experiments were performed in which the samples eluted from TLC plate were frozen, lyophilized, and re-suspended in water for on-line LC/MS and LC/MS/MS analysis.

Figure 9:
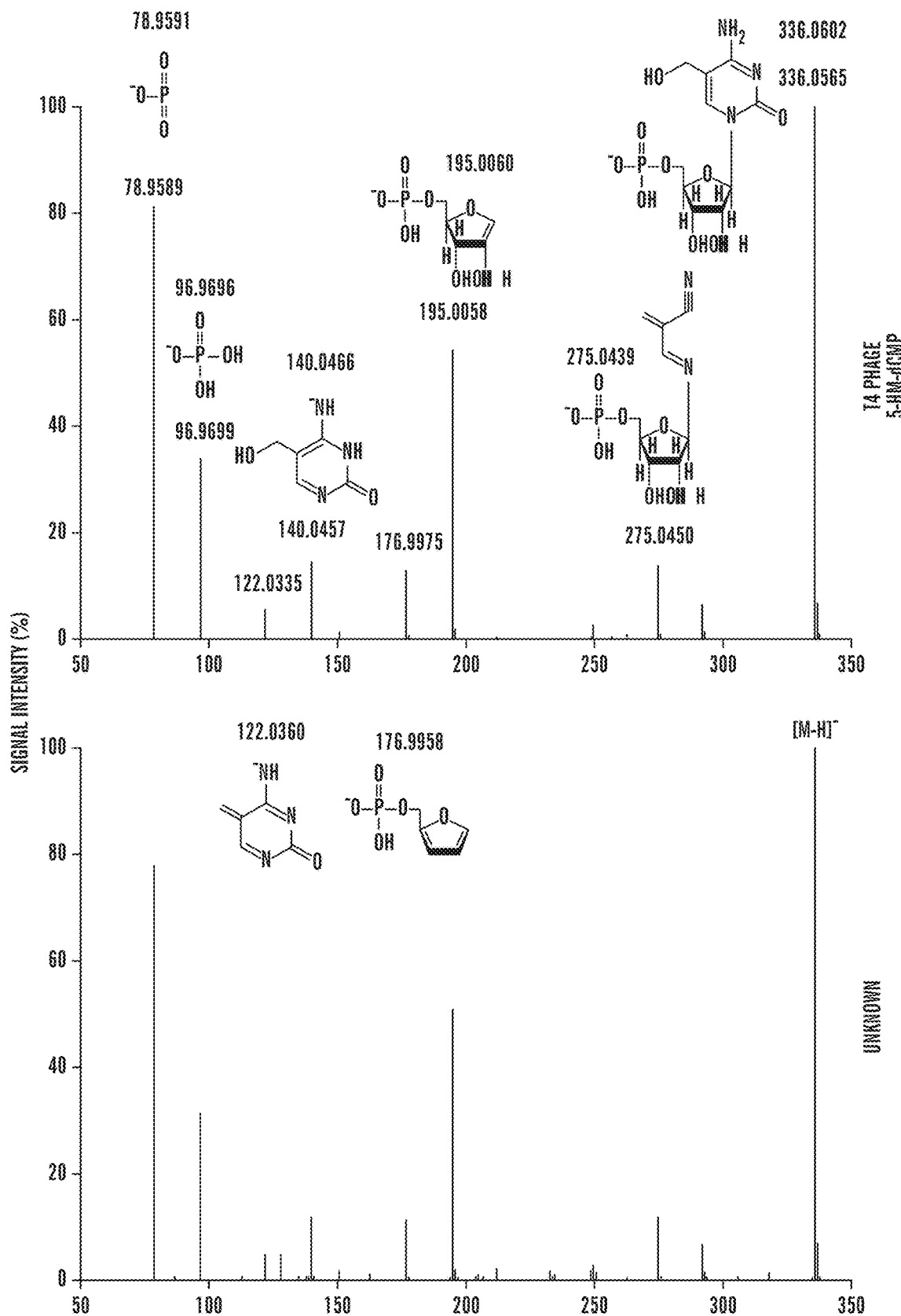
FIG. 9 identifies the novel nucleotide as 5-hydroxymethylcytosine, by determining that the unknown nucleotide is identical to authentic 5-hydroxymethylcytosine obtained from T4 phage grown in GalU-deficient *E. coli* hosts.

The region containing the unknown spot was excised from preparative TLC plates, and XCMS was used to compare the ion intensities of the signals obtained by processing DNA from cells expressing the wild-type versus the mutant version of TET1 C+D (FIG. 9A). After background subtraction (of the values obtained from a control run of the solvent gradient with Milli-Q water injection), a single species of 336.0582 Da was the only one which showed a significant difference in intensity between the two samples. We found that the intensity of the signal from this species in the wildtype sample was ~19-fold greater than that in the wild-type sample, whereas for all other species the signal intensity ratio was smaller than 2. Considering the large errors involved in the extraction of samples by scraping TLC plates, species with signal intensity ratios smaller than 2 can reasonably be ignored. The mass of 336.06 Da is consistent with a molecular formula of $C_{10}H_{15}NO_8P^-$, or 5-hydroxymethyl cytsoine, an oxidation product which from our bioinformatic analysis could reasonably be produced by TET1.

LC/MS/MS runs were carried out at several collision energies: 15, 25, 35V (not shown) and 50V, in both positive and negative modes. 5-hydroxymethylcytosine from T4 phage was used as standard for comparison. For straight comparison, all the LC and MS/MS parameters were kept exactly the same for the unknown nucleotide and the 5-hydroxymethylcytsoine standard in each MS/MS run. After background subtraction (of the MS/MS of wild-type blank sample) by Matlab 7.1 (The MathWorks, Inc.) the MS/MS spectra of the unknown nucleotide looked exactly the same as those corresponding MS/MS spectra from the T4 5-hydroxymethylcytosine standard.

Since 5-hydroxymethylcytosine is not commercially available, a biological source of this nucleotide was sought. The genomes of T-even phages contain hydroxymethylcytosine, which is normally almost completely glucosylated by enzymes in their *E. coli* hosts. This modification protects them from bacterial restriction enzymes such as McrBC, which recognise and cleave DNA containing either 5-methylcytosine or 5-hydroxymethylcytosine. If these phages are grown in *E. coli* ER1656, a strain deficient in the glucose donor molecule UDP glucose, lacking GalU (the enzyme that catalyses formation of the glucose donor UDP-Glucose) and the McrA and McrB1 components of McrBC, they remain unglucosylated and their DNA can be used as a source of 5-hydroxymethylcytosine. Indeed, through TLC analysis we showed that DNA from T4 phage grown in galU, mcrA, mcrB1 *E. coli* hosts yields only 5-hydroxymethylcytosine and no cytsoine or 5-methylcytosine. The 5-hydroxymethylcytosine migrates similarly to the novel nucleotide obtained from TET1-expressing cells. We showed that the novel nucleotide spot is present only in cells expressing the wild-type C+D domains, and migrates similarly by TLC analysis to authentic 5-hydroxymethylcytosine obtained from T4 phage grown in GalU-deficient *E. coli* hosts. As we show in FIG. 9, the unknown nucleotide was determined to be identical to authentic 5-hydroxymethylcytosine obtained from T4 phage grown in GalU-deficient *E. coli* hosts, by using LC/MS/MS runs carried out in negative mode with collision energies of 15V and 25V.

Physiological Importance of TET1 in Gene Regulation.

We have shown that a recombinant protein comprising the catalytic domain (C+D) of human TET1, expressed in baculovirus expression vector in insect Sf9 cells, is active in converting 5-methylcytosine to 5-hydroxymethylcytosine in vitro. Further, the catalytically active TET1 fragments shows an absolute requirement for Fe(II) and 2OG. Omission of ascorbate did not result in a significant decrease in catalytic activity, most likely because dithiothreitol was included in the reaction to counteract the strong tendency of TET1-CD to oxidize (L. Que Jr., et al., Chem. Rev. 96, 2607 (1996); C. Loenarz, and C. J. Schofield, Nat. Chem. Biol. 4, 152 (2008); L. E. Netto and E. R. Stadtman, Arch. Biochem. Biophys. 333, 233 (1996)). We showed that recombinant TET1-CD was specific for 5-methylcytosine, as conversion of thymine to hydroxymethyluracil (hmU) was not detected.

Figure 10:
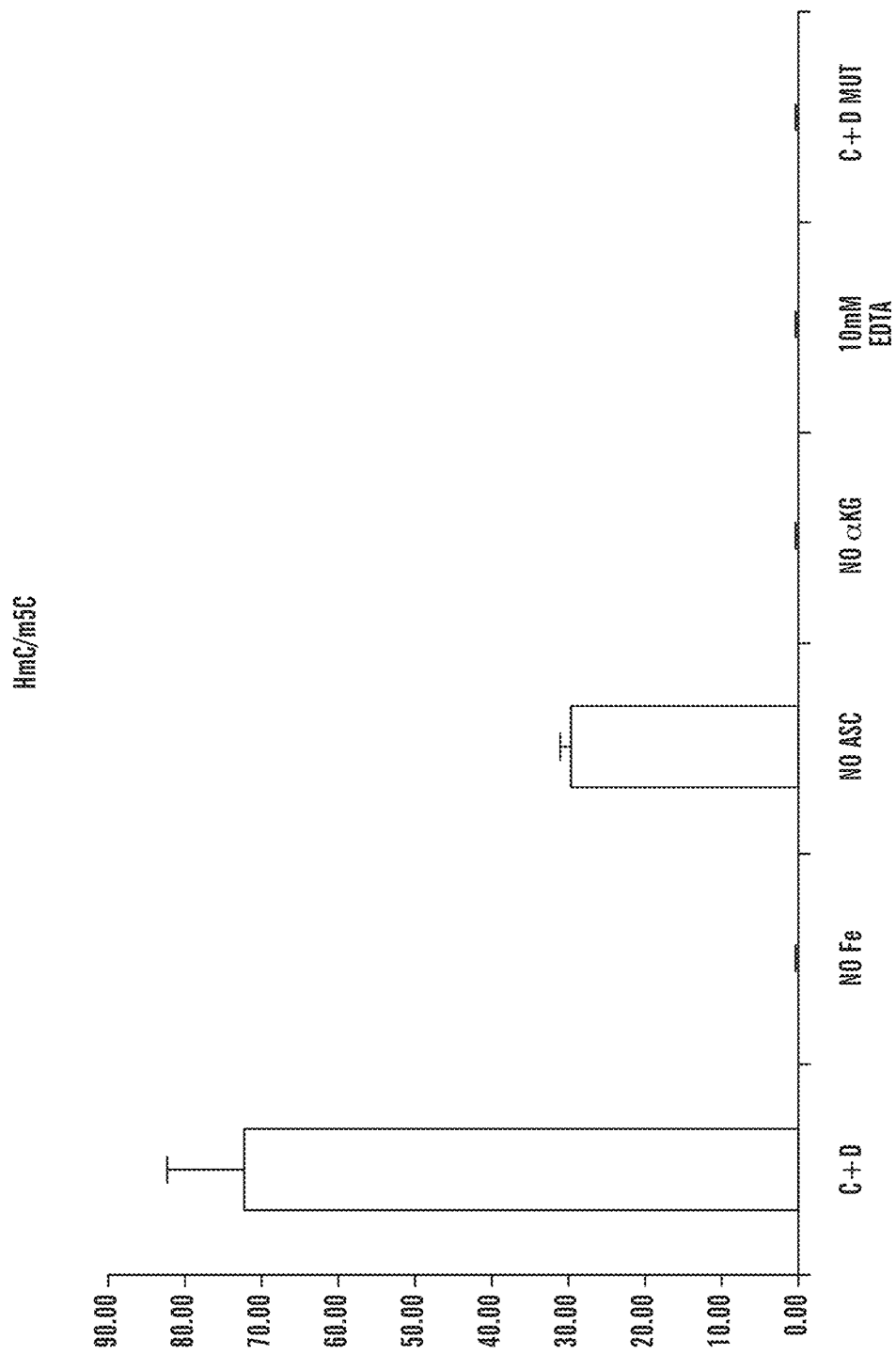
FIG. 10 shows that a recombinant protein comprising the catalytic domain (C+D) of human TET1, expressed in baculovirus expression vector in insect Sf9 cells, is active in converting 5-methylcytosine to 5-hydroxylmethylcytosine in vitro, and depicts the relative activity of the recombinant C+D fragment of TET1 in the presence of various combinations of Fe2+, ascorbic acid, α-KG and EDTA.

We used an SDS polyacrylamide gel stained with Coomassie Blue in which lane 1 had molecular weight markers, lanes 2-4 were loaded with the indicated amounts of bovine serum albumin (BSA) (2, 1 and 0.5 microgram), lanes 5-8 were loaded with eluted protein from the FLAG affinity column used to purify C+D and C+D mutant (mut). Lanes 5 and 6 had 1.6 micrograms of C+D and mut respectively, and lanes 7 and 8 had 5 micrograms of C+D and mut respectively. The band around 90 kDa represents the TET1 fragment and the bands of higher apparent molecular weight are oxidized versions of the same fragment. We used anti-FLAG western blots loaded with different fractions from the FLAG affinity columns used to purify C+D and C+D mut respectively (Lys=cell lysate; sol=soluble; ins=insoluble; FT=flowthrough; W1=wash 1; W2=wash 2; Fg E1=$1^{st}$ elution with FLAG peptide; Fg E2=$2^{nd}$ elution with FLAG peptide; low pH=final elution of column with low pH buffer). We showed that the recombinant C+D fragment of TET1 is catalytically active in vitro, and can produce hydroxymethyl-dCMP (Hm-dCMP) using either the fully-methylated oligo 1 or the hemimethylated oligo 3 as substrate, whereas the catalyticaly-inactive mutant C+D is not. We also showed the relative activity of the recombinant C+D fragment of TET1 in the presence of various combinations of $Fe^{2+}$, ascorbic acid, α-KG and EDTA. Briefly, 10 mg of double-stranded DNA oligonucleotides containing a methylated Taqα1 site were incubated with 3 mg of GST-SMCX in a buffer containing 1 mM a-KG, 2 mM ascorbic acid, 75 mM Fe2+ for 3 hours at 37 C. The enzyme to substrate ratio is 1:10. Oligonucleotides were incubated under identical conditions with purified FlagHA-CD(DHD) as a negative control. Recovered oligonucleotides were digested with Taqα1, end-labeled with T4-PNK and g-32P-ATP and then hydrolyzed to dNMP's with DNaseI and snake venom phosphodiesterase. dNMP's were resolved using cellulose TLC plates and the relative amounts of dNMP's were quantitated using phosphorimager. Each condition was performed in triplicate. FIG. 10 shows the relative activity of the recombinant C+D fragment of TET1 in the presence of various combinations of Fe2+, ascorbic acid, α-KG and EDTA.

Figure 11A:
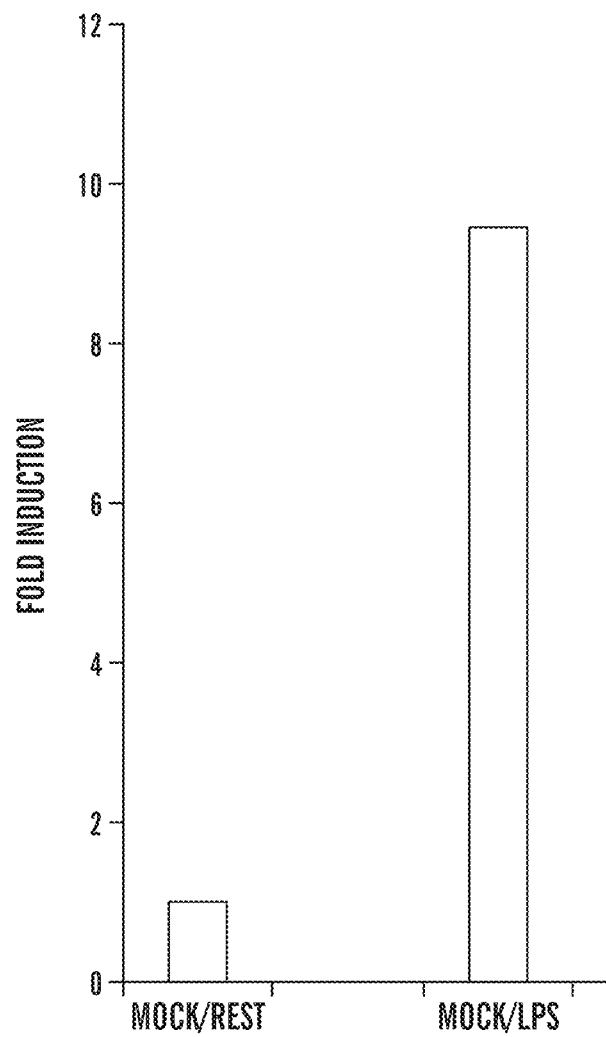
FIG. 11A-11I demonstrates the physiological importance of TET1 in gene regulation.
Figure 11B:
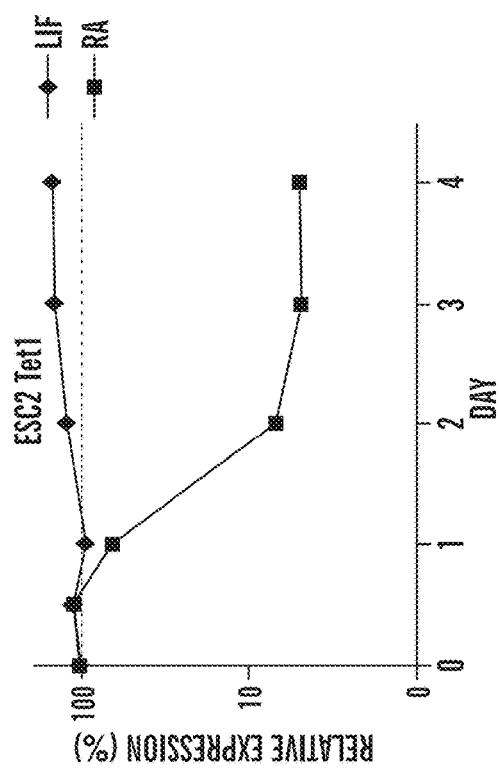
Figure 11C:
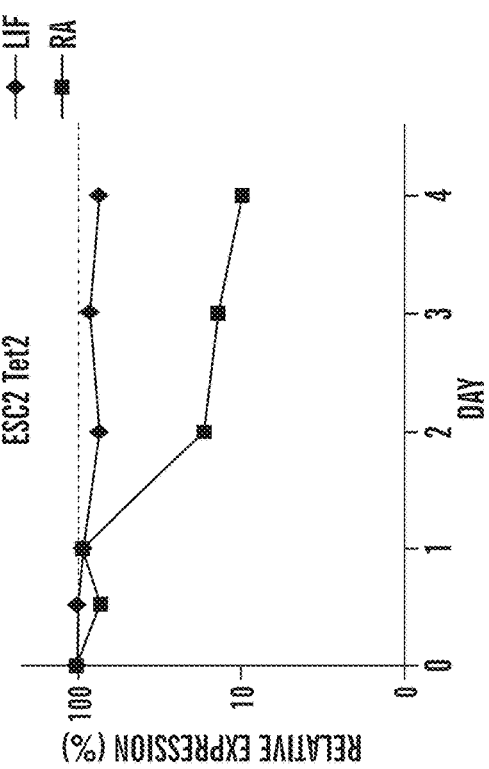
Figure 11D:
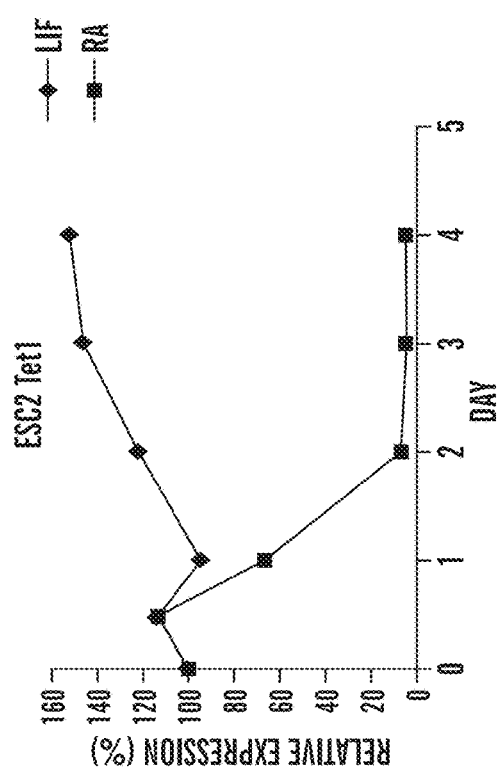
Figure 11E:
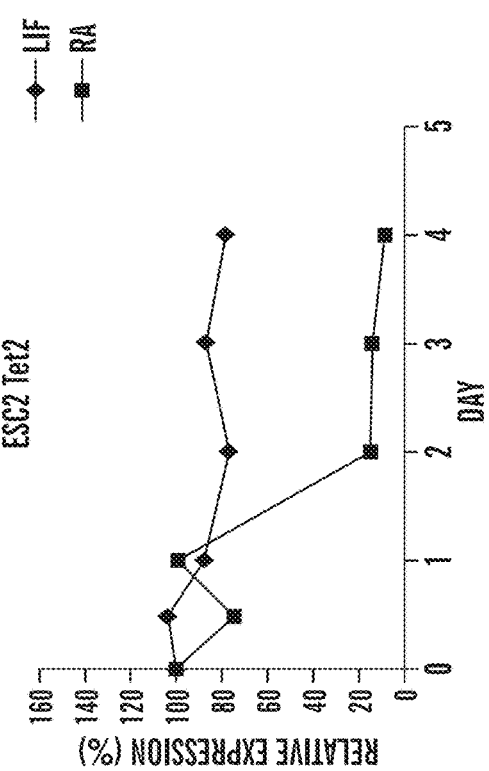
Figure 11F:
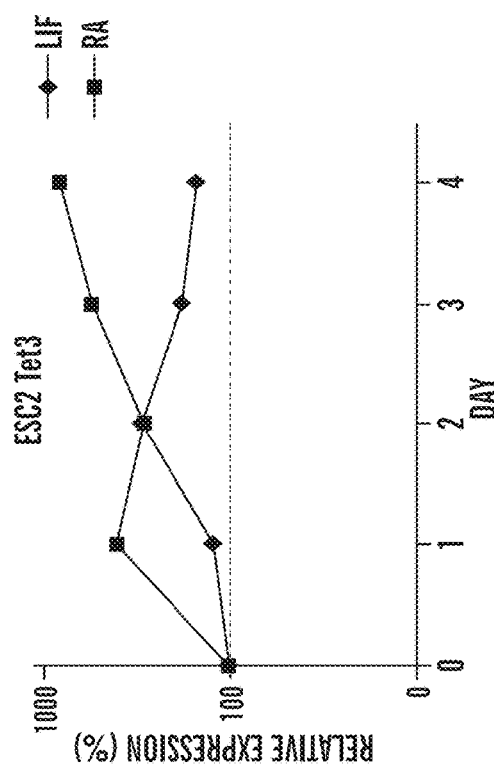
Figure 11G:
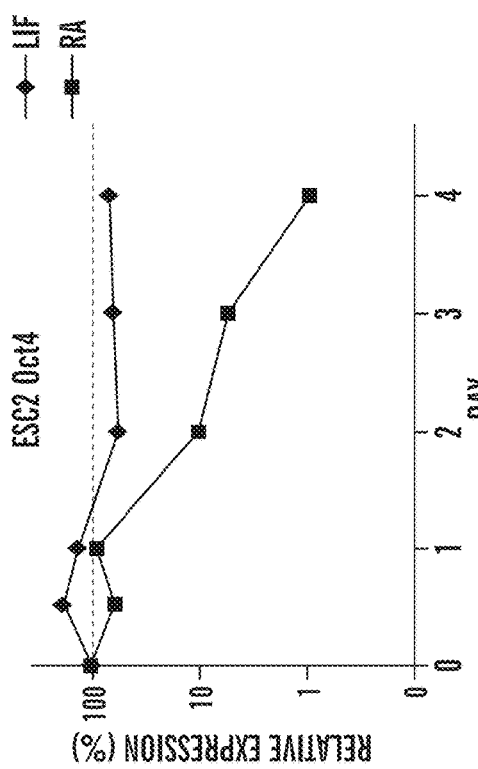
Figure 11H:
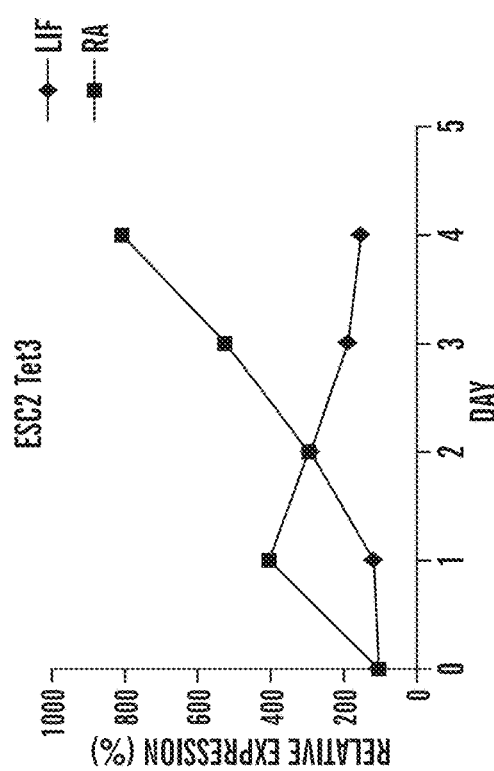
Figure 11I:
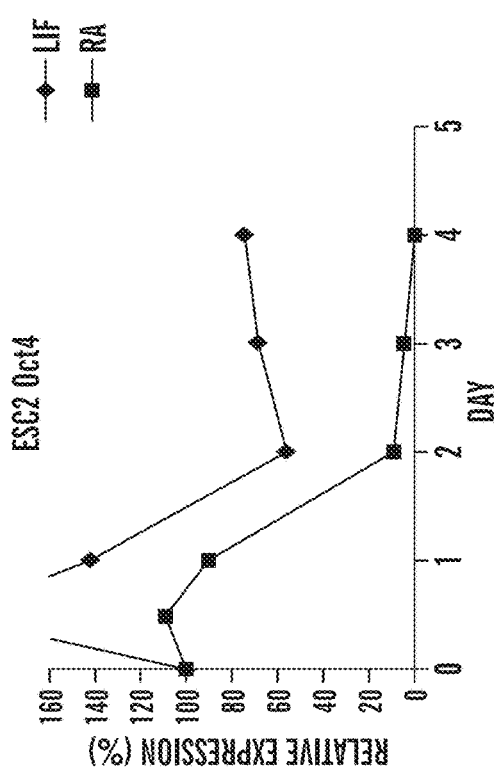
Figure 12B:
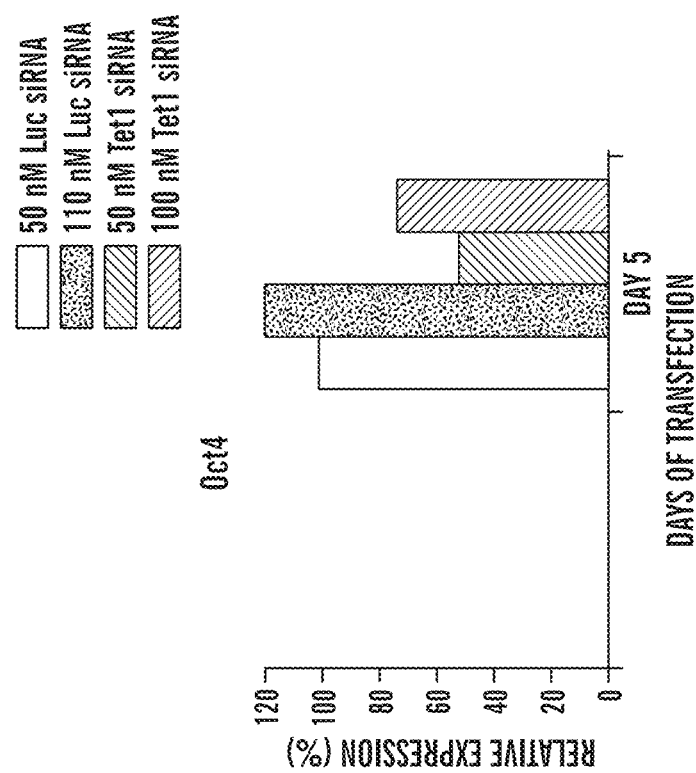
FIG. 12A-12F shows the effect of Tet RNAi on ES cell lineage gene marker expression, using cells treated with Tet1, Tet2 and Tet3 siRNAs.
Figure 12A:
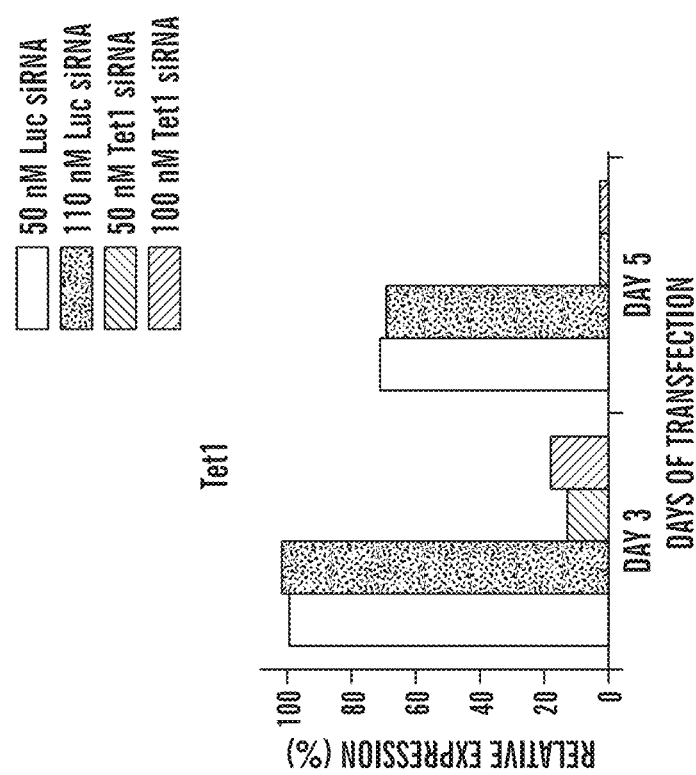
Figure 12C:
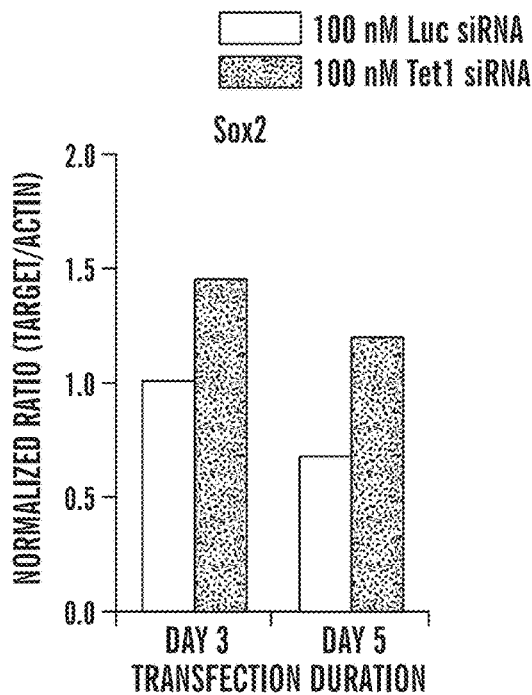
Figure 12D:
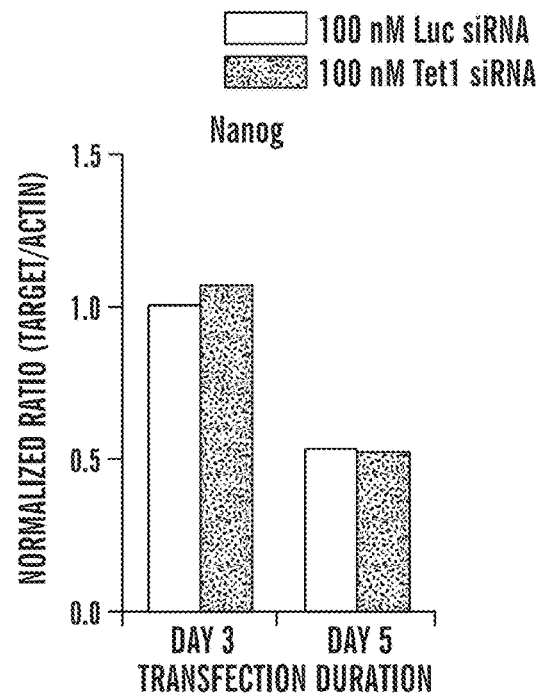
Figure 12E:
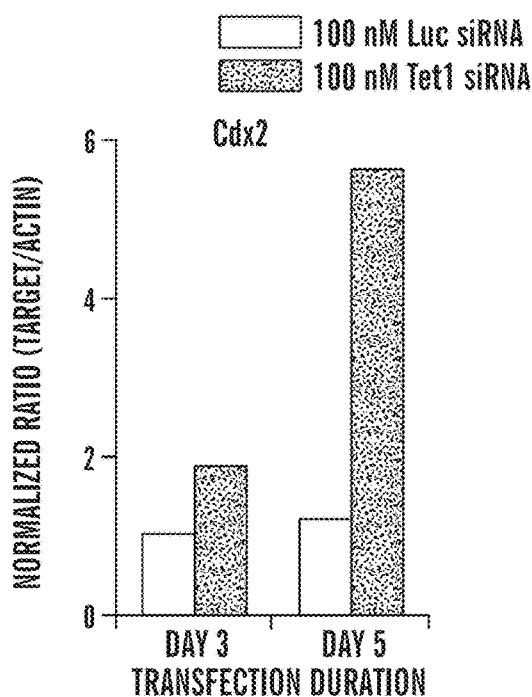
Figure 12F:
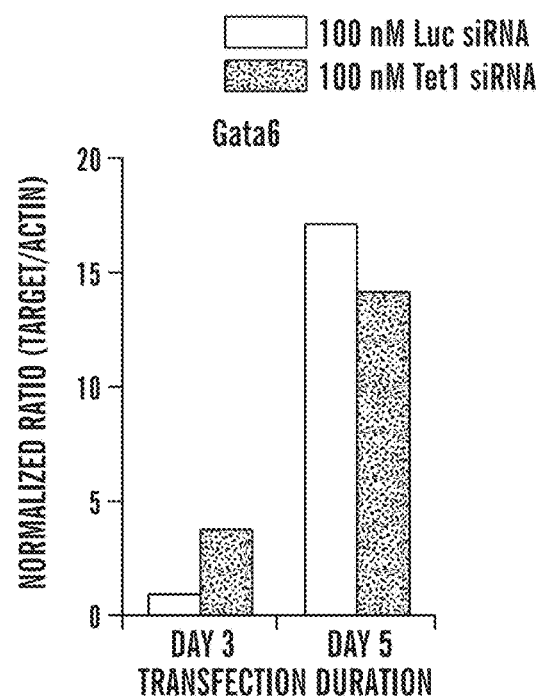

We demonstrated the physiological importance of TET1 in gene regulation. FIG. 11A demonstrates that Tet1 mRNA is strongly upregulated after 8 h of stimulation of mouse dendritic cells (DC) with LPS, a standard activating stimulus for DC. FIGS. 11B-11I shows the changes in Tet1, Tet2 and Tet3 mRNA levels in mouse ES cells that have been induced to differentiate by withdrawal of leukemia inhibitory factor (LIF) and addition of retinoic acid. We cultured v6.5 mouse ES cells on gelatin-coated wells in DMEM media supplemented with 15% FBS and $10^3$ units/ml of LIF. Twenty four hours after plating (D0 time point), cells were either continually cultured in the presence of LIF or treated with 1 mM retinoic acid in the absence of LIF for up to 5 days. We showed phase contrast images of the cells, taken daily using a 20× objective. We collected cell samples daily for RNA extraction. We measured transcript levels of Tet1, Tet2, Tet3 and Oct4, normalized to b-actin levels, by quantitative RT-PCR and expressed relative to levels at D0. Error bars denote mean±SD from 2 experiments. We showed that Tet1 and Tet2 and the positive control pluripotency gene Oct4 are downregulated, whereas Tet3 is upregulated, during RA-induced differentiation.

We asked whether 5-hydroxymethylcytosine was a physiological constituent of mammalian DNA. Using the TLC assay, we observed a clear spot corresponding to labeled 5-hydroxymethylcytosine in mouse embryonic stem (ES) cells. Quantification of multiple experiments indicated that 5-hydroxymethylcytosine and 5-methylcytosine constituted 4 to 6% and 55 to 60%, respectively, of all cytosine species in MspI cleavage sites (CACGG) in ES cells. We showed that Tet1 mRNA levels declined by 80% in response to leukemia inhibitory factor (LIF) withdrawal for 5 days, compared with the levels observed in undifferentiated ES cells; in parallel, 5-hydroxymethylcytosine levels diminished from 4.4 to 2.6% of total C species, a decline of ~40% from control levels. The difference might be due to the compensatory activity of other Tet-family proteins. Similarly, RNA interference (RNAi)-mediated depletion of endogenous Tet1 resulted in an 87% decrease in Tet1 mRNA levels and a parallel ~40% decrease in 5-hydroxymethylcytosine levels. Again, the difference is likely due to the presence of Tet2 and Tet3, which are both expressed in ES cells.

We show the effect of Tet RNAi on ES cell lineage gene marker expression. Twenty four hours after plating on gelatin-coated wells (D0 time point), v6.5 ES cells were transfected with siGENOME SMARTpool (Dharmacon) siRNA targeting Tet1, Tet2 or Tet3, or a luciferase (luc)-targeting siRNA as a negative control, with Lipofectamine RNAiMAX (Invitrogen) in the presence of LIF. Cells were passaged and re-transfected pre-adherent at days 2 and 4 in the presence of LIF. Samples were collected at days 3 (D3) and 5 (D5) for RNA isolation. We took phase contrast images at day 5 (2 fields per transfection). Knockdown of Tet proteins causes appreciable spontaneous ES cell differentiation (especially apparent with Tet3 knockdown, right panels). FIG. 12 shows the degree of knockdown of Tet1, Tet2 and Tet3 RNA, measured by quantitative RT-PCR and normalized to Gapdh levels, in cells treated with Tet1, Tet2 and Tet3 siRNAs. FIG. 12 (middle and bottom rows) show expression of Tet1-Tet3, trophectoderm (Cdx2, Hand1, Psx1), primitive endoderm (Gata4), mesoderm (Brachyury) and primitive ectoderm (Fgf5) markers were measured by quantitative RT-PCR and normalized to Gapdh levels. The expression of D3 control siRNA treatment was set as reference.

Without wishing to be bound by a theory, our data indicate that Tet1, and other Tet family members, are responsible for 5-hydroxymethylcytosine generation in ES cells under physiological conditions. CpG dinucleotides are ~0.8% of all dinucleotides in the mouse genome; thus, 5-hydroxymethylcytosine (which constitutes ~4% of all cytosine species in CpG dinucleotides located in MspI cleavage sites) is ~0.032% of all bases (~1 in every 3000 nucleotides, or ~$2\times10^6$ bases per haploid genome). For comparison, 5-methylcytosine is 55 to 60% of all cytosines in CpG dinucleotides in MspI cleavage sites, about 14 times as high as 5-hydroxymethylcytosine (5-hydroxymethylcytosine may not be confined to CpG). An important question is whether 5-hydroxymethylcytosine and TET proteins are localized to specific regions of ES cell DNA—for instance, genes that are involved in maintaining pluripotency or that are poised to be expressed upon differentiation. A full appreciation of the biological importance of 5-hydroxymethylcytosine will require the development of tools that allow 5-hydroxymethylcytosine, 5-methylcytosine, and cytosine to be distinguished unequivocally.

As a potentially stable base, 5-hydroxymethylcytosine may influence chromatin structure and local transcriptional activity by recruiting selective 5-hydroxymethylcytosine binding proteins or excluding methyl-CpG-binding proteins (MBPs) that normally recognize 5-methylcytosine, thus displacing chromatin-modifying complexes recruited by MBPs. Indeed, it has already been demonstrated that the methylbinding protein MeCP2 does not recognize 5-hydroxymethylcytosine (V. Valinluck et al., Nucleic Acids Res. 32, 4100 (2004)). Alternatively, without wishing to be bound by a theory, conversion of 5-methylcytosine to 5-hydroxymethylcytosine may facilitate passive DNA demethylation by excluding the maintenance DNA methyltransferase DNMT1, which recognizes 5-hydroxymethylcytosine poorly (V. Valinluck and L. C. Sowers, Cancer Res. 67, 946 (2007)). Even a minor reduction in the fidelity of maintenance methylation would be expected to result in an exponential decrease in CpG methylation over the course of many cell cycles. Finally, 5-hydroxymethylcytosine may be an intermediate in a pathway of active DNA demethylation. 5-hydroxymethylcytosine has been shown to yield cytosine through loss of formaldehyde in photooxidation experiments (E. Privat and L. C. Sowers, Chem. Res. Toxicol. 9, 745 (1996)) and at high pH (J. G. Flaks, S. S. Cohen, J. Biol. Chem. 234, 1501 (1959); A. H. Alegria, Biochim. Biophys. Acta 149, 317 (1967)), leaving open the possibility that 5-hydroxymethylcytosine could convert to cytosine under certain conditions in cells. A related possibility is that specific DNA repair mechanisms replace 5-hydroxymethylcytosine or its derivatives with cytosine (S. K. Ooi, T. H. Bestor, Cell 133, 1145 (2008); J. Jiricny, M. Menigatti, Cell 135, 1167 (2008)). In support of this hypothesis, a glycosylase activity specific for 5-hydroxymethylcytosine was reported in bovine thymus extracts (24. S. V. Cannon, et al., Biochem. Biophys. Res. Commun. 151, 1173 (1988)). Moreover, several DNA glycosylases, including TDG and MBD4, have been implicated in DNA demethylation, although none of them has shown convincing activity on 5-methylcytosine in in vitro enzymatic assays (B. Zhu et al., Proc. Natl. Acad. Sci. U.S.A. 97, 5135 (2000). R. Metivier et al., Nature 452, 45 (2008); S. Kangaspeska et al., Nature 452, 112 (2008)). Cytosine deamination has also been implicated in demethylation of DNA (R. Metivier et al., Nature 452, 45 (2008); S. Kangaspeska et al., Nature 452, 112 (2008); K. Rai et al., Cell 135, 1201 (2008)); in this context, deamination of 5-hydroxymethylcytosine yields hmU, and high levels of hmU:G glycosylase activity have been reported in fibroblast extracts (V. Rusmintratip and L. C. Sowers, Proc. Natl. Acad. Sci. U.S.A., 97, 14183 (2000)).

Our studies alter the perception of how cytosine methylation may be regulated in mammalian cells. Notably, disruptions of the TET1 and TET2 genetic loci have been reported in association with hematologic malignancies. A fusion of TET1 with the histone methyltransferase MLL has been identified in several cases of acute myeloid leukemia (AML) associated with t(10;11)(q22;q23) translocation (R. Ono et al., Cancer Res. 62, 4075 (2002); R. B. Lorsbach et al., Leukemia 17, 637 (2003)). Homozygous null mutations and chromosomal deletions involving the TET2 locus have been found in myeloproliferative disorders, suggesting a tumor suppressor function for TET2 (F. Viguie et al., Leukemia 19, 1411 (2005); F. Delhommeau et al., paper presented at the American Society of Hematology Annual Meeting and Exposition, San Francisco, Calif., Dec. 9, 2008). It will be important to test the involvement of TET proteins and 5-hydroxymethylcytosine in oncogenic transformation and malignant progression.

The Role of Tet Oncogene Proteins in Mouse Embryonic Stem Cells

By computational analysis, we identified the TET proteins, TET1, TET2 and TET3, as mammalian homologs of the trypanosome J-binding proteins JBP1 and JBP2 that have been proposed to oxidize the 5-methyl group of thymine. We have found that TET1/CXXC6, previously characterized as a fusion partner of the MLL gene in acute myeloid leukemia, is an iron- and a-ketoglutarate-dependent dioxygenase that catalyzes the conversion of 5-methylcytosine (5mC) to 5-hydroxymethylcytosine (hmC), both as a recombinant protein in vitro and when overexpressed in cultured HEK293 cells (Tahiliani, M., et al., Science, 2009: 324(5929): p. 930-935). We find that 5-hydroxymethylcytosine can be detected in the genome of mouse embryonic stem (ES) cells but not in differentiated cell types. Tet1 and Tet2, but not Tet3, are highly expressed in mouse ES cells and RNAi-mediated depletion of both Tet1 and Tet2 causes loss of 5-hydroxymethylcytosine. Tet1 and Tet2 are repressed rapidly in parallel with Oct4 when ES cells are cultured in the absence of leukemia inhibitory factor (LIF), whereas additional treatment of retinoic acid leads to induction of Tet3 during differentiation. These changes correspond with a decrease in genomic5-hydroxymethylcytosine levels. Loss of pluripotency caused by Oct4 RNAi also downregulates Tet1 and Tet2 expression with loss of 5-hydroxymethylcytosine. On the other hand, gain of pluripotency in induced pluripotent stem (iPS) cell reprogrammed from mouse fibroblasts is associated with induction of both Tet1 and Tet2 and appearance of 5-hydroxymethylcytosine. RNAi-depletion of each Tet member does not decrease mRNA levels of the pluripotency-associated genes Oct4, Sox2 and Nanog, but Tet1 RNAi results in induction of genes that specify trophectodermal lineage. Our results suggest (i) that Tet1 and Tet2 catalyze conversion of 5-methylcytosine to 5-hydroxymethylcytosine in mouse ES cells; (ii) that Tet1, Tet2 and 5-hydroxymethylcytosine are associated with the pluripotent state; (iii) that Tet1 and Tet2 are downstream targets of the transcriptional network regulated by Oct4 and (iv) that Tet1 is a novel factor involved in repression of trophectoderm lineage development during the first cell-fate decision in mouse embryogenesis.

Figure 13A:
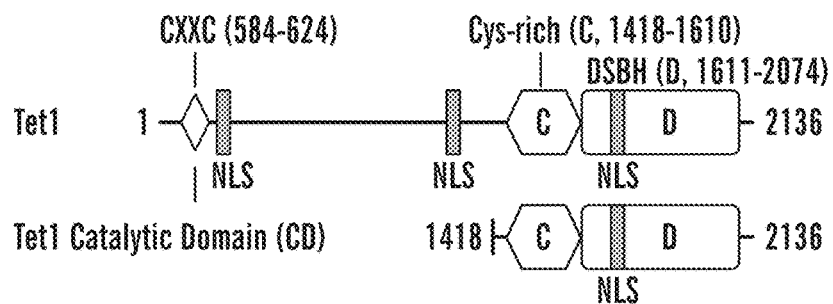
FIG. 13A-C shows the identification of 5-hydroxymethylcytosine as the catalytic product of conversion from 5-methylcytosine by TET1 and detection of 5-hydroxymethylcytosine in the genome of mouse ES cells.

We used the following methods in our analyses. To perform immunofluorescence, we transfected cells with pEF1a expression constructs with HA-epitope N-terminal of full length (FL) TET1 or catalytic domain alone (TET1 CD) or empty vector (mock) for 2 days, as depicted in FIG. 13A. Fixed cells were treated with 2N HCl to denature DNA before co-staining with rabbit anti-HA (Santa Cruz Biotechnology) and mouse anti-5-methylcytosine (Calbiochem) antibodies which were detected using secondary antibodies coupled with Cy2 or Cy3 respectively. Nuclei were stained with DAPI before mounting for fluorescence imaging.

To perform thin-layer chromatography (TLC), genomic DNA was digested with the restriction endonuclease MspI, which cleaves at C^CGG sites, to generate fragments whose 5' ends derive from the dinucleotide CpG and contain either 5-methylcytosine, C or 5-hydroxymethylcytosine. The digested DNA was then radiolabeled at the 5' ends and then hydrolysed from the 3' ends to single dNMPs which were resolved by TLC. Spot intensities were measured by phosphoimaging densitometry and 5-hydroxymethylcytosine levels are represented as percentages of total cytosine (5mC+C+hmC). Values were mean±SD from triplicate samples (FIG. 13A).

To perform cell culture and RNA interference (RNAi), V6.5 mouse ES cells were maintained on feeder layers in standard ES medium but were replated on gelatin-coated wells for the experiments described. RNAi experiments were performed using Dharmacon siGENOME siRNA duplexes. Mouse ES cells were transfected with 50 nM siRNA using Lipofectamine RNAiMAX reagent (Invitrogen) in the presence of LIF. Retransfections were performed on pre-adherent cells every 2 days and cells were harvested at Day 5 for RNA and TLC analyses.

We performed RNA extraction, cDNA synthesis and quantitative real-time PCR analyses. Briefly, total RNA was isolated with an RNeasy kit (Qiagen) with on-column DNase treatment. cDNA was synthesized from 0.5 mg total RNA using SuperScriptIII reverse transcriptase (Invitrogen). Quantitative PCR was performed using FastStart Universal SYBR Green master mix (Roche) on a StepOnePlus real-time PCR system (Applied Biosystems). Gene expression was normalized to Gapdh and referenced to Day 0 samples. Data shown are mean±SEM, n=3-4.

Figure 13B:
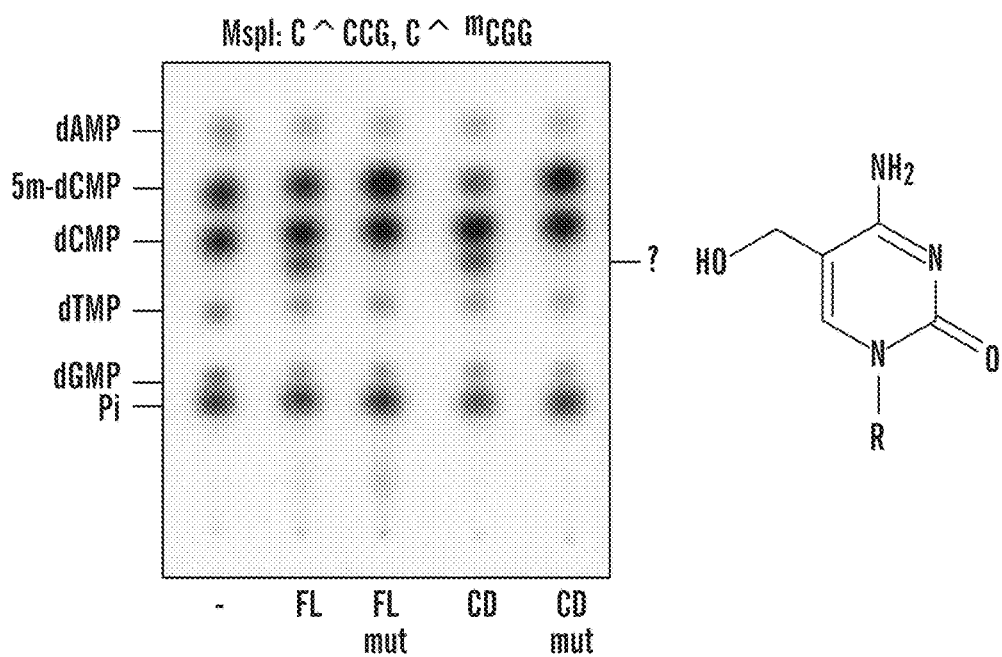
Figure 13C:
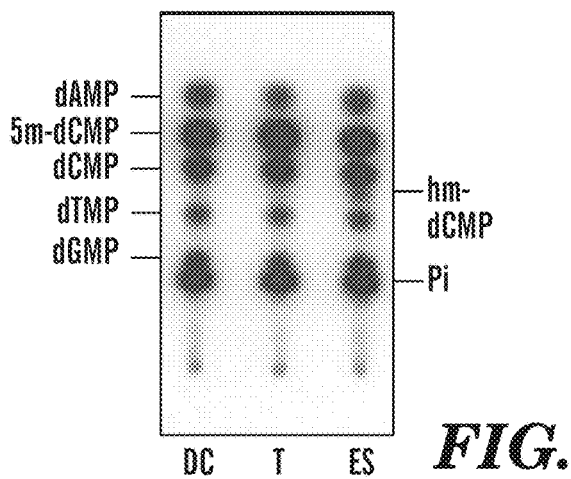

We identified 5-hydroxymethylcytosine as the catalytic product of conversion from 5-methylcytosine by TET1 and detected 5-hydroxymethylcytosine in the genome of mouse ES cells (FIG. 13C). We showed that overexpression of HA-TET1 in HEK293 cells causes loss of staining with an antibody to 5-methylcytosine. We found that TLC of cells overexpressing full-length (FL) TET1 or the predicted catalytic domain (CD) reveals the appearance of an additional nucleotide species identified by mass spectrometry as 5-hydroxymethylcytosine. We found that H1671Y, D1673A mutations at the residues predicted to bind Fe(II) abrogate the ability of TET1 to generate 5-hydroxymethylcytosine, and that 5-hydroxymethylcytosine is detected in the genome of mouse ES cells (FIG. 13B).

Figure 14A:
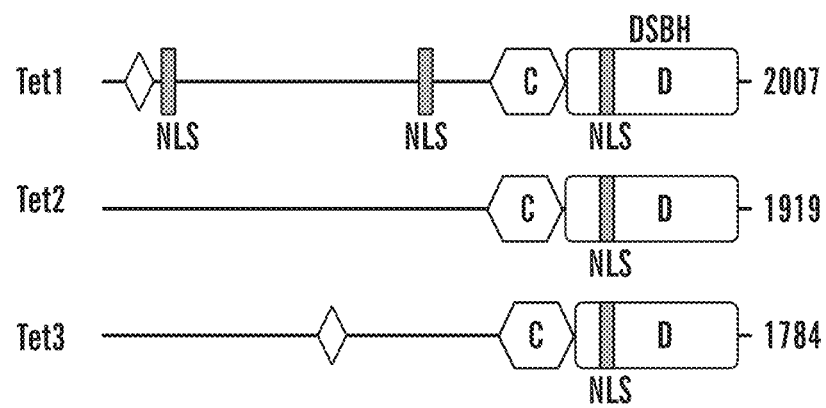
FIG. 14A-B depicts the role of murine Tet1 and Tet2 in the catalytic generation of 5-hydroxymethylcytosine in ES cells.
Figure 14B:
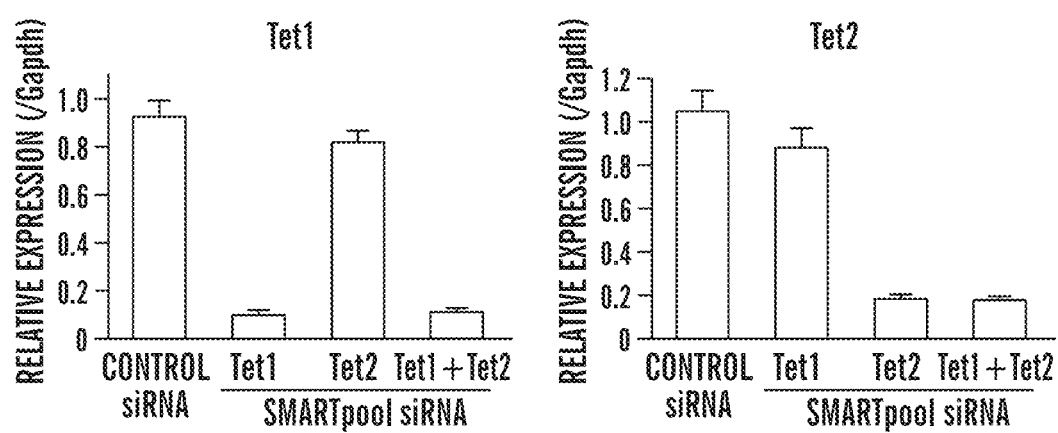

We found a role for murine Tet1 and Tet2 in the catalytic generation of 5-hydroxymethylcytosine in ES cells. The mouse genome expresses three family members—Tet1, Tet2 and Tet3—that share significant sequence homology with the human homologs (FIG. 14A) (Lorsbach, R. B., et al., Leukemia, 2003. 17(3): p. 637-41). Tet1 and Tet3 encode within their first conserved coding exon the CXXC domain. We show that mouse ES cells express high levels of Tet1 and Tet2 (FIG. 15), but not Tet3, which can be depleted with RNAi (FIG. 14). We found that RNAi-depletion of Tet1 or Tet2 alone decreases 5-hydroxymethylcytosine levels partially but combined RNAi reduces 5-hydroxymethylcytosine levels further, suggesting that both Tet1 and Tet2 are enzymes responsible for the catalytic conversion of 5-methylcytosine to 5-hydroxymethylcytosine in mouse ES cells.

Figure 15A:
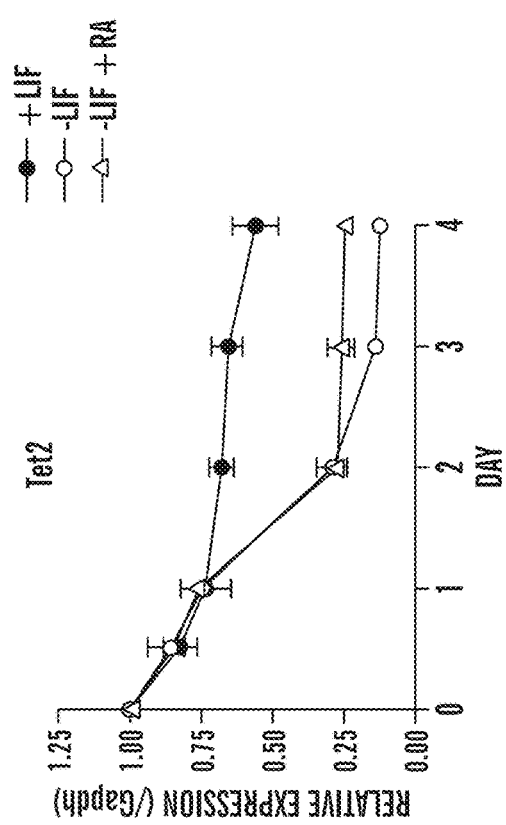
FIG. 15A-D shows the changes in Tet family gene expression that occur in mouse ES cells upon differentiation.
Figure 15B:
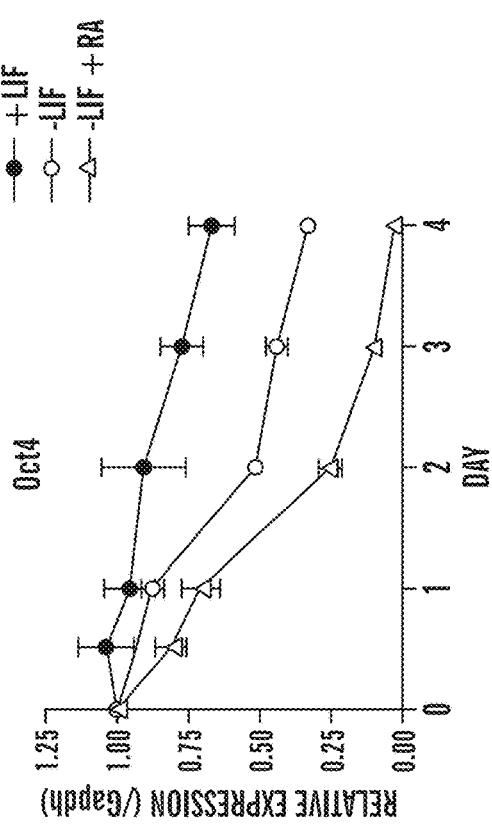
Figure 15C:
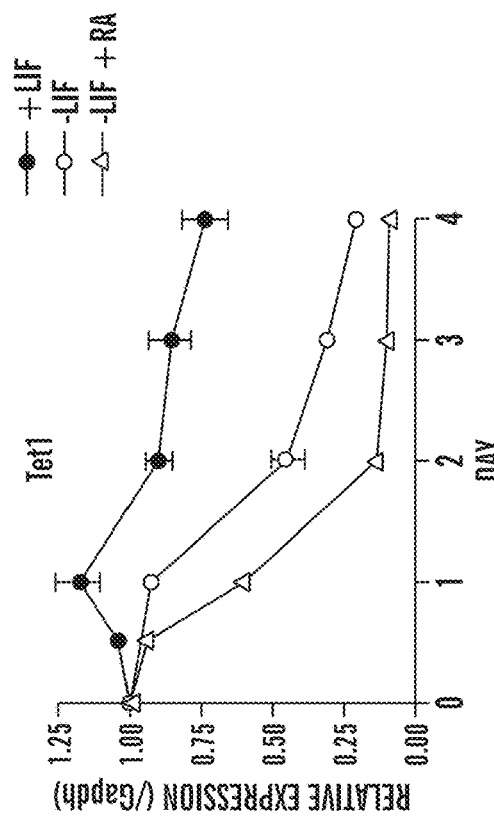
Figure 15D:
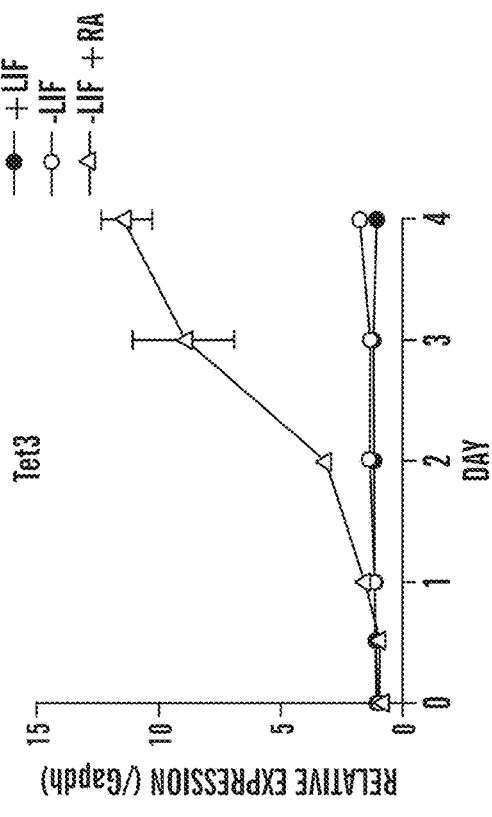

We showed changes in Tet family gene expression occur in mouse ES cells upon differentiation. We found that mRNA levels of Tet1, Tet2 and Oct4 rapidly decline upon LIF withdrawal (FIG. 15). Tet3 level remains low upon LIF withdrawal but increases 10-fold with addition of retinoic acid (FIG. 15C). We found that the decline of Tet1 and Tet2 expression is associated with loss of 5-hydroxymethylcytosine.

We found that Tet1, Tet2 and 5-hydroxymethylcytosine are associated with pluripotency. We show that the loss of pluripotency induced by RNAi-mediated depletion of Oct4 potently suppresses Tet1 and Tet2 expression and upregulates Tet3 (FIGS. 16A-16C). We show that Sox2 RNAi causes a similar, though weaker, effect as Oct4 RNAi and that Nanog RNAi has almost no effect (FIGS. 16A-16C). We found that RNAi-depletion of Oct4 in particular causes loss of 5-hydroxymethylcytosine in ES cells. We show that the gain of pluripotency in iPS clones derived from mouse tail-tip fibroblasts (TTF) by viral transduction of Oct4, Sox2, Klf4 and c-Myc is associated with up-regulation of Tet1 and Tet2 and appearance of 5-hydroxymethylcytosine in the genome (FIGS. 16D-16E).

Figure 17A:
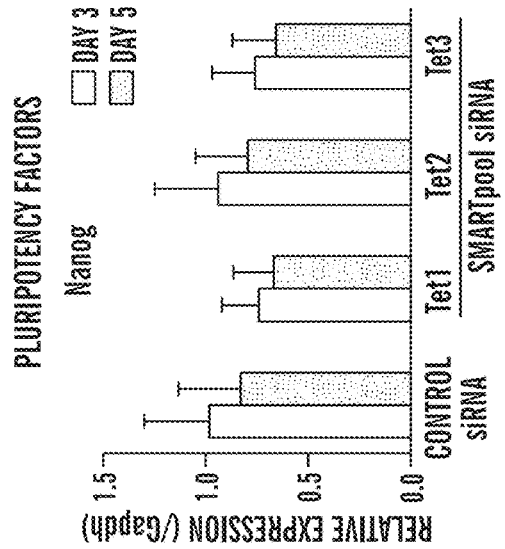
FIG. 17A-I shows the effect of Tet knockdown on ES cell pluripotency and differentiation genes.
Figure 17B:
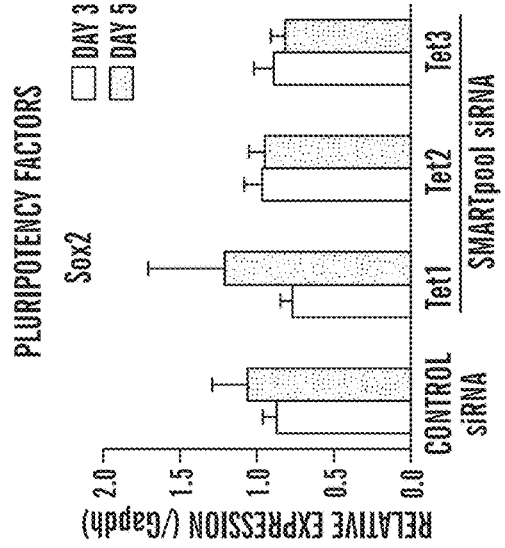
Figure 17C:
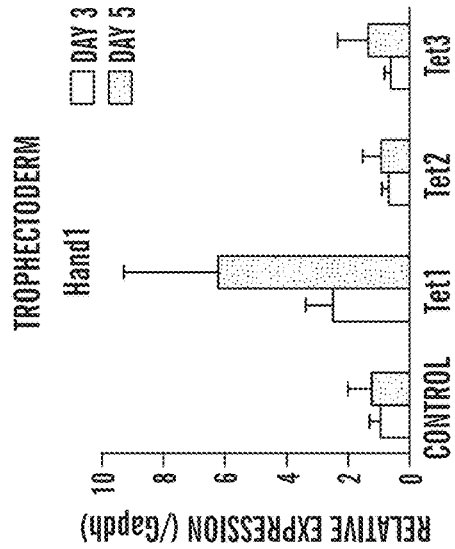
Figure 17D:
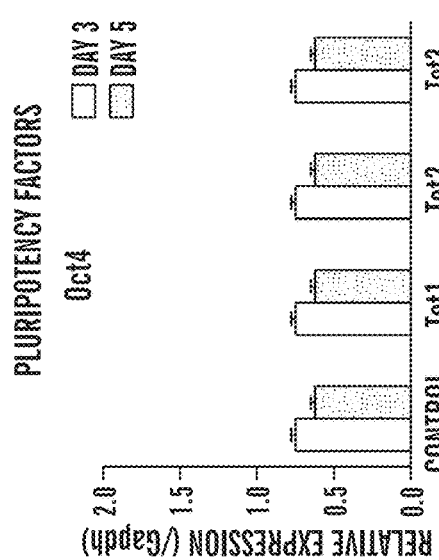
Figure 17E:
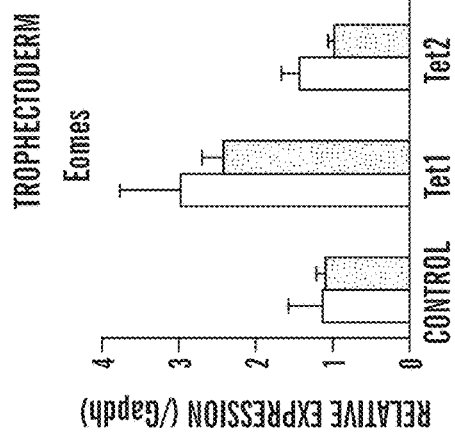
Figure 17F:
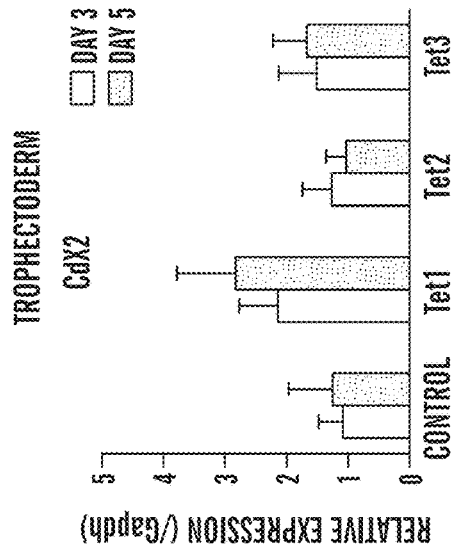
Figures 17G, 17H, 17I:
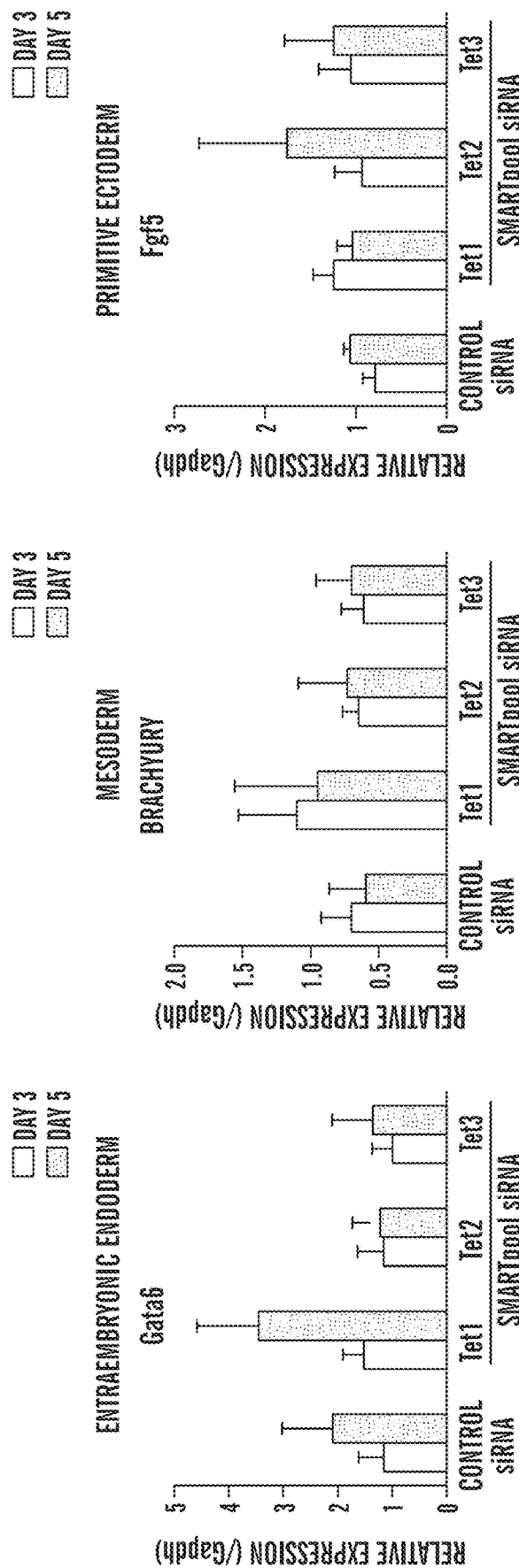
Figure 20B:
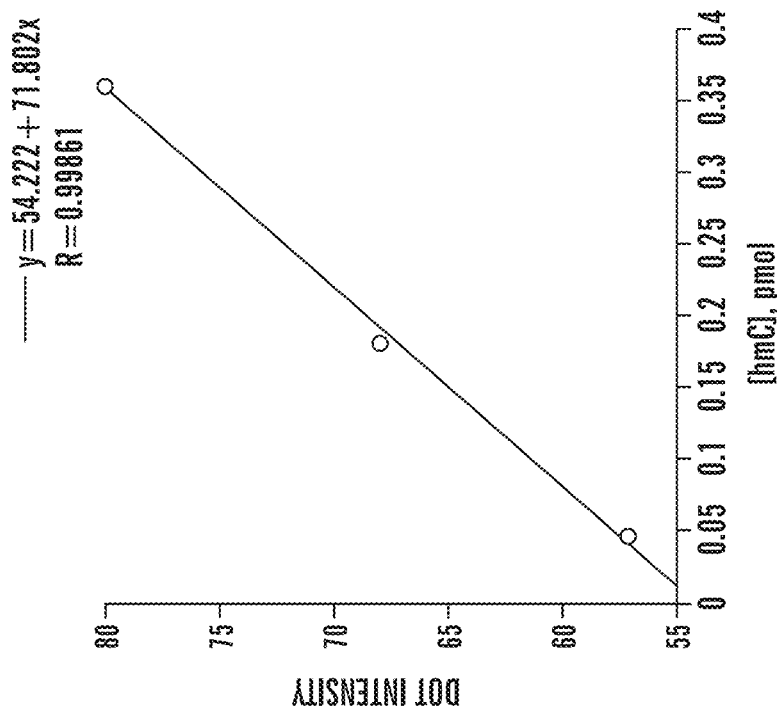
FIGS. 20A-20B compare the correlation between dot intensity and the amount of cytosine methylene sulfonate (FIG. 20A) or 5-hydroxymethylcytosine (FIG. 20B) present in a sample.
Figure 20A:
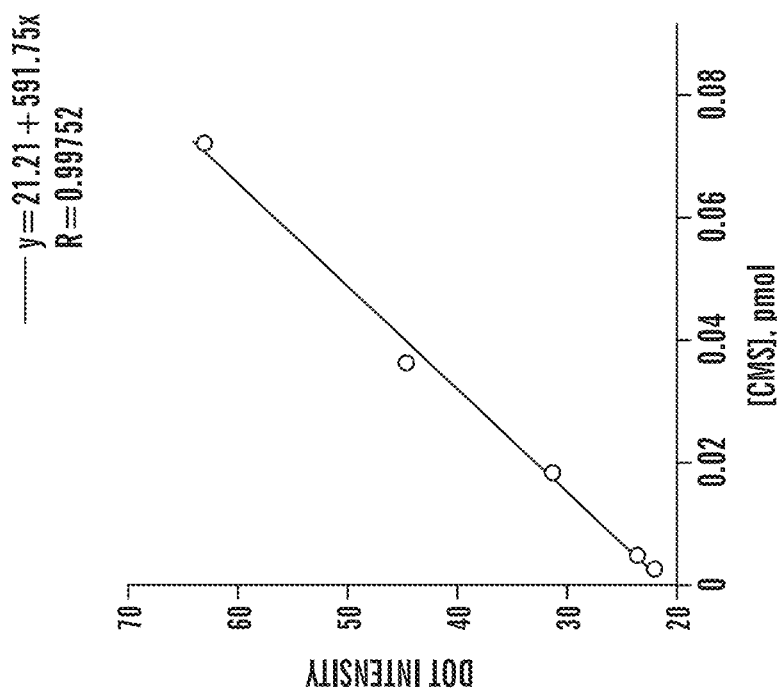
Figure 22B:
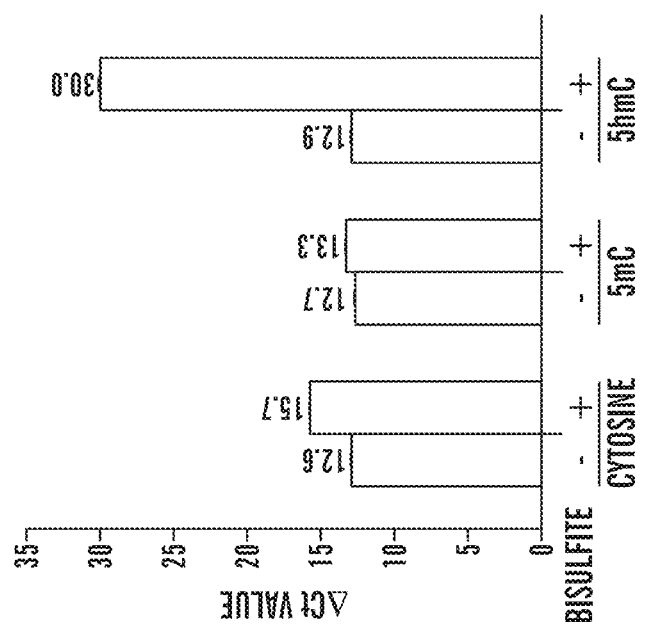
FIG. 22A-B depicts real-time PCR analyses of various oligonucleotides in the presence or absence of bisulfite treatment.
Figure 22A:
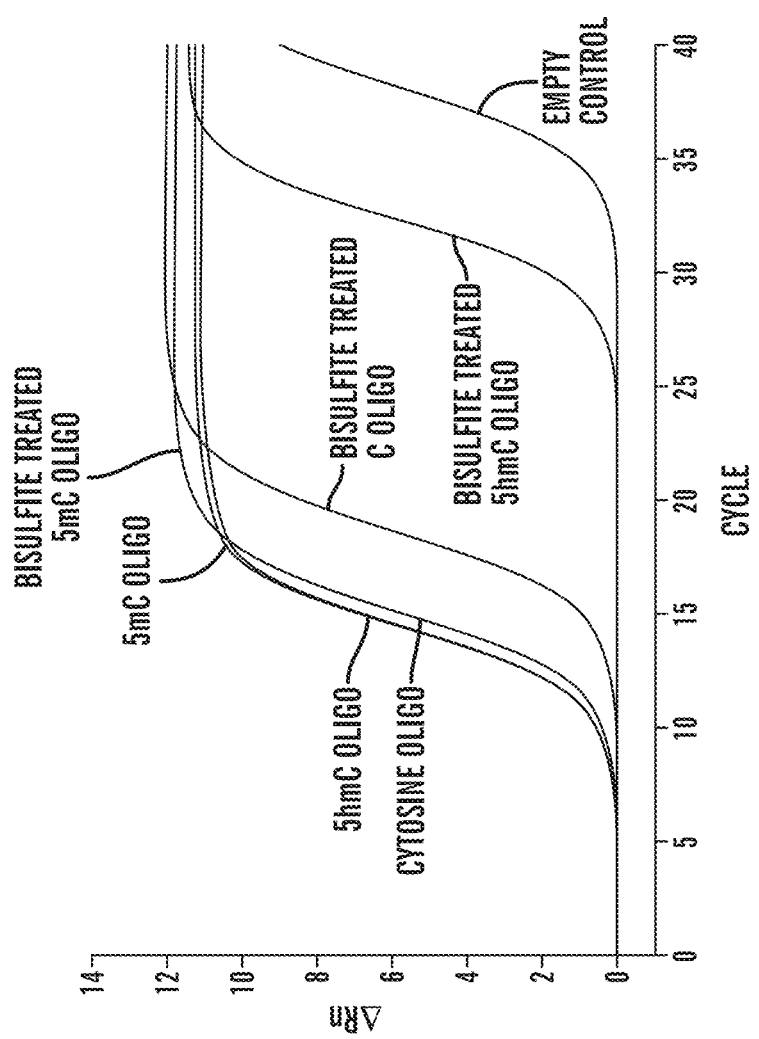

We show that Tet family member knockdown impacts ES cell pluripotency and differentiation genes. We show that RNAi-mediated knockdown of each Tet family member does not affect expression of the pluripotency factors Oct4, Sox2 and Nanog (FIGS. 17A-17C). We show that RNAi-depletion of Tet1, but not of Tet2 or Tet3, increases the expression of the trophectodermal genes Cdx2, Eomes and Hand1 (FIGS. 17D-17F). We show that RNAi-depletion of Tet family members produces small insignificant changes in expression of extraembryonic endoderm, mesoderm and primitive ectoderm markers (FIGS. 17G-17I).

Figure 23:
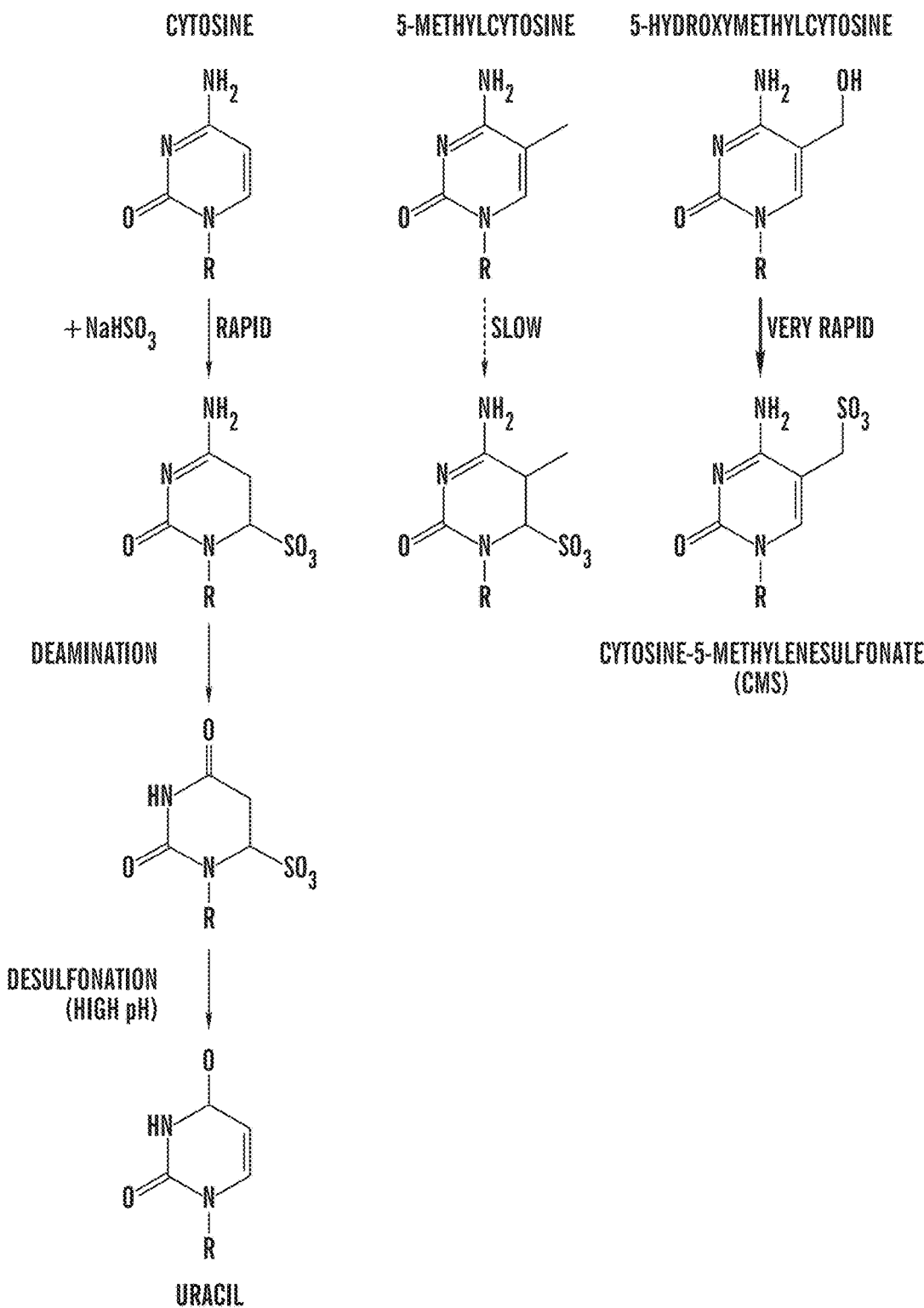
FIG. 23 depicts the reaction of sodium bisulfite with cytosine, 5-methylcytosine, and 5-hydroxymethylcytosine.

The Effect of 5-Hydroxymethylcytosine on Sodium Bisulfite-Based Analysis of DNA Methylation Status Treatment of DNA with sodium bisulfite promotes the deamination of cytosine to uracil, while 5-methylcytosine is deaminated at a far slower rate, allowing the methylation state of a given cytosine to be ascertained. The reaction of sodium bisulfite with cytosine, 5 methylcytosine and 5-hydroxymethylcytosine differs, as depicted in FIG. 23. During bisulfite-mediated deamination of cytosine, $HSO_3^-$ reversibly and quickly adds across the 5,6 double bond of cytosine, promoting deamination at position 4 and conversion to $U$-$SO_3^-$. $U$-$SO_3^-$ is stable under neutral conditions, but is easily desulfonated to uracil at higher pH. 5-methylcytosine is deaminated to thymine by bisulfite conversion, but the rate is approximately two orders of magnitude slower than that of cytosine. Recently, we showed that 5-hydroxymethylcytosine is present in mammalian DNA (S. Kriaucionis and N. Heintz, Science 324, 929 (2009); M. Tahiliani et al., Science 324, 930 (2009)). Bisulfite reacts with 5-hydroxymethylcytosine to form cytosine 5-methylenesulfonate. This adduct does not readily undergo deamination (H. Hayatsu, et al., Biochemistry 9, 2858 (1970); R. Y. Wang, et al., Nucleic Acids Res 8, 4777 (1980); H. Hayatsu and M. Shiragami, Biochemistry 18, 632 (1979)).

Bisulfite sequencing usually entails PCR amplification of a region of bisulfite-treated genomic DNA containing the cytosines of interest, followed by sequencing of PCR clones. Cytosine to thymine transitions will be observed at all unmethylated cytosines (M. Frommer et al., Proc Natl Acad Sci USA 89, 1827 (1992)). To test whether the bulky cytosine 5-methylenesulfonate adduct impedes PCR amplification of the treated DNA, we generated DNA templates containing cytosine, 5-methylcytosine or 5-hydroxymethylcytosine as their sole cytosine species, as shown in FIG. 24. To do this, we PCR-amplified a 201 bp oligonucleotide using the nucleoside triphosphates dATP, dGTP, dTTP with dCTP or its 5-methylcytosine or 5-hydroxymethylcytosine derivatives. The PCR products were treated with bisulfite, exposed to conditions promoting deamination and desulfonation, and amplified with the primers: SEQ ID NO: 7: ATTGTCGTAGGTTAAGTGGATTGTAAGGAGGTAG and SEQ ID NO: 8: ATTCACTACCACTCTCCT-TACTTCTCTTTCTCC (reverse primer used for primer extension).

Under these conditions, 5-hydroxymethylcytosine-containing DNA was very poorly amplified compared to cytosine- and 5-methylcytosine-containing DNA. Sequencing of the amplified DNA confirmed that bisulfite-treated 5-hydroxymethylcytosine did not undergo cytosine→thymine transitions, demonstrating, as expected, that 5-hydroxymethylcytosine and 5-methylcytosine cannot be distinguished by the bisulfite technique. Since 5-hydroxymethylcytosine is present in embryonic stem (ES) cells at a level ~10% of 5-methylcytosine (M. Tahiliani et al., Science 324, 930 (2009)), it is likely that a proportion of the regions identified as methylated in the ES cell genome (C. R. Farthing et al., PLoS Genet 4, e1000116 (2008); B. H. Ramsahoye et al., Proc Natl Acad Sci USA 97, 5237 (2000)) are actually hydroxymethylated.

Figure 25:
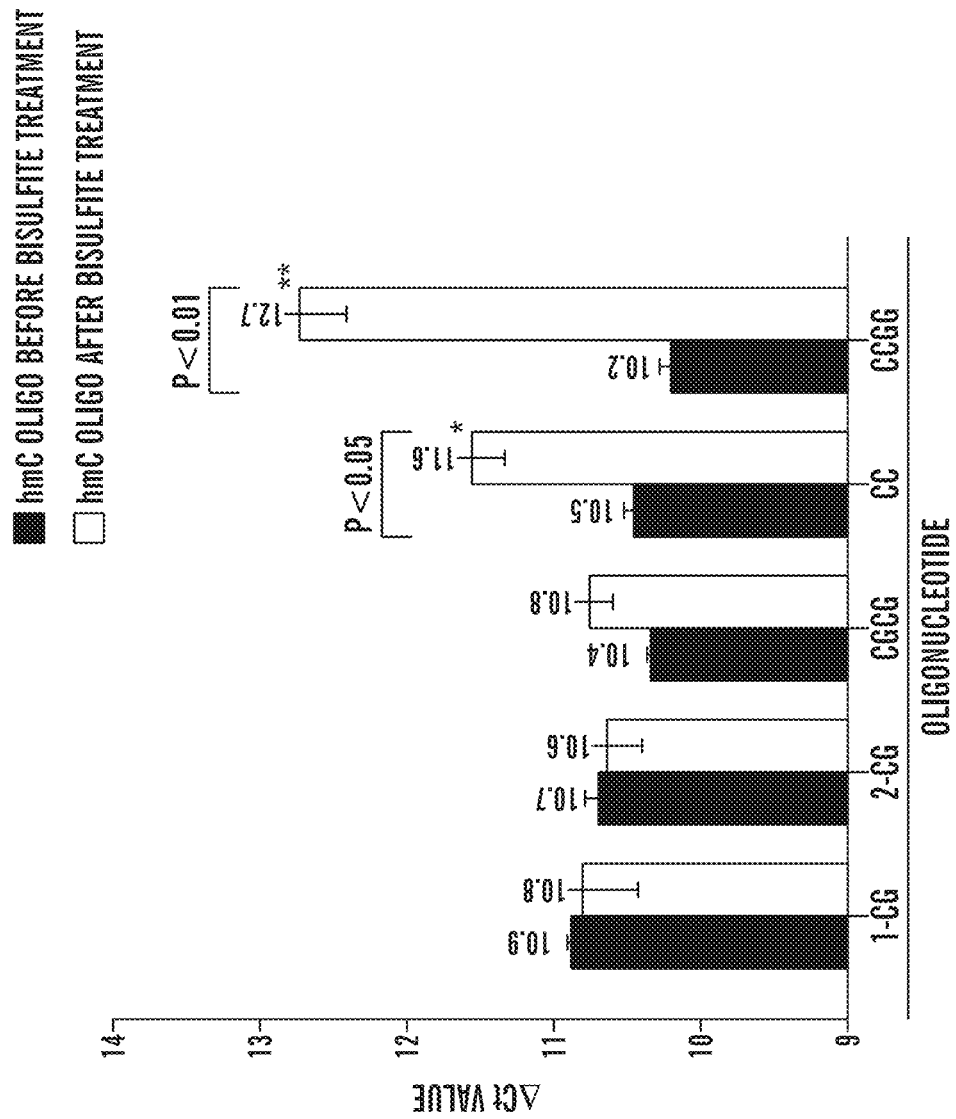
FIG. 25 shows the results of real-time PCR analysis of various oligonucleotides before and after bisulfite treatment, expressed as a change in cycle threshold.

To determine if a block in PCR amplification occurred, we performed primer extension assays using two commercial sources of Taq polymerase. A ladder of incomplete extension products was seen only with bisulfite-treated, 5-hydroxymethylcytosine-containing DNA, in which the 5-hydroxymethylcytosine had been converted to the bulky cytosine 5-methylenesulfonate. The most significant stalling occurred at positions across from a CTC sequence close to the end of the reverse primer, and a CCGC sequence and several CC sequences further away. We also found that there were cytosine residues where stalling was weak or did not occur. Thus, cytosine 5-methylenesulfonate stalls but does not block Taq polymerase, and the stalling is particularly striking when two cytosine 5-methylenesulfonate residues are adjacent (FIG. 25).

In mammalian DNA, 5-methylcytosine (and therefore its hydroxylated derivative, 5-hydroxymethylcytosine) are found almost exclusively in the context of the dinucleotide CpG (B. H. Ramsahoye et al., Proc Natl Acad Sci USA 97, 5237 (2000); Y. Gruenbaum, et al., FEBS Lett 124, 67 (1981); M. Ehrlich, R. Y. Wang, Science 212, 1350 (1981)). To evaluate the degree to which CMS would stall Taq polymerase in this physiological context, we synthesized a set of 158 bp oligonucleotides in which the top strand contained one common CG dinucleotide (in the sequence TCGA, highlighted in FIG. 24B) and a second variable sequence that was one of the following: GGAT, CGAT, CCAT, CGCG, or CCGG (indicated by XXXX in FIG. 24B). After bisulfite treatment, the most significant stalling was observed at the tandem CC sequences in the CC and CCGG oligonucleotides. A minor amount of stalling was observed at the same position in the 2-CG (two non-continuous CGs) and CGCG oligonucleotides. Nevertheless, the 1-CG, 2-CG and CGCG oligonucleotides were efficiently amplified after bisulphite treatment, whereas oligonucleotides containing CC sequences showed a perceptible decrease in amplification efficiency (FIG. 25). The primers used for amplification were: SEQ ID NO: 9: GTGAAATATTGTGGTAGGT-TAAGTGGATTGTAAGGAG and SEQ ID NO: 10: CATCTTAATTAACACTACCACTCTCCT-TACTTCTCTTTCT.

Figure 27A:
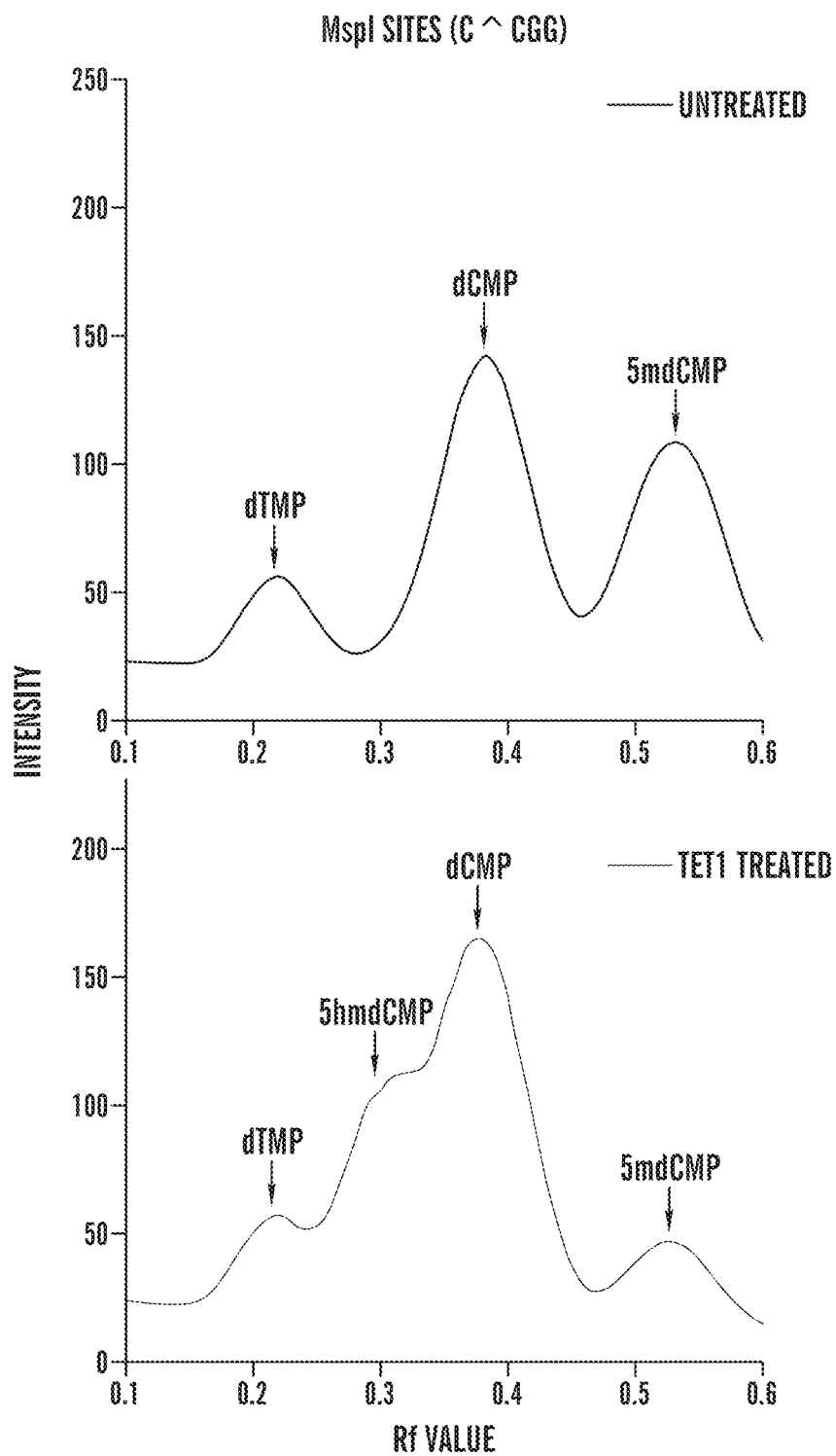
FIG. 27A-27C depicts the line traces of bisulfite treated genomic DNA in the absence or presence of a TET1 catalytic domain.
Figure 27B:
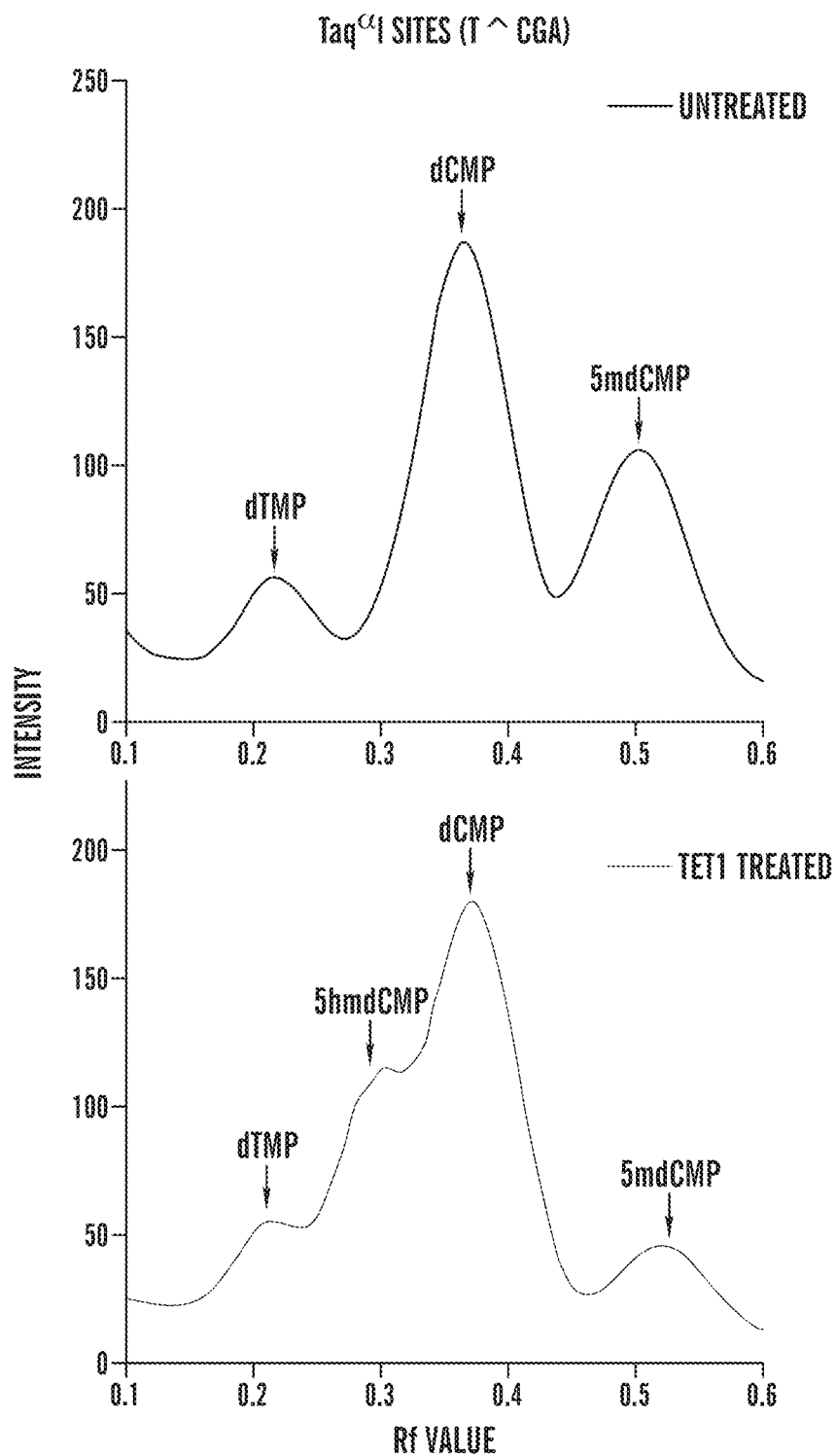
Figure 27C:
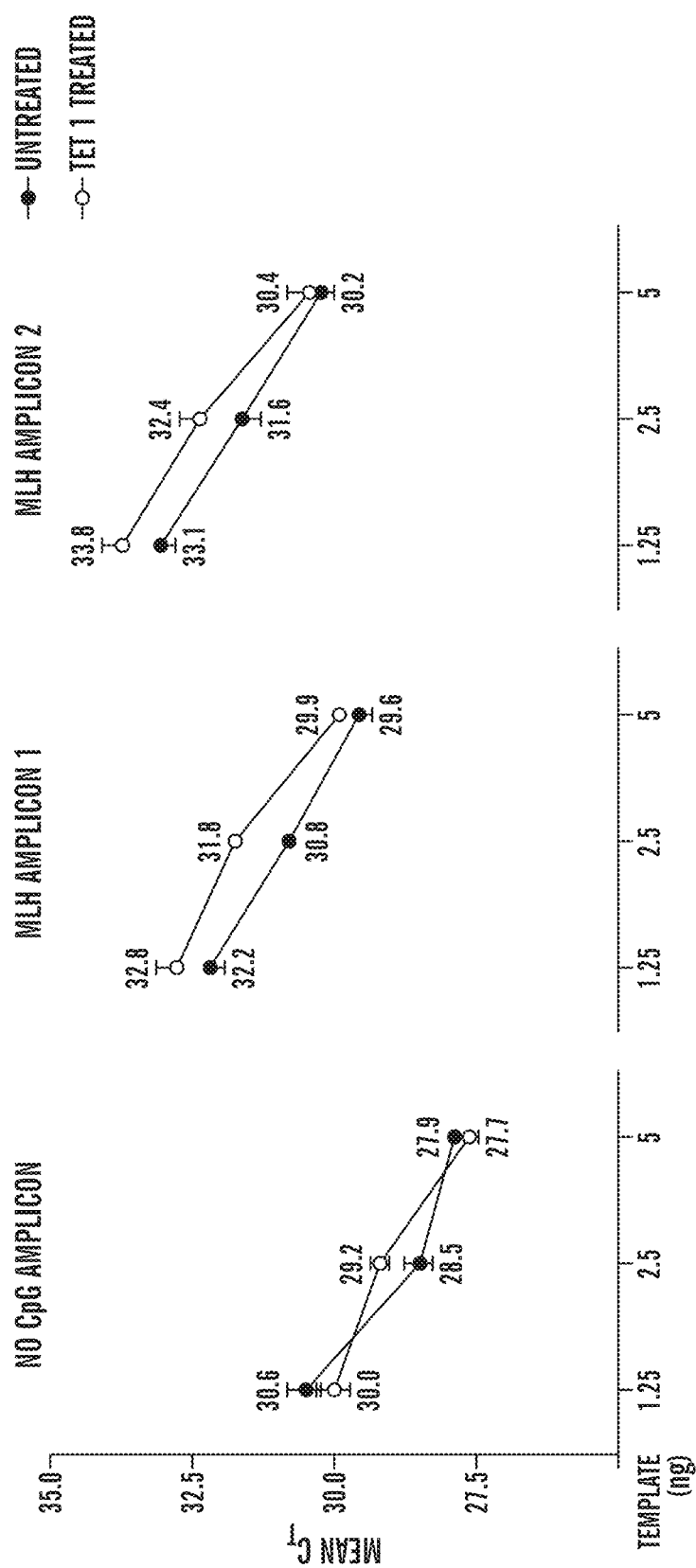

We postulated that if cytosine 5-methylenesulfonate can stall DNA polymerase, genomic loci containing hydroxymethylated DNA might be underrepresented in quantitative methylation analyses. To evaluate this point, we examined the MLH1 locus, which is known to be heavily methylated in HEK293T cells (S. Fukushige, et al., Biochem Biophys Res Commun 377, 600 (2008)). We confirmed this point by bisulfite sequencing of genomic DNA purified from HEK293T cells (FIG. 26). The primers used to sequence were: SEQ ID NO: 11: GTGAATTAAGGAT-TTTTTTGTGTG and SEQ ID NO: 12: AAAAAACAT-TTCCCTACTTC. Two different amplicons in the MLH1 locus were shown to contain more than 10 highly methylated CpGs; methylated cytosines, which do not undergo C→T transitions, are shown in bold, whereas partially methylated C's which yielded a mixture of C and T after bisulfite sequencing, are highlighted and indicated by Y (FIG. 26). The primers we used to amplify the MLH1 locus amplicons were: SEQ ID NO: 13: GTTAGATTATTT-TAGTAGAGGTATATAAGT and SEQ ID NO: 14: ACCAATCAAATTTCTCAACTCTAT; and SEQ ID NO: 15: TGAGAAATTTGATTGGTATTTAAGTTG and SEQ ID NO: 16: CAATCATCTCTTTAATAACAT-TAACTAACC. We then treated the genomic DNA with the recombinant catalytic domain of TET1 in vitro. Roughly 80% of 5-methylcytosine in MspI or Taqα 1 sites was converted to 5-hydroxymethylcytosine (FIG. 27). Real-time PCR analysis showed that untreated and TET1-treated (hydroxymethylated) DNAs were amplified with almost identical efficiency (FIG. 26), even though each amplicon contained more than 10 highly methylated CpGs.

In summary, we have shown that the bisulfite technique for DNA methylation analysis does not distinguish between 5-hydroxymethylcytosine and 5-methylcytosine; that loci containing dense regions of hydroxymethylated DNA may be underrepresented in quantitative methylation analyses; and that primer extension reactions conducted with bisulfite-treated DNA would be predicted to terminate disproportionately at sites of hydroxymethylation. It should be possible to take advantage of our findings, combining ligation-mediated PCR with primer extension under suboptimal extension conditions to determine the location of 5-hydroxymethylcytosine in the genome. It is unclear how CMS inhibits PCR. Rein et al. proposed that CMS would block DNA polymerase by analogy to oxidative pyrimidine adducts such as thymine glycol (T. Rein, et al., Nucleic Acids Res 26, 2255 (1998)). However, CMS retains aromaticity, whereas it has since been demonstrated that polymerases are disrupted by thymine glycol's loss of aromaticity and consequent adoption of a chair geometry (P. Aller, et al., Proc Natl Acad Sci USA 104, 814 (2007)). Whatever the mechanism, the observation that 5-hydroxymethylcytosine can stall Taq polymerase after bisulfite reactions may have important ramifications for our interpretation of previous DNA methylation analyses as discussed above.

Materials and Methods

Minigenes were designed for generation of DNA templates containing cytosine, 5-methylcytosine or 5-hydroxymethylcytosine. Minigenes used as templates to amplify cytosine, 5-methylcytosine or 5-hydroxymethylcytosine containing oligonucleotides were synthesized by Integrated DNA Technologies. DNA containing cytosine 5-methylcytosine or 5-hydroxymethylcytosine was amplified by PCR using nucleoside triphosphates dATP, dGTP, dTTP with dCTP or its derivatives mdCTP (GE healthcare) or hmdCTP (Bioline). PCR products were run on a 2% agarose gel to confirm correct length and further purified by a gel extraction kit (Qiagen).

Bisulfite treatment and recovery of samples were carried out with the EpiTect Bisulfite kit (QIAGEN) by following manufacturer's instructions. In brief, 2 μg DNA in 20 μL volume was used for each reaction and mixed with 85 μL bisulfite mix and 35 μL DNA protect buffer. Bisulfite conversion was performed on a thermocycler as follows: 99° C. for 5 min, 60° C. for 25 min, 99° C. for 5 min, 60° C. for 85 min, 99° C. for 5 min, 60° C. for 175 min and 20° C. indefinitely. The bisulfite treated DNA was recovered by EpiTect spin column and subsequently sequenced to confirm the efficiency of bisulfite conversion.

RealTime PCR of oligonucleotides was performed on the StepONE plus real-time PCR system (Applied Biosystems) by using the FastStart Universal SYBR Green Master kit (Roche). 0.1 μg DNA template and 0.15 mM primers were used in each reaction. The amplification reaction program was set as: 95° C. for 10 min, 40 cycles of 95° C. for 15 sec, 60° C. for 1 min, and a melt curve analysis step at the end. Data were analyzed by StepONE plus real-time PCR software.

To perform the primer extension assays, reverse primers (50 ng) were end labeled with T4 polynucleotide kinase (T4 PNK) (NEB) and 10 μCi of [γ-32P]-ATP (PerkinElmer) for 1 hr at 37° C., and then purified by Illustra MicroSpin G-25 column (GE Healthcare). For the primer extension, 2 ng template, 4 pmol γ32-P-labeled primers were used. PCR reactions were set up according to manufacturer's instructions using two commercial sources of Taq DNA polymerase (Roche and Sigma). For Roche Taq DNA polymerase, the PCR condition was set as: 95° C. for 10 min, 30 cycles of 95° C. for 15 sec, 60° C. for 1 min. For Sigma TagRED polymerase, the PCR condition was set as: 30 cycles of 94° C. for 1 min, 55° C. for 2 min and 72° C. for 1 min. The primer extension products were mixed with 2× gel loading buffer II (Ambion), denatured at 95° C. for 15 min and loaded to 12% polyacrylamide gel denaturing (7 M urea). Sanger sequencing were performed using Thermo Sequenase Dye Primer Manual Cycle Sequencing kit (USB). 2 ng template and 1 pmol [γ32-P]-labeled primer were used for Sanger sequencing. The results were visualized by autoradiography.

Real Time PCR of bisulfite treated genomic DNA was performed by extracting genomic DNA from HEK293 cells (as described in (H. Hayatsu, et al., Biochemistry 9, 2858 (1970)), and shearing the DNA by vortexing to facilitate pipeting. Recombinant human TET1 catalytic domain (CD) was expressed in insect cells as in (H. Hayatsu, et al., Biochemistry 9, 2858 (1970)). 12 μg of DNA was then reacted with 18 μg of TET1-CD in 50 mM HEPES pH 8.0, 50 mM NaCl, 2 mM Ascorbic Acid, 1 mM alpha-ketoglutarate, 100 μM FAS, and 1 mM DTT. The total reaction volume was 300 μL and the reaction ran 90 minutes at 37° C. The WT sample was subjected to the same reaction conditions without enzyme.

The DNA was then ethanol precipitated by the addition of 0.1 volume of 3 M sodium acetate pH 7.4, linear polyacrylimide, and 3 volumes of ethanol, followed by freezing and spinning at 16000 g for 30 minutes at 4° C. The sample was then washed twice with 70% ethanol, air dried, and resuspended in 10 mM Tris 0.1 mM EDTA. Resuspension proceeded overnight with gentle shaking at 45° C. About 500 ng of the DNA was digested with MspI or Taqα I, end labeled, digested to single nucleotides, and run on TLC as described. The data was analyzed on a phosphorimager. The strong cytosine peak seen in this work comes from the fact that we sheared the DNA beforehand, resulting in breaks not created by the enzyme which were end-labeled. This did not confound interpretation of methylation loss or the extent of hydroxymethylation.

The DNA was bisulfite treated as described above, and was quantified afterward using a Nanodrop (NanoDrop DN-1000 spectrophotometer, Thermo Scientific). Bisulfite treated DNA can no longer reanneal, so an absorbance constant typical of single stranded DNA (33 μg DNA/(mL*OD260 units) was used. Bisulfite treatment changes the absorption properties of DNA so the estimated quantities could be off, but any error would be approximately consistent between the TET-CD treated and WT samples.

The primers used in the PCR of the CGless region in FIG. 26 and FIG. 27 were designed with the Bisearch Primer Design tool (R. Y. Wang, et al., Nucleic Acids Res 8, 4777 (1980)). A long stretch of DNA, arbitrarily chosen, lacking CpGs was used as input for the program, though a CpG had to be typed into the middle of the sequence to allow the input sequence to be processed. The primers used for the MLH promoter were taken from (Fukushige), with a couple bases added to raise their melting temperature.

The Real Time PCR was performed using the FastStart Universal SYBR Green Master kit (Roche), with each primer present at a final concentration of 0.15 mM. PCR was run on a StepOnePlus Real Time PCR System (Applied Biosystems), programmed to undergo an initial 10 minute 95° C. step; fifty cycles of 95° C. for 15 s, 50° C. for 30 s, 60° C. for 90 s; and a melt curve analysis step at the end. PCR products were run on an agarose gel to confirm that the correct sized product was formed as the dominant band.

Real Time PCR product was handled using different pipets than were used to set up PCRs, and also handled on different surfaces, to prevent cross-contamination.

The Effect of 5-Hydroxymethylcytosine on Sodium Bisulfite-Based Analysis of DNA Methylation Status DNA methylation at the carbon-5 position of cytosine (5-methylcytosine, also regarded as the "fifth" base) is a stable epigenetic mark found in eukaryotes that imparts an additional layer of heritable information upon DNA. In normal cells, DNA methylation plays vital roles in embryogenesis and development, regulation of gene expression, silencing of transposable elements, and genomic imprinting. In cancer cells, DNA hypermethylation in CpG-island-promoters has been linked to aberrant silencing of tumor suppressor genes. Epigenomic profiling of DNA methylation could serve as marker of cancer cells and indicator for tumor prognosis, as well as useful predictor of response to chemotherapy.

We have shown that 5-hydroxymethylcytosine is present in mammalian DNA, and that a novel family of proteins, the TET proteins, is capable of converting 5-methylcytosine to 5-hydroxymethylcytosine both in vitro and in vivo.

Bisulfite sequencing has been one of the most widely-used techniques for global profiling of cytosine methylation patterns. Bisulfite sequencing relies on the fact that reaction with bisulfite promotes the deamination of unmethylated cytosine to yield uracil (read as thymine after PCR). Deamination occurs orders of magnitude more slowly with 5-methylcytosine and 5-hydroxymethylcytosine; 5-methylcytosine reacts poorly with bisulfite whereas 5-hydroxymethylcytosine forms a distinct adduct, cytosine 5-methylsulfonate. Thus, while unmethylated cytosine will be read as thymine, both 5-methylcytosine and 5-hydroxymethylcytosine will still be read as cytosine in subsequent PCR reactions. As a result, all cytosine methylation analyses to date run the risk of conflating 5-methylcytosine and 5-hydroxymethylcytosine. It is highly likely that genomic loci identified as methylated with traditional methods are actually hydroxymethylated.

To test whether this particular modification on 5-methylcytosine would affect bisulfite sequencing or not, we designed a set of experiments by using synthesized 5-hydroxymethylcytosine oligonucleotides and genomic DNA treated with TET protein.

The experimental design for primer extension assays that we used is outlined below. We showed primer extension assays for DNA containing different cytosine species, and compared it besides a Sanger sequencing ladder. We found that ladders of incomplete extension products were only observed in an 5-hydroxymethylcytosine-containing DNA after bisulfite treatment, at positions corresponding to G in Sanger sequencing ladder. We found that less full length product was observed in the extension reaction with 5-hydroxymethylcytosine-containing DNA treated with bisulfite.

We performed primer extension assays of DNA containing CpG combinations: 1CpG, 2CpG, CGCG, CC and CCGG. We showed that the bands corresponding to stalled PCR reaction were notably observed in the 5-hydroxymethylcytosine-containing CC or CCGG oligonucleotides after bisulfite treatment. The stalling effect, though less obvious, was also observed in bisulfite-treated, 5-hydroxymethylcytosine-containing oligonucleotides with CG or CGCG.

We performed Tet treatment of MLH1 promoter amplicons, both of which contained more than ten fully methylated residues as determined by sequencing of bulk PCR product delayed amplification by less than one cycle. Amplification of a region lacking CpGs, and thus 5-hydroxymethylcytosine, was similar in the WT and TET1 treated populations.

We designed a strategy of incorporating 5-methylcytosine and 5-hydroxymethylcytosine into designed oligonucleotides. We confirmed that the 5-hydroxymethylcytosine was successfully incorporated into the oligonucleotide using TLC. Analyzing sequencing traces of 5-hydroxymethylcytosine-containing oligonucleotides before and after bisulfite treatment indicated that bisulfite treated 5-hydroxymethylcytosine did not undergo cytosine to thymine transitions. The control cytosine-containing oligonucleotides completely underwent cytosine to thymine conversion. We performed real-time PCR amplification curve of an oligonucleotide containing cytosine, 5-methylcytosine or 5-hydroxymethylcytosine before and after bisulfite treatment. The small lag observed for the bisulfite-treated cytosine oligonucleotide is due, in part, to the fact that after conversion of cytosine to uracil, this oligonucleotide can only be amplified from one of the two strands. We quantified the $\Delta$Ct value from experiments performed.

In summary, we have shown that the bisulfite technique for DNA methylation analysis does not distinguish between 5-methylcytosine and 5-hydroxymethylcytosine; that loci containing dense regions of hydroxymethylated DNA may be under-represented in quantitative methylation analyses; and that primer extension reactions conducted with bisulfate-treated DNA would be predicted to terminate disproportionately at sites of hydroxymethylation.

It should be possible to take advantage of our findings, in some embodiments, by combining ligation-mediated PCR with primer extension under suboptimal extension conditions to determine the location of 5-hydroxymethylcytosine in the genome. It is unclear how cytosine-5-methylsulfonate inhibits PCR. Rein et al. proposed that cytosine-5-methylsulfonate would block DNA polymerase by analogy to oxidative pyrimidine adducts such as thymine glycol. However, cytosine-5-methylsulfonate retains aromaticity, whereas it has since been demonstrated that polymerases are disrupted by thymine glycol's loss of aromaticity and consequent adoption of a chair geometry. Whatever the mechanism, the observation that 5-hydroxymethylcytosine can stall Taq polymerase after bisulfate reactions may have important ramifications for our interpretation of previous DNA methylation analyses as discussed herein.

The Effect of 5-Hydroxymethylcytosine on Sodium Bisulfite-Based Analysis of DNA Methylation Status Cytosine methylation, typically found in the context of CpG sequences, is critical in vertebrates and performs functions such as regulation of transcription and silencing of transposable elements (W. Reik, Nature 447, 425 (May 24, 2007)). Recently, we predicted that the TET family of proteins would oxidize 5-methylcytosine to 5-hydroxymethylcytosine (L. M. Iyer, et al., Cell Cycle 8, 1698 (2009)). Acting on this prediction, we found that expression of the catalytic domain (CD) of human TET1 in 293T cells caused formation of 5-hydroxymethylcytosine and a corresponding loss of 5-methylcytosine. Recombinant human TET1 CD efficiently oxidized 5-methylcytosine to 5-hydroxymethylcytosine in vitro. We also found that 5-hydroxymethylcytosine is present in mammalian DNA and is particularly abundant in Embryonic Stem Cells. In murine ES cells, siRNA knockdown of Tet1 and Tet2 causes a reduction in observed hydroxymethylcytosine levels (M. Tahiliani et al., Science 324, 930 (2009)). Independently, another group reported the presence of 5-hydroxymethylcytosine in Purkinje neurons (S. Kriaucionis, N. Heintz, Science 324, 929 (2009)).

TET proteins include three recognizable domains. A CXXC domain, which in other proteins is involved in binding of unmethylated CpG motifs, a double-stranded beta-helix (DSBH) which contains the catalytic residues, and a cysteine rich region. The function of this last domain is unclear, but based on its similarity to zinc finger domains and its position relative to the DSBH, it may be involved in DNA binding.

Very little is known about the physiological role of TET proteins or 5-hydroxymethylcytosine. The DSBH of TET1 is found in a fusion with the oncogene MLL in rare leukemias (R. B. Lorsbach et al., Leukemia 17, 637 (2003); R. Ono et al., Cancer Res 62, 4075 (2002)). Null mutations of TET2 are found in a significant fraction of patients with AML or precancerous myelodysplastic disorders, and TET2 is thus believed to be a tumor suppressor that is lost early in the development of myeloid tumors (S. M. Langemeijer et al., Nat Genet 41, 838 (2009); F. Delhommeau et al., N Engl J Med 360, 2289 (2009)). The mechanism of TET's role in cancer is undetermined. Tet2 deficient mice die shortly after birth, again for unknown reasons (H. Tang, et al., Transgenic Res 17, 599 (2008)).

While 5-hydroxymethylcytosine has no known function, without wishing to be limited by a theory, it is thought that it might facilitate demethylation either by "flagging" methylated cytosines for removal or blocking maintenance methylation. Without wishing to be limited by a theory, it may also have a role in blocking 5-methylcytosine binding proteins or recruiting as yet undiscovered 5-hydroxymethylcytosine binding proteins.

Figure 28A:
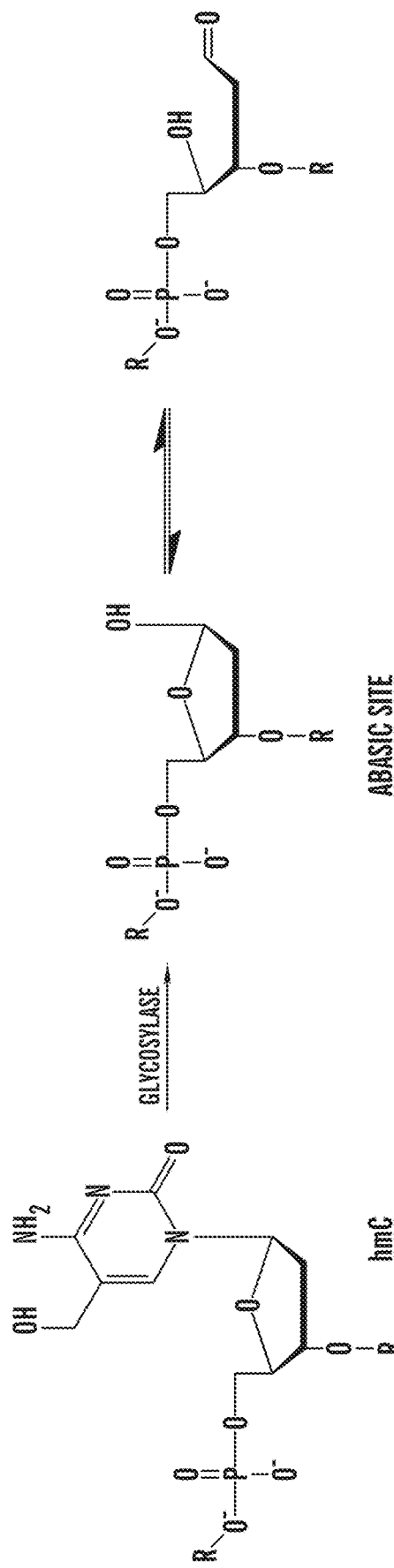
FIG. 28A depicts the generation of abasic sites from 5-hydroxymethylcytosine by glycosylases.
Figure 28B:
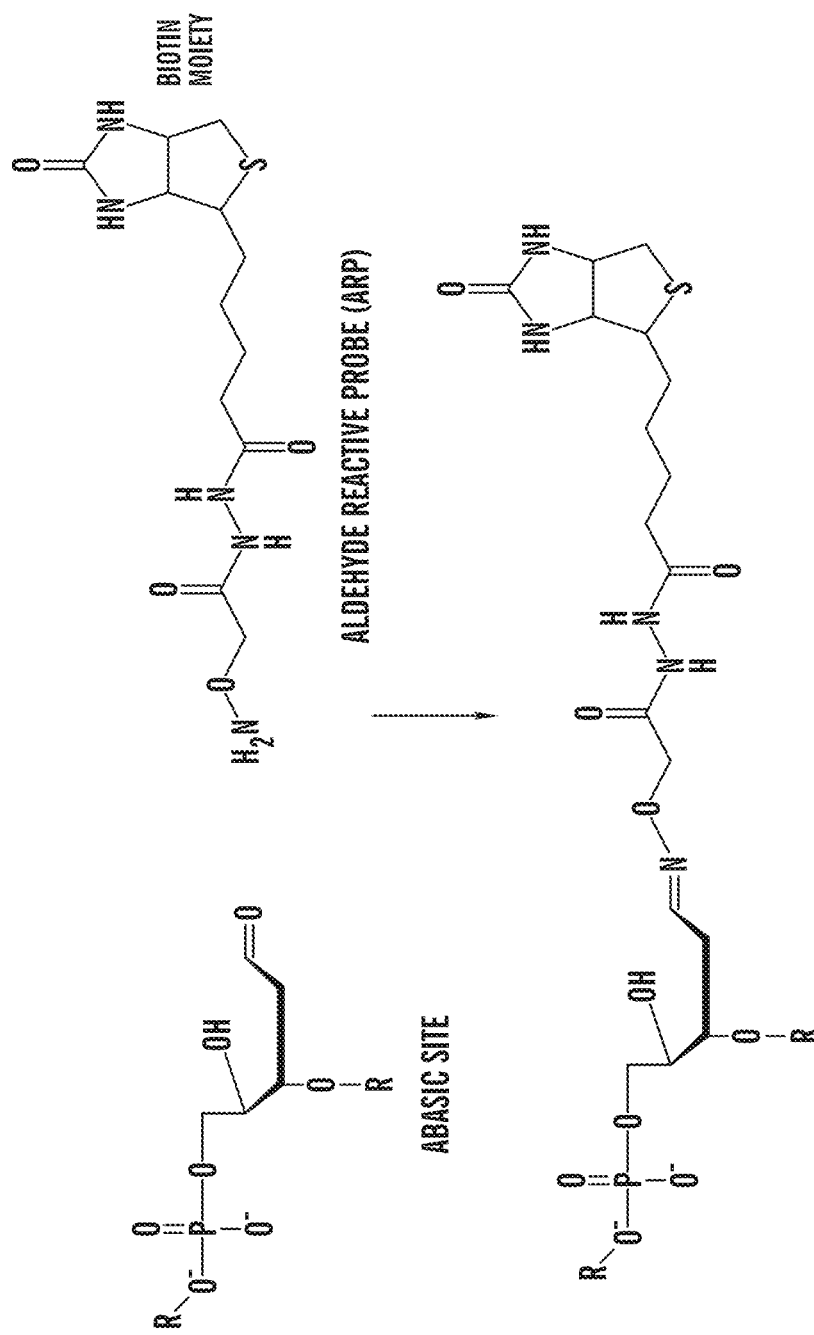
FIG. 28B shows the specific reaction of abasic sites with aldehyde reactive probes.
Figure 29A:
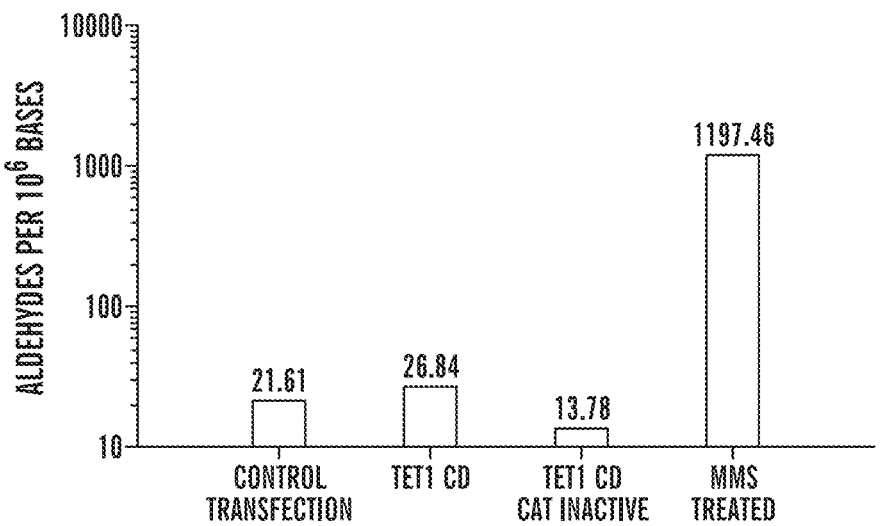
FIG. 29A shows the impact of TET1 expression on aldehyde density.
Figure 29B:
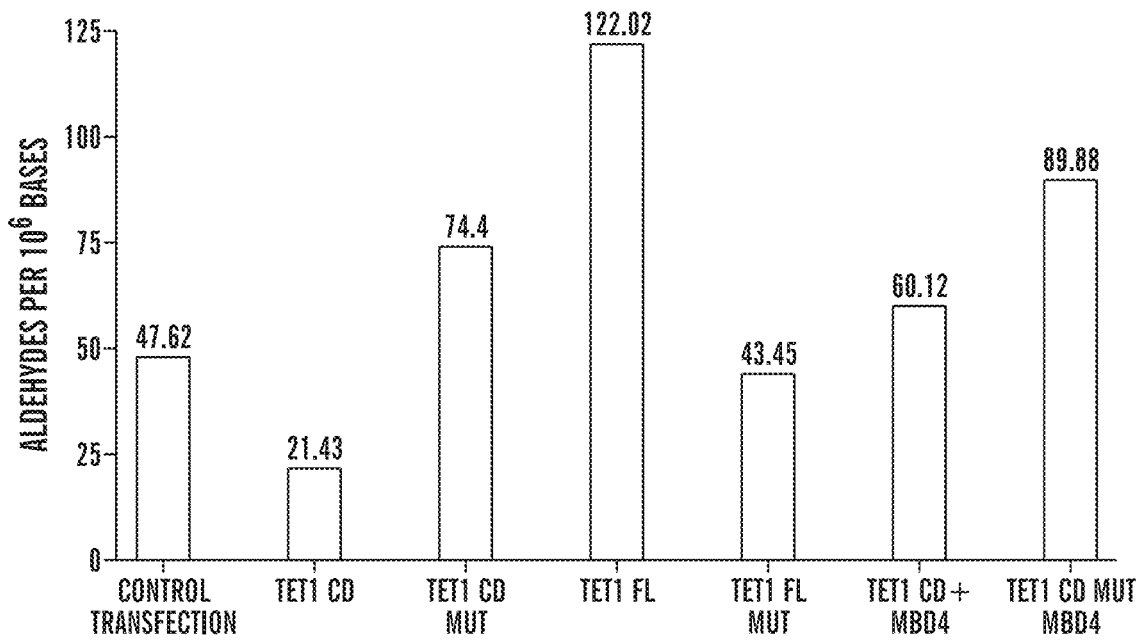
FIG. 29B compares the impact of co-expression of MD4 on abasic sites and aldehyde density.

In one embodiment, we can determine whether hydroxymethylation leads to active and/or passive demethylation of 5-methylcytosine in DNA. As discussed, 5-hydroxymethylcytosine may lead, without wishing to be bound by a theory, to demethylation by an active or passive mechanism. An active mechanism might entail removal of 5-hydroxymethylcytosine by DNA repair machinery, which, without wishing to be limited or bound to a theory, is most likely base excision repair, which is typically used to remove lesions that do not disrupt the broad structure of DNA (V. Valinluck, et al., Nucleic Acids Res 33, 3057 (2005)). Most DNA glycosylases generate abasic sites or 3' phospho a, $\beta$-unsaturated aldehydes, both of which react with an aldehyde specific molecule called ARP (FIG. 28). Removal of these repair intermediates is the rate-limiting step in DNA repair, and thus large scale glycosylase activity would be predicted, without wishing to be constrained by a theory, to generate many aldehydes in DNA which could be measured via ARP. We found that in 293T cells, expression of the TET1 catalytic domain (CD) did not cause a significant increase in aldehyde density (FIG. 29). We considered MBD4 to be a likely glycosylase to remove 5-hydroxymethylcytosine, as it is known to repair the somewhat analogous compound 5-bromocytosine (V. Valinluck, et al., Nucleic Acids Res 33, 3057 (2005)) and it binds to methylated DNA (B. L. Parsons, Proc Natl Acad Sci USA 100, 14601 (2003)). Also, an MBD4 homologue is fused to a distant TET homologue in some algae species (L. M. Iyer, et al., Cell Cycle 8, 1698 (2009)). However, coexpressing MBD4 with TET1 CD did not significantly increase abasic sites (FIG. 29), reduce 5-hydroxymethylcytosine levels, or increase cytosine levels.

Meanwhile, it has become clear that in 293T cells TET's main effect is to convert cytosine to 5-hydroxymethylcytosine. Only a modest rise in cytosine is observed upon TET expression, which could arise via blocking of maintenance methylation as opposed to repair (M. Tahiliani et al., *Science* 324, 930 (2009)). Also, the simple fact that cells can tolerate such high levels of 5-hydroxymethylcytosine would seem to indicate, without wishing to be bound by a theory, that at least in 293T cells, large-scale glycosylase activity is not occurring. We have cloned a number of DNA repair proteins (MBD4, SMUG1, TDG, NTHL1, NEIL1, NEIL2 and APEX1), and can test their involvement in resolution of hydroxymethylcytosine. We can do this by expressing the enzymes in mammalian cells, then determining whether any 5-hydroxymethylcytosine-glycosylase activity is present in lysate by monitoring cleavage of a hydroxymethylcytosine-containing oligo. For example, in one aspect we can express a test glycosylase of interest in 293T cells. We can generate and end-label oligonucleotides, where at least one oligonucleotide has 5-hydroxymethylcytosine residues and another oligonucleotide has a known substrate for the test glycosylase. The glycosylase expressing 293 cells are then lysed and the oligonucleotides are added to the lysate. The oligonucleotides are then exposed to alkaline conditions in order to generate abasic sites on the oligonucleotides. The oligonucleotides are then run on a denaturing gel to detect breaks as described herein. If both the hydroxymethylated and positive control oligonucleotides are cut, it indicates that the test glycosylase recognizes 5-hydroxymethylcytosine. If only positive control oligonucleotide is cut, it indicates that the test glycosylase does not recognize 5-hydroxymethylcytosine. If we observe no cutting of both the hydroxymethylated and positive control oligonucleotides, it indicates that the test glycosylase is not active in conditions used in assay.

In another aspect, we can also determine whether hydroxymethylation blocks maintenance methylation. Without wishing to be bound by a theory, DNMT1 might not efficiently methylate cytosines at CpGs opposite hydroxymethylated CpGs, an observation with some in vitro backing (V. Valinluck, and L. C. Sowers, *Cancer Res* 67, 946 (2007)). Also, it has been observed that methylation activates DNMT1 allosterically (R. Goyal, et al., Nucleic Acids Res 34, 1182 (2006); Z. M. Svedruzic, Curr Med Chem 15, 92 (2008)), and hydroxymethylation may not have this effect. Finally, DNMT1 requires the partner protein UHRF1, which selectively binds hemimethylated CpGs, for localization to newly replicated DNA (M. Bostick et al., Science 317, 1760 (2007); J. Sharif et al., Nature 450, 908 (2007)). Inhibition of UHRF1 binding could also block maintenance methylation.

We have expressed recombinant UHRF1 and showed that it has modestly impaired binding to hemihydroxymethylated, as opposed to hemimethylated, DNA, as determined by an Electromobility Shift Assay (EMSA). We saw some binding to unmethylated DNA, which was not observed in past work (M. Bostick et al., *Science* 317, 1760 (2007); C. Qian et al., *J Biol Chem* 283, 34490 (2008)) possibly because of the use of different blocking agents. We can also better replicate the conditions used in past work and determine the preference for hemimethylated over hemihydroxymethylated DNA under these conditions. We can also determine whether maintenance methylation of hydroxymethylated DNA is impaired. Episomal plasmids have been shown to maintain methylation faithfully through many cell divisions and are relatively easy to manipulate (C. L. Hsieh, *Mol Cell Biol* 14, 5487 (1994)), and we can compare the maintenance of methylated versus hydroxymethylated episomes.

We can also evaluate and discover methods for determining where hydroxymethylcytosine residues are located in DNA.

The discovery of 5-hydroxymethylcytosine in mammalian DNA forces a reassessment of old techniques used to differentiate methylated and unmethylated cytosine. Furthermore, determination of the physiological role of 5-hydroxymethylcytosine requires knowledge of where in the genome 5-hydroxymethylcytosine is located, and we have developed methods of tagging and precipitating 5-hydroxymethylcytosine for use in chromatin immunoprecipitation.

Figure 30:
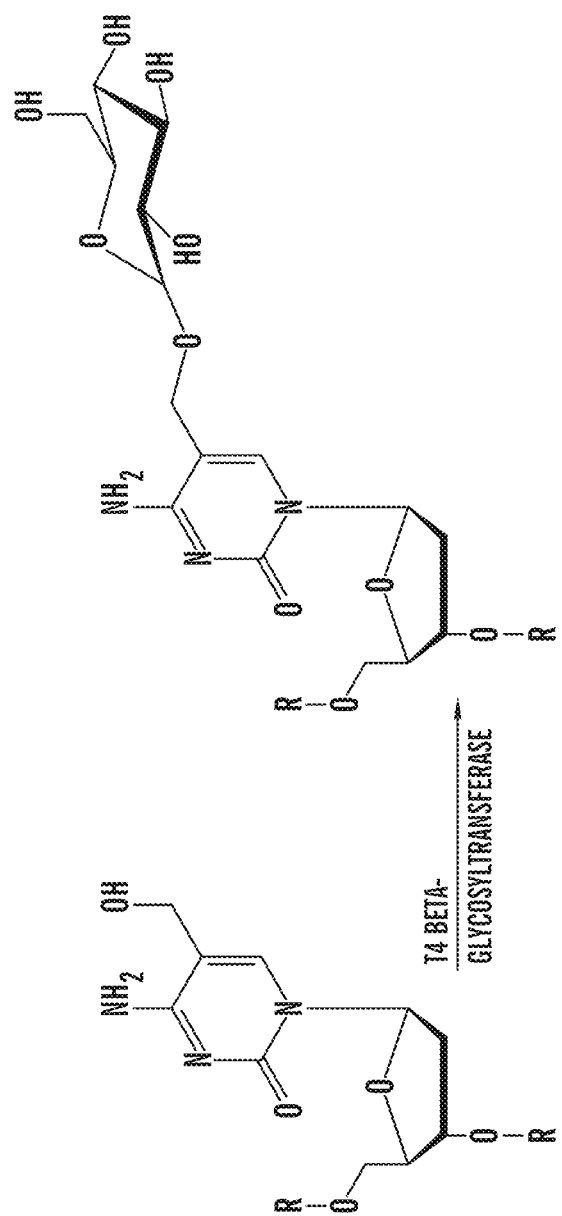
FIG. 30 shows the glucosylation of 5-hydroxymethylcytosine by β-glucosyltransferase.
Figure 31:
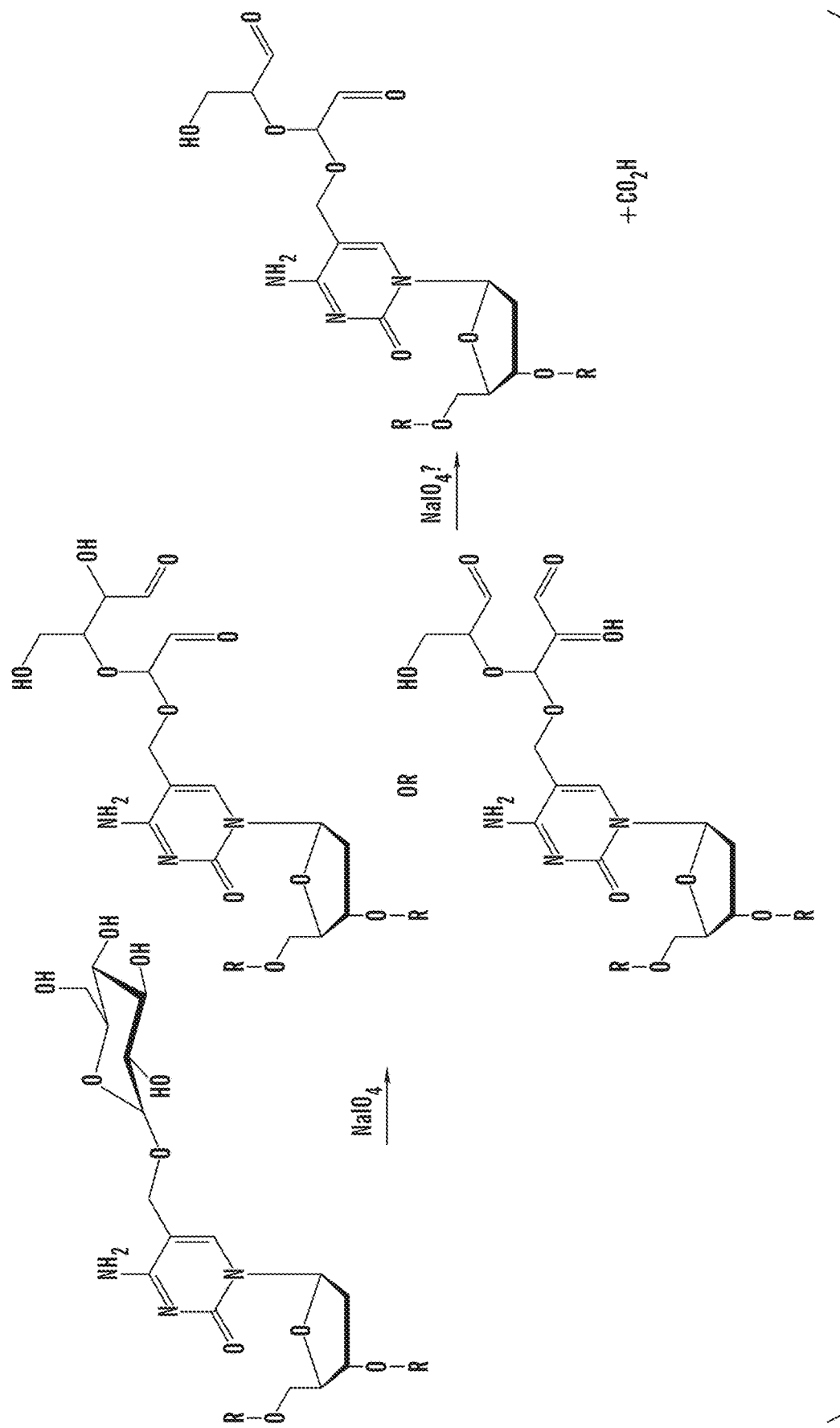
FIG. 31 shows a schematic diagram depicting how the glucosylation of 5-hydroxymethylcytosine can be labeled, using aldehyde quantification.
Figure 32:
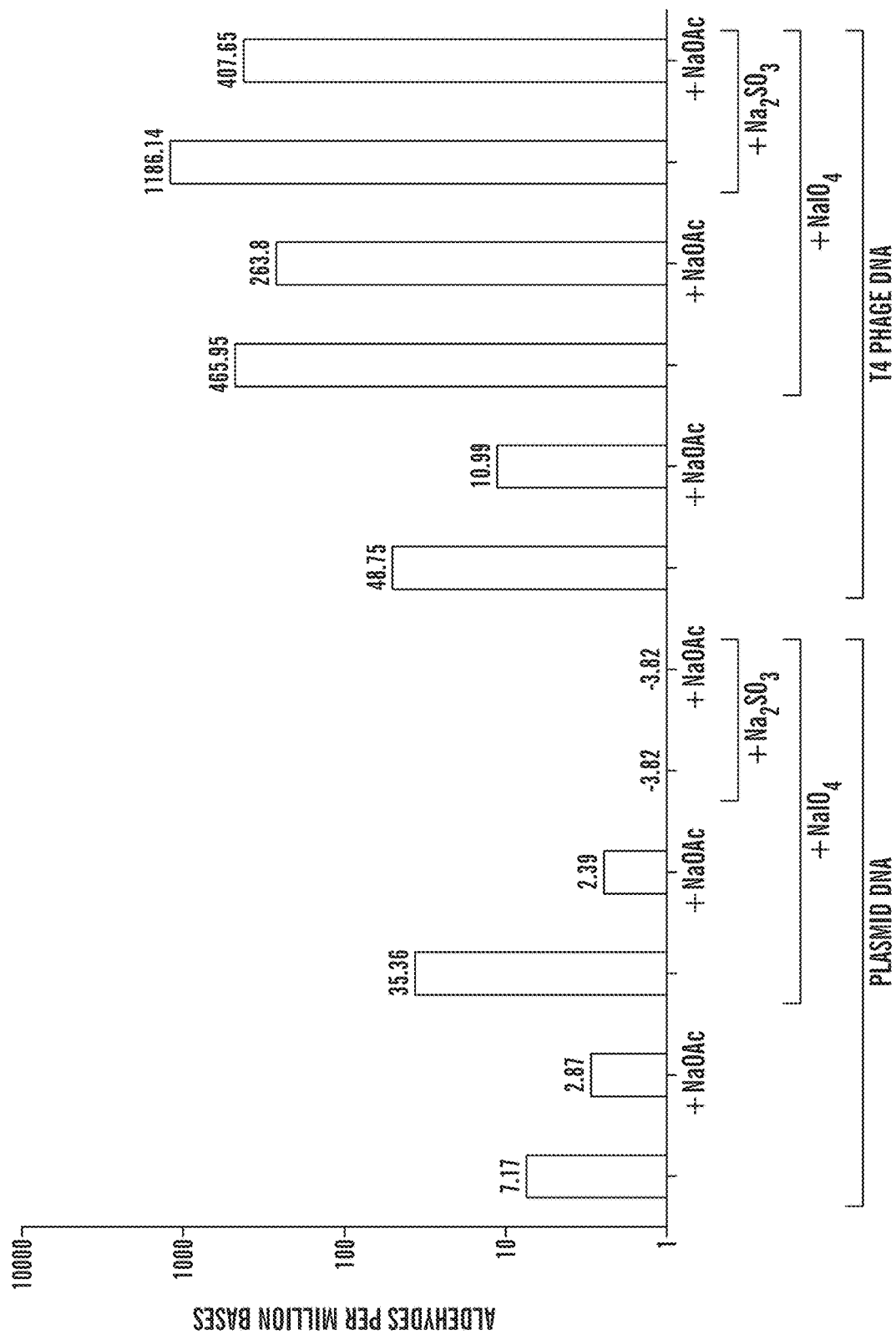
FIG. 32 compares aldehyde quantification of DNA under various conditions, including in the presence of sodium bisulfate treatment and sodium periodate treatment.

In T4 phage, all cytosines are hydroxymethylated and subsequently glucosylated by the enzymes α-glucosyltransferase (AGT) or β-glucosyltransferase (BGT) (S. R. Kornberg, et al., *J Biol Chem* 236, 1487 (1961)) (FIG. 30). We have succeeded in producing recombinant BGT. Thus, we can glucosylate sites of hydroxymethylation, and label them via the mechanism described in FIG. 31. We treated bacterial plasmid and T4 phage DNA with periodate, and then used the same aldehyde quantification method described. Only periodate treated T4 phage DNA showed major aldehyde presence (FIG. 32).

In one embodiment, glucosylation conditions for hydroxymethylated DNA can be optimized, and the extent of glucosylation can be measured by TLC. Periodate treatment can be optimized and binding to beads with hydrazide moieties can be performed, in order to perform specific pulldown of hydroxymethylated and glucosylated DNA. Such methods can be used, for example, to perform chromatin immunoprecipitation (ChIP) to determine sites of in vivo genomic hydroxymethylation.

We can determine likely sites of hydroxymethylation by determining the binding specificities of TET1. We individually expressed domains from TET proteins and tested their DNA binding properties via EMSAs. Other CXXC domains have been found to bind unmethylated CpGs, so we expressed the CXXC domains of TET1 and TET3 to test this specificity. We found that the CXXC domains in TET proteins are very positively charged and seem to bind non-specifically to all DNA in vitro. In parallel, we expressed the CXXC domain of CXXC1, which has been demonstrated to bind to unmethylated CpGs. Under the same conditions used for the TET proteins, this domain bound specifically. We found that the catalytic domain as a whole and the DSBH domain of TET bind DNA, but again with no specificity, not even for methylated CpG, which is TET's substrate. Without wishing to be bound by a theory, this may be due to non-specific binding of DNA to a largely unconserved positively charged region of the DSBH, which is unlikely to actually interact with DNA in vivo because of its predicted position on the protein.

In one aspect, we can also generate mice in which one or more of the TET family genes is genetically ablated ("knock-out mice"), in a lineage specific or inducible manner ("conditional knock-out mice"). We have successfully generated Tet1 and Tet2 conditional knock-out mice. We have successfully generated Tet3 conditional KO mice possessing a high degree of chimerism, and are confirming germline transmission, after which we can breed mice fully deficient for Tet3 and analyze their phenotype. We have shown that Tet3 is expressed in many tissues, so subsequent experiments on the mice will be guided by phenotype.

Identifying 5-Hydroxymethylcytsoine Using Antibodies to Cytosine Methylene Sulfonate The invention also provides, in part, the use of antibodies to cytosine methylene sulfonate to identify 5-hydroxymethylcytosine residues in genomic DNA and for the isolation of such 5-hydroxymethylcytosine residue comprising DNA by immunoprecipitation, for use, for example, in analyses of cancer cells.

We have produced a rabbit antiserum specific for cytosine methylene sulfonate, the product of bisulfite treatment of 5-hydroxymethylcytosine, and have shown that this antiserum is highly specific for, and can be used to quantify, the quantity of 5-hydroxymethylcytosine residues present in a sample, such as genomic DNA. We have shown that this rabbit antiserum can be used to demonstrate the inhibition of TET family activity, for example, when TET family activity is inhibited by the use of one or more siRNAs specific for TET family members, such as TET1 or a combination of TET1 and TET2. For example, a bisulfite treated sample, such as a genomic DNA sample, can be digested with an enzyme, such as Mse1, which cleaves at TTAA sequences. The digested DNA can then be end-labeled with $^{32}$P. The digested and labeled DNA can then be incubated with an antibody or antiserum specific for cytosine methylene sulfonate, and immobilized, for example, with anti-rabbit IgG beads. Radiation counts can then be determined using scintillation counters, and the radiation count data used to ascertain the amount of 5-hydroxymethylcytosine present in the DNA. An example of such an assay is shown in FIG. 19.

In another such example, genomic DNA from ES cells, either transfected with siRNA sequences specific for one or more TET family members, such as TET1 or a combination of TET1 and TET2, is bisulfite treated, digested with an enzyme, and labeled and incubated with antiserum specific for cytosine methylene sulfonate, and the amount of cytosine methylene sulfonate residues can be quantified against a standard curve generated using a known oligo containing cytosine methylene sulfonate. The impact of TET family inhibition on the generation of 5-hydroxymethylcytosine can then be compared between the samples. The presence of less cytosine methylene sulfonate in a sample treated with a TET family inhibitor, such as an siRNA sequence, is indicative of the specificity of that siRNA for the TET family member.

Figure 33:
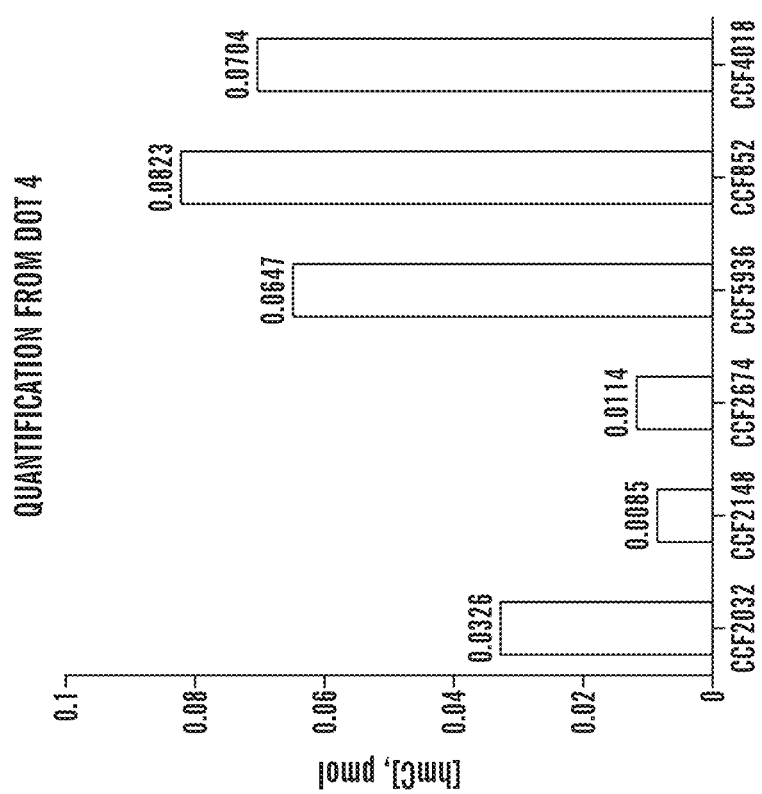
FIG. 33 quantifies the amount of 5-hydroxymethylcytosine present in samples obtained from patients diagnosed with cancer with or without mutations in TET2.

In yet another example, the amount of 5-hydroxymethylcytosine in a patient having mutations in one or more TET family members and suffering from a malignant condition, can be ascertained using bisulfite treatment of DNA obtained from such a patient, where the DNA is then assayed for cytosine methylene sulfonate quantity using the antiserum described herein, as shown in FIG. 21 and FIG. 33. Genomic DNA was isolated from patients having the following mutations in TET2, and diagnosed with the cancerous conditions shown in parentheses:

CCF2032-S631stop-somatic (CD3 negative), heterozygous mutation, (MDS/MPD, MDS/MPD-U<5%)
CCF2148-S509stop-somatic (CD3 negative), hemizygous mutation, pt with del4q24, (MDS, RARS)
CCF2674-ins1310T-somatic (CD3 negative), homozygous mutation, pt with UPD4q, (MDS/MPD, CMML-1)
CCF5936-ins318A-homozygous mutation, SNP-A results pending, (CML)
CCF852-WT TET2, (MDS/MPD, CMML-2)
CCF4018-WT TET2, (MDS/MPD, CMML-1)

The isolated DNA was then either bisulfite treate or left untreated, digested and labeled with $^{32}$P. The bisulfite treated DNA was incubated with antiserum specific for cytosine methylene sulfonate, while the untreated DNA was incubated with antibodies specific for 5-hydroxymethylcytosine to immunoprecipitate the genomic regions having 5-hydroxymethylcytosine. The immunoprecipitated DNA was then run on gels as dot blots and analyzed using phosphoimaging, compared to serial dilutions of a standard control having a known quantity of cytosine methylene sulfonate or 5-hydroxymethylcytosine, such as cytosine methylene sulfonate or 5-hydroxymethylcytosine oligonucleotides. In the examples shown in FIG. 21 and FIG. 33, we show that patients CCF2148 and CCF2674 have significantly less 5-hydroxymethylcytosine, when compared to patients CCF852 and CCF4018, having wild-type TET2. This demonstrated that the somatic mutations in TET2 in patients CCF2148 and CCF2674 directly are functional and directly impact TET2-mediated conversion of 5-methylcytosine to 5-hydroxymethylcytosine.

Role of TET Proteins in Leukemia

It has been observed that there are a high frequency of TET2, but not TET1 and TET3, mutations in various myeloid cancers, including MDS, MPD, AML, secondary AML, systemic mastocytosis, and CMML. It has been shown that TET2 is the most commonly mutated gene in MDS, and thus serves as a very useful prognostic marker.

Figure 34:
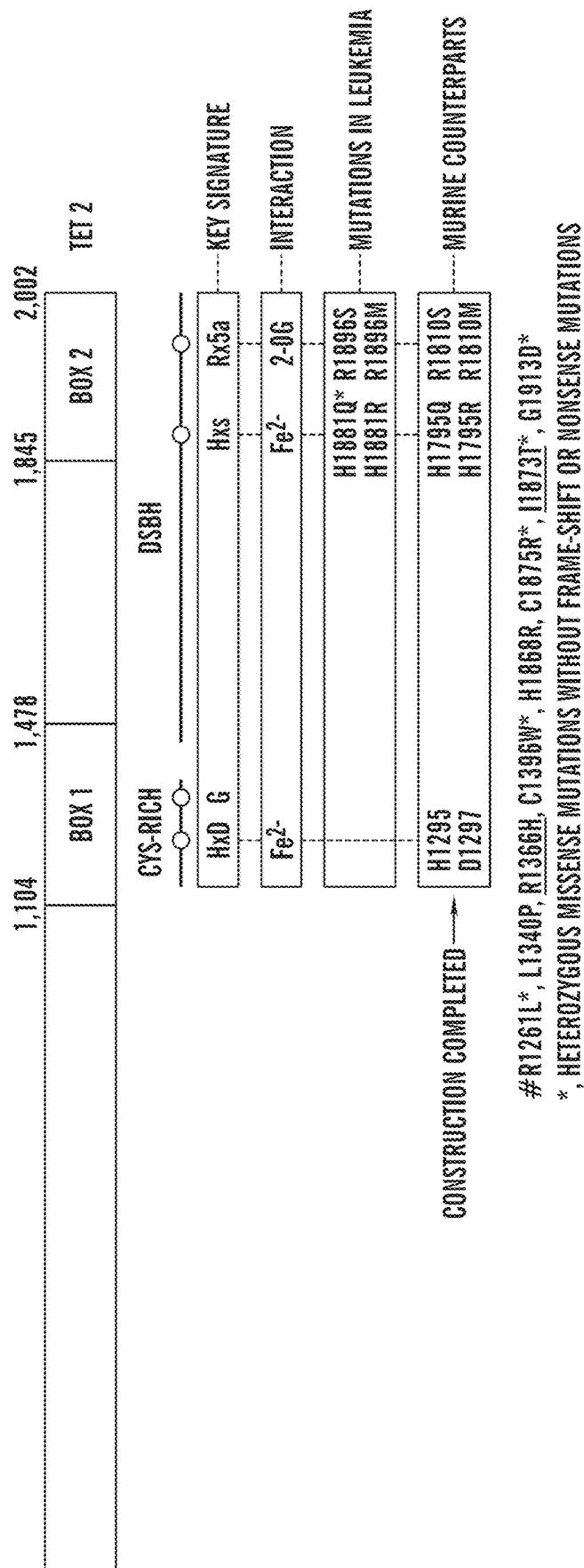
FIG. 34 shows a schematic depicting the sites of various mutations found in TET2.

TET2 mutations are present in both multipotent and committed progenitor cells from MPD patients. TET2 mutations have been found in patients with both JAK2 V617F-positive and -negative MPD, and these mutations have been proposed to be a pre-JAK2 event. It has been shown that there is an enrichment of TET2 missense mutations, without frame shift or nonsense mutations, or deletions, in two conserved regions that cover the catalytic core of TET proteins that contain C and D domains, as shown in FIG. 34. We postulate that these numerous heterozygous missense mutations have dominant negative roles to promote malignant transformation.

Figure 35A:
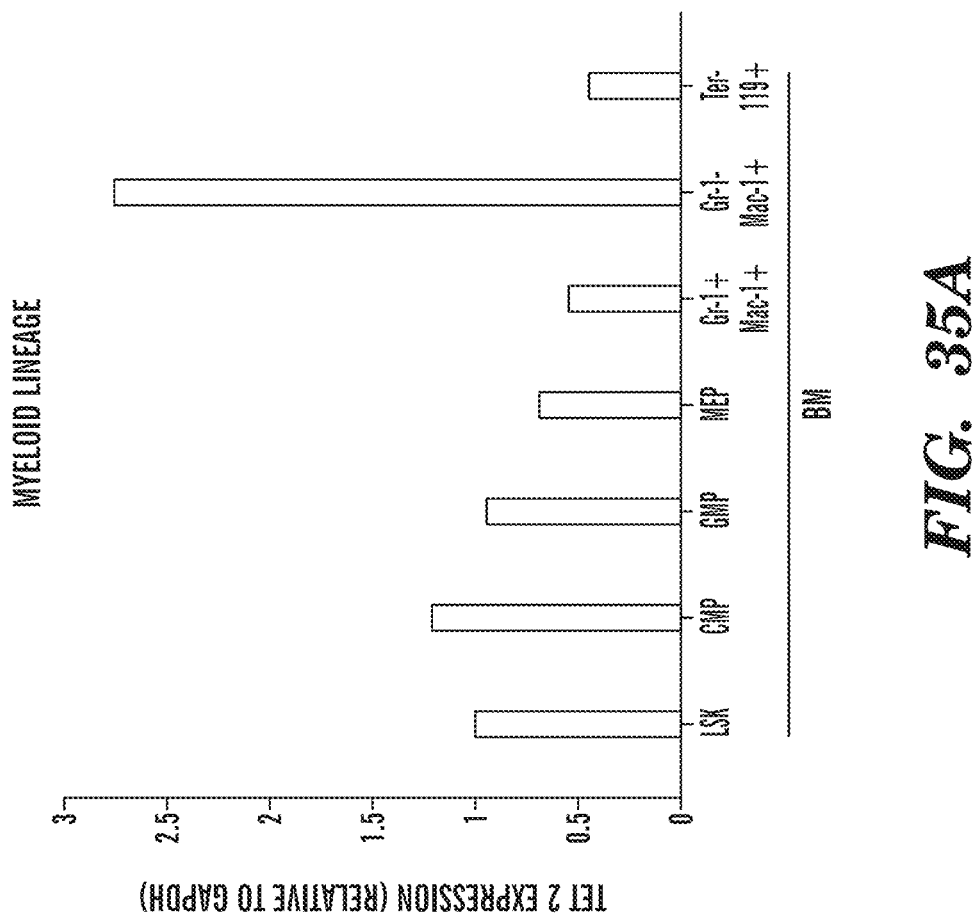
FIGS. 35A-B shows the expression of Tet2 in various myeloid and lymphoid lineage populations isolated from bone marrow and thymus.
Figure 35B:
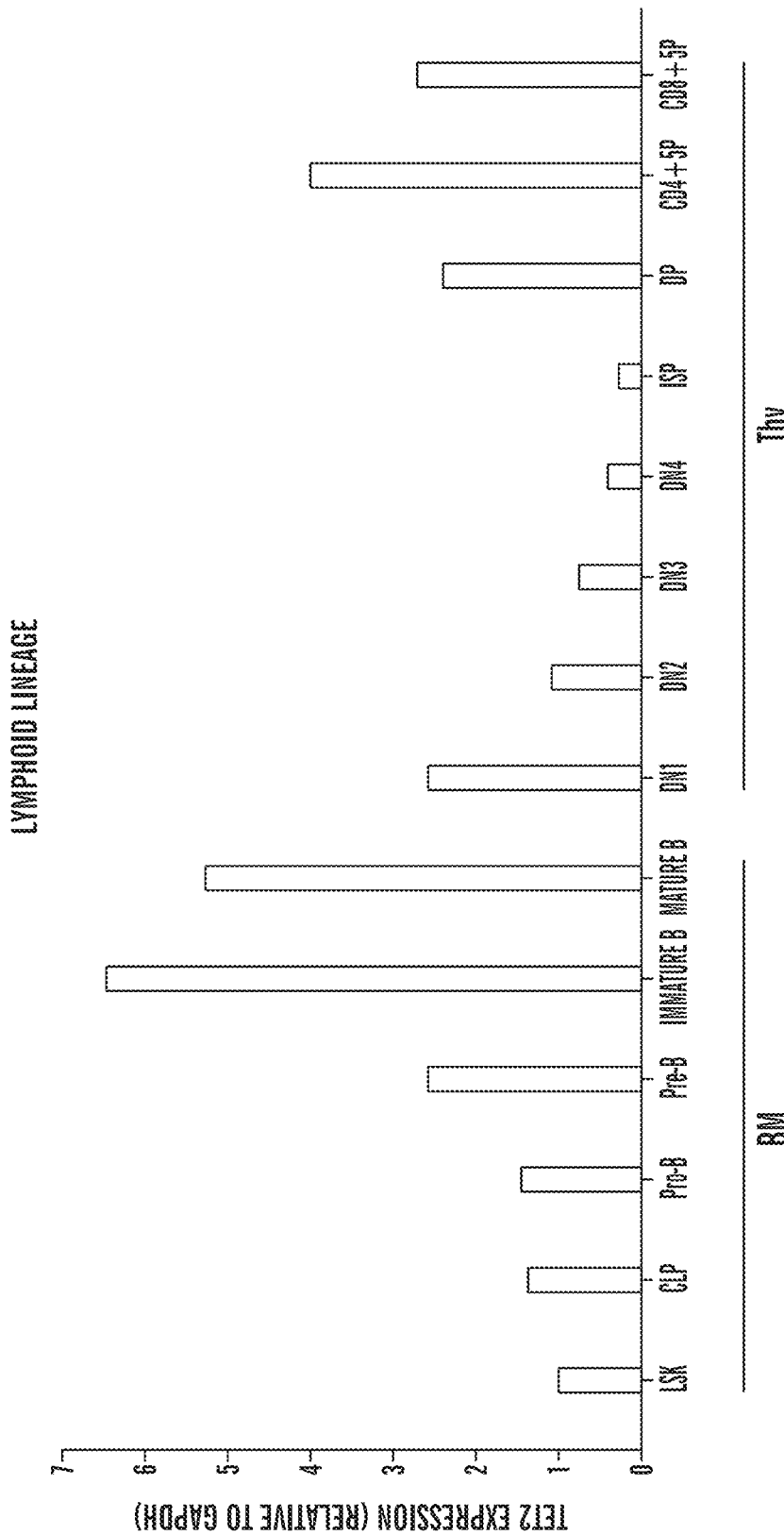
Figure 36A:
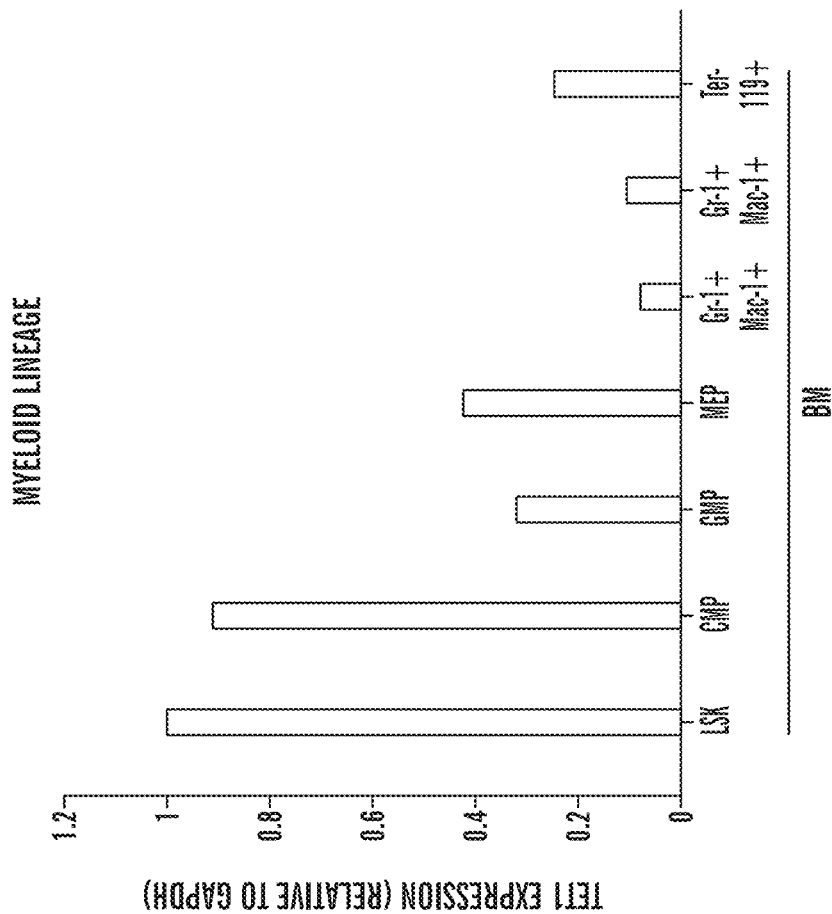
FIG. 36A-B shows the expression of Tet1 in various myeloid and lymphoid lineage populations isolated from bone marrow and thymus.
Figure 36B:
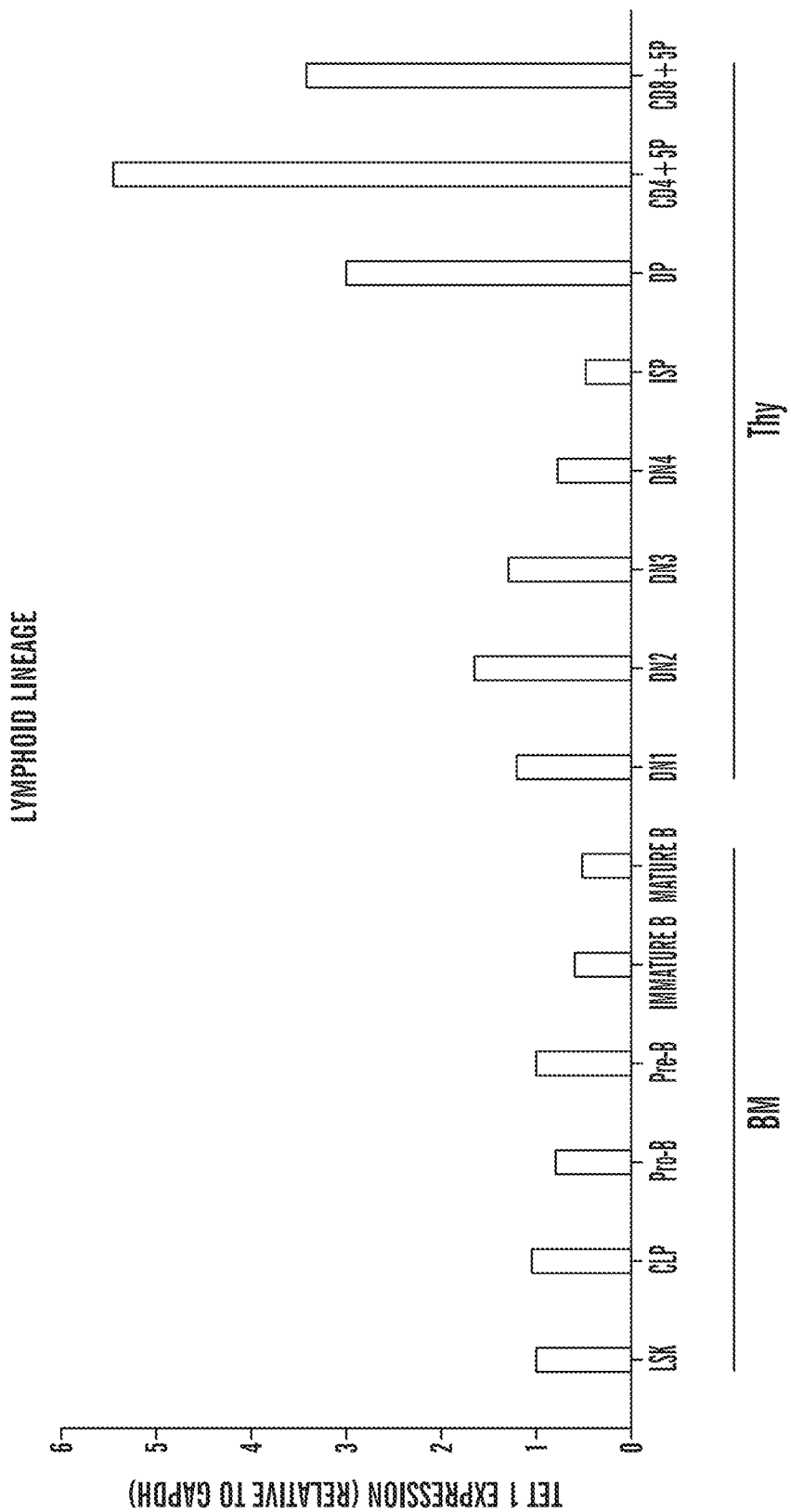

We have shown that TET1 and TET2 have differential expression patterns when both bone marrow and thymic hematopoietic progenitor cell subsets are examined. As shown in FIG. 35, TET2 is expressed most highly in the Gr-1$^-$Mac-1$^+$ myeloid lineage bone marrow cells; pre-B, immature B, and mature B lymphoid lineage bone marrow cells; and in DN1, DP, CD4+ SP, and CD8+ SP thymic lymphoid lineage cells. As shown in FIG. 36, TET1 is expressed most highly in DP, CD4+ SP, and CD8+ SP thymic lymphoid lineage cells.

In order to determine the role of TET2 in leukemia and malignant transformations, and the role of cooperation between TET2 and JAK2 mutations, Lin$^-$c-kit$^+$ cells bone marrow cells can be isolated and transduced with the various combinations of retroviral vectors: LMP-GFP and MSCV-IRES-hCD4; LMP-shTet2-GFP and MSCV-IRES-hCD4; LMP-GFP and MSCV-JAK2 V617F-IRES-hCD4; and LMP-shTet2-GFP and MSCV-JAK2 V617F-IRES-hCD4, where shTet2 is an shRNA specific for Tet2. Cells can then be sorted on the basis of GFP and hCD4 expression, using techniques known to one of skill in the art. The isolated cells can then be compared for their effects on growth kinetics, transforming activity, and in vivo tumorigenesis. For example, isolated cells can be transferred into lethally irradiated mice to investigate in vivo tumorigenesis capacities.

Figures 37A, 37B:
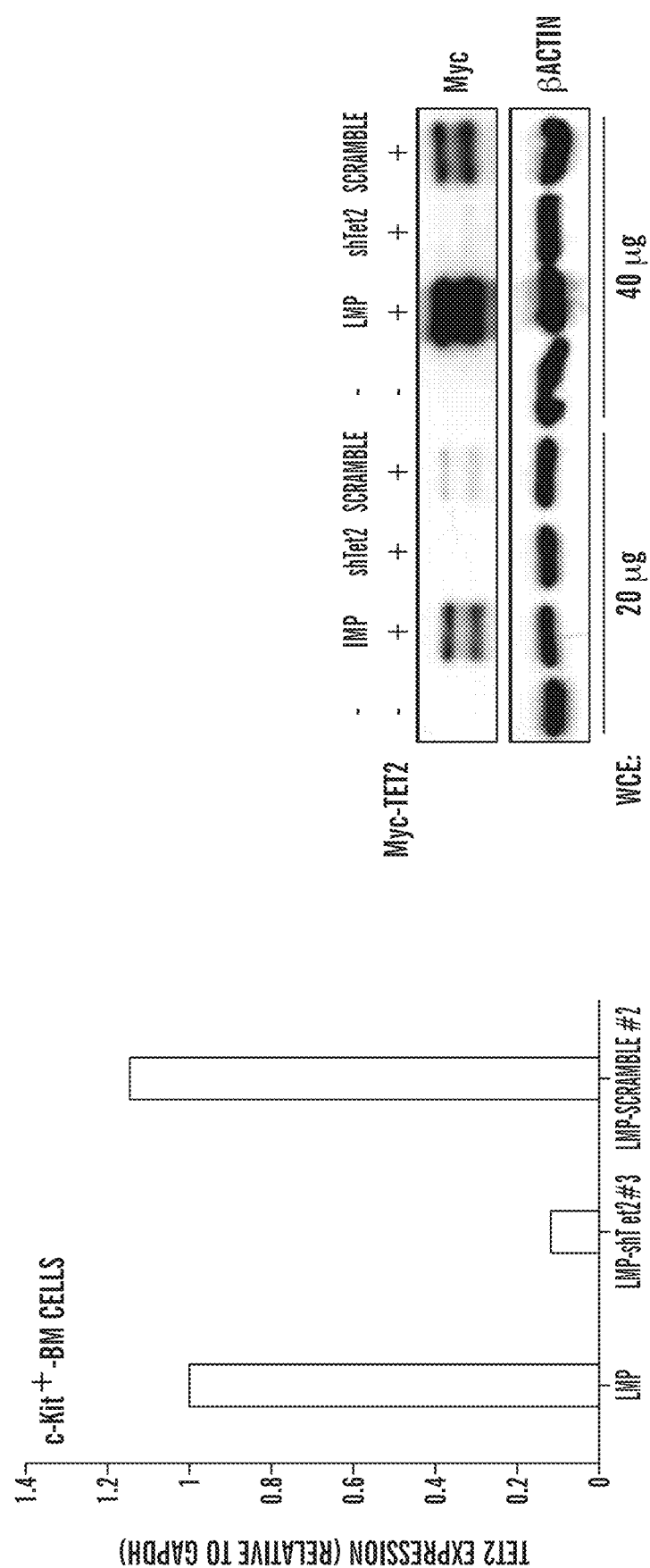
FIG. 37A-B shows the reduction of TET2 mRNA and protein expression in cells upon treatment with siRNA sequence directed against TET2.

As shown in FIG. 37, expression of the shTet2 #3 sequence results in decreased expression of Tet2 in c-kit$^+$ bone marrow cells, as assessed by quantitative PCR analysis. Further, we show that expression of the shTet2 #3 sequence results in decreased protein expression, using a Myc tagged Tet2 protein (FIG. 37).

Figure 38:
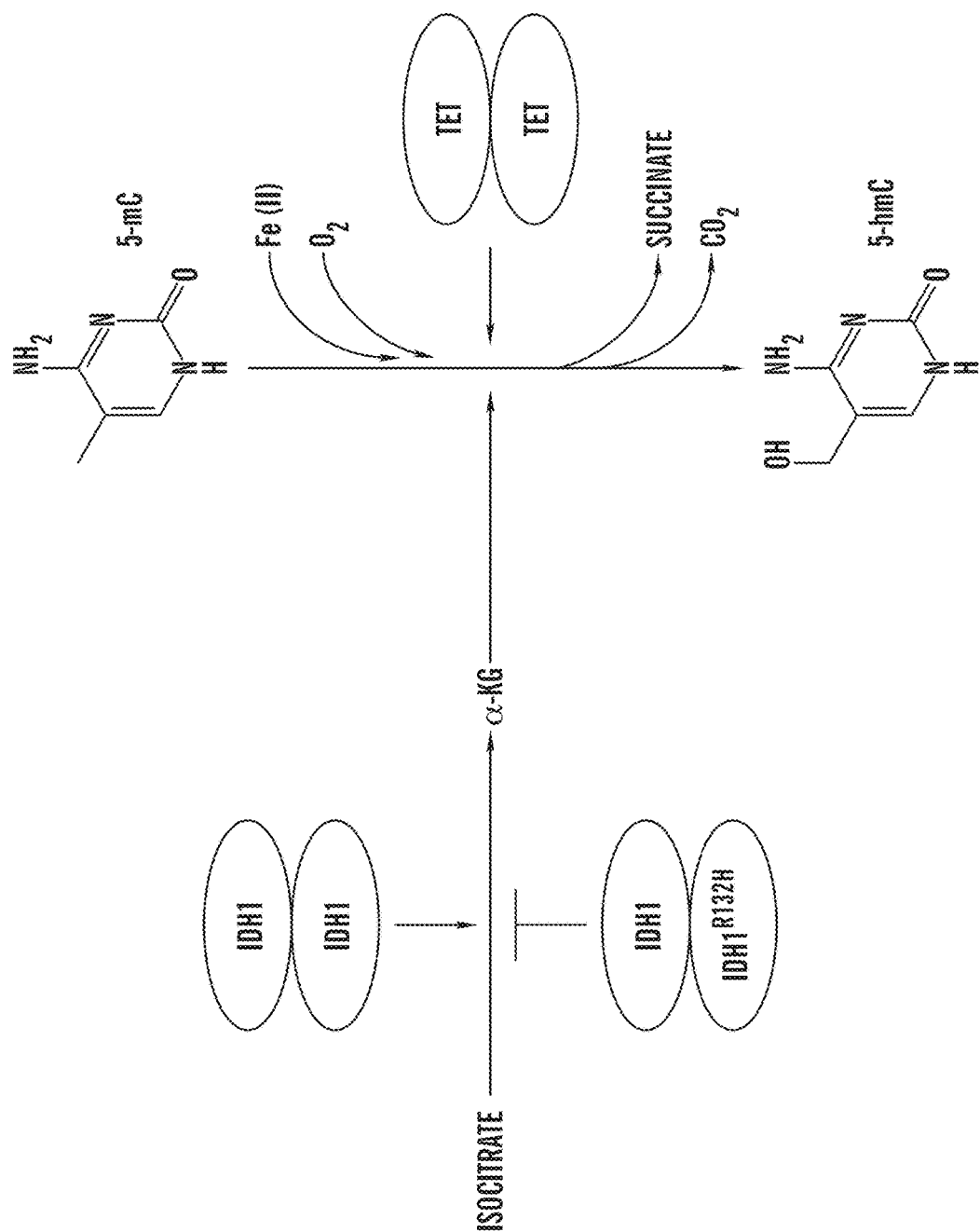
FIG. 38 illustrates a potential link between abnormalities in energy metabolism and tumor suppression mediated by the TET family of enzymes.

Without wishing to be bound or limited by a theory, we postulate that the TET family of epigenetic modulators serve as potential linkers between energy metabolism and tumor suppression. Isocitratedehydrogenases (IDHs) are metabolic enzymes in the TCA cycle and catalyze the oxidative decarboxylation of isocitrate to α-ketoglutarate (α-KG). IDHs can be classified into two groups (depending on the types of e-acceptor): (1) NAD+-dependent isocitratedehydrogenases, such as IDH3A, IDH3B, IDH3G, which form heterotetramer α2βγ, play an irreversible step of TCA cycle, and are found in the mitochondrial matrix; and (2) NDAP+-dependent isocitratedehydrogenases, such as IDH1, IDH2, which form homodimers, are involved in NADPH regeneration for anabolic pathways, and can be found in the mitochondrial matrix (IDH2) or cytoplasm/peroxisome (IDH1). It is known that recurrent somatic, (dominant negative) mutations occur at R132 of IDH1 in glioblastoma multiform (GBM: ~12%) and myeloid leukemia. Without wishing to be bound by a theory, we postulate that the R132 mutation impairs IDH1 homodimer formation, resulting in impaired α-KG generation, which results in TET family inactivation and consequent tumorigenesis, as diagrammed in FIG. 38.

Detection of Radiolabeled Glucose Added to 5-Hydroxymethylcytosine

DNA is incubated with alpha-glucosyltransferase or beta-glucosyltransferase in the presence of radiolabeled uridine diphosphate (UDP) glucose, either UDP-14C-glucose or UDP-3H-glucose, and the DNA is purified. If 5-hydroxymethylcytosine is present in the DNA, the radiolabel is isolated with the DNA and detected by liquid scintillation counting or autoradiography or other means. In some embodiments, the DNA is first contacted with one or more catalytically active TET family enzymes, functional TET family derivatives, or TET catalytic fragments to convert 5-methylcytosine to 5-hydroxymethylcytosine.

Detection of Non-Radiolabeled Glucose Added to 5-Hydroxymethylcytosine

Non-radioactive UDP glucose is used as a substrate and the resulting alpha-glucose-5-hydroxymethylcytosine or beta-glucose-5-hydroxymethylcytosine is detected by further chemical reaction or protein binding. Examples of a protein include an antibody or lectin that recognizes alpha-glucose-5-hydroxymethylcytosine or beta-glucose-5-hydroxymethylcytosine or an enzyme, such as hexokinase or beta-glucosyl-alpha-glucosyl-transferase, that adds further modifications to the alpha-glucose-5-hydroxymethylcytosine or beta-glucose-5-hydroxymethylcytosine. In some embodiments, the DNA is first contacted with one or more catalytically active TET family enzymes, functional TET family derivatives, or TET catalytic fragments to convert 5-methylcytosine to 5-hydroxymethylcytosine.

Detection of Methylcytosine and 5-Hydroxymethylcytosine Using Covalent Trapping

A UDP glucose analog that fosters covalent trapping of the covalent enzyme-DNA intermediate is used as a substrate, such that when DNA is incubated with alpha-glucosyltransferase or beta-glucosyltransferase, any 5-hydroxymethylcytosine containing DNA is tagged with alpha-glucosyltransferase or beta-glucosyltransferase. The DNA either has naturally occurring 5-hydroxymethylcytosine residues or is contacted with one or more catalytically active TET family enzymes, functional TET family derivatives, or TET catalytic fragments to convert 5-methylcytosine to 5-hydroxymethylcytosine. Also, the alpha-glucosyltransferase or beta-glucosyltransferase are created with one or more protein or non-protein tags to facilitate detection or isolation of the covalently linked enzyme-DNA complexes.

Modification and Detection of Methylcytosine and 5-Hydroxymethylcytosine

Naturally-occurring 5-hydroxymethylcytosine or that created by conversion of 5-methylcytosine in nucleic acids, such as DNA, is converted to glucose-5-hydroxymethylcytosine with alpha-glucosyltransferase or beta-glucosyltransferase and is further glycosylated using beta-glucosyl-alpha-glucosyl-transferase. The beta-glucosyl-alpha-glucosyl-transferase adds radioactively labeled glucose in UDPG to glucose-5-hydroxymethylcytosine. Alternatively, beta-glucosyl-alpha-glucosyl-transferase is used with substrates other than UDPG, such as UDP-2-deoxy-2-fluoro-glucose, to covalently trap the enzyme with its substrates. This will allow tagging of methylcytosine or 5-hydroxymethylcytosine with a protein. Beta-glucosyl-alpha-glucosyl-transferase is also created with several protein or non-protein tags to facilitate detection or isolation of the covalently linked beta-glucosyl-alpha-glucosyl-transferase glucose-5-hydroxymethylcytosine DNA complex.

The gentibiosyl (gentiobiosyl) residue in gentibiose-containing 5-hydroxymethylcytosine, which results from addition of a second glucose to glucose-5-hydroxymethylcytosine DNA by beta-glucosyl-alpha-glucosyl-transferase is detected using non-covalent methods. Detection methods include exploiting the binding of gentibiosyl residues to proteins with an affinity for this residue, such as (1) antibodies specific to gentibiose-containing 5-hydroxymethylcytosine or (2) lectins with affinity to gentibiosyl, such as *Musa acuminata* lectin (BanLec).

Lectins and antibodies further modified with several tags such as biotin or beads are used for solid-phase purification of gentibiose-containing 5-hydroxymethylcytosine containing DNA. Lectins and antibodies modified with gold or fluorescent tags are used for electron microscopic or immunofluorescent detection, respectively, of gentibiose-containing 5-hydroxymethylcytosine containing DNA.

Figure 4:
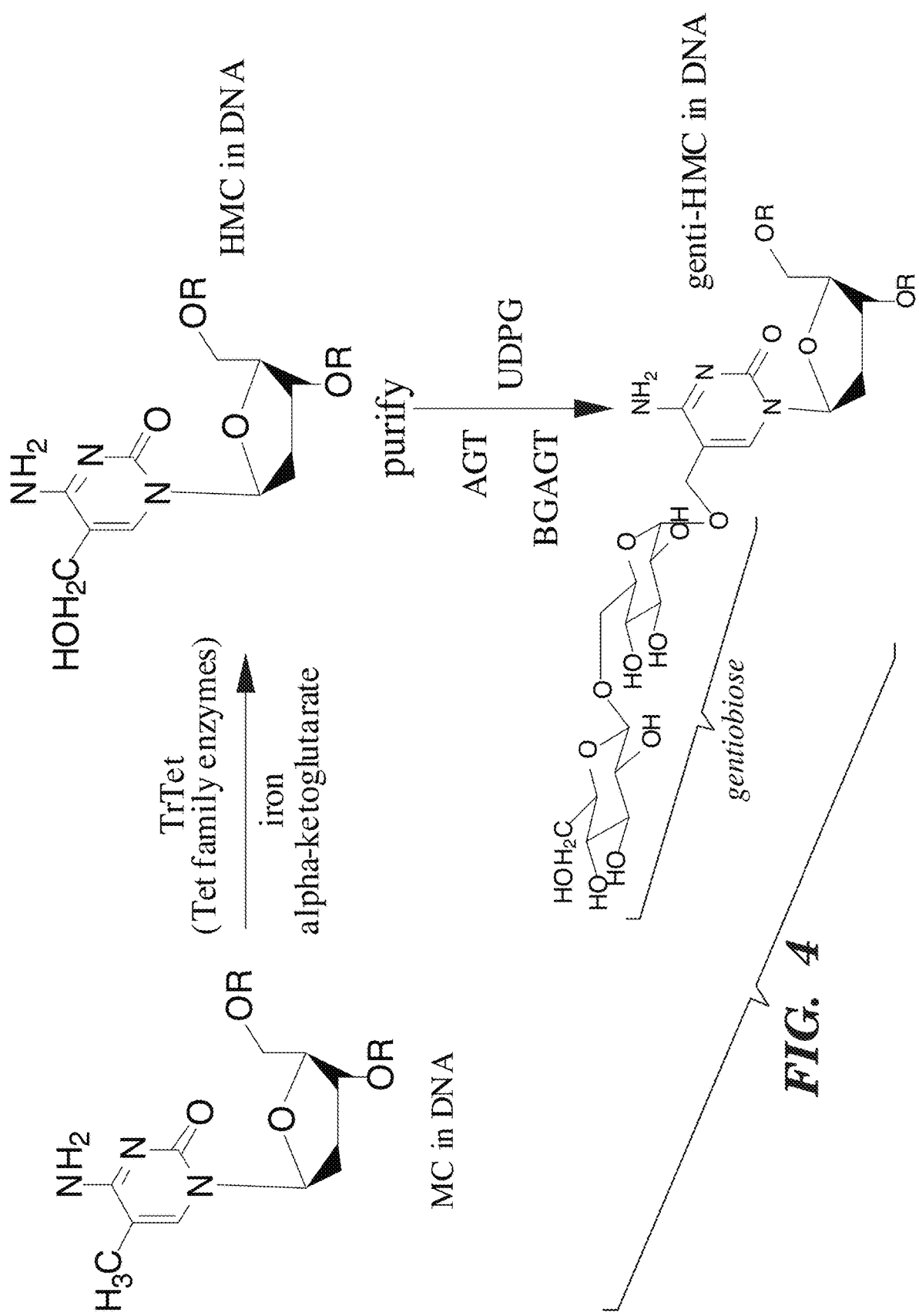
FIG. 4 depicts a method by which methylcytosine and 5-hydroxymethylcytosine can be detected in, and isolated from nucleic acids for use in downstream applications.
Figure 4:
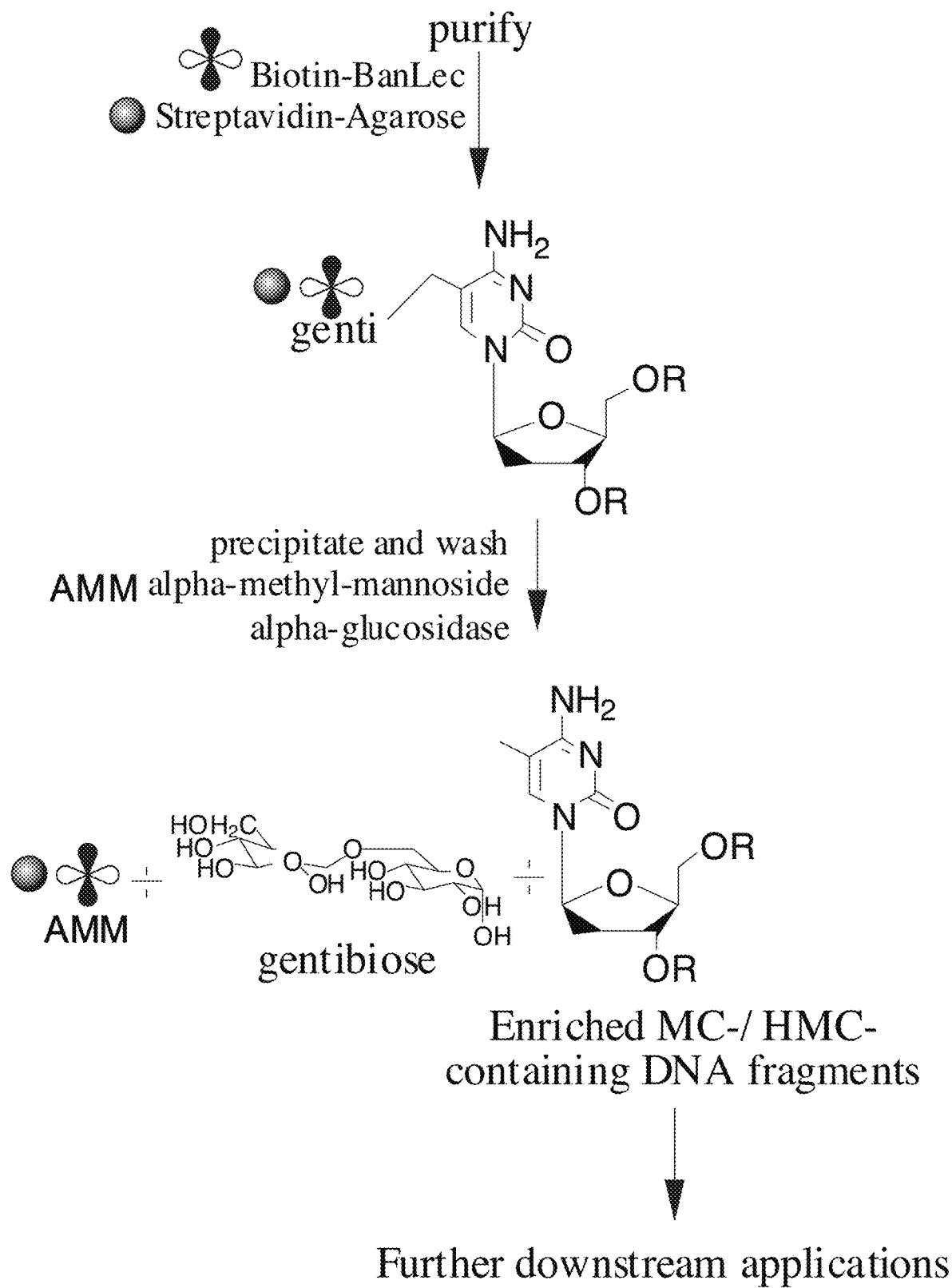

If desired, covalent linkages of glucose and gentibiosyl modifications to gentibiose-containing 5-hydroxymethylcytosine and glucose-containing 5-hydroxymethylcytosine are reversed by chemical means or by enzymes such as alpha- and beta-glucosidases, thus liberating the 5-hydroxymethylcytosine containing DNA for further downstream applications. One example of these methods is shown in FIG. 4.

To detect 5-hydroxymethylcytosine, the 5-hydroxymethyl residue of 5-hydroxymethylcytosine is converted to the 5-hydroxymethylenesulfonate residue by sodium hydrogen sulfite, and then detected with antibodies to the modified residue.

Downstream applications that utilize the covalently and non-covalently tagged methylcytosine and 5-hydroxymethylcytosine include: (i) detection of methylcytosine and 5-hydroxymethylcytosine in cells or tissues directly by fluorescence or electron microscopy; (ii) detection of methylcytosine and 5-hydroxymethylcytosine by assays including blotting or linked enzyme mediated substrate conversion with radioactive, colorimetric, luminescent or fluorescent detection and (iii) separation of the tagged DNA away from untagged DNA by enzymatic, chemical or mechanical treatments, and fractionation of either the tagged or untagged DNA by precipitation with beads, magnetic means, fluorescent sorting, or other means; followed by application to whole genome analyses such as microarray hybridization and high-throughput sequencing Diagnostic Methods for Assessing Global Methylcytosine and 5-Hydroxymethylcytosine Levels Global level of methylcytosine and/or 5-hydroxymethylcytosine, i.e., the "methylome" or "hydroxymethylome"

signatures in diseased tissue samples, such as bone marrow from patients with MDS, MPD, AML, are assessed to aid in disease diagnosis of disease to permits disease classifications, risk stratify patients, direct therapy, and monitor responses to therapy.

Genetic Tests for Methylcytosine and 5-Hydroxymethylcytosine Levels

Levels of methylcytosine and/or 5-hydroxymethylcytosine are determined in cells from family members of people affected with a disease, to determine whether they might harbor the disease. 5-hydroxymethylcytosine levels are determined, in a non-limiting example, in the CD34+ hematopoietic cells of a family member of someone with MDS, MPD, AML to determine whether there is a familial predisposition.

Kits and Methods for Detection of Methylcytosine and 5-Hydroxymethylcytosine in Genomes Whole genomic DNA is mixed with control DNA, and sheared to a desired size (average around 200 bp). The DNA is subjected to one or more catalytically active TET family enzymes, functional TET family derivatives, or TET catalytic fragments mediated conversion of methylcytosine to 5-hydroxymethylcytosine in the appropriate buffer. DNA is purified on spin column. 5-hydroxymethylcytosine converted DNA is then treated simultaneously with alpha-glucosyltransferase or beta-glucosyltransferase and beta-glucosyl-alpha-glucosyl-transferase enzyme in a UDPG containing buffer. DNA is purified on spin column. Biotinylated BanLec is rocked with gentibiose-containing 5-hydroxymethylcytosine converted DNA. Streptavidin agarose beads will be added. Streptavidin-biotin-BanLec-gentibiose-containing 5-hydroxymethylcytosin-containing DNA complexes are precipitated and washed in buffer, and supernatant containing unmethylated cytosine containing DNA is saved for analysis. The beads are treated with methyl-alpha-mannoside to release the lectin, and glucosidases to cleave the gentiobiosyl residue, and solute is purified over DNA spin column. The purified DNA is subjected to further analysis, such as microarray, direct sequencing, or PCR based assays.

An internal standard of lambda DNA carrying cytosine methylation at BamHI residues is used to determine efficiency and specificity of 5-hydroxymethylcytosine detection using PCR primer pairs flanking and not flanking BamHI residues in the lambda genome.

The detection of naturally occurring 5-hydroxymethylcytosine in genomes is performed the same as above but without the conversion of methylcytosine to 5-hydroxymethylcytosine by one or more catalytically active TET family enzymes, functional TET family derivatives, or TET catalytic fragments.

The kit components comprise: one or more catalytically active TET family enzymes, functional TET family derivatives, or TET catalytic fragments; one or more alpha glucosyltransferases, beta-glucosyltransferases, or beta-glucosyl-alpha-glucosyl-transferases; biotinylated BanLec; streptavidin agarose beads; methyl-alpha-mannoside; alpha-glucosidase and beta-glucosidase; appropriate buffers, substrate solutions, and DNA purification spin columns and an internal standard further comprising lambda DNA cytosine methylated with BamHI methyltransferase and PCR primers.

The present invention can be defined in any of the following numbered paragraphs:

1. A method for improving the generation of stable human Foxp3+ T cells, the method comprising contacting with or delivering to a human T cell an effective 5-methylcytosine to 5-hydroxymethylcytosine converting amount of at least one catalytically active TET family enzyme, functional TET family derivative, TET catalytically active fragment, or combination thereof.

2. The method of paragraph 1, wherein the catalytically active TET family enzyme is selected from the group consisting of TET1, TET2, TET3, and CXXC4.

3. The method of paragraph 1, wherein the human T cell is a purified human CD4+ T cell.

4. The method of paragraph 1, further comprising generating stable human Foxp3+ T cells by contacting the human T cell with a composition at least one cytokine, growth factor, or activating reagent.

5. The method of paragraph 5, wherein said composition comprises TGF-β.

6. A method for improving efficiency or rate with which induced pluripotent stem (iPS) cells are produced from somatic cells, the method comprising contacting with, or delivering to, a somatic cell an effective 5-methylcytosine to 5-hydroxymethylcytosine converting amount of at least one catalytically active TET family enzyme, functional TET family derivative, TET catalytically active thereof, or combination thereof.

7. The method of paragraph 6, wherein the catalytically active TET family enzyme is selected from the group consisting of TET1, TET2, TET3, and CXXC4.

8. The method of paragraph 6, wherein the catalytically active TET family enzyme is TET1 or TET2.

9. The method of paragraph 6, further comprising contact with or delivering to the somatic cell an effective amount of a TET family inhibitor.

10. The method of paragraph 9, wherein the TET family inhibitor is a TET3 inhibitor.

11. The method of paragraph 6, further comprising inducing iPS cell production by contacting the adult somatic cell with or delivering to said adult somatic cell a combination of nucleic acid sequences encoding Oct-4, Sox2, c-MYC, and Klf4.

12. The method of paragraph 11, wherein the combination of nucleic acid sequences encoding Oct-4, Sox2, c-MYC, and Klf4 are delivered in a viral vector, selected from the group consisting of an adenoviral vector, a lentiviral vector, and a retroviral vector.

13. The method of paragraph 6, wherein the somatic cell is a fibroblast.

14. A method for improving efficiency of cloning mammals by nuclear transfer or nuclear transplantation, the method comprising contacting a nucleus extracted from a cell to be cloned with an effective 5-methylcytosine to 5-hydroxymethylcytosine hydroxylating amount of at least one catalytically active TET family enzyme, functional TET family derivative, TET catalytically active fragment, or combination thereof, during a nuclear transfer protocol.

15. The method of paragraph 14, wherein the catalytically active TET family enzyme is selected from the group consisting of TET1, TET2, TET3, and CXXC4.

16. The method of paragraph 14, wherein the catalytically active TET family enzyme is TET1 or TET2.

17. The method of paragraph 14, further comprising contact with or delivering to the somatic cell an effective amount of a TET family inhibitor.

18. The method of paragraph 17, wherein the TET family inhibitor is a TET3 inhibitor.

19. A method for detecting a 5-hydroxymethylcytosine nucleotide in a biological sample, the method comprising contacting a biological sample with a detectably labeled antibody or an antigen binding portion thereof, a labeled intrabody, or a labeled protein, that specifically binds to 5-hydroxymethylcytosine, and detecting the amount of bound label, wherein the presence of the bound label is indicative of the 5-methylcytosine being converted to 5-hydroxymethylcytosine.

20. A kit for modulating gene transcription via hydroxylation of 5-methylcytosine to 5-hydroxymethylcytosine, the kit comprising the following separate components:
(a) at least one or more catalytically active TET family enzyme, functional TET family derivative, TET catalytically active fragment, or combination thereof, or nucleic acid molecule that comprises a sequence encoding at least one catalytically active TET family enzyme, functional TET family derivative, TET catalytically active fragment, or combination thereof, in an appropriate buffer or solution; and
(b) packaging materials and instructions therein to use said kit to hydroxylate 5-methylcytosine to 5-hydroxymethylcytosine, for the purposes of modulating gene transcription.

21. The kit of paragraph 20, wherein the catalytically active TET family enzymes are selected from the group consisting of TET1, TET2, TET3, and CXXC4.

22. The kit of paragraph 20, further comprising at least one cytokine, growth factor, activating reagent, or combination thereof, for the purposes of generating stable human Foxp3+ regulatory T cells.

23. The kit of paragraph 22, wherein the composition comprises TGF-β.

24. The kit of paragraph 20, further comprising at least one nucleic acid sequence encoding Oct-4, Sox2, c-MYC, and Klf4, to be contacted with or delivered to a somatic cell for the purposes of improving the efficiency and rate of induced pluripotent stem cell production.

25. The kit of paragraph 24, wherein the nucleic acid sequences encoding Oct-4, Sox2, c-MYC, and Klf4 are delivered in a viral vector selected from the group consisting of an adenoviral vector, a lentiviral vector, and a retroviral vector.

26. The kit of paragraph 20, further comprising at least one reagent suitable for the detection of 5-hydroxymethylcytosine.

27. The kit of paragraph 26, wherein the reagent suitable for the detection of 5-hydroxymethylcytosine is an antibody or an antigen-binding portion thereof, an intrabody, or a protein, that specifically binds to 5-hydroxymethylcytosine.

28. The kit of paragraph 26, wherein said reagent suitable for the detection of 5-hydroxymethylcytosine is specific for cytosine-5-methylsulfonate.

29. A method for improving stem cell therapies, the method comprising contacting with, or delivering to, a stem cell an effective 5-methylcytosine to 5-hydroxymethylcytosine converting amount of at least one catalytically active TET family enzyme, functional TET family derivative, TET catalytically active fragment thereof, or combination thereof, or at least one nucleic acid molecule that comprises a sequence encoding at least one catalytically active TET family enzyme, functional TET family derivative, TET catalytically active fragment, or combination thereof.

30. The method of paragraph 29, wherein the catalytically active TET family enzyme is selected from the group consisting of TET1, TET2, TET3, and CXXC4.

31. A method for treating an individual with or at risk for cancer, the method comprising administering to an individual with or at risk for cancer an effective amount of an agent that specifically modulates hydroxylase activity of at least one catalytically active TET family enzyme, functional TET family derivative, TET catalytically active fragment, or combination thereof involved in transforming 5-methylcytosine into 5-hydroxymethylcytosine.

32. The method of paragraph 31, wherein the catalytically active TET family enzyme is selected from the group consisting of TET1, TET2, TET3, and CXXC4.

33. The method of paragraph 31, wherein the agent that specifically modulates hydroxylase activity is an inhibitor.

34. The method of paragraph 31, wherein the agent that specifically modulates hydroxylase activity is an activator.

35. The method of paragraph 31, wherein the cancer is a leukemia.

36. The method of paragraph 35, wherein the leukemia is an acute myeloid leukemia comprising the t(10:11)(q22:q23) Mixed Lineage Leukemia translocation of TET1.

37. A method for screening for an agent with TET family enzyme modulating activity, the method comprising the steps of:
a) providing a cell comprising at least one TET family enzyme, functional TET family derivative, TET catalytically active fragment, recombinant TET family enzyme, or combination thereof;
b) contacting said cell with a test agent, thereby creating a test sample; and
c) comparing the relative levels of 5-hydroxymethylated cytosine in cells expressing the catalytically active TET family enzyme, functional TET family derivative, TET catalytically active fragment, recombinant TET family enzyme, or combination thereof, in the test sample with the level expressed in a control sample; and
(d) determining whether or not the test agent increases or decreases the level of 5-hydroxymethylated cytosine, wherein a statistically significant decrease in the level of 5-hydroxymethylated cytosine indicates the agent is an inhibitor, and a statistically significant increase in the level of 5-hydroxymethylated cytosine indicates the agent is an activator.

38. The method of paragraph 37, wherein the catalytically active TET family enzyme is selected from the group consisting of TET1, TET2, TET3, and CXXC4.

39. The method of any of the preceding paragraphs, wherein the functional TET family derivative comprises SEQ ID NO: 1.

40. The method of any of the preceding paragraphs, wherein the TET family catalytically active fragment comprises SEQ ID NO: 2, SEQ ID NO: 3, SEQ ID NO: 4, or SEQ ID NO: 5.

41. A method for covalent tagging 5-hydroxymethylcytosine in a nucleic acid, the method comprising contacting a nucleic acid molecule with an enzyme that adds one or more glucose molecules to a 5-hydroxymethylcytosine residue to generate glucosylated-5-hydroxymethylcytosine or gentibiose-containing-5-hydroxymethylcytosine, wherein the enzyme is an alpha-glucosyltransferase, a beta-glucosyltransferase, or a beta-glucosyl-alpha-glucosyl-transferase.

42. The method of paragraph 41, wherein the 5-hydroxymethylcytosine is naturally occurring.

43. The method of paragraph 41, further comprising the step of first contacting said nucleic acid with at least one catalytically active TET family enzyme, functional TET family derivative, TET catalytically active fragment thereof, or combination thereof, thereby converting 5-methylcytosine to hydroxymethylcytosine.

44. The method of paragraph 41, wherein the alpha-glucosyltransferase is encoded by a bacteriophage selected from the group consisting of T2, T4, and T6 bacteriophages.

45. The method of paragraph 41, wherein the beta-glucosyltransferase is encoded by a bacteriophage selected from T4 bacteriophages.

46. The method of paragraph 41, wherein the beta-glucosyl-alpha-glucosyl-transferase is encoded by a bacteriophage selected from the group consisting of T2 and T6 bacteriophages.

47. The method of paragraph 41, wherein the nucleic acid is contacted in vitro, in a cell, or in vivo.

48. A method for detecting 5-hydroxymethylcytosine in a nucleic acid, the method comprising contacting a nucleic acid with an enzyme that utilizes labeled glucose or glucose-derivative donor substrates to add at least one labeled glucose molecules or glucose-derivatives to a 5-hydroxymethylcytosine residue to generate glucosylated-5-hydroxymethylcytosine or gentibiose-containing-5-hydroxymethylcytosine, wherein the enzyme is an alpha-glucosyltransferase, a beta-glucosyltransferase, or a beta-glucosyl-alpha-glucosyl-transferase.

49. The method of paragraph 48, wherein the glucose or glucose-derivative donor substrate is a uridine diphosphate glucose.

50. The method of paragraph 48, wherein the labeled glucose or glucose-derivative donor substrates is radioactively labeled.

51. The method of paragraph 50, wherein the radioactive label is $^{14}C$ or $^{3}H$.

52. The method of paragraph 48, wherein the 5-hydroxymethylcytosine is naturally occurring.

53. The method of paragraph 53, further comprising the step of first contacting said nucleic acid with at least one catalytically active TET family enzyme, functional TET family derivative, TET catalytically active fragment, or combination thereof, thereby converting 5-methylcytosine to 5-hydroxymethylcytosine.

54. The method of paragraph 48, wherein the alpha-glucosyltransferase is encoded by a bacteriophage selected from the group consisting of T2, T4, and T6 bacteriophages.

55. The method of paragraph 48, wherein the beta-glucosyltransferase is encoded by a bacteriophage selected from T4 bacteriophages.

56. The method of paragraph 48, wherein the beta-glucosyl-alpha-glucosyl-transferase is encoded by a bacteriophage selected from the group consisting of T2 and T6 bacteriophages.

57. The method of paragraph 48, wherein the nucleic acid is contacted in vitro, in a cell, or in vivo.

58. A method for detecting 5-hydroxymethylcytosine in a nucleic acid, the method comprising contacting the covalently tagged 5-hydroxymethylcytosine of paragraph 41 with a protein that recognizes a glucose molecule, glucose-derivative or gentibiosyl molecule.

59. The method of paragraph 58, wherein the protein recognizes only the glucose molecule, glucose-derivative, or gentibiosyl.

60. The method of paragraph 58, wherein the protein recognizes the glucose molecule, glucose-derivative, or gentibiosyl only in the context of 5-hydroxymethylcytosine.

61. The method of paragraph 58, wherein the protein is a lectin.

62. The method of paragraph 61, wherein the lectin is Musa acuminata lectin.

63. The method of paragraph 58, wherein the protein is a antibody or antigen-binding fragment thereof.

64. The method of paragraph 63, wherein the antibody or antigen-binding fragment thereof is modified with a tag.

65. The method of paragraph 64, wherein the tag is a biotin molecule, a bead, a gold particle, or a fluorescent molecule.

66. The method of paragraph 58, wherein the protein is an enzyme.

67. The method of paragraph 66, wherein the enzyme is hexokinase or beta-glucosyl-alpha-glucosyl-transferase.

68. A method for detecting 5-hydroxymethylcytosine in a nucleic acid, the method comprising contacting a nucleic acid with an enzyme and utilizing glucose or glucose-derivative donor substrates that trap covalent enzyme-DNA intermediates to detect 5-hydroxymethylcytosine residues, wherein the enzyme is an alpha-glucosyltransferase, a beta-glucosyltransferase, or a beta-glucosyl-alpha-glucosyl-transferase.

69. The method of paragraph 68, wherein the glucose donor substrate is a uridine diphosphate glucose analog.

70. The method of paragraph 69, wherein the uridine diphosphate glucose analog is uridine-2-deoxy-2-fluoro-glucose.

71. The method of paragraph 68, wherein the 5-hydroxymethylcytosine is naturally occurring.

72. The method of paragraph 68, further comprising the step of first contacting said nucleic acid with at least one catalytically active TET family enzyme, functional TET family derivative, TET catalytically active fragment, or combination thereof, thereby converting 5-methylcytosine to 5-hydroxymethylcytosine.

73. The method of paragraph 68, wherein the enzyme is tagged.

74. The method of paragraph 68, wherein the alpha-glucosyltransferase is encoded by a bacteriophage selected from the group consisting of T2, T4, and T6 bacteriophages.

75. The method of paragraph 68, wherein the beta-glucosyltransferase is encoded by a bacteriophage selected from T4 bacteriophages.

76. The method of paragraph 68, wherein the beta-glucosyl-alpha-glucosyl-transferase is encoded by a bacteriophage selected from the group consisting of T2 and T6 bacteriophages.

77. The method of paragraph 68, wherein the nucleic acid is contacted in vitro, in a cell, or in vivo.

78. An method to detect 5-hydroxymethylcytosine in a nucleic acid, the method comprising contacting a nucleic acid with sodium hydrogen sulfite to convert a 5-hydroxymethylcytosine residue in a nucleic acid to a cytosine-5-methylsulfonate, and contacting the sodium hydrogen sulfite contacted nucleic acid with a protein specific for cytosine-5-methylsulfonate.

79. The method of paragraph 78, wherein the protein is an antibody or antigen-binding fragment thereof, an enzyme, or an intrabody.

80. The method of paragraph 79, wherein the antibody comprises an antiserum.

81. The method of paragraph 79, wherein the antibody or antigen-binding fragment thereof, enzyme, or intrabody is modified with a tag.

82. The method of paragraph 81, wherein the tag is a biotin molecule, a bead, a gold particle, or a fluorescent molecule.

83. The method of paragraph 78, further comprising isolating the 5-hydroxymethylcytosine residue containing nucleic acid with the protein specific for cytosine-5-methylsulfonate 84. The method of paragraph 78, wherein the nucleic acid is in vitro, in a cell, or in vivo.

85. A kit for the detection and purification of methylcytosine and 5-hydroxymethylcytosine, the kit comprising:
(a) one or more catalytically active TET family enzymes, functional TET family derivatives, or TET catalytically active fragments thereof for the conversion of methylcytosine to 5-hydroxymethylcytosine;
(b) one or more enzymes encoded by bacteriophages of the "T even" family;
(c) one or more glucose or glucose-derivative donor substrates;
(d) one or more proteins to detect glucose or glucose-derivative modified nucleotides;
(e) standard DNA purification columns, buffers, and substrate solutions; and
(f) packaging materials and instructions therein to use said kits.

86. The kit of paragraph 85, wherein the enzyme encoded by bacteriophages of the "T even" family is selected from the group consisting of alpha-glucosyltransferases, beta-glucosyltransferases, and beta-glucosyl-alpha-glucosyl-transferases.

87. The kit of paragraph 86, wherein the alpha-glucosyltransferase is encoded by a bacteriophage selected from the group consisting of T2, T4, and T6 bacteriophages.

88. The kit of paragraph 86, wherein the beta-glucosyltransferase is encoded by a bacteriophage selected from T4 bacteriophages.

89. The kit of paragraph 86, wherein the beta-glucosyl-alpha-glucosyl-transferase is encoded by a bacteriophage selected from the group consisting of T2 and T6 bacteriophages.

90. The kit of paragraph 85, wherein the glucose or glucose-derivative donor substrate is uridine diphosphate glucose (UDPG).

91. The kit of paragraph 90, wherein the glucose or glucose-derivative donor substrate is radiolabeled.

92. The kit of paragraph 91, wherein the uridine diphosphate glucose is radiolabeled with 14C or 3H.

93. The kit of paragraph 85, wherein the protein that detects glucose or glucose-derivative modified nucleotides is selected from a group comprising a lectin, an antibody or antigen-binding fragment thereof, or an enzyme.

94. The kit of paragraph 85, wherein the protein recognizes only the glucose or glucose-derivative.

95. The kit of paragraph 85, wherein the protein recognizes the glucose or glucose-derivative only in the context of 5-hydroxymethylcytosine.

96. The kit of paragraph 93, wherein the antibody or antigen-binding fragment thereof is modified with at least one tag.

97. The kit of paragraph 96, wherein the tag is a biotin molecule, a bead, a gold particle, or a fluorescent molecule.

98. The kit of paragraph 93, wherein the enzyme is a hexokinase or a beta-glucosyl-alpha-glucosyl-transferase.

99. The kit of paragraph 93, wherein the lectin is Musa *acuminata* lectin (BanLec).

100. The kit of paragraph 99, wherein the lectin is modified with a gold particle or fluorescent tag.

101. A method for diagnosing a myelodysplastic syndrome, a myeloproliferative disorder, acute myelogenous leukemia, systemic mastocytosis, or chronic myelomonocytic leukemia in an individual in need thereof, the method comprising the steps of
(i) determining a level of 5-methylcytsosine, 5-hydroxymethylcytsosine, or a combination thereof, in a tissue or cell sample from an individual in need thereof, and
(ii) comparing the level of 5-methylcytsosine, 5-hydroxymethylcytsosine, or a combination thereof, in the tissue or cell sample from the individual with a level of 5-methylcytsosine, 5-hydroxymethylcytsosine, or a combination thereof, from a normal control sample, wherein a difference in the level of 5-methylcytsosine, 5-hydroxymethylcytsosine, or a combination thereof, between the sample from the individual in need and the normal control sample is indicative of the individual having a myelodysplastic syndrome, a myeloproliferative disorder, acute myelogenous leukemia, systemic mastocytosis, or chronic myelomonocytic leukemia.

102. The method of paragraph 101, further comprising a step of comparing the level of 5-methylcytosine, 5-hydroxymethylcytsosine, or a combination thereof, in a tissue or cell sample of the individual to a level of 5-methylcytsosine, 5-hydroxymethylcytsosine, or a combination thereof, in at least one sample from a diseased tissue or a diseased cell, wherein if the level of 5-methylcytsosine, 5-hydroxymethylcytsosine, or a combination thereof, in the tissue or cell sample from the individual in need is similar to the level of 5-methylcytsosine, 5-hydroxymethylcytsosine, or a combination thereof, from at least one of the samples from the diseased tissue or diseased cell then the individual is diagnosed with a myelodysplastic syndrome, a myeloproliferative disorder, acute myelogenous leukemia, systemic mastocytosis, or chronic myelomonocytic leukemia.

103. A method for monitoring a disease progression or an effect of a therapy on a myelodysplastic syndrome, a myeloproliferative disorder, acute myelogenous leukemia, systemic mastocytosis, or chronic myelomonocytic leukemia, the method comprising the steps of
(i) determining a level of 5-methylcytsosine, 5-hydroxymethylcytsosine, or a combination thereof, in a tissue or a cell sample from an individual in need thereof and establishing a baseline level of 5-methylcytsosine, 5-hydroxymethylcytsosine, or a combination thereof, in the tissue or cell sample from the individual;
(ii) determining a level of 5-methylcytsosine, 5-hydroxymethylcytsosine, or a combination thereof, in a tissue or cell sample from the individual at least one time following the establishment of the baseline level of 5-methylcytsosine, 5-hydroxymethylcytsosine, or a combination thereof, thereby establishing at least one follow-up level of 5-methylcytsosine, 5-hydroxymethylcytsosine, or a combination thereof, wherein a difference in the follow-up level of 5-methylcytsosine, 5-hydroxymethylcytsosine, or a combination thereof, relative to the baseline level of 5-methylcytsosine, 5-hydroxymethylcytsosine, or a combination thereof, is indicative of the progression of, or effect of a therapy on, a myelodysplastic syndrome, a myeloproliferative disorder, acute myelogenous leukemia, systemic mastocytosis, or chronic myelomonocytic leukemia in the individual.

104. A method for determining familial predisposition to a myelodysplastic syndrome, a myeloproliferative disorder, acute myelogenous leukemia, systemic mastocytosis, or chronic myelomonocytic leukemia in an individual in need thereof, the method comprising (i) determining a level of 5-methylcytsosine, 5-hydroxymethylcytsosine, or a combination thereof in CD34+ cells from an individual in need thereof, (ii) determining a level of 5-methylcytsosine, 5-hydroxymethylcytsosine, or a combination thereof, in CD34+ cells from a family member of the individual, wherein the family member is affected with a myelodysplastic syndrome, a myeloproliferative disorder, acute myelogenous leukemia, systemic mastocytosis, or chronic myelomonocytic leukemia, and (iii) comparing the level of 5-methylcytsosine, 5-hydroxymethylcytsosine, or a combination thereof in the CD34+ cells from the individual in need thereof with the level of 5-methylcytsosine, 5-hydroxymethylcytsosine, or a combination thereof, in the CD34+ cells from the affected family member, wherein an increase in the level of 5-methylcytsosine, 5-hydroxymethylcytsosine, or a combination thereof, in the individual relative to the 5-methylcytsosine, 5-hydroxymethylcytsosine, or a combination thereof level in the affected family member is indicative of the individual being predisposed to a myelodysplastic syndrome, a myeloproliferative disorder, acute myelogenous leukemia, systemic mastocytosis, or chronic myelomonocytic leukemia.

105. A method for determining familial predisposition to a myelodysplastic syndrome, a myeloproliferative disorder, acute myelogenous leukemia, systemic mastocytosis, or chronic myelomonocytic leukemia in an individual in need thereof, the method comprising (i) determining a level of 5-methylcytsosine, 5-hydroxymethylcytsosine, or a combination thereof in CD34+ cells from an individual in need thereof, (ii) determining a level of 5-methylcytsosine, 5-hydroxymethylcytsosine, or a combination thereof, in CD34+ cells from a family member of the individual, wherein the family member is affected with a myelodysplastic syndrome, a myeloproliferative disorder, acute myelogenous leukemia, systemic mastocytosis, or chronic myelomonocytic leukemia, and (iii) comparing the level of 5-methylcytsosine, 5-hydroxymethylcytsosine, or a combination thereof in the CD34+ cells from the individual in need thereof with the level of 5-methylcytsosine, 5-hydroxymethylcytsosine, or a combination thereof, in the CD34+ cells from the affected family member, wherein a decrease in the level of 5-methylcytsosine, 5-hydroxymethylcytsosine, or a combination thereof, in the individual relative to the 5-methylcytsosine, 5-hydroxymethylcytsosine, or a combination thereof level in the affected family member is indicative of the individual being predisposed to a myelodysplastic syndrome, a myeloproliferative disorder, acute myelogenous leukemia, systemic mastocytosis, or chronic myelomonocytic leukemia.

106. The method as in any of paragraphs 101-105, wherein the 5-methylcytsosine, 5-hydroxymethylcytsosine, or a combination thereof, level is determined using an assay to detect cytosine-5-methylsulfonate.

107. A kit for the detection and purification of 5-hydroxymethylcytosine, the kit comprising:
(a) at least one catalytically active TET family enzyme, functional TET family derivative, TET catalytically active fragment, or combination thereof for the conversion of 5-methylcytosine to 5-hydroxymethylcytosine;
(b) sodium bisulfite;
(c) at least one protein to detect sodium bisulfite treated nucleotides;
(e) standard DNA purification columns, buffers, and substrate solutions; and
(f) packaging materials and instructions therein to use said kits.

108. The kit of paragraph 107, wherein the protein that recognizes sodium bisulfite treated nucleotide is specific for cytosine-5-methylsulfonate.

109. The kit of paragraph 107, wherein the protein that detects sodium bisulfite treated nucleotides is an antibody or antigen-binding fragment thereof, an intrabody, or an enzyme.

110. The kit of paragraph 107, wherein the antibody or antigen-binding fragment thereof, intrabody, or enzyme is modified with at least one tag.

111. The kit of paragraph 110, wherein the tag is a biotin molecule, a bead, a gold particle, or a fluorescent molecule.

112. The use of at least one catalytically active TET family enzyme, functional TET family derivative, TET catalytically active fragment, or combination thereof, in the manufacture of a medicament for improving the generation of stable human Foxp3+ T cells, wherein an effective amount of o at least one catalytically active TET family enzyme, functional TET family derivative, TET catalytically active fragment, or combination thereof, is contacted with, or delivered to, a human T cell to improve the generation of stable human Foxp3+ T cells.

113. The use of paragraph 112, wherein the human T cell is a purified human CD4+ T cell.

114. The use of paragraph 112, further comprising generating stable human Foxp3+ T cells by contacting the human T cell with a composition comprising at least one cytokine, growth factor, or activating reagent.

115. The use of paragraph 114, wherein said composition comprises TGF-β.

116. The use of at least one catalytically active TET family enzyme, functional TET family derivative, TET catalytically active fragment, or combination thereof, in the manufacture of a medicament for improving efficiency or rate with which an induced pluripotent stem (iPS) cell is produced from a somatic cell, wherein an effective amount of at least one catalytically active TET family enzyme, functional TET family derivative, TET catalytically active fragment, or combination thereof, is contacted with, or delivered to, a somatic cell to improve the efficiency or rate with which an induced pluripotent stem (iPS) cell is produced.

117. The use of paragraph 116, further comprising inducing iPS cell production by contacting with or delivering to the somatic cell at least one of a nucleic acid sequence encoding Oct-4, Sox2, c-MYC, or Klf4, or a combination thereof.

118. The use of paragraph 117, wherein the at least one nucleic acid sequence encoding Oct-4, Sox2, c-MYC, or Klf4 is delivered in a viral vector, selected from the group consisting of an adenoviral vector, a lentiviral vector, and a retroviral vector.

119. The use of paragraph 116, further comprising contacting with, or delivering to, a somatic cell an effective amount of a TET family inhibitor.

120. The use of paragraph 119, wherein the TET family inhibitor is a TET3 inhibitor.

121. The use of paragraph 138, wherein the adult somatic cell is a fibroblast.

122. The use of at least one catalytically active TET family enzyme, functional TET family derivative, TET catalytically active fragment, or combination thereof, in the manufacture of a medicament for improving efficiency of cloning mammals by nuclear transfer or nuclear transplantation, wherein an effective 5-methylcytosine to 5-hydroxymethylcytosine hydroxylating amount of at least one catalytically active TET family enzyme, functional TET family derivative, TET catalytically active fragment, or combination thereof, is contacted with a nucleus extracted from a cell to be cloned during a nuclear transfer protocol.

123. The use of paragraph 122, further comprising contacting a nucleus extracted from a cell to be cloned during a nuclear transfer protocol with an effective amount of a TET family inhibitor.

124. The use of paragraph 123, wherein the TET family inhibitor is a TET3 inhibitor.

125. The use of a detectably labeled antibody or a antigen-binding portion thereof, a labeled intrabody, or a labeled protein, that specifically binds to 5-hydroxymethylcytosine for detecting a 5-hydroxymethylcytosine nucleotide in a sample, wherein the presence of the bound label is indicative of the presence of 5-hydroxymethylcytosine in the sample.

126. The use of at least one catalytically active TET family enzyme, functional TET family derivative, TET catalytically active fragment, or combination thereof, or at least one nucleic acid molecule encoding at least one catalytically active TET family enzyme, functional TET family derivative, TET catalytically active fragment, or combination thereof, in the manufacture of a medicament for improving stem cell therapies, wherein an effective amount of at least one catalytically active TET family enzyme, functional TET family derivative, TET catalytically active fragment, or combination thereof, or at least one nucleic acid molecule encoding at least one catalytically active TET family enzyme, functional TET family derivative, TET catalytically active fragment, or combination thereof, is contacted with, or delivered to, a stem cell for improving stem cell therapies.

127. The use of an agent that specifically modulates hydroxylase activity of a at least one catalytically active TET family enzyme, functional TET family derivative, TET catalytically active fragment, or combination thereof, involved in transforming 5-methylcytosine into 5-hydroxymethylcytosine in the manufacture of a medicament for treating an individual with or at risk for cancer.

128. The use of paragraph 127, wherein the agent that specifically modulates hydroxylase activity is an inhibitor.

129. The use of paragraph 127, wherein the agent that specifically modulates hydroxylase activity is an activator.

130. The use of paragraph 127, wherein the cancer is a myelodysplastic syndrome, a myeloproliferative disorder, acute myelogenous leukemia, systemic mastocytosis, or chronic myelomonocytic leukemia 131. The use of paragraph 127, wherein the cancer is a leukemia.

132. The use of paragraph 131, wherein the leukemia is an acute myeloid leukemia comprising the t(10:11)(q22:q23) Mixed Lineage Leukemia translocation of TET1.

133. The use as in any one of paragraphs 112, 116, 122, 126, or 127, wherein the catalytically active TET family enzyme is selected from the group consisting of TET1, TET2, TET3, and CXXC4.

134. The use as in any one of paragraphs 112, 116, 122, 126, or 127, wherein the functional TET family derivative comprises SEQ ID NO: 1.

135. The use as in any one of paragraphs 112, 116, 122, 126, or 127, wherein the TET family catalytically active fragment comprises SEQ ID NO: 2, SEQ ID NO: 3, SEQ ID NO: 4, or SEQ ID NO: 5.

136. The use of an enzyme that adds one or more glucose molecules to a 5-hydroxymethylcytosine residue in a nucleic acid for covalent tagging 5-hydroxymethylcytosine to generate glucosylated-5-hydroxymethylcytosine or gentibiose-containing-5-hydroxymethylcytosine, wherein the enzyme is an alpha-glucosyltransferase, a beta-glucosyltransferase, or a beta-glucosyl-alpha-glucosyl-transferase.

137. The use of paragraph 136, wherein the 5-hydroxymethylcytosine is naturally occurring.

138. The use of paragraph 136, further comprising the step of first contacting said nucleic acid with a at least one catalytically active TET family enzyme, functional TET family derivative, TET catalytically active fragment, or combination thereof, thereby converting 5-methylcytosine to hydroxymethylcytosine.

139. The use of an enzyme that utilizes labeled glucose or glucose-derivative donor substrates to add one or more labeled glucose molecules or glucose-derivatives to a 5-hydroxymethylcytosine residue in a nucleic acid to generate glucosylated-5-hydroxymethylcytosine or gentibiose-containing-5-hydroxymethylcytosine for detecting 5-hydroxymethylcytosine, wherein the enzyme is an alpha-glucosyltransferase, a beta-glucosyltransferase, or a beta-glucosyl-alpha-glucosyl-transferase.

140. The use of paragraph 139, wherein the glucose or glucose-derivative donor substrate is a uridine diphosphate glucose.

141. The use of paragraph 139, wherein the labeled glucose or glucose-derivative donor substrate is radioactively labeled.

142. The use of paragraph 141, wherein the radioactive label is $^{14}C$ or $^3H$.

143. The use of paragraph 139, wherein the 5-hydroxymethylcytosine is naturally occurring.

144. The use of paragraph 139, further comprising the step of first contacting said nucleic acid with at least one catalytically active TET family enzyme, functional TET family derivative, TET catalytically active fragment, or combination thereof, thereby converting 5-methylcytosine to 5-hydroxymethylcytosine.

145. The use of a protein that recognizes a glucose molecule, glucose-derivative or gentibiosyl molecule for detecting the covalently tagged 5-hydroxymethylcytosine of paragraph 136.

146. The use of paragraph 145, wherein the protein recognizes only the glucose molecule, glucose-derivative, or gentibiosyl.

147. The use of paragraph 145, wherein the protein recognizes the glucose molecule, glucose-derivative, or gentibiosyl only in the context of 5-hydroxymethylcytosine.

148. The use of paragraph 145, wherein the protein is a lectin.

149. The use of paragraph 148, wherein the lectin is *Musa acuminata* lectin.

150. The use of paragraph 145, wherein the protein is a antibody or antibody fragment thereof.

151. The use of paragraph 150, wherein the antibody or antibody fragment thereof is modified with a tag.

152. The use of paragraph 170, wherein the tag is a biotin molecule, a bead, a gold particle, or a fluorescent molecule.

153. The use of paragraph 145, wherein the protein is an enzyme.

154. The use of paragraph 153, wherein the enzyme is a hexokinase or beta-glucosyl-alpha-glucosyl-transferase.

155. The use of an enzyme and a glucose or glucose-derivative donor substrate for trapping covalent enzyme-DNA intermediates to detect a 5-hydroxymethylcytosine residue in a nucleic acid, wherein the enzyme is an alpha-glucosyltransferase, a beta-glucosyltransferase, or a beta-glucosyl-alpha-glucosyl-transferase.

156. The use of paragraph 155, wherein the glucose donor substrate is a uridine diphosphate glucose analog.

157. The use of paragraph 156, wherein the uridine diphosphate glucose analog is uridine-2-deoxy-2-fluoro-glucose.

158. The use of paragraph 155, wherein the 5-hydroxymethylcytosine is naturally occurring.

159. The use of paragraph 155, further comprising the step of first contacting said nucleic acid with at least one catalytically active TET family enzyme, functional TET family derivative, TET catalytically active fragment, or combination thereof, thereby converting 5-methylcytosine to 5-hydroxymethylcytosine.

160. The use of paragraph 155, wherein the enzyme is tagged.

161. The use of an assay to detect 5-hydroxymethylcytosine in a nucleic acid, the assay comprising contacting a nucleic acid with sodium hydrogen sulfite to convert a 5-hydroxymethylcytosine residue in the nucleic acid to cytosine-5- methylsulfonate, and contacting the sodium hydrogen sulfite contacted nucleic acid with a protein specific for cytosine-5-methylsulfonate.

162. The use of paragraph 161, wherein the protein is an antibody or antigen-binding fragment thereof, an enzyme, or an intrabody.

163. The use of paragraph 162, wherein the antibody comprises an antiserum.

164. The use of paragraph 162, wherein the antibody or antigen-binding fragment thereof, enzyme, or intrabody is modified with a tag.

165. The use of paragraph 164, wherein the tag is a biotin molecule, a bead, a gold particle, or a fluorescent molecule.

166. The use as in any one of paragraphs 136, 139, or 155, wherein the alpha-glucosyltransferase is encoded by a bacteriophage selected from the group consisting of T2, T4, and T6 bacteriophages.

167. The use as in any one of paragraphs 136, 139, or 155, wherein the beta-glucosyltransferase is encoded by a bacteriophage selected from T4 bacteriophages.

168. The use as in any one of paragraphs 136, 139, or 155, wherein the beta-glucosyl-alpha-glucosyl-transferase is encoded by a bacteriophage selected from the group consisting of T2 and T6 bacteriophages.

169. The use as in any one of paragraphs 136, 139, 155, or 161, wherein the nucleic acid is contacted in vitro, in a cell, or in vivo.

REFERENCES

The references cited herein and throughout the specification and examples are herein incorporated by reference in their entirety.

1. R. B. Lorsbach et al., Leukemia 17, 637 (March, 2003).
2. R. Ono et al., Cancer Res 62, 4075 (Jul. 15, 2002).
3. F. Delhommeau et al., Blood 112, lba-3 (November, 2008).
4. F. Viguie et al., Leukemia 19, 1411 (August, 2005).
5. C. Bogani et al., Stem Cells 26, 1920 (August, 2008).
6. G. Leone, M. T. Voso, L. Teofili, M. Lubbert, Clin Immunol 109, 89 (October, 2003).
7. L. Teofili et al., Int J Cancer 123, 1586 (Oct. 1, 2008).
8. S. R. Kornberg, S. B. Zimmerman, A. Kornberg, J Biol Chem 236, 1487 (May, 1961).
9. M. Winkler, W. Ruger, Nucleic Acids Res 21, 1500 (Mar. 25, 1993).
10. S. Kuno, I. R. Lehman, J Biol Chem 237, 1266 (April, 1962).
11. H. Hayatsu, M. Shiragami, Biochemistry 18, 632 (Feb. 20, 1979).
12. D. Zilberman, S. Henikoff, Development 134, 3959 (November, 2007).
13. L. Lariviere, N. Sommer, S. Morera, J Mol Biol 352, 139 (Sep. 9, 2005).
14. L. Lariviere, V. Gueguen-Chaignon, S. Morera, J Mol Biol 330, 1077 (Jul. 25, 2003).
15. J. Wicki, D. R. Rose, S. G. Withers, Methods Enzymol 354, 84 (2002).
16. I. J. Goldstein et al., Eur J Biochem 268, 2616 (May, 2001).

---

We claim:

1. A composition comprising a mixture of a methylcytosine dioxygenase, a DNA glucosyltransferase, and nucleic acid comprising glucosylated 5-hydroxymethylcytosine.

2. The composition of claim 1, wherein said methylcytosine dioxygenase is a ten eleven translocation (TET) enzyme.

3. The composition of claim 2, wherein said TET enzyme comprises TET1, TET2, TET3, CXXC4, or a combination thereof.

4. The composition of claim 1, wherein said DNA glucosyltransferase is a DNA glucosyltransferase encoded by a bacteriophage of the T even family.

5. The composition of claim 1, wherein said DNA glucosyltransferase is a beta-glucosyltransferase.

6. The composition of claim 1, wherein said DNA glucosyltransferase is an alpha-glucosyltransferase.

7. The composition of claim 1, wherein said mixture comprises a DNA methyltransferase.

8. The composition of claim 7, wherein said DNA methyltransferase is DNMT1.

9. The composition of claim 1, further comprising a glucose donor substrate.

10. The composition of claim 9, wherein said glucose donor substrate comprises uridine diphosphate glucose (UDPG).

11. The composition of claim 1, further comprising a buffer.

12. The composition of claim 1, further comprising 5-methylcytosine.

* * * * *

SEQUENCE LISTING

```
<160> NUMBER OF SEQ ID NOS: 102

<210> SEQ ID NO 1
<211> LENGTH: 24
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Leu, Ile or Val
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Leu, Ile or Val
<220> FEATURE:
<221> NAME/KEY: MOD_RES
<222> LOCATION: (17)..(17)
<223> OTHER INFORMATION: Arg or Lys
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(20)
<223> OTHER INFORMATION: Leu, Ile or Val

<400> SEQUENCE: 1

Gly Val Ala Xaa Ala Pro Xaa His Gly Ser Xaa Leu Ile Glu Cys Ala
1               5                   10                  15

Xaa Xaa Glu Xaa His Ala Thr Thr
            20
```

<210> SEQ ID NO 2
<211> LENGTH: 719
<212> TYPE: PRT
<213> ORGANISM: Homo sapiens

<400> SEQUENCE: 2

```
Glu Leu Pro Thr Cys Ser Cys Leu Asp Arg Val Ile Gln Lys Asp Lys
1               5                   10                  15

Gly Pro Tyr Tyr Thr His Leu Gly Ala Gly Pro Ser Val Ala Ala Val
            20                  25                  30

Arg Glu Ile Met Glu Asn Arg Tyr Gly Gln Lys Gly Asn Ala Ile Arg
        35                  40                  45

Ile Glu Ile Val Val Tyr Thr Gly Lys Glu Gly Lys Ser Ser His Gly
50                  55                  60

Cys Pro Ile Ala Lys Trp Val Leu Arg Arg Ser Ser Asp Glu Glu Lys
65                  70                  75                  80

Val Leu Cys Leu Val Arg Gln Arg Thr Gly His His Cys Pro Thr Ala
            85                  90                  95

Val Met Val Val Leu Ile Met Val Trp Asp Gly Ile Pro Leu Pro Met
            100                 105                 110

Ala Asp Arg Leu Tyr Thr Glu Leu Thr Glu Asn Leu Lys Ser Tyr Asn
        115                 120                 125

Gly His Pro Thr Asp Arg Arg Cys Thr Leu Asn Glu Asn Arg Thr Cys
130                 135                 140

Thr Cys Gln Gly Ile Asp Pro Glu Thr Cys Gly Ala Ser Phe Ser Phe
145                 150                 155                 160

Gly Cys Ser Trp Ser Met Tyr Phe Asn Gly Cys Lys Phe Gly Arg Ser
            165                 170                 175

Pro Ser Pro Arg Arg Phe Arg Ile Asp Pro Ser Ser Pro Leu His Glu
        180                 185                 190

Lys Asn Leu Glu Asp Asn Leu Gln Ser Leu Ala Thr Arg Leu Ala Pro
    195                 200                 205

Ile Tyr Lys Gln Tyr Ala Pro Val Ala Tyr Gln Asn Gln Val Glu Tyr
210                 215                 220

Glu Asn Val Ala Arg Glu Cys Arg Leu Gly Ser Lys Glu Gly Arg Pro
225                 230                 235                 240

Phe Ser Gly Val Thr Ala Cys Leu Asp Phe Cys Ala His Pro His Arg
            245                 250                 255

Asp Ile His Asn Met Asn Asn Gly Ser Thr Val Val Cys Thr Leu Thr
        260                 265                 270

Arg Glu Asp Asn Arg Ser Leu Gly Val Ile Pro Gln Asp Glu Gln Leu
    275                 280                 285

His Val Leu Pro Leu Tyr Lys Leu Ser Asp Thr Asp Glu Phe Gly Ser
290                 295                 300

Lys Glu Gly Met Glu Ala Lys Ile Lys Ser Gly Ala Ile Glu Val Leu
305                 310                 315                 320

Ala Pro Arg Arg Lys Lys Arg Thr Cys Phe Thr Gln Pro Val Pro Arg
            325                 330                 335

Ser Gly Lys Lys Arg Ala Ala Met Met Thr Glu Val Leu Ala His Lys
        340                 345                 350

Ile Arg Ala Val Glu Lys Lys Pro Ile Pro Arg Ile Lys Arg Lys Asn
    355                 360                 365

Asn Ser Thr Thr Thr Asn Asn Ser Lys Pro Ser Ser Leu Pro Thr Leu
370                 375                 380
```

```
Gly Ser Asn Thr Glu Thr Val Gln Pro Glu Val Lys Ser Glu Thr Glu
385                 390                 395                 400

Pro His Phe Ile Leu Lys Ser Ser Asp Asn Thr Lys Thr Tyr Ser Leu
                405                 410                 415

Met Pro Ser Ala Pro His Pro Val Lys Glu Ala Ser Pro Gly Phe Ser
            420                 425                 430

Trp Ser Pro Lys Thr Ala Ser Ala Thr Pro Ala Pro Leu Lys Asn Asp
        435                 440                 445

Ala Thr Ala Ser Cys Gly Phe Ser Glu Arg Ser Ser Thr Pro His Cys
    450                 455                 460

Thr Met Pro Ser Gly Arg Leu Ser Gly Ala Asn Ala Ala Ala Ala Asp
465                 470                 475                 480

Gly Pro Gly Ile Ser Gln Leu Gly Glu Val Ala Pro Leu Pro Thr Leu
                485                 490                 495

Ser Ala Pro Val Met Glu Pro Leu Ile Asn Ser Glu Pro Ser Thr Gly
            500                 505                 510

Val Thr Glu Pro Leu Thr Pro His Gln Pro Asn His Gln Pro Ser Phe
        515                 520                 525

Leu Thr Ser Pro Gln Asp Leu Ala Ser Ser Pro Met Glu Glu Asp Glu
    530                 535                 540

Gln His Ser Glu Ala Asp Glu Pro Pro Ser Asp Glu Pro Leu Ser Asp
545                 550                 555                 560

Asp Pro Leu Ser Pro Ala Glu Glu Lys Leu Pro His Ile Asp Glu Tyr
                565                 570                 575

Trp Ser Asp Ser Glu His Ile Phe Leu Asp Ala Asn Ile Gly Gly Val
            580                 585                 590

Ala Ile Ala Pro Ala His Gly Ser Val Leu Ile Glu Cys Ala Arg Arg
        595                 600                 605

Glu Leu His Ala Thr Thr Pro Val Glu His Pro Asn Arg Asn His Pro
    610                 615                 620

Thr Arg Leu Ser Leu Val Phe Tyr Gln His Lys Asn Leu Asn Lys Pro
625                 630                 635                 640

Gln His Gly Phe Glu Leu Asn Lys Ile Lys Phe Glu Ala Lys Glu Ala
                645                 650                 655

Lys Asn Lys Lys Met Lys Ala Ser Glu Gln Lys Asp Gln Ala Ala Asn
            660                 665                 670

Glu Gly Pro Glu Gln Ser Ser Glu Val Asn Glu Leu Asn Gln Ile Pro
        675                 680                 685

Ser His Lys Ala Leu Thr Leu Thr His Asp Asn Val Val Thr Val Ser
    690                 695                 700

Pro Tyr Ala Leu Thr His Val Ala Gly Pro Tyr Asn His Trp Val
705                 710                 715

<210> SEQ ID NO 3
<211> LENGTH: 879
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
```

```
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(26)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(45)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (56)..(835)
<223> OTHER INFORMATION: Any amino acid and this region may encompass 0
      to 780 residues
<220> FEATURE:
<221> NAME/KEY: MOD_RES
<222> LOCATION: (839)..(839)
<223> OTHER INFORMATION: Any amino acid
<220> FEATURE:
<221> NAME/KEY: MOD_RES
<222> LOCATION: (842)..(842)
<223> OTHER INFORMATION: Any amino acid
<220> FEATURE:
<221> NAME/KEY: MOD_RES
<222> LOCATION: (846)..(846)
<223> OTHER INFORMATION: Any amino acid
<220> FEATURE:
<221> NAME/KEY: MOD_RES
<222> LOCATION: (852)..(853)
<223> OTHER INFORMATION: Any amino acid
<220> FEATURE:
<221> NAME/KEY: MOD_RES
<222> LOCATION: (855)..(855)
<223> OTHER INFORMATION: Any amino acid
<220> FEATURE:
<221> NAME/KEY: MOD_RES
<222> LOCATION: (860)..(870)
<223> OTHER INFORMATION: Any amino acid
<220> FEATURE:
<221> NAME/KEY: MOD_RES
<222> LOCATION: (872)..(872)
<223> OTHER INFORMATION: Any amino acid
<220> FEATURE:
```

<221> NAME/KEY: MOD_RES
<222> LOCATION: (876)..(876)
<223> OTHER INFORMATION: Any amino acid

<400> SEQUENCE: 3

```
Pro Phe Xaa Gly Xaa Thr Ala Cys Xaa Asp Phe Xaa Ala His Xaa His
1               5                   10                  15

Xaa Asp Xaa Xaa Asn Xaa Xaa Xaa Xaa Xaa Thr Xaa Val Xaa Thr Leu
            20                  25                  30

Xaa Xaa Xaa Xaa Xaa Xaa Xaa Xaa Xaa Xaa Xaa Xaa Xaa Asp Glu Gln
        35                  40                  45

Xaa His Val Leu Pro Xaa Tyr Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa
```

```
            385                 390                 395                 400

Xaa Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Xaa Xaa
    515                 520                 525

Xaa Xaa Xaa Xaa Xaa Xaa Xaa Xaa Xaa Xaa Xaa Xaa Xaa Xaa Xaa Xaa
530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa Xaa
        580                 585                 590

Xaa Xaa Xaa Xaa Xaa Xaa Xaa Xaa Xaa Xaa Xaa Xaa Xaa Xaa Xaa Xaa
    595                 600                 605

Xaa Xaa Xaa Xaa Xaa Xaa Xaa Xaa Xaa Xaa Xaa Xaa Xaa Xaa Xaa Xaa
610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa Xaa
        660                 665                 670

Xaa Xaa Xaa Xaa Xaa Xaa Xaa Xaa Xaa Xaa Xaa Xaa Xaa Xaa Xaa Xaa
    675                 680                 685

Xaa Xaa Xaa Xaa Xaa Xaa Xaa Xaa Xaa Xaa Xaa Xaa Xaa Xaa Xaa Xaa
690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa Xaa Xaa Xaa
        740                 745                 750

Xaa Xaa Xaa Xaa Xaa Xaa Xaa Xaa Xaa Xaa Xaa Xaa Xaa Xaa Xaa Xaa
    755                 760                 765

Xaa Xaa Xaa Xaa Xaa Xaa Xaa Xaa Xaa Xaa Xaa Xaa Xaa Xaa Xaa Xaa
770                 775                 780

Xaa Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
            805                 810                 815
```

```
Xaa Xaa Xaa Xaa Xaa Xaa Xaa Xaa Xaa Xaa Xaa Xaa Xaa Xaa Xaa
            820                 825                 830

Xaa Xaa Xaa Gly Val Ala Xaa Ala Pro Xaa His Gly Ser Xaa Leu Ile
        835                 840                 845

Glu Cys Ala Xaa Xaa Glu Xaa His Ala Thr Thr Xaa Xaa Xaa Xaa Xaa
850                 855                 860

Xaa Xaa Xaa Xaa Xaa Xaa Arg Xaa Ser Leu Val Xaa Tyr Gln His
865                 870                 875

<210> SEQ ID NO 4
<211> LENGTH: 878
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(26)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(44)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (55)..(834)
<223> OTHER INFORMATION: Any amino acid and this region may encompass 0
      to 780 residues
<220> FEATURE:
```

```
<221> NAME/KEY: MOD_RES
<222> LOCATION: (838)..(838)
<223> OTHER INFORMATION: Any amino acid
<220> FEATURE:
<221

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa
            595                 600                 605

Xaa Xaa Xaa Xaa Xaa Xaa Xaa Xaa Xaa Xaa Xaa Xaa Xaa Xaa Xaa
            610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa

```
                  660                 665                 670
Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa Xaa Xaa
            820                 825                 830

Xaa Xaa Gly Val Ala Xaa Ala Pro Xaa His Gly Ser Xaa Leu Ile Glu
            835                 840                 845

Cys Ala Xaa Xaa Glu Xaa His Ala Thr Thr Xaa Xaa Xaa Xaa Xaa Xaa
            850                 855                 860

Xaa Xaa Xaa Xaa Xaa Arg Xaa Ser Leu Val Xaa Tyr Gln His
865                 870                 875

<210> SEQ ID NO 5
<211> LENGTH: 887
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
```

```
<222> LOCATION: (22)..(32)
<223> OTHER INFORMATION: Any amino acid and this region may encopass 2
      to 11 residues
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (39)..(51)
<223> OTHER INFORMATION: Any amino acid and this region may encompass 9
      to 13 residues
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (62)..(841)
<223> OTHER INFORMATION: Any amino acid and this region may encompass 0
      to 780 residues
<220> FEATURE:
<221> NAME/KEY: MOD_RES
<222> LOCATION: (845)..(845)
<223> OTHER INFORMATION: Any amino acid
<220> FEATURE:
<221> NAME/KEY: MOD_RES
<222> LOCATION: (848)..(848)
<223> OTHER INFORMATION: Any amino acid
<220> FEATURE:
<221> NAME/KEY: MOD_RES
<222> LOCATION: (852)..(852)
<223> OTHER INFORMATION: Any amino acid
<220> FEATURE:
<221> NAME/KEY: MOD_RES
<222> LOCATION: (858)..(859)
<223> OTHER INFORMATION: Any amino acid
<220> FEATURE:
<221> NAME/KEY: MOD_RES
<222> LOCATION: (861)..(861)
<223> OTHER INFORMATION: Any amino acid
<220> FEATURE:
<221> NAME/KEY: MOD_RES
<222> LOCATION: (866)..(878)
<223> OTHER INFORMATION: Any amino acid and this region may encompass 5
      to 13 residues
<220> FEATURE:
<221> NAME/KEY: MOD_RES
<222> LOCATION: (880)..(880)
<223> OTHER INFORMATION: Any amino acid
<220> FEATURE:
<221> NAME/KEY: MOD_RES
<222> LOCATION: (884)..(884)
<223> OTHER INFORMATION: Any amino acid

<400> SEQUENCE: 5

Pro Phe Xaa Gly Xaa Thr Ala Cys Xaa Asp Phe Xaa Xaa His Xaa His
1               5                   10                  15

Xaa Asp Xaa Xaa Asn Xaa Xaa Xaa Xaa Xaa Xaa Xaa Xaa Xaa Xaa Xaa
            20                  25                  30

Thr Xaa Val Xaa Thr Leu Xaa Xaa Xaa Xaa Xaa Xaa Xaa Xaa Xaa Xaa
        35                  40                  45

Xaa Xaa Xaa Asp Glu Gln Xaa His Val Leu Pro Xaa Tyr Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80
```

```
Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
                115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
                195                 200                 205

Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa Xaa Xaa Xaa Xaa Xaa Xaa
                370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa
                435                 440                 445

Xaa Xaa Xaa Xaa Xaa Xaa Xaa Xaa Xaa Xaa Xaa Xaa Xaa Xaa Xaa
                450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
                485                 490                 495
```

Xaa Xaa Xaa Xaa Xaa Xaa Xaa Xaa Xaa Xaa Xaa Xaa Xaa
          500                 505                 510

Xaa Xaa Xaa Xaa Xaa Xaa Xaa Xaa Xaa Xaa Xaa Xaa Xaa
          515                 520                 525

Xaa Xaa Xaa Xaa Xaa Xaa Xaa Xaa Xaa Xaa Xaa Xaa Xaa
          530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa
          565                 570                 575

Xaa Xaa Xaa Xaa Xaa Xaa Xaa Xaa Xaa Xaa Xaa Xaa Xaa
          580                 585                 590

Xaa Xaa Xaa Xaa Xaa Xaa Xaa Xaa Xaa Xaa Xaa Xaa Xaa
          595                 600                 605

Xaa Xaa Xaa Xaa Xaa Xaa Xaa Xaa Xaa Xaa Xaa Xaa Xaa
          610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa
          645                 650                 655

Xaa Xaa Xaa Xaa Xaa Xaa Xaa Xaa Xaa Xaa Xaa Xaa Xaa
          660                 665                 670

Xaa Xaa Xaa Xaa Xaa Xaa Xaa Xaa Xaa Xaa Xaa Xaa Xaa
          675                 680                 685

Xaa Xaa Xaa Xaa Xaa Xaa Xaa Xaa Xaa Xaa Xaa Xaa Xaa
          690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa
          725                 730                 735

Xaa Xaa Xaa Xaa Xaa Xaa Xaa Xaa Xaa Xaa Xaa Xaa Xaa
          740                 745                 750

Xaa Xaa Xaa Xaa Xaa Xaa Xaa Xaa Xaa Xaa Xaa Xaa Xaa
          755                 760                 765

Xaa Xaa Xaa Xaa Xaa Xaa Xaa Xaa Xaa Xaa Xaa Xaa Xaa
          770                 775                 780

Xaa Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa
          805                 810                 815

Xaa Xaa Xaa Xaa Xaa Xaa Xaa Xaa Xaa Xaa Xaa Xaa Xaa
          820                 825                 830

Xaa Xaa Xaa Xaa Xaa Xaa Xaa Xaa Xaa Gly Val Ala Xaa Ala Pro Xaa
          835                 840                 845

His Gly Ser Xaa Leu Ile Glu Cys Ala Xaa Xaa Glu Xaa His Ala Thr
          850                 855                 860

Thr Xaa Xaa Xaa Xaa Xaa Xaa Xaa Xaa Xaa Xaa Xaa Xaa Xaa Arg Xaa
865                 870                 875                 880

Ser Leu Val Xaa Tyr Gln His
          885

<210> SEQ ID NO 6
<211> LENGTH: 1776
<212> TYPE: PRT

<213> ORGANISM: Homo sapiens

<400> SEQUENCE: 6

```
Met Ser Gln Phe Gln Val Pro Leu Ala Val Gln Pro Asp Leu Pro Gly
 1               5                  10                  15
Leu Tyr Asp Phe Pro Gln Arg Gln Val Met Val Gly Ser Phe Pro Gly
                20                  25                  30
Ser Gly Leu Ser Met Ala Gly Ser Glu Ser Gln Leu Arg Gly Gly Gly
            35                  40                  45
Asp Gly Arg Lys Lys Arg Lys Arg Cys Gly Thr Cys Glu Pro Cys Arg
        50                  55                  60
Arg Leu Glu Asn Cys Gly Ala Cys Thr Ser Cys Thr Asn Arg Arg Thr
65                  70                  75                  80
His Gln Ile Cys Lys Leu Arg Lys Cys Glu Val Leu Lys Lys Lys Val
                85                  90                  95
Gly Leu Leu Lys Glu Thr Gly Ser Glu Leu Ser Pro Val Asp Gly Pro
                100                 105                 110
Val Pro Gly Gln Met Asp Ser Gly Pro Val Tyr His Gly Asp Ser Arg
                115                 120                 125
Gln Leu Ser Ala Ser Gly Val Pro Val Asn Gly Ala Arg Glu Pro Ala
        130                 135                 140
Gly Pro Ser Leu Leu Gly Thr Gly Gly Pro Trp Arg Val Asp Gln Lys
145                 150                 155                 160
Pro Asp Trp Glu Ala Ala Pro Gly Pro Ala His Thr Ala Arg Leu Glu
                165                 170                 175
Asp Ala His Asp Leu Val Ala Phe Ser Ala Val Ala Glu Ala Val Ser
                180                 185                 190
Ser Tyr Gly Ala Leu Ser Thr Arg Leu Tyr Glu Thr Phe Asn Arg Glu
            195                 200                 205
Met Ser Arg Glu Ala Gly Asn Asn Ser Arg Gly Pro Arg Pro Gly Pro
        210                 215                 220
Glu Gly Cys Ser Ala Gly Ser Glu Asp Leu Asp Thr Leu Gln Thr Ala
225                 230                 235                 240
Leu Ala Leu Ala Arg His Gly Met Lys Pro Pro Asn Cys Asn Cys Asp
                245                 250                 255
Gly Pro Glu Cys Pro Asp Tyr Leu Glu Trp Leu Glu Gly Lys Ile Lys
                260                 265                 270
Ser Val Val Met Glu Gly Gly Glu Glu Arg Pro Arg Leu Pro Gly Pro
            275                 280                 285
Leu Pro Pro Gly Glu Ala Gly Leu Pro Ala Pro Ser Thr Arg Pro Leu
        290                 295                 300
Leu Ser Ser Glu Val Pro Gln Ile Ser Pro Gln Glu Gly Leu Pro Leu
305                 310                 315                 320
Ser Gln Ser Ala Leu Ser Ile Ala Lys Glu Lys Asn Ile Ser Leu Gln
                325                 330                 335
Thr Ala Ile Ala Ile Glu Ala Leu Thr Gln Leu Ser Ser Ala Leu Pro
                340                 345                 350
Gln Pro Ser His Ser Thr Pro Gln Ala Ser Cys Pro Leu Pro Glu Ala
            355                 360                 365
Leu Ser Pro Pro Ala Pro Phe Arg Ser Pro Gln Ser Tyr Leu Arg Ala
        370                 375                 380
Pro Ser Trp Pro Val Val Pro Pro Glu Glu His Ser Ser Phe Ala Pro
385                 390                 395                 400
```

Asp Ser Ser Ala Phe Pro Pro Ala Thr Pro Arg Thr Glu Phe Pro Glu
            405                 410                 415

Ala Trp Gly Thr Asp Thr Pro Ala Thr Pro Arg Ser Ser Trp Pro
    420                 425                 430

Met Pro Arg Pro Ser Pro Asp Pro Met Ala Glu Leu Glu Gln Leu Leu
        435                 440                 445

Gly Ser Ala Ser Asp Tyr Ile Gln Ser Val Phe Lys Arg Pro Glu Ala
    450                 455                 460

Leu Pro Thr Lys Pro Lys Val Lys Val Glu Ala Pro Ser Ser Ser Pro
465                 470                 475                 480

Ala Pro Ala Pro Ser Pro Val Leu Gln Arg Glu Ala Pro Thr Pro Ser
            485                 490                 495

Ser Glu Pro Asp Thr His Gln Lys Ala Gln Thr Ala Leu Gln Gln His
            500                 505                 510

Leu His His Lys Arg Ser Leu Phe Leu Glu Gln Val His Asp Thr Ser
    515                 520                 525

Phe Pro Ala Pro Ser Glu Pro Ser Ala Pro Gly Trp Trp Pro Pro
    530                 535                 540

Ser Ser Pro Val Pro Arg Leu Pro Asp Arg Pro Pro Lys Glu Lys Lys
545                 550                 555                 560

Lys Lys Leu Pro Thr Pro Ala Gly Gly Pro Val Gly Thr Glu Lys Ala
                565                 570                 575

Ala Pro Gly Ile Lys Pro Ser Val Arg Lys Pro Ile Gln Ile Lys Lys
            580                 585                 590

Ser Arg Pro Arg Glu Ala Gln Pro Leu Phe Pro Val Arg Gln Ile
    595                 600                 605

Val Leu Glu Gly Leu Arg Ser Pro Ala Ser Gln Glu Val Gln Ala His
    610                 615                 620

Pro Pro Ala Pro Leu Pro Ala Ser Gln Gly Ser Ala Val Pro Leu Pro
625                 630                 635                 640

Pro Glu Pro Ser Leu Ala Leu Phe Ala Pro Ser Pro Ser Arg Asp Ser
            645                 650                 655

Leu Leu Pro Pro Thr Gln Glu Met Arg Ser Pro Ser Pro Met Thr Ala
                660                 665                 670

Leu Gln Pro Gly Ser Thr Gly Pro Leu Pro Pro Ala Asp Asp Lys Leu
        675                 680                 685

Glu Glu Leu Ile Arg Gln Phe Glu Ala Glu Phe Gly Asp Ser Phe Gly
            690                 695                 700

Leu Pro Gly Pro Pro Ser Val Pro Ile Gln Asp Pro Glu Asn Gln Gln
705                 710                 715                 720

Thr Cys Leu Pro Ala Pro Glu Ser Pro Phe Ala Thr Arg Ser Pro Lys
                725                 730                 735

Gln Ile Lys Ile Glu Ser Ser Gly Ala Val Thr Val Leu Ser Thr Thr
        740                 745                 750

Cys Phe His Ser Glu Glu Gly Gly Gln Glu Ala Thr Pro Thr Lys Ala
    755                 760                 765

Glu Asn Pro Leu Thr Pro Thr Leu Ser Gly Phe Leu Glu Ser Pro Leu
770                 775                 780

Lys Tyr Leu Asp Thr Pro Thr Lys Ser Leu Leu Asp Thr Pro Ala Lys
785                 790                 795                 800

Arg Ala Gln Ala Glu Phe Pro Thr Cys Asp Cys Val Glu Gln Ile Val
            805                 810                 815

Glu Lys Asp Glu Gly Pro Tyr Tyr Thr His Leu Gly Ser Gly Pro Thr

```
                820                 825                 830
Val Ala Ser Ile Arg Glu Leu Met Glu Glu Arg Tyr Gly Glu Lys Gly
            835                 840                 845

Lys Ala Ile Arg Ile Glu Lys Val Ile Tyr Thr Gly Lys Glu Gly Lys
    850                 855                 860

Ser Ser Arg Gly Cys Pro Ile Ala Lys Trp Val Ile Arg His Thr
865                 870                 875                 880

Leu Glu Glu Lys Leu Leu Cys Leu Val Arg His Arg Ala Gly His His
                885                 890                 895

Cys Gln Asn Ala Val Ile Val Ile Leu Ile Leu Ala Trp Glu Gly Ile
            900                 905                 910

Pro Arg Ser Leu Gly Asp Thr Leu Tyr Gln Glu Leu Thr Asp Thr Leu
        915                 920                 925

Arg Lys Tyr Gly Asn Pro Thr Ser Arg Arg Cys Gly Leu Asn Asp Asp
    930                 935                 940

Arg Thr Cys Ala Cys Gln Gly Lys Asp Pro Asn Thr Cys Gly Ala Ser
945                 950                 955                 960

Phe Ser Phe Gly Cys Ser Trp Ser Met Tyr Phe Asn Gly Cys Lys Tyr
                965                 970                 975

Ala Arg Ser Lys Thr Pro Arg Lys Phe Arg Leu Ala Gly Asp Asn Pro
            980                 985                 990

Lys Glu Glu Val Leu Arg Lys Ser Phe Gln Asp Leu Ala Thr Glu
        995                 1000                1005

Val Ala Pro Leu Tyr Lys Arg Leu Ala Pro Gln Ala Tyr Gln Asn
   1010                 1015                 1020

Gln Val Thr Asn Glu Glu Ile Ala Ile Asp Cys Arg Leu Gly Leu
   1025                 1030                 1035

Lys Glu Gly Arg Pro Phe Ala Gly Val Thr Ala Cys Met Asp Phe
   1040                 1045                 1050

Cys Ala His Ala His Lys Asp Gln His Asn Leu Tyr Asn Gly Cys
   1055                 1060                 1065

Thr Val Val Cys Thr Leu Thr Lys Glu Asp Asn Arg Cys Val Gly
   1070                 1075                 1080

Lys Ile Pro Glu Asp Glu Gln Leu His Val Leu Pro Leu Tyr Lys
   1085                 1090                 1095

Met Ala Asn Thr Asp Glu Phe Gly Ser Glu Glu Asn Gln Asn Ala
   1100                 1105                 1110

Lys Val Gly Ser Gly Ala Ile Gln Val Leu Thr Ala Phe Pro Arg
   1115                 1120                 1125

Glu Val Arg Arg Leu Pro Glu Pro Ala Lys Ser Cys Arg Gln Arg
   1130                 1135                 1140

Gln Leu Glu Ala Arg Lys Ala Ala Ala Glu Lys Lys Lys Ile Gln
   1145                 1150                 1155

Lys Glu Lys Leu Ser Thr Pro Glu Lys Ile Lys Gln Glu Ala Leu
   1160                 1165                 1170

Glu Leu Ala Gly Ile Thr Ser Asp Pro Gly Leu Ser Leu Lys Gly
   1175                 1180                 1185

Gly Leu Ser Gln Gln Gly Leu Lys Pro Ser Leu Lys Val Glu Pro
   1190                 1195                 1200

Gln Asn His Phe Ser Ser Phe Lys Tyr Ser Gly Asn Ala Val Val
   1205                 1210                 1215

Glu Ser Tyr Ser Val Leu Gly Asn Cys Arg Pro Ser Asp Pro Tyr
   1220                 1225                 1230
```

```
Ser Met Asn Ser Val Tyr Ser Tyr His Ser Tyr Ala Gln Pro
1235             1240             1245

Ser Leu Thr Ser Val Asn Gly Phe His Ser Lys Tyr Ala Leu Pro
1250             1255             1260

Ser Phe Ser Tyr Tyr Gly Phe Pro Ser Ser Asn Pro Val Phe Pro
1265             1270             1275

Ser Gln Phe Leu Gly Pro Gly Ala Trp Gly His Ser Gly Ser Ser
1280             1285             1290

Gly Ser Phe Glu Lys Lys Pro Asp Leu His Ala Leu His Asn Ser
1295             1300             1305

Leu Ser Pro Ala Tyr Gly Gly Ala Glu Phe Ala Glu Leu Pro Ser
1310             1315             1320

Gln Ala Val Pro Thr Asp Ala His His Pro Thr Pro His His Gln
1325             1330             1335

Gln Pro Ala Tyr Pro Gly Pro Lys Glu Tyr Leu Leu Pro Lys Ala
1340             1345             1350

Pro Leu Leu His Ser Val Ser Arg Asp Pro Ser Pro Phe Ala Gln
1355             1360             1365

Ser Ser Asn Cys Tyr Asn Arg Ser Ile Lys Gln Glu Pro Val Asp
1370             1375             1380

Pro Leu Thr Gln Ala Glu Pro Val Pro Arg Asp Ala Gly Lys Met
1385             1390             1395

Gly Lys Thr Pro Leu Ser Glu Val Ser Gln Asn Gly Gly Pro Ser
1400             1405             1410

His Leu Trp Gly Gln Tyr Ser Gly Gly Pro Ser Met Ser Pro Lys
1415             1420             1425

Arg Thr Asn Gly Val Gly Gly Ser Trp Gly Val Phe Ser Ser Gly
1430             1435             1440

Glu Ser Pro Ala Ile Val Pro Asp Lys Leu Ser Ser Phe Gly Ala
1445             1450             1455

Ser Cys Leu Ala Pro Ser His Phe Thr Asp Gly Gln Trp Gly Leu
1460             1465             1470

Phe Pro Gly Glu Gly Gln Gln Ala Ala Ser His Ser Gly Gly Arg
1475             1480             1485

Leu Arg Gly Lys Pro Trp Ser Pro Cys Lys Phe Gly Asn Ser Thr
1490             1495             1500

Ser Ala Leu Ala Gly Pro Ser Leu Thr Glu Lys Pro Trp Ala Leu
1505             1510             1515

Gly Ala Gly Asp Phe Asn Ser Ala Leu Lys Gly Ser Pro Gly Phe
1520             1525             1530

Gln Asp Lys Leu Trp Asn Pro Met Lys Gly Glu Glu Gly Arg Ile
1535             1540             1545

Pro Ala Ala Gly Ala Ser Gln Leu Asp Arg Ala Trp Gln Ser Phe
1550             1555             1560

Gly Leu Pro Leu Gly Ser Ser Glu Lys Leu Phe Gly Ala Leu Lys
1565             1570             1575

Ser Glu Glu Lys Leu Trp Asp Pro Phe Ser Leu Glu Glu Gly Pro
1580             1585             1590

Ala Glu Glu Pro Pro Ser Lys Gly Ala Val Lys Glu Glu Lys Gly
1595             1600             1605

Gly Gly Gly Ala Glu Glu Glu Glu Glu Leu Trp Ser Asp Ser
1610             1615             1620
```

```
Glu His Asn Phe Leu Asp Glu Asn Ile Gly Gly Val Ala Val Ala
    1625                1630                1635

Pro Ala His Gly Ser Ile Leu Ile Glu Cys Ala Arg Arg Glu Leu
    1640                1645                1650

His Ala Thr Thr Pro Leu Lys Lys Pro Asn Arg Cys His Pro Thr
    1655                1660                1665

Arg Ile Ser Leu Val Phe Tyr Gln His Lys Asn Leu Asn Gln Pro
    1670                1675                1680

Asn His Gly Leu Ala Leu Trp Glu Ala Lys Met Lys Gln Leu Ala
    1685                1690                1695

Glu Arg Ala Arg Ala Arg Gln Glu Glu Ala Ala Arg Leu Gly Leu
    1700                1705                1710

Gly Gln Gln Glu Ala Lys Leu Tyr Gly Lys Lys Arg Lys Trp Gly
    1715                1720                1725

Gly Thr Val Val Ala Glu Pro Gln Gln Lys Glu Lys Lys Gly Val
    1730                1735                1740

Val Pro Thr Arg Gln Ala Leu Ala Val Pro Thr Asp Ser Ala Val
    1745                1750                1755

Thr Val Ser Ser Tyr Ala Tyr Thr Lys Val Thr Gly Pro Tyr Ser
    1760                1765                1770

Arg Trp Ile
    1775

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attgtcgtag gttaagtgga ttgtaaggag gtag                              34

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attcactacc actctcctta cttctctttc tcc                               33

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgaaatatt gtggtaggtt aagtggattg taaggag                           37

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 10
catcttaatt aacactacca ctctccttac ttctctttct                    40

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgaattaag gatttttttg tgtg                                    24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaaaaacatt tccctacttc                                         20

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttagattat tttagtagag gtatataagt                              30

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accaatcaaa tttctcaact ctat                                    24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgagaaattt gattggtatt taagttg                                 27

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 16
caatcatctc tttaataaca ttaactaacc                                          30

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ile Arg Leu
1

<210> SEQ ID NO 18
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
attgtggtag gttaagtgga ttgtaaggag gtaggtgtga tatctgtagc catcgaggaa         60
gatttaaata ctggaattcc acaatcagaa ctttagggac caggctctcc gggaccttat        120
aacttccaag ggtggtgacg actgtgaagt ggccgcgggg agctctgtgg agaaagagaa        180
gtaaggagag tggtagtgaa t                                                  201

<210> SEQ ID NO 19
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (103)..(106)
<223> OTHER INFORMATION: a, c, g, t, unknown or other

<400> SEQUENCE: 19
gtgaaatatt gtggtaggtt aagtggattg taaggaggta ggtgttgtag agatcgagga         60
agatttaaat agtggagaat gagaagttta gaagaggatg ttnnnnatgt gttataagag        120
aaagagaagt aaggagagtg gtagtgttaa ttaagatg                                158

<210> SEQ ID NO 20
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gtgaattaag gatttttttg tgtgttttg gttttaggag agtttatttt gtgtgattga          60
tttgaggttt taaaagtttt tgagtaatat taagaatgtt ttattaggat tttttttta        120 aaaatatttt aaagattttt ttttgtttt tgttggtgaa gttttttagg gaattagaga        180
tatgggaaga tgaattggag gtttaagaag tattagagag aggatttgta agaaaagttg        240
gggttagatg tgtatttgag tggtatgaag tagggaaatg tttttt                      286

<210> SEQ ID NO 21
<211> LENGTH: 221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gttagattat tttagtagag gtatataagt tcggtttcgg tattttgtt tttattggtt      60 ggatatttcg tattttcga gttttaaaa aygaattaat aggaagagcg gatagcgatt     120
tttaacgcgt aagcgtatat ttttttaggt agcgggtagt agtcgtttta gggagggacg   180
aagagattta gtaatttata gagttgagaa atttgattgg t                       221

<210> SEQ ID NO 22
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
tgagaaattt gattggtatt taagttgttt aattaatagt tgtcgttgaa gggtggggtt    60
ggatggcgta agttatagtt gaaggaagaa cgtgagtayg aggtattgag gtgattggtt   120
gaaggtattt tcgttgagta tttagacgtt tttttggttt ttttggcgtt aaaatgtcgt   180
tcgtggtagg ggttattcgg cggttggacg agatagtggt gaatcgtatc gcggcggggg   240 aagttatttta gyggttagtt aatgttatta aagagatgat tg                     282

<210> SEQ ID NO 23
<211> LENGTH: 9601
<212> TYPE: DNA
<213> ORGANISM: Homo sapiens

<400> SEQUENCE: 23
agacactgct gctccggggg gctgacctgg cggggagtgg ccgcgcagtc tgctccggcg    60
ccgctttgtg cgcgcagccg ctggcccctc tactcccggg tctgccccc gggacacccc    120 tctgcctcgc ccaagtcatg cagccctacc tgcctctcca ctgtggacct ttgggaaccg   180
actcctcacc tcggggctc gggccttgac tgtgctggga gccggtaggc gtcctccgcg   240
acccgcccgc gccctcgcg cccgccgggg ccccgggctc caaagttgtg gggaccggcg   300
cgagttggaa agtttgcccg agggctggtg caggcttgga gctgggggcc gtgcgctgcc   360
ctgggaatgt gacccggcca gcgaccaaaa ccttgtgtga ctgagctgaa gagcagtgca   420
tccagattct cctcagaagt gagactttcc aaaggaccaa tgactctgtt tcctgcgccc   480
tttcattttt tcctactctg tagctatgtc tcgatcccgc catgcaaggc cttccagatt   540
agtcaggaag gaagatgtaa acaaaaaaaa gaaaaacagc caactacgaa agacaaccaa   600
gggagccaac aaaaatgtgg catcagtcaa gactttaagc cctggaaaat taaagcaatt   660
aattcaagaa agagatgtta agaaaaaaac agaacctaaa ccacccgtgc cagtcagaag   720
ccttctgaca agagctggag cagcacgcat gaatttggat aggactgagg ttctttttca   780
gaacccagag tccttaacct gcaatggggt tacaatggcg ctacgaagca cctctcttag   840
caggcgactc tcccaacccc cactggtcgt agccaaatcc aaaaaggttc cactttctaa   900

```
gggtttagaa aagcaacatg attgtgatta taagatactc cctgctttgg gagtaaagca    960
ctcagaaaat gattcggttc caatgcaaga cacccaagtc cttcctgata tagagactct   1020
aattggtgta caaaatccct ctttacttaa aggtaagagc caagagacaa ctcagttttg   1080
gtcccaaaga gttgaggatt ccaagatcaa tatccctacc cacagtggcc ctgcagctga   1140
gatccttcct gggccactgg aagggacacg ctgtggtgaa ggactattct ctgaagagac   1200
attgaatgat accagtggtt ccccaaaaat gtttgctcag gacacagtgt gtgctccttt   1260
tccccaaaga gcaaccccca agttacctc tcaaggaaac cccagcattc agttagaaga   1320
gttgggttca cgagtagaat ctcttaagtt atctgattct tacctggatc ccattaaaag   1380
tgaacatgat tgctaccc ca cctccagtct taataaggtt atacctgact tgaaccttag   1440
aaactgcttg gctcttggtg ggtctacgtc tcctacctct gtaataaaat tcctcttggc   1500
aggctcaaaa caagcgaccc ttggtgctaa accagatcat caagaggcct tcgaagctac   1560
tgcaaatcaa caggaagttt ctgataccac ctctttccta ggacaggcct ttggtgctat   1620
cccacatcaa tgggaacttc ctggtgctga cccagttcat ggtgaggccc tgggtgagac   1680
cccagatcta ccagagattc ctggtgctat tccagtccaa ggagaggtct ttggtactat   1740
tttagaccaa caagaaactc ttggtatgag tgggagtgtt gtcccagact tgcctgtctt   1800
ccttcctgtt cctccaaatc caattgctac ctttaatgct ccttccaaat ggcctgagcc   1860
ccaaagcact gtctcatatg gacttgcagt ccagggtgct atacagattt tgcctttggg   1920
ctcaggacac actcctcaat catcatcaaa ctcagagaaa aattcattac ctccagtaat   1980
ggctataagc aatgtagaaa atgagaagca ggttcatata agcttcctgc cagctaacac   2040
tcagggggttc ccattagccc ctgagagagg actcttccat gcttcactgg gtatagccca   2100
actctctcag gctggtccta gcaaatcaga cagagggagc tcccaggtca gtgtaaccag   2160
cacagttcat gttgtcaaca ccacagtggt gactatgcca gtgccaatgg tcagtacctc   2220
ctcttcttcc tataccactt tgctaccgac tttggaaaag aagaaaagaa agcgatgtgg   2280
ggtctgtgaa ccctgccagc agaagaccaa ctgtggtgaa tgcacttact gcaagaacag   2340
aaagaacagc catcagatct gtaagaaaag aaaatgtgag gagctgaaaa agaaaccatc   2400
tgttgttgtg cctctggagg ttataaagga aaacaagagg ccccagaggg aaaagaagcc   2460
caaagtttta aaggcagatt ttgacaacaa accagtaaat ggccccaagt cagaatccat   2520
ggactacagt agatgtggtc atggggaaga acaaaaattg gaattgaacc cacatactgt   2580
tgaaaatgta actaaaaatg aagacagcat gacaggcatc gaggtggaga agtggacaca   2640
aaacaagaaa tcacagttaa ctgatcacgt gaaaggagat tttagtgcta atgtcccaga   2700
agctgaaaaa tcgaaaaact ctgaagttga caagaaacga accaaatctc caaaattgtt   2760
tgtacaaacc gtaagaaatg gcattaaaca tgtacactgt ttaccagctg aaacaaatgt   2820
ttcatttaaa aaattcaata ttgaagaatt cggcaagaca ttggaaaaca attcttataa   2880
attcctaaaa gacactgcaa accataaaaa cgctatgagc tctgttgcta ctgatatgag   2940
ttgtgatcat ctcaagggga gaagtaacgt tttagtattc cagcagcctg gctttaactg   3000
cagttccatt ccacattctt cacactccat cataaatcat catgctagta tacacaatga   3060
aggtgatcaa ccaaaaactc ctgagaatat accaagtaaa gaaccaaaag atggatctcc   3120
cgttcaacca gtctcttat cgttaatgaa agataggaga ttaacattgg agcaagtggt   3180
agccatagag gccctgactc aactctcaga agccccatca gagaattcct ccccatcaaa   3240
gtcagagaag gatgaggaat cagagcagag aacagccagt ttgcttaata gctgcaaagc   3300
```

-continued

```
tatcctctac actgtaagaa aagacctcca agacccaaac ttacagggag agccaccaaa    3360
acttaatcac tgtccatctt tggaaaaaca aagttcatgc aacacggtgg ttttcaatgg    3420
gcaaactact acccttttcca actcacatat caactcagct actaaccaag catccacaaa   3480
gtcacatgaa tattcaaaag tcacaaattc attatctctt tttataccaa aatcaaattc    3540
atccaagatt gacaccaata aaagtattgc tcaagggata attactcttg acaattgttc    3600
caatgatttg catcagttgc caccaagaaa taatgaagtg gagtattgca accagttact    3660
ggacagcagc aaaaaattgg actcagatga tctatcatgt caggatgcaa cccatacccca   3720 aattgaggaa gatgttgcaa cacagttgac acaacttgct tcgataatta agatcaatta    3780
tataaaacca gaggacaaaa aagttgaaag tacaccaaca agccttgtca catgtaatgt    3840
acagcaaaaa tacaatcagg agaagggcac aatacaacag aaaccacctt caagtgtaca    3900
caataatcat ggttcatcat taacaaaaca aaagaaccca acccagaaaa agacaaaatc    3960
caccccatca agagatcggc ggaaaaagaa gcccacagtt gtaagttatc aagaaaatga    4020
tcggcagaag tgggaaaagt tgtcctatat gtatggcaca atatgcgaca tttggatagc    4080
atcgaaattt caaaattttg ggcaattttg tccacatgat tttcctactg tatttgggaa    4140
aatttcttcc tcgaccaaaa tatggaaacc actggctcaa acgaggtcca ttatgcaacc    4200
caaaacagta tttccaccac tcactcagat aaaattacag agatatcctg aatcagcaga    4260
ggaaaaggtg aaggttgaac cattggattc actcagctta tttcatctta aaacggaatc    4320
caacgggaag gcattcactg ataaagctta taattctcag gtacagttaa cggtgaatgc    4380
caatcagaaa gcccatcctt tgacccagcc ctcctctcca cctaaccagt gtgctaacgt    4440
gatggcaggc gatgaccaaa tacggtttca gcaggttgtt aaggagcaac tcatgcatca    4500
gagactgcca acattgcctg gtatctctca tgaaacaccc ttaccggagt cagcactaac    4560
tctcaggaat gtaaatgtag tgtgttcagg tggaattaca gtggtttcta ccaaaagtga    4620
agaggaagtc tgttcatcca gttttggaac atcagaattt tccacagtgg acagtgcaca    4680
gaaaaatttt aatgattatg ccatgaactt ctttactaac cctacaaaaa acctagtgtc    4740
tataactaaa gattctgaac tgcccacctg cagctgtctt gatcgagtta tacaaaaaga    4800
caaaggccca tattatacac accttggggc aggaccaagt gttgctgctg tcagggaaat    4860
catggagaat aggtatggtc aaaaaggaaa cgcaataagg atagaaatag tagtgtacac    4920
cggtaaagaa gggaaaagct ctcatgggtg tccaattgct aagtgggttt taagaagaag    4980
cagtgatgaa gaaaaagttc tttgtttggt ccggcagcgt acaggccacc actgtccaac    5040
tgctgtgatg gtggtgctca tcatggtgtg ggatggcatc cctcttccaa tggccgaccg    5100
gctatacaca gagctcacag agaatctaaa gtcatacaat gggcacccta ccgacagaag    5160 atgcacccctc aatgaaaatc gtacctgtac atgtcaagga attgatccag agacttgtgg    5220
agcttcattc tctttggct gttcatggag tatgtacttt aatggctgta agtttggtag    5280
aagcccaagc cccagaagat ttagaattga tccaagctct cccttacatg aaaaaaacct    5340
tgaagataac ttacagagtt tggctacacg attagctcca attataagc agtatgctcc    5400 agtagcttac caaaatcagg tggaatatga aaatgttgcc cgagaatgtc ggcttggcag    5460
caaggaaggt cgtcccttct ctggggtcac tgcttgcctg gacttctgtg ctcatcccca    5520
cagggacatt cacaacatga ataatggaag cactgtggtt tgtaccttaa ctcgagaaga    5580
taaccgctct ttgggtgtta ttcctcaaga tgagcagctc catgtgctac ctcttttataa   5640
```

```
gctttcagac acagatgagt ttggctccaa ggaaggaatg gaagccaaga tcaaatctgg   5700
ggccatcgag gtcctggcac cccgccgcaa aaaagaacg tgtttcactc agcctgttcc   5760
ccgttctgga agaagaggg ctgcgatgat gacagaggtt cttgcacata agataagggc   5820
agtggaaaag aaacctattc cccgaatcaa gcggaagaat aactcaacaa caacaaacaa   5880
cagtaagcct tcgtcactgc caaccttagg gagtaacact gagaccgtgc aacctgaagt   5940
aaaaagtgaa accgaacccc attttatctt aaaaagttca gacaacacta aaacttattc   6000
gctgatgcca tccgctcctc acccagtgaa agaggcatct ccaggcttct cctggtcccc   6060
gaagactgct tcagccacac cagctccact gaagaatgac gcaacagcct catgcgggtt   6120
ttcagaaaga agcagcactc cccactgtac gatgccttcg ggaagactca gtggtgccaa   6180
tgcagctgct gctgatggcc ctggcatttc acagcttggc gaagtggctc ctctccccac   6240
cctgtctgct cctgtgatgg agcccctcat taattctgag ccttccactg gtgtgactga   6300
gccgctaacg cctcatcagc caaaccacca gccctccttc ctcacctctc ctcaagacct   6360
tgcctcttct ccaatggaag aagatgagca gcattctgaa gcagatgagc ctccatcaga   6420 cgaacccta tctgatgacc ccctgtcacc tgctgaggag aaattgcccc acattgatga   6480
gtattggtca gacagtgagc acatcttttt ggatgcaaat attggtgggg tggccatcgc   6540
acctgctcac ggctcggttt tgattgagtg tgcccggcga gagctgcacg ctaccactcc   6600
tgttgagcac cccaaccgta atcatccaac ccgcctctcc cttgtctttt accagcacaa   6660
aaacctaaat aagccccaac atggttttga actaaacaag attaagtttg aggctaaaga   6720
agctaagaat aagaaaatga aggcctcaga gcaaaaagac caggcagcta atgaaggtcc   6780
agaacagtcc tctgaagtaa atgaattgaa ccaaattcct tctcataaag cattaacatt   6840
aacccatgac aatgttgtca ccgtgtcccc ttatgctctc acacacgttg cggggcccta   6900
taaccattgg gtctgaaggc ttttctcccc ctcttaatgc ctttgctagt gcagtgtatt   6960
ttttcaaggt gctgttaaaa gaaagtcatg ttgtcgttta ctatcttcat ctcacccatt   7020
tcaagtctga ggtaaaaaaa taataatgat aacaaaacgg ggtgggtatt cttaactgtg   7080
actatatttt gacaattggt agaaggtgca cattttaagc aaaaataaaa gttttatagt   7140
tttaaataca taagaaaatg tttcagttag gcattaacct tgatagaatc actcagtttg   7200
gtgctttaaa ttaagtctgt ttactatgaa acaagagtca ttttagagg attttaacag   7260 gttcatgttc tatgatgtaa aatcaagaca cacagtgtta actctacaca gcttctggtg   7320
cttaaccaca tccacacagt taaaaataag ctgaattatt atttcatggt gccattgttc   7380
caacatcttc caatcattgc tagaaaattg gcatattcct ttgaaataaa cttatgaaat   7440
gttttctctc ttaaaatatt tctcctgtgt aaaataaatc attgttgtta gtaatggttg   7500
gaggctgttc ataaattgta aatatatatt ttaaaagcac tttctatttt taaaagtaac   7560
ttgaaataat atagtataag aatcctattg tctattgttt gtgcatattt gcatacaaga   7620
gaaatcattt atccttgctg tgtagagttc catcttgtta actgcagtat gtattctaat   7680
catgtatatg gtttgtgttc ttttactgtg tcctctcaca ttcaagtatt agcaacttgc   7740
agtatataaa atagttagat aatgagaagt tgttaattat ctctaaaatt ggaattagga   7800
agcatatcac caatactgat taacattctc tttggaacta ggtaagagtg gtctcttctt   7860
attgaacaac ctcaatttag tttcatccca cctttctcag tataatccat gagaggtgtt   7920
tccaaaagga gatgagggaa caggataggt ttcagaagag tcaaatgctt ctaatgtctc   7980
aaggtgataa aatacaaaaa ctaagtagac agatatttgt actgaagtct gatacagaat   8040
```

-continued

```
tagaaaaaaa aaattcttgt tgaaatattt tgaaaacaaa ttccctacta tcatcacatg    8100
cctccccaac cccaagtcaa aaacaagagg aatggtacta caaacatggc tttgtccatt    8160
aagagctaat tcatttgttt atcttagcat actagatttg ggaaatgat aactcatctt     8220 ttctgataat tgcctatgtt ctaggtaaca ggaaaacagg cattaagttt attttagtct    8280
tcccattttc ttcctattac tttattgact cattttattg caaaacaaaa aggattaccc    8340
aaacaacatg tttcgaacaa ggagaatttt caatgaaata cttgattctg ttaaaatgca    8400
gaggtgctat aacattcaaa gtgtcagatt ccttgggagt atggaaaacc taatggtgct    8460
tctcccttgg aaatgccata ggaagcccac aaccgctaac acttacaatt ttggtgcaaa    8520
agcaaacagt tccagcaggc tctctaaaga aaaactcatt gtaacttatt aaaataatat    8580
ctggtgcaaa gtatctgttt tgagcttttg actaatccaa gtaaaggaat atgaagggat    8640
tgtaaaaaac aaaatgtcca ttgatagacc atcgtgtaca agtagatttc tgcttgttga    8700
atatgtaaaa tagggtaatt cattgacttg ttttagtatt ttgtgtgcct tagatttccg    8760
ttttaagaca tgtatatttt tgtgagccta aggtttctta tatacatata agtatataaa    8820
taagtgattg tttattgctt cagctgcttc aacaagatat ttactagtat tagactatca    8880
ggaatacacc cttgcgagat tatgttttag attttaggcc ttagctccca ctagaaatta    8940
tttcttcacc agatttaatg gataaagttt tatggctctt tatgcatcca ctcatctact    9000
cattcttcga gtctacactt attgaatgcc tgcaaaatct aagtatcact tttattttc     9060 tttggatcac cacctatgac atagtaaact tgaagaataa aaactaccct cagaaatatt    9120
tttaaaagaa gtagcaaatt atcttcagta taatccatgg taatgtatgc agtaattcaa    9180
attgatctct ctctcaatag gtttcttaac aatctaaact tgaaacatca atgttaattt    9240
ttggaactat tgggatttgt gacgcttgtt gcagtttacc aaaacaagta tttgaaaata    9300
tatagtatca actgaaatgt ttccattccg ttgttgtagt taacatcatg aatggacttc    9360
ttaagctgat taccccactg tgggaaccaa attggattcc tactttgttg gactctcttt    9420
cctgatttta acaatttacc atcccattct ctgccctgtg attttttta aaagcttatt     9480 caatgttctg cagcattgtg attgtatgct ggctacactg cttttagaat gctctttctc    9540
atgaagcaag gaaataaatt tgtttgaaat gacattttct ctcaaaaaaa aaaaaaaaa     9600 a                                                                    9601
```

<210> SEQ ID NO 24
<211> LENGTH: 9677
<212> TYPE: DNA
<213> ORGANISM: Homo sapiens

<400> SEQUENCE: 24

```
gcggccgccc cgagacgccg gccccgctga gtgatgagaa cagacgtcaa actgccttat      60
gaatattgat gcggaggcta ggctgctttc gtagagaagc agaaggaagc aagatggctg    120 cccctttagga tttgttagaa aggagacccg actgcaactg ctggattgct gcaaggctga    180
gggacgagaa cgaggctggc aaacattcag cagcacaccc tctcaagatt gtttacttgc    240
cttgtctcct gttgagttac aacgcttgga agcaggagat gggctcagca gcagccaata    300
ggacatgatc caggaagagc agtaagggac tgagctgctg aattcaacta gagggcagcc    360
ttgtggatgg ccccgaagca agcctgatgg aacaggatag aaccaaccat gttgagggca    420
acagactaag tccattcctg ataccatcac ctcccatttg ccagacagaa cctctggcta    480
```

```
caaagctcca gaatggaagc ccactgcctg agagagctca tccagaagta aatggagaca    540
ccaagtggca ctcttcaaa agttattatg gaatacctg tatgaaggga agccagaata    600
gtcgtgtgag tcctgacttt acacaagaaa gtagagggta ttccaagtgt ttgcaaaatg   660
gaggaataaa acgcacagtt agtgaaccct ctctctctgg gctccttcag atcaagaaat    720
tgaaacaaga ccaaaaggct aatggagaaa gacgtaactt cggggtaagc caagaaagaa    780
atccaggtga aagcagtcaa ccaaatgtct ccgatttgag tgataagaaa gaatctgtga    840
gttctgtagc ccagaaaat gcagttaaag atttcaccag ttttcaaca cataactgca      900 gtgggcctga aaatccagag cttcagattc tgaatgagca ggaggggaaa agtgctaatt    960
accatgacaa gaacattgta ttacttaaaa acaaggcagt gctaatgcct aatggtgcta   1020
cagtttctgc ctcttccgtg gaacacacac atggtgaact cctggaaaaa acactgtctc   1080
aatattatcc agattgtgtt tccattgcgg tgcagaaaac cacatctcac ataaatgcca   1140
ttaacagtca ggctactaat gagttgtcct gtgagatcac tcacccatcg catacctcag   1200
ggcagatcaa ttccgcacag acctctaact ctgagctgcc tccaaagcca gctgcagtgg   1260
tgagtgaggc ctgtgatgct gatgatgctg ataatgccag taaactagct gcaatgctaa   1320
atacctgttc ctttcagaaa ccagaacaac tacaacaaca aaaatcagtt tttgagatat   1380
gcccatctcc tgcagaaaat aacatccagg gaaccacaaa gctagcgtct ggtgaagaat   1440
tctgttcagg ttccagcagc aatttgcaag ctcctggtgg cagctctgaa cggtatttaa   1500
aacaaaatga aatgaatggt gcttacttca gcaaagctc agtgttcact aaggattcct    1560
tttctgccac taccacacca ccaccaccat cacaattgct tctttctccc cctcctcctc   1620
ttccacaggt tcctcagctt ccttcagaag gaaaaagcac tctgaatggt ggagttttag   1680
aagaacacca ccactacccc aaccaaagta acacaacact tttaagggaa gtgaaaatag   1740
agggtaaacc tgaggcacca ccttcccaga gtcctaatcc atctacacat gtatgcagcc   1800
cttctccgat gctttctgaa aggcctcaga ataattgtgt gaacaggaat gacatacaga   1860
ctgcagggac aatgactgtt ccattgtgtt ctgagaaaac aagaccaatg tcagaacacc   1920
tcaagcataa cccaccaatt tttggtagca gtggagagct acaggacaac tgccagcagt   1980
tgatgagaaa caaagagcaa gagattctga agggtcgaga caaggagcaa acacgagatc   2040
ttgtgccccc aacacagcac tatctgaaac caggatggat tgaattgaag gcccctcgtt   2100
ttcaccaagc ggaatcccat ctaaaacgta atgaggcatc actgccatca attcttcagt   2160
atcaacccaa tctctccaat caaatgacct ccaaacaata cactgaaat tccaacatgc     2220 ctgggggct cccaaggcaa gcttacaccc agaaaacaac acagctggag cacaagtcac   2280
aaatgtacca agttgaaatg aatcaagggc agtcccaagg tacagtggac caacatctcc   2340
agttccaaaa accctcacac caggtgcact tctccaaaac agaccattta ccaaaagctc   2400
atgtgcagtc actgtgtggc actagatttc attttcaaca aagagcagat tcccaaactg   2460
aaaaacttat gtcccagtg ttgaaacagc acttgaatca acaggcttca gagactgagc    2520
cattttcaaa ctcacaccctt ttgcaacata gcctcataa acaggcagca caaacacaac   2580
catcccagag ttcacatctc cctcaaaacc agcaacagca gcaaaaatta caaataagga    2640
ataaagagga aatactccag acttttcctc acccccaaag caacaatgat cagcaaagag   2700
aaggatcatt ctttggccag actaaagtgg aagaatgttt tcatggtgaa atcagtatt    2760 caaaatcaag cgagttcgag actcataatg tccaaatggg actggaggaa gtacagaata   2820
taaatcgtag aaattcccct tatagtcaga ccatgaaatc aagtgcatgc aaaatacagg   2880
```

```
tttcttgttc aaacaataca cacctagttt cagagaataa agaacagact acacatcctg    2940 aacttttgc aggaaacaag acccaaaact tgcatcacat gcaatatttt ccaaataatg     3000
tgatcccaaa gcaagatctt cttcacaggt gctttcaaga acaggagcag aagtcacaac    3060
aagcttcagt tctacaggga tataaaaata gaaaccaaga tatgtctggt caacaagctg    3120
cgcaacttgc tcagcaaagg tacttgatac ataaccatgc aaatgttttt cctgtgcctg    3180
accagggagg aagtcacact cagacccctc cccagaagga cactcaaaag catgctgctc    3240
taaggtggca tctcttacag aagcaagaac agcagcaaac acagcaaccc caaactgagt    3300
cttgccatag tcagatgcac aggccaatta aggtggaacc tggatgcaag ccacatgcct    3360
gtatgcacac agcaccacca gaaaacaaaa catggaaaaa ggtaactaag caagagaatc    3420
cacctgcaag ctgtgataat gtgcagcaaa agagcatcat tgagaccatg gagcagcatc    3480
tgaagcagtt tcacgccaag tcgttatttg accataaggc tcttactctc aaatcacaga    3540
agcaagtaaa agttgaaatg tcagggccag tcacagtttt gactagacaa accactgctg    3600
cagaacttga tagccacacc ccagctttag agcagcaaac aacttcttca gaaaagacac    3660
caaccaaaag aacagctgct tctgttctca ataattttat agagtcacct tccaaattac    3720
tagatactcc tataaaaaat ttattggata cacctgtcaa gactcaatat gatttcccat    3780
cttgcagatg tgtagagcaa attattgaaa aagatgaagg tccttttttat acccatctag    3840 gagcaggtcc taatgtggca gctattagag aaatcatgga agaaaggttt ggacagaagg    3900
gtaaagctat taggattgaa agagtcatct atactggtaa agaaggcaaa agttctcagg    3960
gatgtcctat tgctaagtgg gtggttcgca gaagcagcag tgaagagaag ctactgtgtt    4020
tggtgcggga gcgagctggc cacacctgtg aggctgcagt gattgtgatt ctcatcctgg    4080
tgtgggaagg aatcccgctg tctctggctg acaaactcta ctcggagctt accgagacgc    4140
tgaggaaata cggcacgctc accaatcgcc ggtgtgcctt gaatgaagag agaacttgcg    4200
cctgtcaggg gctggatcca gaaacctgtg gtgcctcctt ctcttttggt tgttcatgga    4260
gcatgtacta caatggatgt aagtttgcca gaagcaagat cccaaggaag tttaagctgc    4320 ttgggggatga cccaaaagag gaagagaaac tggagtctca tttgcaaaac ctgtccactc    4380
ttatggcacc aacatataag aaacttgcac ctgatgcata taataatcag attgaatatg    4440
aacacagagc accagagtgc cgtctgggtc tgaaggaagg ccgtccattc tcagggttca    4500
ctgcatgttt ggacttctgt gctcatgccc acagagactt gcacaacatg cagaatggca    4560
gcacattggt atgcactctc actagagaag acaatcgaga atttggagga aaacctgagg    4620
atgagcagct tcacgttctg cctttataca agtctctga cgtggatgag tttgggagtg    4680
tggaagctca ggaggagaaa aaacggagtg gtgccattca ggtactgagt tcttttcggc    4740
gaaaagtcag gatgttagca gagccagtca agacttgccg acaaaggaaa ctagaagcca    4800
agaaagctgc agctgaaaag ctttcctccc tggagaacag ctcaaataaa aatgaaaagg    4860
aaaagtcagc cccatcacgt acaaaacaaa ctgaaaacgc aagccaggct aaacagttgg    4920
cagaactttt gcgactttca ggaccagtca tgcagcagtc ccagcagccc cagcctctac    4980
agaagcagcc accacagccc cagcagcagc agagacccca gcagcagcag ccacatcacc    5040
ctcagacaga gtctgtcaac tcttattctg cttctggatc caccaatcca tacatgagac    5100
ggcccaatcc agttagtcct tatccaaaact cttcacacac ttcagatatc tatgaagca    5160 ccagccctat gaacttctat tccacctcat ctcaagctgc aggttcatat ttgaattctt    5220
```

```
ctaatcccat gaacccttac cctgggcttt tgaatcagaa tacccaatat ccatcatatc   5280
aatgcaatgg aaacctatca gtggacaact gctccccata tctgggttcc tattctcccc   5340
agtctcagcc gatggatctg tataggtatc caagccaaga ccctctgtct aagctcagtc   5400
taccacccat ccatacactt taccagccaa ggtttggaaa tagccagagt tttacatcta   5460
aatacttagg ttatggaaac caaaatatgc agggagatgg tttcagcagt tgtaccatta   5520
gaccaaatgt acatcatgta gggaaattgc ctccttatcc cactcatgag atggatggcc   5580
acttcatggg agccacctct agattaccac ccaatctgag caatccaaac atggactata   5640
aaaatggtga acatcattca ccttctcaca taatccataa ctacagtgca gctccgggca   5700
tgttcaacag ctctcttcat gccctgcatc tccaaaacaa ggagaatgac atgctttccc   5760
acacagctaa tgggttatca agatgcttc cagctcttaa ccatgataga actgcttgtg    5820
tccaaggagg cttacacaaa ttaagtgatg ctaatggtca ggaaaagcag ccattggcac   5880
tagtccaggg tgtggcttct ggtgcagagg acaacgatga ggtctggtca gacagcgagc   5940
agagctttct ggatcctgac attggggag tggccgtggc tccaactcat gggtcaattc     6000
tcattgagtg tgcaaagcgt gagctgcatg ccacaacccc tttaaagaat cccaatagga   6060
atcaccccac caggatctcc ctcgtctttt accagcataa gagcatgaat gagccaaaac   6120
atggcttggc tctttgggaa gccaaaatgg ctgaaaaagc ccgtgagaaa gaggaagagt   6180
gtgaaaagta tgcccagac tatgtgcctc agaaatccca tggcaaaaaa gtgaaacggg    6240
agcctgctga gccacatgaa acttcagagc ccacttacct gcgtttcatc aagtctcttg   6300
ccgaaaggac catgtccgtg accacagact ccacagtaac tacatctcca tatgccttca   6360
ctcgggtcac agggccttac aacagatata tatgatatca ccccttttg ttggttacct    6420 cacttgaaaa gaccacaacc aacctgtcag tagtatagtt ctcatgacgt gggcagtggg   6480
gaaaggtcac agtattcatg acaaatgtgg tgggaaaaac ctcagctcac cagcaacaaa   6540
agaggttatc ttaccatagc acttaatttt cactggctcc caagtggtca cagatggcat   6600
ctaggaaaag accaaagcat tctatgcaaa agaaggtgg ggaagaaagt gttccgcaat    6660
ttacattttt aaacactggt tctattattg gacgagatga tatgtaaatg tgatcccccc   6720
cccccgctta caactctaca catctgtgac cacttttaat aatatcaagt ttgcatagtc   6780
atggaacaca atcaaacaa gtactgtagt attacagtga caggaatctt aaaataccat    6840
ctggtgctga atatatgatg tactgaaata ctggaattat ggcttttga aatgcagttt    6900 ttactgtaat cttaactttt atttatcaaa atagctacag gaaacatgaa tagcaggaaa   6960
acactgaatt tgtttggatg ttctaagaaa tggtgctaag aaaatggtgt ctttaatagc   7020
taaaaattta atgcctttat atcatcaaga tgctatcagt gtactccagt gcccttgaat   7080 aatagggta ccttttcatt caagttttta tcataattac ctattcttac acaagcttag     7140 ttttaaaat gtggacattt taaaggcctc tggattttgc tcatccagtg aagtccttgt    7200
aggacaataa acgtatatat gtacatatat acacaaacat gtatatgtgc acacacatgt   7260
atatgtataa atattttaaa tggtgttta gaagcacttt gtctacctaa gctttgacaa    7320
cttgaacaat gctaaggtac tgagatgttt aaaaaacaag tttactttca ttttagaatg   7380
caaagttgat ttttttaagg aaacaaagaa agcttttaaa atattttgc ttttagccat     7440 gcatctgctg atgagcaatt gtgtccattt ttaacacagc cagttaaatc caccatgggg   7500
cttactggat tcagggggaat acgttagtcc acaaaacatg ttttctggtg ctcatctcac   7560
atgctatact gtaaaacagt tttatacaaa attgtatgac aagttcattg ctcaaaaatg   7620
```

```
tacagtttta agaattttct attaactgca ggtaataatt agctgcatgc tgcagactca    7680
acaaagctag ttcactgaag cctatgctat tttatggatc ataggctctt cagagaactg    7740
aatggcagtc tgccttttgtg ttgataatta tgtacattgt gacgttgtca tttcttagct   7800
taagtgtcct ctttaacaag aggattgagc agactgatgc ctgcataaga tgaataaaca    7860
gggttagttc catgtgaatc tgtcagttaa aaagaaacaa aaacaggcag ctggtttgct    7920
gtggtggttt taaatcatta atttgtataa agaagtgaaa gagttgtata gtaaattaaa    7980
ttgtaaacaa aactttttta atgcaatgct ttagtatttt agtactgtaa aaaaattaaa    8040
tatatacata tatatatata tatatatata tatatatatg agtttgaagc agaattcaca    8100
tcatgatggt gctactcagc ctgctacaaa tatatcataa tgtgagctaa gaattcatta    8160
aatgtttgag tgatgttcct acttgtcata tacctcaaca ctagtttggc aataggatat    8220
tgaactgaga gtgaaagcat tgtgtaccat cattttttc caagtccttt tttttattgt     8280
taaaaaaaaa agcatacctt ttttcaatac ttgatttctt agcaagtata acttgaactt    8340
caacctttt gttctaaaaa ttcagggata tttcagctca tgctctccct atgccaacat     8400
gtcacctgtg tttatgtaaa attgttgtag gttaataaat atattctttg tcagggattt    8460
aacccttta ttttgaatcc cttctatttt acttgtacat gtgctgatgt aactaaaact     8520
aattttgtaa atctgttggc tcttttttatt gtaaagaaaa gcattttaaa agtttgagga   8580
atcttttgac tgtttcaagc aggaaaaaaa aattacatga aaatagaatg cactgagttg    8640
ataaagggaa aaattgtaag gcaggagttt ggcaagtggc tgttggccag agacttactt    8700
gtaactctct aaatgaagtt ttttgatcc tgtaatcact gaaggtacat actccatgtg     8760
gacttcccctt aaacaggcaa acacctacag gtatggtgtg caacagattg tacaattaca   8820
ttttggccta aatacatttt tgcttactag tatttaaaat aaattcttaa tcagaggagg    8880
cctttgggtt ttattggtca aatctttgta agctggcttt tgtcttttta aaaaatttct    8940
tgaatttgtg gttgtgtcca atttgcaaac atttccaaaa atgtttgctt tgcttacaaa    9000
ccacatgatt ttaatgtttt ttgtatacca taatatctag ccccaaacat ttgattacta    9060
catgtgcatt ggtgattttg atcatccatt cttaatattt gatttctgtg tcacctactg    9120
tcatttgtta aactgctggc caacaagaac aggaagtata gtttgggggg ttggggagag    9180
tttacataag gaagagaaga aattgagtgg catattgtaa atatcagatc tataattgta    9240
aatataaaac ctgcctcagt tagaatgaat ggaaagcaga tctacaattt gctaatatag    9300
gaatatcagg ttgactatat agccatactt gaaaatgctc ctgagtggtg tcaactttac    9360
ttgaatgaat ttttcatctt gattgacgca cagtgatgta cagttcactt ctgaagctag    9420
tggttaactt gtgtaggaaa cttttgcagt ttgacactaa gataacttct gtgtgcattt    9480
ttctatgctt ttttaaaaac tagtttcatt tcattttcat gagatgtttg gtttataaga    9540
tctgaggatg gttataaata ctgtaagtat tgtaatgtta tgaatgcagg ttatttgaaa    9600
gctgtttatt attatatcat tcctgataat gctatgtgag tgttttaat aaaatttata    9660
tttatttaat gcactct                                                   9677

<210> SEQ ID NO 25
<211> LENGTH: 10983
<212> TYPE: DNA
<213> ORGANISM: Homo sapiens

<400> SEQUENCE: 25
```

-continued

| | | | | |
|---|---|---|---|---|
| atggactcag | ggccagtgta | ccatggggac | tcacggcagc | taagcgcctc agggggtgccg | 60 |
| gtcaatggtg | ctagagagcc | cgctggaccc | agtctgctgg | ggactggggg tccttggcgg | 120 |
| gtagaccaaa | agcccgactg | ggaggctgcc | ccaggcccag | ctcatactgc tcgcctggaa | 180 |
| gatgcccacg | atctggtggc | cttttcggct | gtggccgaag | ctgtgtcctc ttatggggcc | 240 |
| cttagcaccc | ggctctatga | aaccttcaac | cgtgagatga | gtcgtgaggc tgggaacaac | 300 |
| agcaggggac | cccggccagg | gcctgagggc | tgctctgctg | gcagcgaaga ccttgacaca | 360 |
| ctgcagacgg | ccctggccct | cgcgcggcat | ggtatgaaac | acccaactg caactgcgat | 420 |
| ggcccagaat | gccctgacta | cctcgagtgg | ctggagggga | agatcaagtc tgtggtcatg | 480 |
| gaaggagggg | aggagcggcc | caggctccca | gggcctctgc | ctcctggtga ggccggcctc | 540 |
| ccagcaccaa | gcaccaggcc | actcctcagc | tcagaggtgc | cccagatctc tccccaagag | 600 |
| ggcctgcccc | tgtcccagag | tgccctgagc | attgccaagg | aaaaaaacat cagcttgcag | 660 |
| accgccattg | ccattgaggc | cctcacacag | ctctcctctg | ccctcccgca gccttctcat | 720 |
| tccaccccc | aggcttcttg | cccccttcct | gaggccttgt | cacctcctgc ccctttcaga | 780 |
| tctccccagt | cttacctccg | ggctccctca | tggcctgtgg | ttcctcctga agagcactca | 840 |
| tcttttgctc | ctgatagctc | tgccttccct | ccagcaactc | ctagaactga gttccctgaa | 900 |
| gcctggggca | ctgacacccc | tccagcaacg | ccccggagct | cctggcccat gcctcgccca | 960 |
| agccccgatc | ccatggctga | actggagcag | ttgttgggca | cgccagtga ttacatccag | 1020 |
| tcagtattca | agcggcctga | ggccctgcct | accaagccca | aggtcaaggt ggaggcaccc | 1080 |
| tcttcctccc | cggccccggc | cccatcccct | gtacttcaga | gggaggctcc cacgccatcc | 1140 |
| tcggagcccg | acacccacca | gaaggcccag | accgccctgc | agcagcacct ccaccacaag | 1200 |
| cgcagcctct | tcctagaaca | ggtgcacgac | acctccttcc | ctgctccttc agagccttct | 1260 |
| gctcctggct | ggtggccccc | accaagttca | cctgtcccac | ggcttccaga cagaccaccc | 1320 |
| aaggagaaga | agaagaagct | cccaacacca | gctggaggtc | ccgtgggaac ggagaaagct | 1380 |
| gcccctggga | tcaagcccag | tgtccgaaag | cccattcaga | tcaagaagtc caggcccc gg | 1440 |
| gaagcacagc | ccctcttccc | acctgtccga | cagattgtcc | tggaagggct taggtcccca | 1500 |
| gcctcccagg | aagtgcaggc | tcatccaccg | gcccctctgc | ctgcctcaca gggctctgct | 1560 |
| gtgcccctgc | cccagaaacc | ttctcttgcg | ctatttgcac | ctagtccctc cagggacagc | 1620 |
| ctgctgcccc | ctactcagga | aatgaggtcc | cccagcccca | tgacagcctt gcagccaggc | 1680 |
| tccactggcc | ctcttccccc | tgccgatgac | aagctggaag | agctcatccg gcagtttgag | 1740 |
| gctgaatttg | gagatagctt | tgggcttccc | ggccccctt | ctgtgcccat tcaggacccc | 1800 |
| gagaaccagc | aaacatgtct | cccagcccct | gagagcccct | tgctacccg ttcccccaag | 1860 |
| caaatcaaga | ttgagtcttc | ggggctgtg | actgtgctct | caaccacctg cttccattca | 1920 |
| gaggagggag | gacaggaggc | cacacccacc | aaggctgaga | acccactcac acccaccctc | 1980 |
| agtggcttct | tggagtcacc | tcttaagtac | ctggacacac | ccaccaagag tctgctggac | 2040 |
| acacctgcca | agagagccca | ggccgagttc | cccacctgcg | attgcgtcga caaatagtg | 2100 |
| gagaaagatg | aagtccata | ttatactcac | ttgggatctg | gccccacggt cgcctctatc | 2160 |
| cgggaactca | tggaggagcg | gtatggagag | aaggggaaag | ccatccggat cgagaaggtc | 2220 |
| atctacacgg | ggaaggaggg | aaagagctcc | cgcggttgcc | ccattgcaaa gtgggtgatc | 2280 |
| cgcaggcaca | cgctggagga | gaagctactc | tgcctggtgc | ggcaccgggc aggccaccac | 2340 |
| tgccagaacg | ctgtgatcgt | catcctcatc | ctggcctggg | agggcattcc ccgtagcctc | 2400 |

```
ggagacaccc tctaccagga gctcaccgac accctccgga agtatgggaa ccccaccagc    2460
cggagatgcg gcctcaacga tgaccggacc tgcgcttgcc aaggcaaaga ccccaacacc    2520
tgtggtgcct ccttctcctt tggttgttcc tggagcatgt acttcaacgg ctgcaagtat    2580
gctcggagca agacacctcg caagttccgc ctcgcagggg acaatcccaa agaggaagaa    2640
gtgctccgga agagtttcca ggacctggcc accgaagtcg ctcccctgta caagcgactg    2700 gccccctcagg cctatcagaa ccaggtgacc aacgaggaaa tagcgattga ctgccgtctg    2760
gggctgaagg aaggacggcc cttcgcgggg gtcacggcct gcatggactt ctgtgcccac    2820
gcccacaagg accagcataa cctctacaat gggtgcaccg tggtctgcac cctgaccaag    2880
gaagacaatc gctgcgtggg caagattccc gaggatgagc agctgcatgt tctcccctg     2940 tacaagatgg ccaacacgga tgagtttggt agcgaggaga accagaatgc aaaggtgggc    3000
agcggagcca tccaggtgct caccgccttc ccccgcgagg tccgacgcct gcccgagcct    3060
gccaagtcct gccgccagcg gcagctggaa gccagaaagg cagcagccga gaagaagaag    3120
attcagaagg agaagctgag cactccggag aagatcaagc aggaggccct ggagctggcg    3180
ggcattacgt cggacccagg cctgtctctg aagggtggat tgtcccagca aggcctgaag    3240
ccctccctca aggtggagcc gcagaaccac ttcagctcct tcaagtacag cggcaacgcg    3300
gtggtggaga gctactcggt gctgggcaac tgccggccct ccgacccttta cagcatgaac    3360 agcgtgtact cctaccactc ctactatgca cagcccagcc tgacctccgt caatggcttc    3420
cactccaagt acgctctccc gtcttttagc tactatggct ttccatccag caaccccgtc    3480
ttcccctctc agttcctggg tcctggtgcc tgggggcaca gtggcagcag tggcagtttt    3540
gagaagaagc cagacctcca cgctctgcac aacagcctga gcccggccta cggtggtgct    3600
gagtttgccg agctgcccag ccaggctgtt cccacagacg cccaccaccc cactcctcac    3660
caccagcagc ctgcgtaccc aggccccaag gagtatctgc ttcccaaggc cccctactc    3720 cactcagtgt ccagggaccc ctccccctttt gcccagagct ccaactgcta caacagatcc    3780
atcaagcaag agccagtaga cccgctgacc caggctgagc ctgtgcccag agacgctggc    3840
aagatgggca agacacctct gtccgaggtg tctcagaatg aggacccag tcacctttgg     3900 ggacagtact caggaggccc aagcatgtcc cccaagagga ctaacggtgt gggtggcagc    3960
tggggtgtgt tctcgtctgg ggagagtcct gccatcgtcc ctgacaagct cagttccttt    4020
ggggccagct gcctggcccc ttcccacttc acagatggcc agtgggggct gttccccggt    4080
gaggggcagc aggcagcttc ccactctgga ggacggctgc gaggcaaacc gtggagcccc    4140
tgcaagtttg ggaacagcac ctcggccttg gctgggccca gctgactga aagccgtgg     4200 gcgctggggg cagggatttt caactcggcc ctgaaaggta gtcctgggtt ccaagacaag    4260
ctgtggaacc ccatgaaagg agaggagggc aggattccag ccgcagggc cagccagctg     4320 gacagggcct ggcagtcctt tggtctgccc ctgggatcca gcgagaagct gtttggggct    4380
ctgaagtcag aggagaagct gtgggacccc ttcagcctgg aggagggcc ggctgaggag     4440 cccccccagca agggagcgt gaaggaggag aaggggcggtg tggtgcgga ggaggaagag     4500 gaggagctgt ggtcggacag tgaacacaac ttcctggacg agaacatcgg cggcgtggcc    4560
gtggccccag cccacggctc catcctcatc gagtgtgccc ggcgggagct gcacgccacc    4620
acgccgctta agaagcccaa ccgctgccac cccaccgca tctcgctggt cttctaccag     4680
cacaagaacc tcaaccagcc caaccacggg ctggccctct gggaagccaa gatgaagcag    4740
```

```
ctggcggaga gggcacgggc acggcaggag gaggctgccc ggctgggcct gggccagcag    4800
gaggccaagc tctacgggaa gaagcgcaag tgggggggca ctgtggttgc tgagcccag     4860 cagaaagaga agaaggggt cgtccccacc cggcaggcac tggctgtgcc cacagactcg     4920
gcggtcaccg tgtcctccta tgcctacacg aaggtcactg gccccacag ccgctggatc     4980 taggtgccag ggagccagcg tacctcagcg tcgggcctgg cccgagctgt ctctgtggtg    5040
cttttgccct catacctggg ggcggggttgg gggtgcagaa gtcttttat ctctatatac    5100 atatatagat gcgcatatca tatatatgta tttatggtcc aaacctcaga actgacccgc   5160
ccctccctta cccccacttc cccagcactt tgaagaagaa actacggctg tcgggtgatt    5220
tttccgtgat cttaatattt atatctccaa gttgtccccc cccttgtct gggggttt      5280 tattttatt ttctctttgt ttttaaaact ctatccttgt atatcacaat aatggaaaga    5340
aagtttatag tatcctttca caaggagta gtttaaatt ccattaaaaa tgtgtattta     5400 ttggatttt taaaagcgac aatagtaatg gtaaaggatg ggcaggaaag gccagtagtg    5460
ctcccccgcc cagtctcgct gggtctggcg agccaagccc ctcgggcgct ggcgaggtcc   5520
tcagccatct gcccctcgag agccaagcgc ggacggtagc cacccagttc atccctcccg   5580
acatacaccc cttcccttg gggaagggag cctcaggaca gcttctgtcc tctctgatag    5640
gatgggagag tctgcagaaa accatctggg gtcccttttc cagtccccgg cttggagtcg   5700
aagggcagat gcaccccagg ccagccccac gagatgctgg catagctttc cccagaaacc   5760
aggttggaag tagatggctt caagcttgct agtctccaca ctgaatcctc tgtccgttat    5820
ttatggagtc acacgatgtc atggttcact aggcagcacc tcacgctgga gctggagtgc   5880
gaggttctta ggggccgtgc ccaccatgtt gccaagccaa tgcatgctga gctgaaggaa    5940
tttgtcttag tggcagtttt ttaaaaaatg cccccaaagt ctatgctgat actgaaaaag   6000
ggctactgta tctttaaaaa caggaagttg aacccaagct gtgaaaagcc agtggtgctc    6060
tgtgcatggt gctgtgcgga gcctggtgct gtagtgttgt gctgggactt tcttgactct    6120
tgggcaggtc acatcctaca ggagctcagc agaccagtgt aacaacagtt aatgcatcta    6180
tcctgatccc tgaatttcca cattggacaa tggtgcatgc ctcacacctg agcctgcttc    6240
ctccatgctg tcattgggtt cgggggccta cacttaacaa ttttaaagtg caagagtcaa    6300
acattttcaa caggttgcta taattttcct ccctaattgg tgccatttct ccatttgatc    6360 atttctttt tttcctttct cccctcttca tccactttaa tatagctgtt ctgaaattct    6420
ggtgcattca ttcggttctt tgaaatgaga atgtggtgct taattttgt gacgttgtcg   6480 agagaggttg ggcctgatgg gagcaacact catcatcacc aagtcaaact tgttggagt    6540 gttggttttt cttgtgatat tagcagaaat gatctcatgc tagccatgtg gatgtgtgtg    6600
tggtgaatgg ggggcttcat caggacacac agaggggaat gtggccacac ggtggatgac   6660
caccaagccc tgagatgaac aggtatttac tgagcagttg tattcagata tgggtcttca    6720
tgaatcatgt ttaacaatca gatgaccgct ataggcaagt tcctgagctt ccgggtgcct    6780
tgagtaagag ctgagaaccg gcctgctggg tgtttactgt atctgtttgg aagcactggc    6840
ggagggtcgt tgtaagatgt cctgagcatt tatgtggtct ggttttaact gtaaatagtg    6900
aaagattttt ttaagcactt tgcctagat ttaaacagca acttgaaaaa aaagtatgt     6960 tttaacatgt aattgtggga gaaattgtaa atagtagccg aatatttaat gtgctttgtc    7020
tatcctccac ttttaccata ttctgtaaag ttgcatttat tttacaggac aaaaaaatga   7080
aatattattg cttttgaaat aaataccca gagcttatca ggacttagaa ttattcagaa     7140
```

```
ctcagattta taggaaaaacc tctgaccttc agtttgacaa gctaaaggaa gcagagtctt   7200
taatgagcat gctaattttc tagttttgag gaaaaattgg gtcctttaaa tgctattttg   7260
cttatcgcat cagtactttt atgcaggtct catttgactc cgtgcttagg tagatgcggg   7320
ggtgccttga aaacttcatt ttaaatgatc ttaagcaaga aatacaatat tttacgaaac   7380
atttggagaa tgtgaccgtc tgtatgaccc gtggaagccc caggttggct gttggtttgg   7440
aaggtcccga gtgtaaccca ggtgattctg atacttggca tgtgtgaatc ttcctgatgt   7500
atgttaaata aactcttccc ctcatcaccc tttggtagga aagccattag atgaaaggag   7560
aaaccaatac aagctaaaag catgcgacgt ctgtccccca gcccaaacag ccttggttca   7620
tcagtttctg cagtaggaga taggctgctg agaggtgagt caagaggcag tctccattgg   7680
atgtccccac tccccgcaga atggcgtttc cagagttagg cggtgtggtt gccgtgctca   7740
agcccatgct gatttgtaca ctacatgtct aacctacctc aaatctcagt cattaaaatt   7800
agcatgcttt agacatatat ttaaaaagta actatgcaca gctctttatc ccccccttgc   7860
tgctgaagct ttcttaaaga gaaaaatcaa atttttattt tttactggca ctatcatttt   7920
ttaagtccta aagatgatta acagacattt ttatcatgag aagaaaaata aagccattgc   7980
aactaaagaa cctaacagca tgaccaagtt cgaagagtca tattatagca acggaaatcg   8040
atggcgtctt agtcatctcc ccagtgtgcc ctgtccacgg acaccatcca cgtgcagtgc   8100
aaacatttgg ttccttttct gctctgtttt gttttccctg cctgttgcgt gcaagggaag   8160
tgcttgtaaa gttctgtgct acgagatttt taaaataaaa atcgcttcgc agcaggttct   8220
cacaaaataa ctggtgctag ctcaagaaat catcatctga ccatcagaaa tcttgactaa   8280
aggtgttgca tggatttggg ggtctttcgg ttttggttt tgggtctggc ttttagcagg   8340
gccaatgttt cccacacccc ggcttcatgg gtactgcttt gccttctcac caaggtgacg   8400
atggtgtgcg tggaaagaga tgataccca ccgcccctc ttggtccttc caccagcctc   8460 tttttgggaac agtagtttgc agagcaaggg attttaaag cgctaaagca aggaaagaag   8520
tagcagagct taactgcttt gtaccacaca gcagtagatg tgcaaggacg gttgacaatg   8580
agtcgatgat aacctaattt cattgagaga aacccagcca gacttgcttc tagaggttta   8640
atcaccatga gatctcaaac caaggcaaag ctggtggaaa actatatgat atccctgacg   8700
tgcctcaacc agtatctctt tccttttgtt actgaagtgt gttttatgga ctaggaagca   8760 ttttatgaa ttgaaatagt ctaaataaaa tggtgctatg gtgttttaat gtgactgtcc   8820
ctgatcctgt cttgctgagg tgctatcaac gttctgaaac cacaaccaac caaaaacaag   8880
gtgggctcca gtctcttggc tttttttttt ccctccctc ttttggtgct gtcttagacc   8940
cgtttaccgt gctataatct gctctgagca gtgtgtgtt gtgttgtatt gttcttccct   9000
tggtggccaa acaaagcaag tcgagaaggc agctatctcc ctttctgtga tcgggagtgg   9060
gcctgcctgg cttggcaggt gcttttggt tccacacctg tcttctcagg cttgatgtga   9120
aagaaagggc gaagggtttt tgagtttttt gtttttgagg aaggggagtt gggtacttct   9180
gcctctccta gcatgatagg cattctcata gccagggaca gatttctcc tgcagcccag   9240 ggtgctaagc agacatctct gggagtccca agggcacacc aagggagacc agatggatct   9300
ccttcctccc ctggcactgg ctgggaccat ggtgggcagg ggcttcattc tctgacccag   9360
cgttgcttct gcctctcatt ggtaaccct tatgttcgga ctaaaggaag gagctttctt   9420
tgctcactcg atgccactga ggctgctttt tagttggtgc taacctaaat ttcttcttgg   9480
```

```
gtccacagaa gttgatgttt taaaaactca ccaggaagct ccattttgtg tcatccactg    9540
tcacaataat ttttttaaat acctcaaaaa caggacatca tgacaacttc agtaaagtag    9600
attccatgag ggtctgatac ctgcaggttg tccgtctgat gacatacttg accttgaaaa    9660
atctggggtc attttgtttt tcattcttca gcagttaaga tagcggaacg ccgaaaggaa    9720
ggagcgtagt tggctgtatt tcatgtttaa gttttgcttt tgaataaaat gtgaatttcc    9780
tatgcccatc tcattgagct ttctcagtca ttgttgctgt catttgaaat gactccctca    9840
aaacctagtt ttattagcca gctgcctctg ctgtagtaca tggccaactt caacataccc    9900
tggaccaaaa catttttgag gtgcataccc ccaacataag ttacacagtc ccacatccag    9960
gtgcacagag tgcgagtgca ctccgcgagt gcgggggggag gggcggcccc ctctggtgct   10020 cccagcccctt cctcctgcag agctgcaggc aagagcagag caataggctt ctcccctgag   10080
cagagaccgc agcacagaaa tgcaaggtct aaagttgctt tttgcctaag aatcagcgag   10140
cgatttggcc tacttcctca ttggcttcta ttctgatatc agggatgctt tttgtagtgg   10200
tattgtttgc tccctcttcg cgttttgact acccgtcatt caggggtaac tcatcactct   10260
tcacacgggg atttaaatta agaaactaat tggctcatgt gaacattcca aattttcttg   10320
gtttcaatac cctttttttt cttttgaggg gaaagaggg gagaaaaaca ggagtgatgt   10380
catttctttt tcatgtattc caattaaaga aacaagggca ggtcgtataa tggcatatta   10440
atacattaga cttaatctag aacccctgta gcttttttgat gtgtttttatt tcttatctct   10500 ttgaattcct gtttggttac ttggcttcca atggaggtga acttaacaac catacttgaa   10560
tattccgtct tgactttgta aactgtggct acttgaaatg aagttatct ggggttgatg    10620 gatgaatggt agattttgc aatgtctcaa ggcaatagga tgtgtattaa actgtagata   10680
ttcttagtac agtaaattta tgctgataat tttatttgt ataattttta ccttttttgtt   10740 aatatttttt ccttccactt tattggtttg cctcctgagc tacccctcct taccctccct   10800
tctccctcag tgtttcagta aatttaattt agggtgccta gaaattgcaa gtatgtatcc   10860
tttttgattt gtattttatt ataatttaca caaacaactg ggtttgtgaa ctgtattact   10920
cctggtatct ttaaaatatt gtgggtgttt taataaattt tatatttatt ttttgcactc   10980
aaa                                                                  10983
```

<210> SEQ ID NO 26
<211> LENGTH: 761
<212> TYPE: DNA
<213> ORGANISM: Homo sapiens

<400> SEQUENCE: 26

```
ggcggcagga ccagcatgca ccaccgaaac gactcccaga ggctggggaa agctggctgc      60
ccgccagagc cgtcgttgca aatggcaaat actaatttcc tctccacctt atcccctgaa     120
cactgcagac ctttggcggg ggaatgcatg aacaagctca aatgcggcgc tgctgaagca     180
gagataatga atctccccga gcgcgtgggg acttttttccg ctatcccggc tttagggggc     240
atctcattac ctccaggggt catcgtcatg acagcccttc actccccgc agcagcctca     300 gcagccgtca cagacagtgc gtttcaaatt gccaatctgg cagactgccc gcagaatcat     360
tcctcctcct cctcgtcctc ctcaggggga gctggcggag ccaacccagc caagaagaag     420
aggaaaaggt gtgggggtctg cgtgccctgc aagaggctca tcaactgtgg cgtctgcagc     480
agttgcagga accgcaaaac gggacaccag atctgcaaat ttagaaaatg tgaagagcta     540
aagaaaaaac ctggcacttc actagagaga acacctgttc ccagcgctga agcattccga     600
```

```
tggttctttt aaagcagtag tatatcttat tttcaaggca tttggaaatg aagggcaaac    660
taatgtcttg ttttaagaaa ctgcttagtc caccactgaa gaaatatcc agaaattatt    720 ttcattttat gtatagggat ttcttcaaaa aaaaaaaaa a                          761
```

<210> SEQ ID NO 27
<211> LENGTH: 2136
<212> TYPE: PRT
<213> ORGANISM: Homo sapiens

<400> SEQUENCE: 27

```
Met Ser Arg Ser Arg His Ala Arg Pro Ser Arg Leu Val Arg Lys Glu
1               5                   10                  15

Asp Val Asn Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Asp Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
    210                 215                 220

Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
        275                 280                 285

Pro Ile Lys Ser Glu His Asp Cys Tyr Pro Thr Ser Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
```

-continued

```
                340                 345                 350
Ala Asn Gln Gln Glu Val Ser Asp Thr Thr Ser Phe Leu Gly Gln Ala
            355                 360                 365

Phe Gly Ala Ile Pro His Gln Trp Glu Leu Pro Gly Ala Asp Pro Val
        370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
            420                 425                 430

Leu Pro Val Pro Pro Asn Pro Ile Ala Thr Phe Asn Ala Pro Ser Lys
        435                 440                 445

Trp Pro Glu Pro Gln Ser Thr Val Ser Tyr Gly Leu Ala Val Gln Gly
    450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
            500                 505                 510

Gln Gly Phe Pro Leu Ala Pro Glu Arg Gly Leu Phe His Ala Ser Leu
        515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Lys Arg Lys Arg Cys Gly
            580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
    610                 615                 620

Glu Glu Leu Lys Lys Lys Pro Ser Val Val Val Pro Leu Glu Val Ile
625                 630                 635                 640

Lys Glu Asn Lys Arg Pro Gln Arg Glu Lys Lys Pro Lys Val Leu Lys
                645                 650                 655

Ala Asp Phe Asp Asn Lys Pro Val Asn Gly Pro Lys Ser Glu Ser Met
            660                 665                 670

Asp Tyr Ser Arg Cys Gly His Gly Glu Glu Gln Lys Leu Glu Leu Asn
        675                 680                 685

Pro His Thr Val Glu Asn Val Thr Lys Asn Glu Asp Ser Met Thr Gly
    690                 695                 700

Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
                725                 730                 735

Lys Asn Ser Glu Val Asp Lys Lys Arg Thr Lys Ser Pro Lys Leu Phe
            740                 745                 750

Val Gln Thr Val Arg Asn Gly Ile Lys His Val His Cys Leu Pro Ala
        755                 760                 765
```

-continued

```
Glu Thr Asn Val Ser Phe Lys Phe Asn Ile Glu Phe Gly Lys
    770             775             780
Thr Leu Glu Asn Asn Ser Tyr Lys Phe Leu Lys Asp Thr Ala Asn His
785             790             795             800
Lys Asn Ala Met Ser Ser Val Ala Thr Asp Met Ser Cys Asp His Leu
                805             810             815
Lys Gly Arg Ser Asn Val Leu Val Phe Gln Gln Pro Gly Phe Asn Cys
            820             825             830
Ser Ser Ile Pro His Ser Ser His Ser Ile Ile Asn His His Ala Ser
        835             840             845
Ile His Asn Glu Gly Asp Gln Pro Lys Thr Pro Glu Asn Ile Pro Ser
    850             855             860
Lys Glu Pro Lys Asp Gly Ser Pro Val Gln Pro Ser Leu Leu Ser Leu
865             870             875             880
Met Lys Asp Arg Arg Leu Thr Leu Glu Gln Val Val Ala Ile Glu Ala
                885             890             895
Leu Thr Gln Leu Ser Glu Ala Pro Ser Glu Asn Ser Ser Pro Ser Lys
            900             905             910
Ser Glu Lys Asp Glu Glu Ser Glu Gln Arg Thr Ala Ser Leu Leu Asn
        915             920             925
Ser Cys Lys Ala Ile Leu Tyr Thr Val Arg Lys Asp Leu Gln Asp Pro
    930             935             940
Asn Leu Gln Gly Glu Pro Pro Lys Leu Asn His Cys Pro Ser Leu Glu
945             950             955             960
Lys Gln Ser Ser Cys Asn Thr Val Val Phe Asn Gly Gln Thr Thr Thr
                965             970             975
Leu Ser Asn Ser His Ile Asn Ser Ala Thr Asn Gln Ala Ser Thr Lys
            980             985             990
Ser His Glu Tyr Ser Lys Val Thr Asn Ser Leu Ser Leu Phe Ile Pro
        995             1000            1005
Lys Ser Asn Ser Ser Lys Ile Asp Thr Asn Lys Ser Ile Ala Gln
    1010            1015            1020
Gly Ile Ile Thr Leu Asp Asn Cys Ser Asn Asp Leu His Gln Leu
    1025            1030            1035
Pro Pro Arg Asn Asn Glu Val Glu Tyr Cys Asn Gln Leu Leu Asp
    1040            1045            1050
Ser Ser Lys Lys Leu Asp Ser Asp Asp Leu Ser Cys Gln Asp Ala
    1055            1060            1065
Thr His Thr Gln Ile Glu Glu Asp Val Ala Thr Gln Leu Thr Gln
    1070            1075            1080
Leu Ala Ser Ile Ile Lys Ile Asn Tyr Ile Lys Pro Glu Asp Lys
    1085            1090            1095
Lys Val Glu Ser Thr Pro Thr Ser Leu Val Thr Cys Asn Val Gln
    1100            1105            1110
Gln Lys Tyr Asn Gln Glu Lys Gly Thr Ile Gln Gln Lys Pro Pro
    1115            1120            1125
Ser Ser Val His Asn Asn His Gly Ser Ser Leu Thr Lys Gln Lys
    1130            1135            1140
Asn Pro Thr Gln Lys Lys Thr Lys Ser Thr Pro Ser Arg Asp Arg
    1145            1150            1155
Arg Lys Lys Lys Pro Thr Val Val Ser Tyr Gln Glu Asn Asp Arg
    1160            1165            1170
```

```
Gln Lys Trp Glu Lys Leu Ser Tyr Met Tyr Gly Thr Ile Cys Asp
    1175                1180                1185

Ile Trp Ile Ala Ser Lys Phe Gln Asn Phe Gly Gln Phe Cys Pro
    1190                1195                1200

His Asp Phe Pro Thr Val Phe Gly Lys Ile Ser Ser Ser Thr Lys
    1205                1210                1215

Ile Trp Lys Pro Leu Ala Gln Thr Arg Ser Ile Met Gln Pro Lys
    1220                1225                1230

Thr Val Phe Pro Pro Leu Thr Gln Ile Lys Leu Gln Arg Tyr Pro
    1235                1240                1245

Glu Ser Ala Glu Glu Lys Val Lys Val Glu Pro Leu Asp Ser Leu
    1250                1255                1260

Ser Leu Phe His Leu Lys Thr Glu Ser Asn Gly Lys Ala Phe Thr
    1265                1270                1275

Asp Lys Ala Tyr Asn Ser Gln Val Gln Leu Thr Val Asn Ala Asn
    1280                1285                1290

Gln Lys Ala His Pro Leu Thr Gln Pro Ser Ser Pro Pro Asn Gln
    1295                1300                1305

Cys Ala Asn Val Met Ala Gly Asp Asp Gln Ile Arg Phe Gln Gln
    1310                1315                1320

Val Val Lys Glu Gln Leu Met His Gln Arg Leu Pro Thr Leu Pro
    1325                1330                1335

Gly Ile Ser His Glu Thr Pro Leu Pro Glu Ser Ala Leu Thr Leu
    1340                1345                1350

Arg Asn Val Asn Val Val Cys Ser Gly Gly Ile Thr Val Val Ser
    1355                1360                1365

Thr Lys Ser Glu Glu Glu Val Cys Ser Ser Ser Phe Gly Thr Ser
    1370                1375                1380

Glu Phe Ser Thr Val Asp Ser Ala Gln Lys Asn Phe Asn Asp Tyr
    1385                1390                1395

Ala Met Asn Phe Phe Thr Asn Pro Thr Lys Asn Leu Val Ser Ile
    1400                1405                1410

Thr Lys Asp Ser Glu Leu Pro Thr Cys Ser Cys Leu Asp Arg Val
    1415                1420                1425

Ile Gln Lys Asp Lys Gly Pro Tyr Tyr Thr His Leu Gly Ala Gly
    1430                1435                1440

Pro Ser Val Ala Ala Val Arg Glu Ile Met Glu Asn Arg Tyr Gly
    1445                1450                1455

Gln Lys Gly Asn Ala Ile Arg Ile Glu Ile Val Val Tyr Thr Gly
    1460                1465                1470

Lys Glu Gly Lys Ser Ser His Gly Cys Pro Ile Ala Lys Trp Val
    1475                1480                1485

Leu Arg Arg Ser Ser Asp Glu Glu Lys Val Leu Cys Leu Val Arg
    1490                1495                1500

Gln Arg Thr Gly His His Cys Pro Thr Ala Val Met Val Val Leu
    1505                1510                1515

Ile Met Val Trp Asp Gly Ile Pro Leu Pro Met Ala Asp Arg Leu
    1520                1525                1530

Tyr Thr Glu Leu Thr Glu Asn Leu Lys Ser Tyr Asn Gly His Pro
    1535                1540                1545

Thr Asp Arg Arg Cys Thr Leu Asn Glu Asn Arg Thr Cys Thr Cys
    1550                1555                1560

Gln Gly Ile Asp Pro Glu Thr Cys Gly Ala Ser Phe Ser Phe Gly
```

```
            1565                1570                1575

Cys Ser Trp Ser Met Tyr Phe Asn Gly Cys Lys Phe Gly Arg Ser
        1580                1585                1590

Pro Ser Pro Arg Arg Phe Arg Ile Asp Pro Ser Ser Pro Leu His
        1595                1600                1605

Glu Lys Asn Leu Glu Asp Asn Leu Gln Ser Leu Ala Thr Arg Leu
        1610                1615                1620

Ala Pro Ile Tyr Lys Gln Tyr Ala Pro Val Ala Tyr Gln Asn Gln
        1625                1630                1635

Val Glu Tyr Glu Asn Val Ala Arg Glu Cys Arg Leu Gly Ser Lys
        1640                1645                1650

Glu Gly Arg Pro Phe Ser Gly Val Thr Ala Cys Leu Asp Phe Cys
        1655                1660                1665

Ala His Pro His Arg Asp Ile His Asn Met Asn Asn Gly Ser Thr
        1670                1675                1680

Val Val Cys Thr Leu Thr Arg Glu Asp Asn Arg Ser Leu Gly Val
        1685                1690                1695

Ile Pro Gln Asp Glu Gln Leu His Val Leu Pro Leu Tyr Lys Leu
        1700                1705                1710

Ser Asp Thr Asp Glu Phe Gly Ser Lys Glu Gly Met Glu Ala Lys
        1715                1720                1725

Ile Lys Ser Gly Ala Ile Glu Val Leu Ala Pro Arg Arg Lys Lys
        1730                1735                1740

Arg Thr Cys Phe Thr Gln Pro Val Pro Arg Ser Gly Lys Lys Arg
        1745                1750                1755

Ala Ala Met Met Thr Glu Val Leu Ala His Lys Ile Arg Ala Val
        1760                1765                1770

Glu Lys Lys Pro Ile Pro Arg Ile Lys Arg Lys Asn Asn Ser Thr
        1775                1780                1785

Thr Thr Asn Asn Ser Lys Pro Ser Ser Leu Pro Thr Leu Gly Ser
        1790                1795                1800

Asn Thr Glu Thr Val Gln Pro Glu Val Lys Ser Glu Thr Glu Pro
        1805                1810                1815

His Phe Ile Leu Lys Ser Ser Asp Asn Thr Lys Thr Tyr Ser Leu
        1820                1825                1830

Met Pro Ser Ala Pro His Pro Val Lys Glu Ala Ser Pro Gly Phe
        1835                1840                1845

Ser Trp Ser Pro Lys Thr Ala Ser Ala Thr Pro Ala Pro Leu Lys
        1850                1855                1860

Asn Asp Ala Thr Ala Ser Cys Gly Phe Ser Glu Arg Ser Ser Thr
        1865                1870                1875

Pro His Cys Thr Met Pro Ser Gly Arg Leu Ser Gly Ala Asn Ala
        1880                1885                1890

Ala Ala Ala Asp Gly Pro Gly Ile Ser Gln Leu Gly Glu Val Ala
        1895                1900                1905

Pro Leu Pro Thr Leu Ser Ala Pro Val Met Glu Pro Leu Ile Asn
        1910                1915                1920

Ser Glu Pro Ser Thr Gly Val Thr Glu Pro Leu Thr Pro His Gln
        1925                1930                1935

Pro Asn His Gln Pro Ser Phe Leu Thr Ser Pro Gln Asp Leu Ala
        1940                1945                1950

Ser Ser Pro Met Glu Glu Asp Glu Gln His Ser Glu Ala Asp Glu
        1955                1960                1965
```

```
Pro Pro Ser Asp Glu Pro Leu Ser Asp Asp Pro Leu Ser Pro Ala
    1970                1975                1980

Glu Glu Lys Leu Pro His Ile Asp Glu Tyr Trp Ser Asp Ser Glu
    1985                1990                1995

His Ile Phe Leu Asp Ala Asn Ile Gly Gly Val Ala Ile Ala Pro
    2000                2005                2010

Ala His Gly Ser Val Leu Ile Glu Cys Ala Arg Arg Glu Leu His
    2015                2020                2025

Ala Thr Thr Pro Val Glu His Pro Asn Arg Asn His Pro Thr Arg
    2030                2035                2040

Leu Ser Leu Val Phe Tyr Gln His Lys Asn Leu Asn Lys Pro Gln
    2045                2050                2055

His Gly Phe Glu Leu Asn Lys Ile Lys Phe Glu Ala Lys Glu Ala
    2060                2065                2070

Lys Asn Lys Lys Met Lys Ala Ser Glu Gln Lys Asp Gln Ala Ala
    2075                2080                2085

Asn Glu Gly Pro Glu Gln Ser Ser Glu Val Asn Glu Leu Asn Gln
    2090                2095                2100

Ile Pro Ser His Lys Ala Leu Thr Leu Thr His Asp Asn Val Val
    2105                2110                2115

Thr Val Ser Pro Tyr Ala Leu Thr His Val Ala Gly Pro Tyr Asn
    2120                2125                2130

His Trp Val
    2135

<210> SEQ ID NO 28
<211> LENGTH: 2002
<212> TYPE: PRT
<213> ORGANISM: Homo sapiens

<400> SEQUENCE: 28

Met Glu Gln Asp Arg Thr Asn His Val Glu Gly Asn Arg Leu Ser Pro
1               5                   10                  15

Phe Leu Ile Pro Ser Pro Ile Cys Gln Thr Glu Pro Leu Ala Thr
                20                  25                  30

Lys Leu Gln Asn Gly Ser Pro Leu Pro Glu Arg Ala His Pro Glu Val
            35                  40                  45

Asn Gly Asp Thr Lys Trp His Ser Phe Lys Ser Tyr Tyr Gly Ile Pro
50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95

Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
```

-continued

```
                180                 185                 190
His Asp Lys Asn Ile Val Leu Leu Lys Asn Lys Ala Val Leu Met Pro
            195                 200                 205

Asn Gly Ala Thr Val Ser Ala Ser Val Glu His Thr His Gly Glu
        210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Ala Asp Asn Ala
        290                 295                 300

Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
            340                 345                 350

Cys Ser Gly Ser Ser Asn Leu Gln Ala Pro Gly Gly Ser Ser Glu
        355                 360                 365

Arg Tyr Leu Lys Gln Asn Glu Met Asn Gly Ala Tyr Phe Lys Gln Ser
        370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Leu Pro Gln Val Pro
                405                 410                 415

Gln Leu Pro Ser Glu Gly Lys Ser Thr Leu Asn Gly Gly Val Leu Glu
            420                 425                 430

Glu His His His Tyr Pro Asn Gln Ser Asn Thr Thr Leu Leu Arg Glu
        435                 440                 445

Val Lys Ile Glu Gly Lys Pro Glu Ala Pro Pro Ser Gln Ser Pro Asn
        450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
            500                 505                 510

Lys His Asn Pro Pro Ile Phe Gly Ser Ser Gly Glu Leu Gln Asp Asn
        515                 520                 525

Cys Gln Gln Leu Met Arg Asn Lys Glu Gln Glu Ile Leu Lys Gly Arg
        530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                565                 570                 575

Ser His Leu Lys Arg Asn Glu Ala Ser Leu Pro Ser Ile Leu Gln Tyr
            580                 585                 590

Gln Pro Asn Leu Ser Asn Gln Met Thr Ser Lys Gln Tyr Thr Gly Asn
        595                 600                 605
```

```
Ser Asn Met Pro Gly Gly Leu Pro Arg Gln Ala Tyr Thr Gln Lys Thr
    610             615                 620
Thr Gln Leu Glu His Lys Ser Gln Met Tyr Gln Val Glu Met Asn Gln
625             630                 635                 640
Gly Gln Ser Gln Gly Thr Val Asp Gln His Leu Gln Phe Gln Lys Pro
            645                 650                 655
Ser His Gln Val His Phe Ser Lys Thr Asp His Leu Pro Lys Ala His
        660                 665                 670
Val Gln Ser Leu Cys Gly Thr Arg Phe His Phe Gln Gln Arg Ala Asp
    675                 680                 685
Ser Gln Thr Glu Lys Leu Met Ser Pro Val Leu Lys Gln His Leu Asn
690                 695                 700
Gln Gln Ala Ser Glu Thr Glu Pro Phe Ser Asn Ser His Leu Leu Gln
705                 710                 715                 720
His Lys Pro His Lys Gln Ala Ala Gln Thr Gln Pro Ser Gln Ser Ser
            725                 730                 735
His Leu Pro Gln Asn Gln Gln Gln Gln Lys Leu Gln Ile Lys Asn
        740                 745                 750
Lys Glu Glu Ile Leu Gln Thr Phe Pro His Pro Gln Ser Asn Asn Asp
    755                 760                 765
Gln Gln Arg Glu Gly Ser Phe Phe Gly Gln Thr Lys Val Glu Glu Cys
770                 775                 780
Phe His Gly Glu Asn Gln Tyr Ser Lys Ser Ser Glu Phe Glu Thr His
785             790                 795                 800
Asn Val Gln Met Gly Leu Glu Glu Val Gln Asn Ile Asn Arg Arg Asn
            805                 810                 815
Ser Pro Tyr Ser Gln Thr Met Lys Ser Ser Ala Cys Lys Ile Gln Val
        820                 825                 830
Ser Cys Ser Asn Asn Thr His Leu Val Ser Glu Asn Lys Glu Gln Thr
    835                 840                 845
Thr His Pro Glu Leu Phe Ala Gly Asn Lys Thr Gln Asn Leu His His
850                 855                 860
Met Gln Tyr Phe Pro Asn Asn Val Ile Pro Lys Gln Asp Leu Leu His
865             870                 875                 880
Arg Cys Phe Gln Glu Gln Glu Gln Lys Ser Gln Gln Ala Ser Val Leu
            885                 890                 895
Gln Gly Tyr Lys Asn Arg Asn Gln Asp Met Ser Gly Gln Gln Ala Ala
        900                 905                 910
Gln Leu Ala Gln Gln Arg Tyr Leu Ile His Asn His Ala Asn Val Phe
    915                 920                 925
Pro Val Pro Asp Gln Gly Gly Ser His Thr Gln Thr Pro Pro Gln Lys
930                 935                 940
Asp Thr Gln Lys His Ala Ala Leu Arg Trp His Leu Leu Gln Lys Gln
945             950                 955                 960
Glu Gln Gln Gln Thr Gln Gln Pro Gln Thr Glu Ser Cys His Ser Gln
            965                 970                 975
Met His Arg Pro Ile Lys Val Glu Pro Gly Cys Lys Pro His Ala Cys
        980                 985                 990
Met His Thr Ala Pro Pro Glu Asn Lys Thr Trp Lys Lys Val Thr Lys
    995                 1000                1005
Gln Glu Asn Pro Pro Ala Ser Cys Asp Asn Val Gln Gln Lys Ser
    1010                1015                1020
```

-continued

| | | | | | | | | | | | |
|---|---|---|---|---|---|---|---|---|---|---|---|
| Ile | Ile | Glu | Thr | Met | Glu | Gln | His | Leu | Lys | Gln | Phe | His | Ala | Lys |
| 1025 | | | | | 1030 | | | | | 1035 | | | | |

Ile Ile Glu Thr Met Glu Gln His Leu Lys Gln Phe His Ala Lys
    1025                1030             1035

Ser Leu Phe Asp His Lys Ala Leu Thr Leu Lys Ser Gln Lys Gln
    1040                1045             1050

Val Lys Val Glu Met Ser Gly Pro Val Thr Val Leu Thr Arg Gln
    1055                1060             1065

Thr Thr Ala Ala Glu Leu Asp Ser His Thr Pro Ala Leu Glu Gln
    1070                1075             1080

Gln Thr Thr Ser Ser Glu Lys Thr Pro Thr Lys Arg Thr Ala Ala
    1085                1090             1095

Ser Val Leu Asn Asn Phe Ile Glu Ser Pro Ser Lys Leu Leu Asp
    1100                1105             1110

Thr Pro Ile Lys Asn Leu Leu Asp Thr Pro Val Lys Thr Gln Tyr
    1115                1120             1125

Asp Phe Pro Ser Cys Arg Cys Val Glu Gln Ile Ile Glu Lys Asp
    1130                1135             1140

Glu Gly Pro Phe Tyr Thr His Leu Gly Ala Gly Pro Asn Val Ala
    1145                1150             1155

Ala Ile Arg Glu Ile Met Glu Glu Arg Phe Gly Gln Lys Gly Lys
    1160                1165             1170

Ala Ile Arg Ile Glu Arg Val Ile Tyr Thr Gly Lys Glu Gly Lys
    1175                1180             1185

Ser Ser Gln Gly Cys Pro Ile Ala Lys Trp Val Val Arg Arg Ser
    1190                1195             1200

Ser Ser Glu Glu Lys Leu Leu Cys Leu Val Arg Glu Arg Ala Gly
    1205                1210             1215

His Thr Cys Glu Ala Ala Val Ile Val Ile Leu Ile Leu Val Trp
    1220                1225             1230

Glu Gly Ile Pro Leu Ser Leu Ala Asp Lys Leu Tyr Ser Glu Leu
    1235                1240             1245

Thr Glu Thr Leu Arg Lys Tyr Gly Thr Leu Thr Asn Arg Arg Cys
    1250                1255             1260

Ala Leu Asn Glu Glu Arg Thr Cys Ala Cys Gln Gly Leu Asp Pro
    1265                1270             1275

Glu Thr Cys Gly Ala Ser Phe Ser Phe Gly Cys Ser Trp Ser Met
    1280                1285             1290

Tyr Tyr Asn Gly Cys Lys Phe Ala Arg Ser Lys Ile Pro Arg Lys
    1295                1300             1305

Phe Lys Leu Leu Gly Asp Asp Pro Lys Glu Glu Lys Leu Glu
    1310                1315             1320

Ser His Leu Gln Asn Leu Ser Thr Leu Met Ala Pro Thr Tyr Lys
    1325                1330             1335

Lys Leu Ala Pro Asp Ala Tyr Asn Asn Gln Ile Glu Tyr Glu His
    1340                1345             1350

Arg Ala Pro Glu Cys Arg Leu Gly Leu Lys Glu Gly Arg Pro Phe
    1355                1360             1365

Ser Gly Val Thr Ala Cys Leu Asp Phe Cys Ala His Ala His Arg
    1370                1375             1380

Asp Leu His Asn Met Gln Asn Gly Ser Thr Leu Val Cys Thr Leu
    1385                1390             1395

Thr Arg Glu Asp Asn Arg Glu Phe Gly Gly Lys Pro Glu Asp Glu
    1400                1405             1410

Gln Leu His Val Leu Pro Leu Tyr Lys Val Ser Asp Val Asp Glu

```
              1415                1420                1425
Phe Gly Ser Val Glu Ala Gln Glu Lys Lys Arg Ser Gly Ala
        1430                1435                1440
Ile Gln Val Leu Ser Ser Phe Arg Arg Lys Val Arg Met Leu Ala
        1445                1450                1455
Glu Pro Val Lys Thr Cys Arg Gln Arg Lys Leu Glu Ala Lys Lys
        1460                1465                1470
Ala Ala Ala Glu Lys Leu Ser Ser Leu Glu Asn Ser Ser Asn Lys
        1475                1480                1485
Asn Glu Lys Glu Lys Ser Ala Pro Ser Arg Thr Lys Gln Thr Glu
        1490                1495                1500
Asn Ala Ser Gln Ala Lys Gln Leu Ala Glu Leu Leu Arg Leu Ser
        1505                1510                1515
Gly Pro Val Met Gln Gln Ser Gln Gln Pro Gln Pro Leu Gln Lys
        1520                1525                1530
Gln Pro Pro Gln Pro Gln Gln Gln Arg Pro Gln Gln Gln
        1535                1540                1545
Pro His His Pro Gln Thr Glu Ser Val Asn Ser Tyr Ser Ala Ser
        1550                1555                1560
Gly Ser Thr Asn Pro Tyr Met Arg Arg Pro Asn Pro Val Ser Pro
        1565                1570                1575
Tyr Pro Asn Ser Ser His Thr Ser Asp Ile Tyr Gly Ser Thr Ser
        1580                1585                1590
Pro Met Asn Phe Tyr Ser Thr Ser Ser Gln Ala Ala Gly Ser Tyr
        1595                1600                1605
Leu Asn Ser Ser Asn Pro Met Asn Pro Tyr Pro Gly Leu Leu Asn
        1610                1615                1620
Gln Asn Thr Gln Tyr Pro Ser Tyr Gln Cys Asn Gly Asn Leu Ser
        1625                1630                1635
Val Asp Asn Cys Ser Pro Tyr Leu Gly Ser Tyr Ser Pro Gln Ser
        1640                1645                1650
Gln Pro Met Asp Leu Tyr Arg Tyr Pro Ser Gln Asp Pro Leu Ser
        1655                1660                1665
Lys Leu Ser Leu Pro Pro Ile His Thr Leu Tyr Gln Pro Arg Phe
        1670                1675                1680
Gly Asn Ser Gln Ser Phe Thr Ser Lys Tyr Leu Gly Tyr Gly Asn
        1685                1690                1695
Gln Asn Met Gln Gly Asp Gly Phe Ser Ser Cys Thr Ile Arg Pro
        1700                1705                1710
Asn Val His His Val Gly Lys Leu Pro Pro Tyr Pro Thr His Glu
        1715                1720                1725
Met Asp Gly His Phe Met Gly Ala Thr Ser Arg Leu Pro Pro Asn
        1730                1735                1740
Leu Ser Asn Pro Asn Met Asp Tyr Lys Asn Gly Glu His His Ser
        1745                1750                1755
Pro Ser His Ile Ile His Asn Tyr Ser Ala Ala Pro Gly Met Phe
        1760                1765                1770
Asn Ser Ser Leu His Ala Leu His Leu Gln Asn Lys Glu Asn Asp
        1775                1780                1785
Met Leu Ser His Thr Ala Asn Gly Leu Ser Lys Met Leu Pro Ala
        1790                1795                1800
Leu Asn His Asp Arg Thr Ala Cys Val Gln Gly Gly Leu His Lys
        1805                1810                1815
```

```
Leu Ser Asp Ala Asn Gly Gln Glu Lys Gln Pro Leu Ala Leu Val
    1820            1825                1830

Gln Gly Val Ala Ser Gly Ala Glu Asp Asn Asp Glu Val Trp Ser
    1835            1840                1845

Asp Ser Glu Gln Ser Phe Leu Asp Pro Asp Ile Gly Gly Val Ala
    1850            1855                1860

Val Ala Pro Thr His Gly Ser Ile Leu Ile Glu Cys Ala Lys Arg
    1865            1870                1875

Glu Leu His Ala Thr Thr Pro Leu Lys Asn Pro Asn Arg Asn His
    1880            1885                1890

Pro Thr Arg Ile Ser Leu Val Phe Tyr Gln His Lys Ser Met Asn
    1895            1900                1905

Glu Pro Lys His Gly Leu Ala Leu Trp Glu Ala Lys Met Ala Glu
    1910            1915                1920

Lys Ala Arg Glu Lys Glu Glu Cys Glu Lys Tyr Gly Pro Asp
    1925            1930                1935

Tyr Val Pro Gln Lys Ser His Gly Lys Lys Val Lys Arg Glu Pro
    1940            1945                1950

Ala Glu Pro His Glu Thr Ser Glu Pro Thr Tyr Leu Arg Phe Ile
    1955            1960                1965

Lys Ser Leu Ala Glu Arg Thr Met Ser Val Thr Thr Asp Ser Thr
    1970            1975                1980

Val Thr Thr Ser Pro Tyr Ala Phe Thr Arg Val Thr Gly Pro Tyr
    1985            1990                1995

Asn Arg Tyr Ile
    2000

<210> SEQ ID NO 29
<211> LENGTH: 198
<212> TYPE: PRT
<213> ORGANISM: Homo sapiens

<400> SEQUENCE: 29

Met His His Arg Asn Asp Ser Gln Arg Leu Gly Lys Ala Gly Cys Pro
1               5                   10                  15

Pro Glu Pro Ser Leu Gln Met Ala Asn Thr Asn Phe Leu Ser Thr Leu
            20                  25                  30

Ser Pro Glu His Cys Arg Pro Leu Ala Gly Glu Cys Met Asn Lys Leu
        35                  40                  45

Lys Cys Gly Ala Ala Glu Ala Glu Ile Met Asn Leu Pro Glu Arg Val
    50                  55                  60

Gly Thr Phe Ser Ala Ile Pro Ala Leu Gly Ile Ser Leu Pro Pro
65                  70                  75                  80

Gly Val Ile Val Met Thr Ala Leu His Ser Pro Ala Ala Ser Ala
                85                  90                  95

Ala Val Thr Asp Ser Ala Phe Gln Ile Ala Asn Leu Ala Asp Cys Pro
                100                 105                 110

Gln Asn His Ser Ser Ser Ser Ser Ser Ser Gly Gly Ala Gly Gly
            115                 120                 125

Ala Asn Pro Ala Lys Lys Lys Arg Lys Arg Cys Gly Val Cys Val Pro
    130                 135                 140

Cys Lys Arg Leu Ile Asn Cys Gly Val Cys Ser Ser Cys Arg Asn Arg
145                 150                 155                 160

Lys Thr Gly His Gln Ile Cys Lys Phe Arg Lys Cys Glu Glu Leu Lys
```

```
                    165                 170                 175
Lys Lys Pro Gly Thr Ser Leu Glu Arg Thr Pro Val Pro Ser Ala Glu
            180                 185                 190

Ala Phe Arg Trp Phe Phe
        195

<210> SEQ ID NO 30
<211> LENGTH: 19
<212> TYPE: DNA
<213> ORGANISM: Mus musculus

<400> SEQUENCE: 30
gaacggcatc aaggtgaac                                                  19

<210> SEQ ID NO 31
<211> LENGTH: 19
<212> TYPE: DNA
<213> ORGANISM: Mus musculus

<400> SEQUENCE: 31
gttcaccttg atgccgttc                                                  19

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccccgaa cggcatcaag gtgaacttca agagagttca ccttgatgcc gttcttttta    60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agcttaaaaa gaacggcatc aaggtgaact ctcttgaagt tcaccttgat gccgttcggg    60

<210> SEQ ID NO 34
<211> LENGTH: 19
<212> TYPE: DNA
<213> ORGANISM: Mus musculus

<400> SEQUENCE: 34
caacttgcat ccacgatta                                                  19

<210> SEQ ID NO 35
<211> LENGTH: 19
<212> TYPE: DNA
<213> ORGANISM: Mus musculus

<400> SEQUENCE: 35
taatcgtgga tgcaagttg                                                  19

<210> SEQ ID NO 36
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 36
gatcccccaa cttgcatcca cgattattca agagataatc gtggatgcaa gttgttttta    60

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agcttaaaaa caacttgcat ccacgattat ctcttgaata atcgtggatg caagttgggg    60

<210> SEQ ID NO 38
<211> LENGTH: 19
<212> TYPE: DNA
<213> ORGANISM: Mus musculus

<400> SEQUENCE: 38
gaattacagt tgttacgga                                                 19

<210> SEQ ID NO 39
<211> LENGTH: 19
<212> TYPE: DNA
<213> ORGANISM: Mus musculus

<400> SEQUENCE: 39
tccgtaacaa ctgtaattc                                                 19

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gatccccgaa ttacagttgt tacggattca agagatccgt aacaactgta attctttta    60

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agcttaaaaa gaattacagt tgttacggat ctcttgaatc cgtaacaact gtaattcggg    60

<210> SEQ ID NO 42
<211> LENGTH: 19
<212> TYPE: DNA
<213> ORGANISM: Mus musculus

<400> SEQUENCE: 42
cgtagaatat gtacctggt                                                 19

<210> SEQ ID NO 43
```

```
<211> LENGTH: 19
<212> TYPE: DNA
<213> ORGANISM: Mus musculus

<400> SEQUENCE: 43
accaggtaca tattctacg                                                   19

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 gatccccgt agaatatgta cctggtttca agagaaccag gtacatattc tacgttttta       60

<210> SEQ ID NO 45
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agcttaaaaa cgtagaatat gtacctggtt ctcttgaaac caggtacata ttctacgggg      60

<210> SEQ ID NO 46
<211> LENGTH: 19
<212> TYPE: DNA
<213> ORGANISM: Mus musculus

<400> SEQUENCE: 46
gaaagcagct cgaaagcgt                                                   19

<210> SEQ ID NO 47
<211> LENGTH: 19
<212> TYPE: DNA
<213> ORGANISM: Mus musculus

<400> SEQUENCE: 47
acgctttcga gctgctttc                                                   19

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatccccgaa agcagctcga aagcgttca agagaacgct ttcgagctgc tttcttttta      60

<210> SEQ ID NO 49
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agcttaaaaa gaaagcagct cgaaagcgtt ctcttgaaac gctttcgagc tgctttcggg    60
```

<210> SEQ ID NO 50
<211> LENGTH: 19
<212> TYPE: DNA
<213> ORGANISM: Mus musculus

<400> SEQUENCE: 50
actactaact ccaccctaa                                              19

<210> SEQ ID NO 51
<211> LENGTH: 19
<212> TYPE: DNA
<213> ORGANISM: Mus musculus

<400> SEQUENCE: 51
ttagggtgga gttagtagt                                              19

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gatccccact actaactcca ccctaattca agagattagg gtggagttag tagtttttta    60

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agcttaaaaa actactaact ccaccctaat ctcttgaatt agggtggagt tagtagtggg    60

<210> SEQ ID NO 54
<211> LENGTH: 19
<212> TYPE: DNA
<213> ORGANISM: Mus musculus

<400> SEQUENCE: 54
gaaggatgtg gttcgagta                                              19

<210> SEQ ID NO 55
<211> LENGTH: 19
<212> TYPE: DNA
<213> ORGANISM: Mus musculus

<400> SEQUENCE: 55
tactcgaacc acatccttc                                              19

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gatccccgaa ggatgtggtt cgagtattca agagatactc gaaccacatc cttcttttta    60

```
<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agcttaaaaa gaaggatgtg gttcgagtat ctcttgaata ctcgaaccac atccttcggg    60

<210> SEQ ID NO 58
<211> LENGTH: 19
<212> TYPE: DNA
<213> ORGANISM: Mus musculus

<400> SEQUENCE: 58
gaactattct tgcttacaa                                                 19

<210> SEQ ID NO 59
<211> LENGTH: 19
<212> TYPE: DNA
<213> ORGANISM: Mus musculus

<400> SEQUENCE: 59
ttgtaagcaa gaatagttc                                                 19

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gatccccgaa ctattcttgc ttacaattca agagattgta agcaagaata gttcttttta    60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
agcttaaaaa gaactattct tgcttacaat ctcttgaatt gtaagcaaga atagttcggg    60

<210> SEQ ID NO 62
<211> LENGTH: 19
<212> TYPE: DNA
<213> ORGANISM: Mus musculus

<400> SEQUENCE: 62
gaaggagcac ccggattat                                                 19

<210> SEQ ID NO 63
<211> LENGTH: 19
<212> TYPE: DNA
<213> ORGANISM: Mus musculus

<400> SEQUENCE: 63
ataatccggg tgctccttc                                                 19
```

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gatccccgaa ggagcacccg gattatttca agagaataat ccgggtgctc cttcttttta    60

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agcttaaaaa gaaggagcac ccggattatt ctcttgaaat aatccgggtg ctccttcggg    60

<210> SEQ ID NO 66
<211> LENGTH: 21
<212> TYPE: DNA
<213> ORGANISM: Mus musculus

<400> SEQUENCE: 66
gcgtagaata tgtaactggt a                                              21

<210> SEQ ID NO 67
<211> LENGTH: 21
<212> TYPE: DNA
<213> ORGANISM: Mus musculus

<400> SEQUENCE: 67
taccagttac atattctacg c                                              21

<210> SEQ ID NO 68
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccgggcgtag aatatgtaac tggtactcga gtaccagtta catattctac gcttttttg     58

<210> SEQ ID NO 69
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aattcaaaaa gcgtagaata tgtaactggt actcgagtac cagttacata ttctacgc     58

<210> SEQ ID NO 70
<211> LENGTH: 19
<212> TYPE: DNA
<213> ORGANISM: Mus musculus

```
<400> SEQUENCE: 70
gaaagcagct cgaaagcgt                                           19

<210> SEQ ID NO 71
<211> LENGTH: 19
<212> TYPE: DNA
<213> ORGANISM: Mus musculus

<400> SEQUENCE: 71
actactaact ccaccctaa                                           19

<210> SEQ ID NO 72
<211> LENGTH: 21
<212> TYPE: DNA
<213> ORGANISM: Mus musculus

<400> SEQUENCE: 72
agaaagcagc tcgaaagcgt t                                        21

<210> SEQ ID NO 73
<211> LENGTH: 21
<212> TYPE: DNA
<213> ORGANISM: Mus musculus

<400> SEQUENCE: 73
aacgctttcg agctgctttc t                                        21

<210> SEQ ID NO 74
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ccggagaaag cagctcgaaa gcgttctcga gaacgctttc gagctgcttt cttttttg    58

<210> SEQ ID NO 75
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aattcaaaaa agaaagcagc tcgaaagcgt tctcgagaac gctttcgagc tgctttct     58

<210> SEQ ID NO 76
<211> LENGTH: 21
<212> TYPE: DNA
<213> ORGANISM: Mus musculus

<400> SEQUENCE: 76
cactactaac tccaccctaa a                                        21

<210> SEQ ID NO 77
<211> LENGTH: 21
<212> TYPE: DNA
<213> ORGANISM: Mus musculus

<400> SEQUENCE: 77
tttagggtgg agttagtagt g                                        21
```

<210> SEQ ID NO 78
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ccggcactac taactccacc ctaaactcga gtttagggtg gagttagtag tgttttg       58

<210> SEQ ID NO 79
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aattcaaaaa cactactaac tccaccctaa actcgagttt agggtggagt tagtagtg      58

<210> SEQ ID NO 80
<211> LENGTH: 21
<212> TYPE: DNA
<213> ORGANISM: Mus musculus

<400> SEQUENCE: 80
gcagctggtt tatggtgatt t                                              21

<210> SEQ ID NO 81
<211> LENGTH: 21
<212> TYPE: DNA
<213> ORGANISM: Mus musculus

<400> SEQUENCE: 81
aaatcaccat aaaccagctg c                                              21

<210> SEQ ID NO 82
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccgggcagct ggtttatggt gatttctcga gaaatcacca taaaccagct gcttttg       58

<210> SEQ ID NO 83
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aattcaaaaa gcagctggtt tatggtgatt tctcgagaaa tcaccataaa ccagctgc      58

<210> SEQ ID NO 84
<211> LENGTH: 19
<212> TYPE: DNA
<213> ORGANISM: Mus musculus

```
<400> SEQUENCE: 84
caacttgcat ccacgatta                                                      19

<210> SEQ ID NO 85
<211> LENGTH: 22
<212> TYPE: DNA
<213> ORGANISM: Mus musculus

<400> SEQUENCE: 85
cccaacttgc atccacgatt aa                                                  22

<210> SEQ ID NO 86
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgctgttgac agtgagcgac caacttgcat ccacgattaa tagtgaagcc acagatgtat        60
taatcgtgga tgcaagttgg gtgcctactg cctcgga                                 97

<210> SEQ ID NO 87
<211> LENGTH: 19
<212> TYPE: DNA
<213> ORGANISM: Mus musculus

<400> SEQUENCE: 87
gaattacagt tgttacgga                                                      19

<210> SEQ ID NO 88
<211> LENGTH: 22
<212> TYPE: DNA
<213> ORGANISM: Mus musculus

<400> SEQUENCE: 88
tggaattaca gttgttacgg ag                                                  22

<210> SEQ ID NO 89
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tgctgttgac agtgagcgcg gaattacagt tgttacggag tagtgaagcc acagatgtac        60
tccgtaacaa ctgtaattcc atgcctactg cctcgga                                 97

<210> SEQ ID NO 90
<211> LENGTH: 19
<212> TYPE: DNA
<213> ORGANISM: Mus musculus

<400> SEQUENCE: 90
gaaagcagct cgaaagcgt                                                      19

<210> SEQ ID NO 91
<211> LENGTH: 22
<212> TYPE: DNA
<213> ORGANISM: Mus musculus
```

```
<400> SEQUENCE: 91
aagaaagcag ctcgaaagcg tt                                              22

<210> SEQ ID NO 92
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tgctgttgac agtgagcgca gaaagcagct cgaaagcgtt tagtgaagcc acagatgtaa     60
acgctttcga gctgctttct ttgcctactg cctcgga                              97

<210> SEQ ID NO 93
<211> LENGTH: 19
<212> TYPE: DNA
<213> ORGANISM: Mus musculus

<400> SEQUENCE: 93
actactaact ccaccctaa                                                  19

<210> SEQ ID NO 94
<211> LENGTH: 22
<212> TYPE: DNA
<213> ORGANISM: Mus musculus

<400> SEQUENCE: 94
tcactactaa ctccaccctr aa                                              22

<210> SEQ ID NO 95
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgctgttgac agtgagcgcc actactaact ccaccctaaa tagtgaagcc acagatgtat     60
ttagggtgga gttagtagtg atgcctactg cctcgga                              97

<210> SEQ ID NO 96
<211> LENGTH: 21
<212> TYPE: DNA
<213> ORGANISM: Mus musculus

<400> SEQUENCE: 96
gcgtagaata tgtacctggt a                                               21

<210> SEQ ID NO 97
<211> LENGTH: 21
<212> TYPE: DNA
<213> ORGANISM: Mus musculus

<400> SEQUENCE: 97
taccaggtac atattctacg c                                               21

<210> SEQ ID NO 98
<211> LENGTH: 97
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 98
tgctgttgac agtgagcgag cgtagaatat gtacctggta tagtgaagcc acagatgtat        60
accaggtaca tattctacgc gtgcctactg cctcgga                                 97

<210> SEQ ID NO 99
<211> LENGTH: 21
<212> TYPE: DNA
<213> ORGANISM: Mus musculus

<400> SEQUENCE: 99
gcacgaagcg tatggataca a                                                  21

<210> SEQ ID NO 100
<211> LENGTH: 21
<212> TYPE: DNA
<213> ORGANISM: Mus musculus

<400> SEQUENCE: 100
ttgtatccat acgcttcgtg c                                                  21

<210> SEQ ID NO 101
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgctgttgac agtgagcgcg cacgaagcgt atggatacaa tagtgaagcc acagatgtat        60
tgtatccata cgcttcgtgc ttgcctactg cctcgga                                 97

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, g, t, unknown or other

<400> SEQUENCE: 102
aannnnnnnn nnnnnnnnnn ntt                                                23
```